US007655460B2

(12) United States Patent
Rouleau et al.

(10) Patent No.: US 7,655,460 B2
(45) Date of Patent: Feb. 2, 2010

(54) NUCLEIC ACIDS ENCODING SODIUM CHANNEL SCN1A ALPHA SUBUNIT PROTEINS WITH MUTATIONS ASSOCIATED WITH EPILEPSY

(75) Inventors: Guy A. Rouleau, Montreal (CA); Ronald G. Lafrenière, Verdun (CA); Daniel Rochefort, Laval (CA)

(73) Assignee: McGill University, Montreal, Quebec (CA)

( * ) Notice: Subject to any disclaimer, the term of this patent is extended or adjusted under 35 U.S.C. 154(b) by 338 days.

(21) Appl. No.: 10/664,423

(22) Filed: Sep. 17, 2003

(65) Prior Publication Data

US 2004/0096886 A1 May 20, 2004

Related U.S. Application Data

(62) Division of application No. 09/718,355, filed on Nov. 24, 2000.

(60) Provisional application No. 60/167,623, filed on Nov. 26, 1999.

(51) Int. Cl.

| | |
|---|---|
| ***C12N 5/10*** | (2006.01) |
| ***C12N 15/12*** | (2006.01) |
| ***C07H 21/04*** | (2006.01) |

(52) U.S. Cl. .................... 435/325; 435/320.1; 536/23.5

(58) Field of Classification Search ....................... None
See application file for complete search history.

(56) References Cited

U.S. PATENT DOCUMENTS

| | | | | |
|---|---|---|---|---|
| 5,223,409 A | 6/1993 | Ladner et al. | .............. | 435/69.7 |
| 6,110,672 A * | 8/2000 | Mandel et al. | ................. | 435/6 |
| 6,673,549 B1 * | 1/2004 | Furness et al. | ................. | 435/6 |
| 7,078,515 B2 * | 7/2006 | Wallace et al. | ............. | 536/23.5 |

FOREIGN PATENT DOCUMENTS

| | | | |
|---|---|---|---|
| WO | 96/14077 | * | 5/1996 |
| WO | 97/01577 | * | 1/1997 |
| WO | WO 99/21875 | | 5/1999 |

OTHER PUBLICATIONS

Rudinger, in "Peptide Hormones" (ed., J.A. Parsons) University Park Press, Baltimore, pp. 1-7 (1976).*

Noda 1986. Nature 320:188-192.*

Sequence alignment for NCBI Accession No. X03638.*

Wang 1997. J Clin Invest 99:1714-1720.*

Sequence alignment for US 6,110,672 sequence 14.*

Stratagene Catalog 1991, p. 66.*

Current Protocols in Molecular Biology (1989-1996), pp. 6.0.3-6.0.5, 6.1.1-6.1.4, 6.3.1-6.3.6, and 6.5.1-6.5.2.*

Ahmed et al., "Primary structure, chromosomal localization, and functional expression of a voltage-gated sodium channel from human brain," Proc. Natl. Acad. Sci. USA, 89:8220-8224, 1992.

Lu and Brown, "Isolation of a human-brain sodium-channel gene encoding two isoforms of the subtype III α-subunit," J. Mol. Neuro., 10:67-70, 1998.

Andermann, E., Genetic Basis of the Epilepsies, Raven Press, New York, pp. 355-374, 1982.

Anderson et al., "Use of cyclosporin A in establishing Epstein-Barr virus-transformed human lymphoblastoid cell lines," In Vitro, 20:856-858, 1984.

Annegers et al., Genetic Basis of the Epilepsies, Raven Press, New York, pp. 151-159, 1982.

Baker et al., "Cell proloferation kinetics of normal and tumor tissue in vitro: quiescent reproductive cells and the cycling reproductive fraction," *Cell Prolif.*, 28:1-15, 1995.

Barker et al., "GABA actions on the excitability of cultured CNS neurons ," *Neurosci. Lett.*, 47:313-318, 1984.

Bar-Sagi et al., "Negative modulation of sodium channels in cultured chick muscle cells by the channel activator batrachotoxin," *J. Biol. Chem.*, 260:4740-4744, 1985.

Baulac et al., "A second locus for familial generalized epilepsy with febrile seizures plus maps to chromosome 2q21-q33," *Am. J. Hum. Genet.*, 65:1078-1085, 1999.

Baunoch et al., "R-ELISA: repeated use of antigen-coated plates for ELISA and its application for testing of antibodies to HIV and other pathogens," *Biotechniques*, 12:412-417, 1992.

Berkovic et al., "Epilepsies in twins: genetics of the major epilepsy syndromes," *Ann. Neurol.*, 43:435-445, 1998.

Biervert et al., "A potassium channel mutation in neonatal human epilepsy," *Science*, 279:403-406, 1998.

Bu et al., "The exon-intron organization of the genes (GAD1 and GAD2) encoding two human glutamate decarboxylases (GAD67 and GAD65) suggests that they derive from a common ancestral GAD," *Genomics*, 21:222-228, 1994.

Cardell et al., Agnew. Chem. Int. Ed. Engl., 33:2061-2063, 1994.

Charlier et al., "A pore mutation in a novel KQT-like potassium channel gene in an idiopathic epilepsy family," *Nat. Genet*, 18:53-55, 1998.

Cheviron et al., "The antiproliferative activity of the tetrapeptide Acetyl-N-SerAspLysPro, an inhibitor of haematopoietic stem cell proliferation, is not mediated by a thymosin beta 4-like effect on actin assembly," *Cell Prolif.*, 29:437-446, 1996.

Chia et al., "Cytoskeletal association of an esterase in *Dictyostelium discoideum," Exp.Cell Res.*, 244:340-348, 1998.

(Continued)

*Primary Examiner*—Daniel E. Kolker
(74) *Attorney, Agent, or Firm*—Fulbright & Jaworski L.L.P.

(57) ABSTRACT

The present invention relates to epilepsy. More particularly, the present invention relates to idiopathic generalized epilepsy (IGE) and to the identification of three genes mapping to chromosome 2, which show mutations in patients with epilepsy. The invention further relates to nucleic acid sequences, and protein sequences of these loci (SCNA) and to the use thereof to assess, diagnose, prognose or treat epilepsy, to predict an epileptic individual's response to medication and to identify agents which modulate the function of the SCNA. The invention also provides screening assays using SCN1A, SCN2A and/or SCN3A which can identify compounds which have therapeutic benefit for epilepsy and related neurological disorders.

23 Claims, 21 Drawing Sheets

OTHER PUBLICATIONS

Cho et al., "An Unnatural Biopolymer," *Science*, 261:1303-1305, 1993.
Clare et al., "Voltage-gated sodium channels as therapeutic targets," *Drug Discovery Today*, 5:506-520, 2000.
Corey et al., "The occurrence of epilepsy and febrile seizures in Virginian and Norwegian twins," *Neurology*, 41:1433:1436, 1991.
Cull et al., "Screening for receptor ligands using large libraries of peptides linked to the C terminus of the lac repressor," *Proc. Natl. Acad. Sci. USA*, 89:1865-1869, 1992.
Denyer et al., "HTS approaches to voltage-gated ion channel drug discovery," *Drug Discovery Today*, 3:323-332, 1998.
DeWitt et al., ""Diversomers": an approach to nonpeptide, nonoligomeric chemical diversity," *Proc. Natl. Acad. Sci. USA*, 90:6909-6913, 1993.
Elliot et al., "Bin1 functionally interacts with Myc and inhibits cell proliferation via multiple mechanisms," *Oncogene*, 18:3564-3573, 1999.
Elmslie et al., "Genetic mapping of a major susceptibility locus for juvenile myoclonic epilepsy on chromosome 15q," *Hum. Mol. Genet*., 6:1329-1334, 1997.
Engel et al., Epilepsy: A Comprehensive Textbook, Lippincott-Raven, Phildelphia, 1-7 (1), 1997.
Erb et al., "Recursive deconvolution of combinatorial chemical libraries," *Proc. Natl. Acad. Sci, USA*, 91:11422-11426, 1994.
Escayg et al., "Mutations of SCN1A, encoding a neuronal sodium channel, in two families with GEFS+," *Nat. Genet*., 24:343-345, 2000.
Fodor et al., "Multiplexed biochemical assays with biological chips," *Nature*, 364:555-556, 1993.
Gallop et al., "Applications of combinatorial technologies to drug discovery. 1. Background and peptide combinatorial libraries," *J. Med. Chem*., 37:1233-1251, 1994.
Gonzalez et al., "Cell-based assays and instrumentation for screening ion-channel targets," *Drug Discovery Today*, 4:431-439, 1999.
Gonzalez et al., "Modification of tau to an Alzheimer's type protein interferes with its interaction with microtubules," *Cell. Mol. Biol*., 44:1117-1127, 1998.
Greenberg et al., "Juvenile myoclonic epilepsy (JME) may be linked to the BF and HLA loci on human chromosome 6," *Am. J. Med. Genet*., 31:185-192, 1988.
Guipponi et al., "Linkage mapping of benign familial infantile convulsions (BFIC) to chromosome 19q," *Hum. Mol. Genet*., 6:473-477, 1997.
Gyapay et al., "The 1993-94 Genethon human genetic linkage map," *Nat Genet*. 7:246-339, 1994.
Hamill et al., "Improved patch-clamp techniques for high-resolution current recording from cells and cell-free membrane patches," *PflÜgers Archiv*., 391:85-100, 1981.
Hu et al., "alpha1-Adrenergic receptor stimulation of mitogenesis in human vascular smooth muscle cells: role of tyrosine protein kinases and calcium in activation of mitogen-activated protein kinase," *Journ. Pharmacology Experimental therapeutics*, 290:28-37, 1999.
Kawai et al., "Death-associated protein kinase 2 is a new calcium/calmodulin-dependent protein kinase that signals apoptosis through its catalytic activity," *Oncogene*, 18:3471-3480, 1999.
Komada et al., "Hrs, a FYVE finger protein localized to early endosomes, is implicated in vesicular traffic and required for ventral folding morphogenesis," *Genes & Dev*., 13:1475-1485, 1999.
Lam et al., "A new type of synthetic peptide library for identifying ligand-binding activity," *Nature*, 354:82-84, 1991.
Lam, K.S., "Application of combinatorial library methods in cancer research and drug discovery," *Anti-Cancer Drug Design*, 12:145-167, 1997.
Lanthrop et al., "Easy calculations of lod scores and genetic risks on small computers," *Am. J. Genet*., 36:460-465, 1984.
Lennox et al., Epilepsy and related disorders, Little Brown, pp. 532-574, 1960.
Leppert et al., "Benign familial neonatal convulsions linked to genetic markers on chromosome 20," *Nature*, 337:647-648, 1989.
Lewis et al., "Genetic heterogeneity in benign familial neonatal convulsions: identification of a new locus on chromosome 8q," *Am. J. Hum. Genet*., 53:670-675, 1993.
Liu, L., "Calcium-dependent self-association of annexin II: a possible implication in exocytosis," *Cell. Signal*., 11:317-324, 1999.
Malo et al., "Localization of a putative human brain sodium channel gene (SCN1A) to chromosome band 2q24," *Cytogenet. Cell Genet*., 67:178-186, 1994.
Malo et al., "Targeted gene walking by low stringency polymerase chain reaction: assignment of a putative human brain sodium channel gene (SCN3A) to chromosome 2q24-31," *Proc. Natl. Acad. Sci., USA*, 91:2975-2979, 1994.
McConnell et al., "The cytosensor microphysiometer: biological applications of silicon technology," *Science*, 257:1906-1912, 1992.
McPhee et al., "A critical role for the S4-S5 intracellular loop in domain IV of the sodium channel alpha-subunit in fast inactivation," *J. Biol. Chem*., 273:1121-1129, 1998.
Miyaji-Yamaguchi et al., "Coiled-coil structure-mediated dimerization of template activating factor-I is critical for its chromatin remodeling activity," *Journal of Mol. Biol*., 290:547-557, 1999.
Morvan et al., "alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)].," *Nucleic Acids Research*, 14:5019-5035, 1986.
Moulard et al., "Identification of a new locus for generalized epilepsy with febrile seizures plus (GEFS+) on chromosome 2q24-q33," *Am. J. Hum. Genet*., 65:1396-1400, 1999.
Muir et al., "Phase II clinical trial of sipatrigine (619C89) by continuous infusion in acute stroke," *Cerebrovascular Diseases*, 10:431-436, 2000.
Nakashima et al., "Signaling pathways for tumor necrosis factor-alpha and interleukin-6 expression in human macrophages exposed to titanium-alloy particulate debris in vitro," *J. Bone Joint Surg. Am*., 81:603-615, 1999.
Nielsen, P.E., "Applications of peptide nucleic acids," *Curr. Opin. Biotechnol*., 10:71-75, 1999.
Okuwaki et al., "Template activating factor-I remodels the chromatin structure and stimulates transcription from the chromatin template," *J. Biol. Chem*., 273:34511-34518, 1998.
Ottaman et al., "Localization of a gene for partial epilepsy to chromosome 10q," *Nat. Genet*., 10:56-60, 1995.
Ottaman et al., "Segregation analysis of cryptogenic epilepsy and an empirical test of the validity of the results," *Am. J. Hum. Genet*., 60:667-675, 1997.
Ottman et al., "Seizure risk in offspring of parents with generalized versus partial epilepsy," *Epilepsia*, 30:157-161, 1989.
Plummer and Meisler, "Evolution and diversity of mammalian sodium channel genes," *Genomics*, 57:323-331, 1999.
Pugsley et al., "Effects of bisaramil, a novel class I antiarrhythmic agent, on heart, skeletal muscle and brain Na+ channels," *Eur. J. Pharmacol*., 342:93-104, 1998.
Schroeder et al., "Moderate loss of function of cyclic-AMP-modulated KCNQ2/KCNQ3 K+ channels causes epilepsy," *Nature*, 396:687-690, 1998.
Scott et al., "Searching for peptide ligands with an epitope library,"*Science*, 249:386-390, 1990.
Sillampää et al., "Genetic factors in epileptic seizures: evidence from a large twin population," *ActaNeurol. Scand*., 84:523, 1991.
Singh et al., "A novel potassium channel gene, KCNQ2, is mutated in an inherited epilepsy of newborns," *Nat. Genet*., 18:25-29, 1998.
Sjolander et al., "Integrated fluid handling system for biomolecular interaction analysis," *Anal. Chem*., 63:2338-2345, 1991.
Steinlein et al., "A missense mutation in the neuronal nicotinic acetylcholine receptor alpha 4 subunit is associated with autosomal dominant nocturnal frontal lobe epilepsy," *Nat. Genet*., 11:201-203, 1995.
Szabo et al., "Surface plasmon resonance and its use in biomolecular interaction analysis (BIA).," *Curr. Opinion, Struct. Biol*., 5:699-705, 1995.
Tamaskovic et al., "Enzyme-linked immunosorbent assay for the measurement of JNK activity in cell extracts," *Biological Chemistry*, 380:569-578, 1999.

Taylor et al., "Sodium channels and therapy of central nervous system diseases," *Adv. Pharmacol.*, 39:47-98, 1997.
Wallace et al., "Febrile seizures and generalized epilepsy associated with a mutation in the Na+-channel beta1 subunit gene SCNIB," *Nature Genet.*, 19:366-370, 1998.
Zuchermann et al., "Discovery of nanomolar ligands for 7-transmembrane G-protein-coupled receptors from a diverse N-(substituted)glycine peptoid library," *J. Med. Chem.*, 37:2678-2685, 1994.
Commission on classification and terminology of the international league against epilepsy, *Epilepsia*, 30:389-399, 1989.
"Molecular and Functional Diversity of Ion Channels and Receptors. Proceedings of a conference. New York City, New York, USA. May 14-17, 1998." *Ann. N.Y. Acad. Sci.*, 868:1, 1999 (PubMed Citation downloaded Nov. 14, 2006).
Birch et al., "Strategies to identify ion channel mosulators: current and novel approaches to target neuropathic pain," *Drug Discovery Today*, 9:410-418, 2004.
Kohling, "Voltage-gated Sodium Channels in Epilepsy," *Epilepsia*, 43:1278-1295, 2002.
"Table of Contents," *Annals of the New York Academy of Sciences*, 868, 1999.
Clare et al., "Cloning and Functional Analysis of the Type III Na+ Channel from Human Brain," *Annals of the New York Academy of Sciences*, 868:80-83, 1999.
"Molecular and Functional Diversity of Ion Channels and Receptors," *Annals of The New York Academy of Sciences*, 868: Table of Contents, 1999.
Clare et al., "Cloning of Functional Analysis of the Type III Na+ Channel from Human Brain," *Annals of the New York Academy of Sciences*, 868:80-83, 1999.
Goldin, "Diversity of Mammalian Voltage-Gated Sodium Channels," *Annals of the New York Academy of Sciences*, 868:38-50, 1999.
Rudy, "Introduction: Molecular Diversity of Ion Channels and Cell Function," *Annals of the New York Academy of Sciences*, 868:1-12, 1999.
Honig, "Protein Folding: From the Levinthal Paradox to Structure Prediction," *J. Mol. Biol.*, 293:283-293, 1999.
Avanzini et al., "Physiological properties of immature neocortical neurons relevant to pathophysiology of infantile epileptic encephalopathies," *Prog Nat. Epileptogenesis* (*Epilepsy Res. Suppl.*), 12:53-61, 1996.
Hartshorne and Catterall, "The sodium channel from rat brain. Purification and subunit composition," *J. Biol. Chem.*, 259:1667-1675, 1984.
Kienle et al., "Electropolymerization of a phenol-modified peptide for use in receptor-ligand interactions studied by surface plasmon resonance," *Biosensors and Bioelectronics*, 12:779-786, 1997.
Noda and Numa, "Structure and Function of Sodium Channel," *J. Receptor Res.*, 7:467-497, 1987.
Reckziegel et al., "Electrophysiological characterization of Na+ currents in acutely isolated human hippocampal dentate granule cells," *J. Physiology*, 509.1:139-150, 1998.
Tian et al., "Endogenous bursting due to altered sodium channel function in rat hippocampal CA1 neurons," *Brain Res.*, 680:164-172, 1995.
"Decision of A Delegate of the Commissioner of Patents," issued in Australian Patent Application No. 18465/01, entitled 'Loci for idiopathic generalised epilepsy, mutations thereof and method using same to assess, diagnose, prognose or treatepilepsy,' dated Jan. 29, 2007.

* cited by examiner

Figure 1:
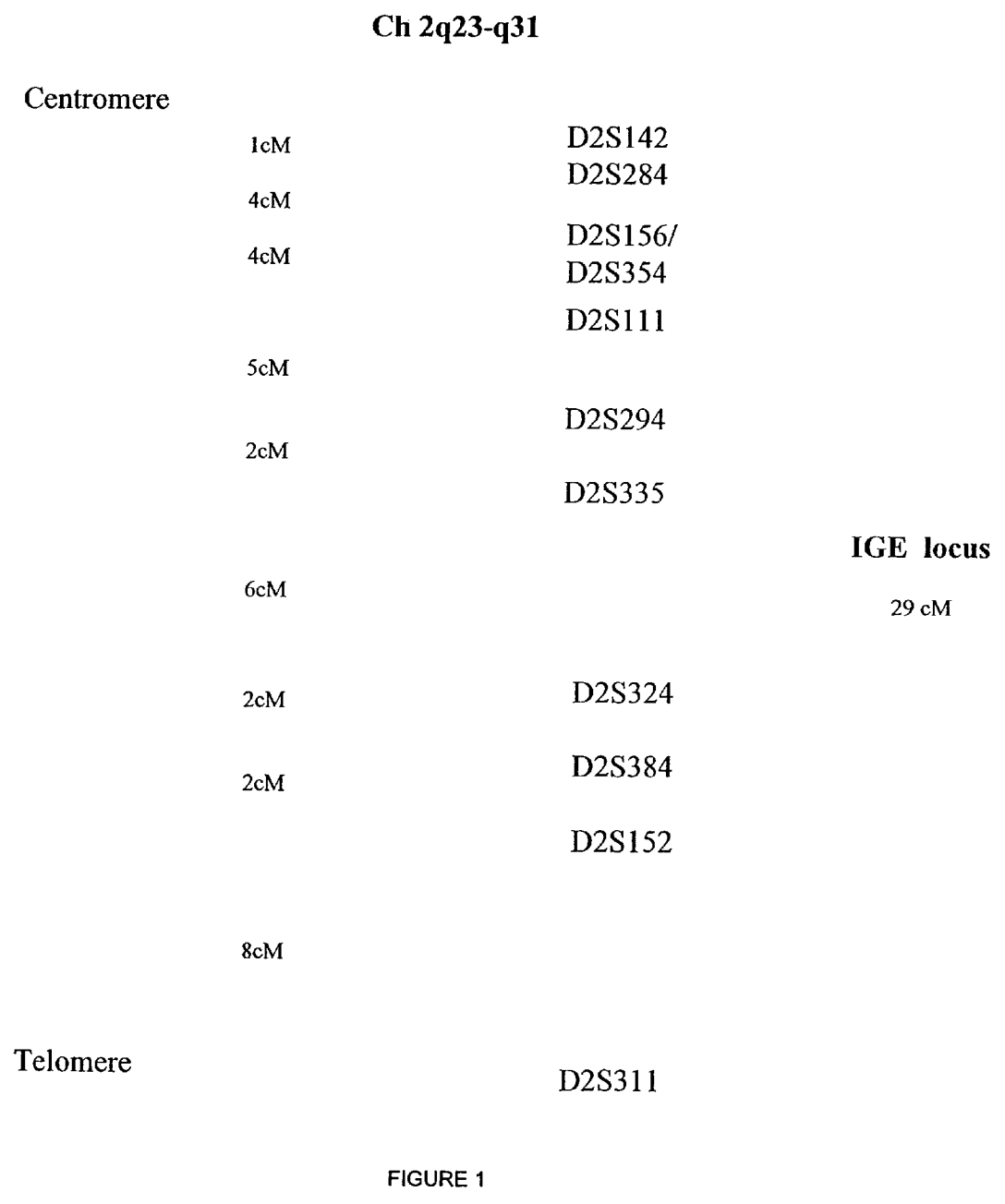

Ch 2q23-q31

Centromere

1cM D2S142

D2S284

4cM

4cM D2S156/

D2S354

D2S111

5cM

D2S294

2cM

D2S335

IGE locus

6cM 29 cM

2cM D2S324

2cM D2S384

D2S152

8cM

Telomere

1Ax00.1
NaC-340 TGTGTTCTGCCCCAGTGAGACT
NaC-341 CTTCCTGCTCTGCCCAAACTGAAT
257 bp 53.4C

1Ax00.2
NaC-342 GGCGATGTAATGTAAGGTGCTGTC
NaC-343 GTGCCTTCAGTTGCAATTGTTCAG
259bp 54.5C

1Ax01.1
NaC-268, TTAGGAATTTCATATGCAGAATAA,
NaC-269 TGGGCCATTTTTCGTCGTC
201 bp 50.9C

1Ax01.2
NaC-270 GAAAGACGCATTGCAGAAGAAAAGG,
NaC-271 CTATTGGCATGTGTTGGTGCTACA
277bp54.4C

1Ax02
NaC-45 GTGCTGGTTTCTCATTTAACTTTAC,
NaC-46 TTCCCAACTTAATTTGATATTTAGC,
319 bp 49.9C

1Ax03
NaC-87, GCAGTTTGGGCTTTTCAATGTTAG,
NaC-88, GACACAGTTTCARAATCCCRAATG,
234 bp 48.9C

1Ax04
NaC-63, TTAGGGCTACGTTTCATTTGTATG,
NaC-64, AGCACTGATGGAAAACCAAACTAT,
338 bp 50.8C

1Ax05
NaC-164 AGCCCATGCAGTAATATAAATCCT
NaC-165 TCCAGGCTGATAAGCTATGTCTAA,
488 bp 52.8C

FIGURE 2

1Ax06
NaC-276, CTGTGGCCTGCCTGAGCGTATT,
NaC-277 CCAATTCTACTTTTTAAGGAAATG,
248bp 50.3C

1Ax07
NaC-272, AAATACTTGTGCCTTTGAA,
NaC-273, GTACATACAATATACACAGATGC
240 bp 46.7C

1Ax08
Nac-89, AGGCAGCAGAACGACTTGTAATA,
NaC-90, ATCCGGTTTTAATTTCATAACTCA,
267 bp 51.9C

1Ax09.2
NaC-217 GTTGAGCACCCTTAGTGAATAATA,
NaC-218 TCACACGCTCTAGACTACTTCTCT
337bp 52.7C

1Ax10a NaC-29, TGCAAATACTTCAGCCCTTTCAAA,
NaC-30, TTCCCCACCAGACTGCTCTTTC,
239bp, 55.1C

1Ax10a
NaC-31, GCAGCAGGCAGGCTCTCA,
NaC-32, TCTCCCATGTTTTAATTTTCAACC,
293bp, 54.5C

1Ax10b
NaC-67, ATAATCTTGCAAAATGAAATCACA,
NaC-68, ATCCGGGATGACCTACTGG
307 bp 53.7C

1Ax10b
NaC-65, GATAACGAGAGCCGTAGAGATTCC,
NaC-66, AGCCAGCCATGCCTGAACTA
282bp 56.4C

FIGURE 2 (cont'd)

1Ax10c
NaC-39, TGTTTGCTTGTCATATTGCTCAA,
NaC-40, TGCACTATTCCCAACTCACAAA,
286bp, 50.7C

1Ax11.1
NaC-69 AAGGGTGTCTCTGTAACAAAAATG,
NaC-70, GTGATGGCCAGGTCAACAAA
269bp 50.8C

1Ax11.2
NaC-71 CTGGGACTGTTCTCCATATTGGTT,
NaC-72, TTTGCAGGGGCCAGGAAG
294 bp 53.3°C

1Ax12
NaC-41 CATTGTGGGAAAATAGCATAAGC,
NaC-42, GCAAGAACCCTGAATGTTAGAAA,
334bp, 51.2C

1Ax13.1
NaC-92 TAATGCTTTTAAGAATCATACAAA,
NaC-93, CCAGCGTGGGAGTTGACAATC,
256bp, 51.1C

1Ax13.2
NaC-75 CGGCATGCAGCTCTTTGGTA,
NaC-91, ATGTGCCATGCTGGTGTATTTC,
277 bp 55.6C

1Ax14.1
NaC-79 CACCCATCTTCTAATCACTATGC,
NaC-80, CAGCAATTTGGAGATTATTCATT,
254 bp 50.4C

1Ax14.2
NaC-81 GCAGCCACTGATGATGATAA,
NaC-82, CTGCCAGTTCCTATACCACTT,
269 bp 49.4C

FIGURE 2 (cont'd)

1Ax14.3
NaC-83 TACAGCAGAAATTGGGAAAGAT,
NaC-84, GTATTCATACCTACCCACACCTAT,
269 bp 50.2C

1Ax15
NaC-202 TTCTTGGCAGGCAACTTATTACC,
NaC-203 TAAGCTGCACTCCAAATGAAAGAT
233bp 53.1C

1Ax16.1
NaC-187, GGCTGAATGTTTCCACAACT,
NaC-168 GTTCAACTATTCGGAAACACG
277 bp, 51.4C

1Ax16.2
NaC-188, AGGCAGAGGAAAACAATGG,
NaC-189, ACAAGGTGGGATAATTAAAAATG
234 bp, 50.3C

1Ax17
NaC-143, GTTTCTCTGCCCTCCTATTCC,
NaC-144, AAGCTACCTTGAACAGAGACA,
330 bp, 48.8C

1Ax18
NaC-139, AATGATGATTCTGTTTATTA,
NaC-140, AATTTGCCATTCCTTTTG,
272 bp, 46.1C

1Ax19.1
NaC-219 TTGACATCGAAGACGTGAATAATC,
NaC-220 CCATCTGGGCTCATAAACTTGTA
285bp 49.3C

1Ax20
NaC-338 CCCTTTGAAAATTATATCAGTAA,
NaC-339 ATTTGGTCGTTTATGCTTTATTC
230 bp 47.6C

FIGURE 2 (cont'd)

1Ax21
NaC-252, TCCAGCACTAAAATGTATGGTAAT,
NaC-253, ATTTGGCAGAGAAAACACTCC
261 bp 49.8C

1Ax22
NaC-254, TTTTAGCCATCCATTTTCTATTTT,
NaC-255, TATTTTCCCCCATATCATTTGA
223 bp 49.1C

1Ax23.1
NaC-256 TTTGCAAGAAACTAGAAAGTC,
NaC-257 TTGATGCGTGACAAAATGG
250bp 48.3C

1Ax23.2
NaC-258 GACCAGAGTGAATATGTGACTACC,
NaC-259 CTGGGATGATCTTGAATCTAATC
246bp 49.5C

1Ax24.1
NaC-221 GCAACTCAGTTCATGGAATTTGAA,
NaC-222 CTTGTTTTCGTTTTAAAGTAGTA
289bp 56.1C

1Ax24.2
NaC-213 CAAAGATCACCCTGGAAGCTCAGTT,
NaC-223 TTCAAGCGCAGCTGCAAACTGAGAT
277bp 55.8C

1Ax24.3
NaC-260 ACATCGGCCTCCTACTCTTCCTA,
NaC-261 ACAGATGGGTTCCCACAGTCC
268 bp 55.3C

1Ax24.4
NaC-262 TAACGCATGATTTCTTCACTGGTT,
NaC-263 ATCCCAAAGATGGCGTAGATGA
262 bp 54.9C

FIGURE 2 (cont'd)

1Ax24.5
NaC-308, TGAGAAATAGGCTAAGGACCTCTA,
NaC-309 CCTAGGGGCTGGATTCC
244 bp 53.2C

1Ax24.6
NaC-310, AAGGGGTGCAAACCTGTGATTTT,
NaC-311 AGGGCCATGTGGTTGCCATAC
252 bp 53.4C

1Ax24.7
NaC-312 CTTCCGGTTTATGTTTTCATTTCT,
NaC-313 TCTTTATTAGTTTTGCACATTTTA
278bp 48.4C

1Ax24.8
NaC-364 CAATCCTTCCAAGGTCTCCTATC,
NaC-365 TTTCATCTTTGCCTTCTTGCTCAT
326bp 52.4C

1Ax24.9
NaC-366 CATGTCCACTGCAGCTTGTCCA,
NaC-367 TCCCCTTTACACAGAGTCACAGTT
292bp 53.1C

FIGURE 2 (cont'd)

a. Glu1238Asp:

| | |
|---|---|
| normal: | GCA TTT GAA GAT ATA; |
| patient R10191 with IGE: | GCA TTT GAC GAT ATA. |

b. Ser1773Tyr:

| | |
|---|---|
| normal: | ATC ATA TcC TTC CTG; |
| patient R9049 with IGE: | ATC ATA TmC TTC CTG; TCC>TAC |

FIGURE 3

2Ax00.1 NaC-235 ATGGGTTGAATGACTTTCTGACAT, NaC-236 AGGCATTTCCTGTACAGGGACTAC
266bp 52.7C

2Ax00.2 NaC-237 ACAGGAAATGCCTCTTCTTACTTC, NaC-238 TTTCCCCAAGGATTCTACTACTGT
277bp 50.6C

2Ax01 NaC-100, AGTGCATGTAACTGACACAATCAC, NaC-101, CTTGCGTTCCTGTTTGGGTCTCT
241 bp 53.7C

2Ax01 NaC-11 TCCGCTTCTTTACCAGGGAATC, NaC-102, AGGCAGTGAAGGCAACTTGACTAA, 259
bp 55.1C

2Ax02 NaC-96, CAGGGCAATATTTATAAATAATGG, NaC-97, TTTGGAAAATGTGTAGCTCAATAA,
289 bp 48.7C

2Ax03 NaC-43, AAGGCATGGTAGTGCATAAAAG, NaC-44, ATGAAACATAAAGGGAGGTCAA, 201
bp, 49.3°C

2Ax04 NaC-47, AATGTGAGCTTGGCTATTGTCTCT, NaC-48, ATAGGCTCCCACCAGTGATTTAC,
213 bp,50.9°C

2Ax05 NaC-49, AGGCCCCTTATATCTCCAACTG, NaC-50, CAACAAGGCTTCTGCACAAAAG, 241
bp, 53.9°C

2Ax05.2 NaC-110, CTTGGTGGCTTGCCTTGAC, NaC-111, TCATGAGTGTCGCCATCAGC, 223
bp, 51.1C

2Ax05.3 NaC-112, GGAAAGCTGATGGCGACACT, NaC-113, CTGAGACATTGCCCAGGTCC, 329
bp 53.0C

FIGURE 4

2Ax05.4 NaC-114, TTTTTACCCGTTGCTTTCTTTA, NaC-115, TATCCCTTGCTCTTTCATTTATCT
224bp 50.9C

2Ax06.1 NaC-169, GCCGGTAAAATAGCTGTTGAGTAG, NaC-170, GCCATTGCAAACATTTATTTCGTA 206bp 53.3C

2Ax06.2 NaC-171, GCGTGTTTGCGCTAATAG, NaC-172, CTAAGTCACTTGATTCACATCTAA
295bp 48.0C

2Ax07 Nac-196, ACAGGGTGGCTGAAGTGTTTA, NaC-197, GTGGGAGGTGGCAGGTTATT, 199
bp, 52.6C

2Ax08 NaC-118, CAATTAGCAGACTTGCCGTTATT, NaC-119, TCTCTTGAGTTCGGTGTTTTATGA
252bp 52.9C

2Ax09 NaC-120, ACCGAACTCAAGAGAATTGCTGTA, NaC-121, AAAGGACCGTATGCTTGTTCACTA
334bp 52.9C

2Ax10a.1 NaC-161 TATGAATGCGCATTTTACTCTTTG, NaC-156 TGGAGCTCAACTTAGATGCTACTG
286 bp 52.1C

2Ax10a.2 NaC-13 GGTGCTGGTGGGATAGGAGTTTTT, NaC-162 TCCATTAAATTCTGGCATATTCTT,
316 bp 50.9C

2Ax10b.1 NaC-145 TCAGAGGGGTGCTTTCTTCCACAT, NaC-14 CTTCGGCTGTCATTGTCCTCAAAG,
298bp 55.6C

2Ax10b.2 NaC-146,GCAAAGGACATTGGCTCTGAGAAT, NaC-147,CTGCCTGCACCAGTCACAACTCT
324bp 59.4C

FIGURE 4 (cont'd)

2Ax10c NaC-190, TGGGCTTTGCTGCTTTCAA, NaC-191, AGTAACTGTGACGCAGGACTTTTA, 218 bp 51.5C

2Ax11.1 NaC-148, CCCTGTTCCTCCAGCAGATTA, NaC-70 GTGATGGCCAGGTCAACAAA, 283 bp, 51.5C

2Ax11.2 NaC-149,TTTGATTTGGGACTGTTGTAAAC, NaC-150,AAGGCAATTATAAACTCTTTCAAG 233bp 52.0C
2Ax12 NaC-159, TGGGAGTTAAATTAAGTTGCTCAA, NaC-160, ACATTTTATGAACACTCCCAGTTA 285bp 50.4C

2Ax13.1 NaC-239 ATTAACACTGTTCTTGCTTTTAT, NaC-240 GTGCCAGCGTGGGAGTTC 239 bp 51.1C

2Ax13.2 NaC-241 GTGGGGGCTCTAGGAAACCT, NaC-242 TTTAATGAAAATGAGGAAAATGTT 324 bp 53.7C

2Ax14.1 NaC-134, GACCAAGCATTTTTATTTCATTC, NaC-135, AGTGGCAGCAAGATTGTCA 234 bp, 49.6C

2Ax14.2 NaC-136, GGCCTTGCTTTTGAGTTCC, NaC-137, GGTCTTTGCCTATTTCTATGGTG, 257 bp, 51.1C

2Ax14.3 NaC-266, TTAAACCGCTTGAAGATCTAAATA, NaC-267 TATACACCAAAATATCTCCTTAT 319bp 48.5C

2Ax15 NaC-314 GGGGCACACCTAATTAATTTTTAT, NaC-315 AAAGAGGATACTCAAGACCACATA (247bp) 51.5C

FIGURE 4 (cont'd)

2Ax16 NaC-344 CCCACCAACACAAATATACCTAAT, NaC-345 TGAAGGGAAAGGGAAAAGATTT
283bp 52.2C

2Ax17 NaC-346 TCCAGCCTTAGGCACCTGATAA NaC-347 ATAAAGCAGCAAAGTGCAGCATAC 310bp
52.4C

2Ax18 NaC-348 AAGGCTGAACTGTGTAGACATTTT NaC-349 TGACATTTCCATGGTACAAAGTGT
262bp 52.2C

2Ax19.1 NaC-350 TTTGTTGTTGGCTTTTCACTTAT NaC-351 CCACCTGGCAGTTTGATTG 268bp 51.9C

2Ax19.2 NaC-352 TAAGCGTGGTCAACAACTACAGT NaC-353 ATTCTTGCCAGCATTTATTGTC
260bp 50.2C

2Ax20 NaC-354 CAAAACATTGCCCCAAAAG NaC-355 TCAAACTAAACAATTTCCCTCTAA 239 bp 48.1C

2Ax21 NaC-306, GATAATTAAAAACTCACTGATGTA, NaC-307 GGAGGCTAAAGGAAAGAGTATG
288bp 46.6C

2Ax22 NaC-356 ATTTTATAGCCAGCAAAGAACAC NaC-357 CTAGAAATTCGGGCTGTGAA 230 bp 49.6C

2Ax23.1 NaC-358 CTGCTTTGTGACCTAAGGCAAGTT NaC-359 GTGACCATGTTAAGGCAGATGAGG
290bp 51.4C

2Ax23.2 NaC-360 GGAATGGTCTTTGATTTTGTAACC NaC-361 TCCTTAACTGAATAAAAGCACCTC
290bp 51.6C

2Ax24.1 NaC-207 TGGAACACCCATCAAAGAAGATACT, NaC-208 GTGGGAGTCCTGTTGACACAAAC
278bp52.8C

FIGURE 4 (cont'd)

2Ax24.2 NaC-209 AGCGATTCATGGCATCAAAC, NaC-210 ACGTGGTGGAAGGCGTCATA 270 bp, 52.9C

2Ax24.3 NaC-211 GCGACCCAGTTTATAGAGTTTGCC, NaC-212 CTTGTTTGCGTTTCAACGTGGTC 289bp 56.1C

2Ax24.4 NaC-213 CAAAGATCACCCTGGAAGCTCAGTT,NaC-214 ATCCAGGGCATCTGCAAAATCAGAA 277bp55.8C

2Ax24.5 NaC-215 TGCCTATGTTAAGAGGGAAGTTGGG, NaC-216 ATGACCGCGATGTACATGTTCAG 279bp 55.3C

2Ax24.6 NaC-278 TCAATTGTTTACAGCCCGTGATG, NaC-279 TTTATACAAAGGCAGACAACAT 302bp 52.0C

2Ax24.7 NaC-280 AGGCGTAATGGCTACTCAGACGA, NaC-281 GTAATCCCTCTCCCCGAACATAAAC 251bp 53.8C

2Ax24.8 NaC-282 TTTGATTCACGGGTTGTTTACTCTTA, NaC-283 TTCTATGGAACATTTACAGGCACATT 294bp 52.1C

2Ax24.9 NaC-284 TAATGTGCCTGTAAATGTTCCATAGA, NaC-285 CAGGCTTCTTAGAAAGGACTGATAGG 264bp 50.6C

2Ax24.10 NaC-286 GTCCCAGCAGCATGACTATC, NaC-287 CCCACTGGGTAAAATTACTAAC 249bp 49.4C

2Ax24.11 NaC-288 TAGCCATCTTCTGCTCTTGGT, NaC-289 TGGCTTCCCATATTAGACTTCTG 307bp 51.3C

2Ax24.12 NaC-290 TCTTGCCTATGCTGCTGTATCTTA, NaC-291 AGTCGGGCTTTTCATCATTGAG 207bp 51.8C

FIGURE 4 (cont'd)

2Ax24.13 NaC-292 TTCTTCATGTCATTAAGCAATAGG, NaC-293 TTCAATTTAAAAGTGCTAGGAACA
299bp49.4C

2Ax24.14 NaC-294 CTTCAGGTGGATGTCACAGTCACTA NaC-295 ATTCAAGCAATGCCAAGAGTATCA
263bp51.5C

2Ax24.15 NaC-296 CTTTCAATAGTAATGCCTTATCAT NaC-297 TCCTGCATGCATTTCACCAAC
348bp 49.6C

2Ax24.16 NaC-362 CTGTTCACATTTTGTAAAACTAAT, NaC-263 ATCCCAAAGATGGCGTAGATGA
309 bp 50.8C

2Ax24.17 NaC-325 CACGCTGCTCTTTGCTTTGA, NaC-363 GATCTTTGTCAGGGTCACAGTCT 269
bp 54.0C

FIGURE 4 (cont'd)

a. Lys908Arg:

| | |
|---|---|
| normal: | TAC AAA GAA; |
| 9782 (Patient with IGE): | TAC AGA GAA; |

b. leu768val, in individuals 8197, 9062 et 9822 (all IGE patients).

FIGURE 5

3Ax00a.1 NaC-390 TGTGTCCGCCAGTAGATGG, NaC-391 TTTTTGACCACAGAGGTTTACAA 233bp
51.4C

3Ax00a.2 NaC-392 GAAGCGGAGGCATAAGCAGA, NaC-393 GGTGCAGATAATGAAATGTTTTGT
253bp 51.3C

3Ax00b NaC-394 CACCCCTATGCCAAATGTCAAAGA NaC-395 CAAAAACAAACTTATACCCAGAAG
293bp 51.6C

3Ax00c NaC-396 CAAATATTGGGCAAACCCTAAT, NaC-397 AAGGTGCCATCACAAAATCAT 225bp
50.7C

3Ax01.1 NaC-51 ATCGCTTGCTTTCCTAACTCTTGT, NaC-52 AAGTCACTATTTGGCTTTGGTTG,
260bp, 53.1C

3Ax01.2 NaC-53 AGAAGCCCAAAAAGGAACAAGATA, NaC-54 GGCCCAGAAAAGTATATTACAGTT,
231bp, 50.8C

3Ax02 NaC-85, TCCTTAAATAAGCCCATGTCTAAT, NaC-86, TCTCAAAGAAATTTTACAGATACT,
273bp, 47.3C

3Ax03 NaC-27, AATGGCCATGGTAACCTACTAACA, NaC-28, CAGGCTATACCCACAAGGAGATT,
212 bp 51.8C

3Ax04 NaC-94, TGTTAATTTTGGCTTGGATGTT, NaC-95, TCACTCCTTTGCGCTTATCAA, 198 bp
50.8C

3Ax05.1 NaC-247, AGGGCTCTATGTGCCAAACC, NaC-248, AGGGGCCTACTACCTTACACCAG 213
bp 52.2C

FIGURE 6

3Ax05.2 NaC-249 TGTAATCCCAGGTAAGAAGAAAC, NaC-250 TACCGGGATGAACTGTAATAATAA
304 bp 51.8C

3Ax06.1 NaC-192,TTCTGGCACTCTTCCTCAGGTAAC, NaC-193,GTCCCATTTGAATCCATTGTGC,
261bp 55.4C

3Ax06.2 NaC-194,GGCCCCCAAGCGATTCTG, NaC-195, TGTACACCCACAGTCTCAACTATT,
209bp, 50.3C

3Ax07 NaC-204, ACAGCCACCTTTGTAAATAA, NaC-205, TTTTTCGCAAAGAGTTCTAT
220 bp, 46.6C

3Ax08 NaC-98, AAACTGACCCTACCTCCATTTCTC, NaC-99, ACTCAGCCTATGCTTTTCATTTCA,
247 bp 53.2C

3Ax09 NaC-37 CAGATATTTATTTGGGGACATTAT, NaC-38 AAATCTTTGCKTTTATCACTCAGT, 295 bp, 52.0C

3Ax10a.1 NaC-198 TAGTGCCTGGCTTTGTTTTATGAC, NaC-199 CGGATTTGGGAAAGCTGTCTCT
225 bp 54.3C

3Ax10a.2 NaC-200 AGAGCACCTTGAAGGAAACAACAA, NaC-274, TCCCTCAACTGAAGTACAGATAGT, 253 bp 51.2C

3Ax10b NaC-33, ATAATTGCGTTCTTCCCCTACCC, NaC-34, AAGCCCTGGCACCATCCTG, 301 bp, 56.2°C

3Ax10c NaC-35, _TTTGCAAAGAAATGCTATGT, NaC-36, CTGGGTAACAGACTTCAGTAAT, 303 bp, 51.4°C

3Ax11.1 NaC-122, ATGGGATTGTCTTCTCAAGTTTCT, NaC-123, GATGGCAAGATCAACAAATGGA
294bp 50.3C

FIGURE 6 (cont'd)

3Ax11.2 NaC-124, CTTGATCTGGGACTGCTGTGATG, NaC-125, AGGATATAATTTTTGGTTCAACA
284bp 51.5C

3Ax12 NaC-61, TTTTCAGTGCTCTTGATAGTAGTG, NaC-62, GTGCCAATGAGCGACAGG, 254 bp,
50.7°C
3Ax13.1 NaC-73, CCACGTGTGGTTCTATGATACC, NaC-74, ACCGTGGGAGCGTACAGTCA 298 bp
52.3C

3Ax13.2 NaC-75, CGGCATGCAGCTCTTTGGTA, NaC-76, TGGCCACGTTCCTAGCTACTGTC 291
bp 55.9C

3Ax14.1 NaC-55, GAGTTCCCTTTTTAGGCTGTTATT, NaC-56 TCTTATTGCCTTCATGGATTTCTA,
285bp,50.5C

3Ax14.2 NaC-57, TGAAAAATAAGATGCGGGAGTG, NaC-58, GTGAGGCTGGGGTTGTTTATG, 247
bp, 51.7C

3Ax14.3 NaC-59, GAGATGGGAATGGAACCACCA, NaC-60, TTCGATAATGCATATAAGCACAA, 297
bp, 51.7C

3Ax15 NaC-318 AAGGGGGAAAATCACATCTTT, NaC-319 TTAAATGAGGCATATTCAGTCTCC 235bp
51.8C

3Ax16 NaC-116, GGAAGTGGAGTGGGGAAGG, NaC-117, ATTCTTGCCAATATGCATTTCACT, 271
bp, 51.1C

3Ax17 NaC-157,TTCTTTTGTACTCACTATTATACTAA, NaC-158,AAACTTGCCTCTTTTAAAAACAAT
317bp 46.6C

3Ax18 NaC-374 TACCACACCCTATACCTTCAGTCA, NaC-375 GAGTATGGCACCCTTTTCTATCTA
275bp 51.4C

FIGURE 6 (cont'd)

3Ax19.1 NaC-386 GCTATGTTCCCCTCGCTGTCT, NaC-387 TGCTTGCCAAGAGCCTGAC
231bp 53.6C

3Ax19.2 NaC-388 GCTGGCAAGTTCTACCACTGTG, NaC-389 CAAACGAAGAACATCAGGGAAATA
247bp 53.0C

3Ax20 NaC-376 TTCACAATATTGTACAAAAAGTTA, NaC-377 ATTACCACCAATATTCACCATAAG
230 bp 46.4C

3Ax21 NaC-378 TCAGGGTAAGGCAAAAGTAGCAC, NaC-379 GAACCCCAGAATGAAGAAAGGTAA 294 bp 50.2C

3Ax22 NaC-380 TTTGTGAAAGTACTATTGGAACAC, NaC-381 ACGCATGGCTTTGGAACAT 204bp 49.6C

3Ax23.1 NaC-382 CCCGTATGTGGAAGGGCTTTAT, NaC-383 CTAGGTTGATCCGGGACAAAACTA
246bp 52.9C

3Ax23.2 NaC-384 AACGGATGACCAGGGCAAATAC, NaC-385 CTAGAAGGTCCTGGGGCAACTG
234bp 54.8C

3Ax24.1 NaC-317 AAGCCATCATGTAAAGTGAAAAG, NaC-320 ATCCCAAAGATGGCATAGATA 274 bp, 52.5C

3Ax24.2 NaC-325 CACGCTGCTCTTTGCTTTGA, NaC-326 TGAGCTGCCAGGGTGAATTG
282 bp 54.9C

3Ax24.3 NaC-327 TTGCTAGCACCTATTCTTAATAGTGC NaC-328 CCAGGGCAGCTGCAAAATCAGAG
318bp 54.2C

3Ax24.4 NaC-329 CCCGATGCGACCCAGTTTA, NaC-330 TGGAGGGGTTTGATGCCATA
250 bp, 55.2C

FIGURE 6 (cont'd)

3Ax24.5 NaC-331 GATGGATGCCCTTCGAATACAGA, NaC-332 TTCCCATTTAGTTTGTCAATAATC
258 bp 50.6C

3Ax24.6 NaC-321 AAGGGGAGGATTGACTTACCTAT, NaC-333 TTGGCATGGACCTCCTCTTGA 302
bp 51.5C

FIGURE 6 (cont'd)

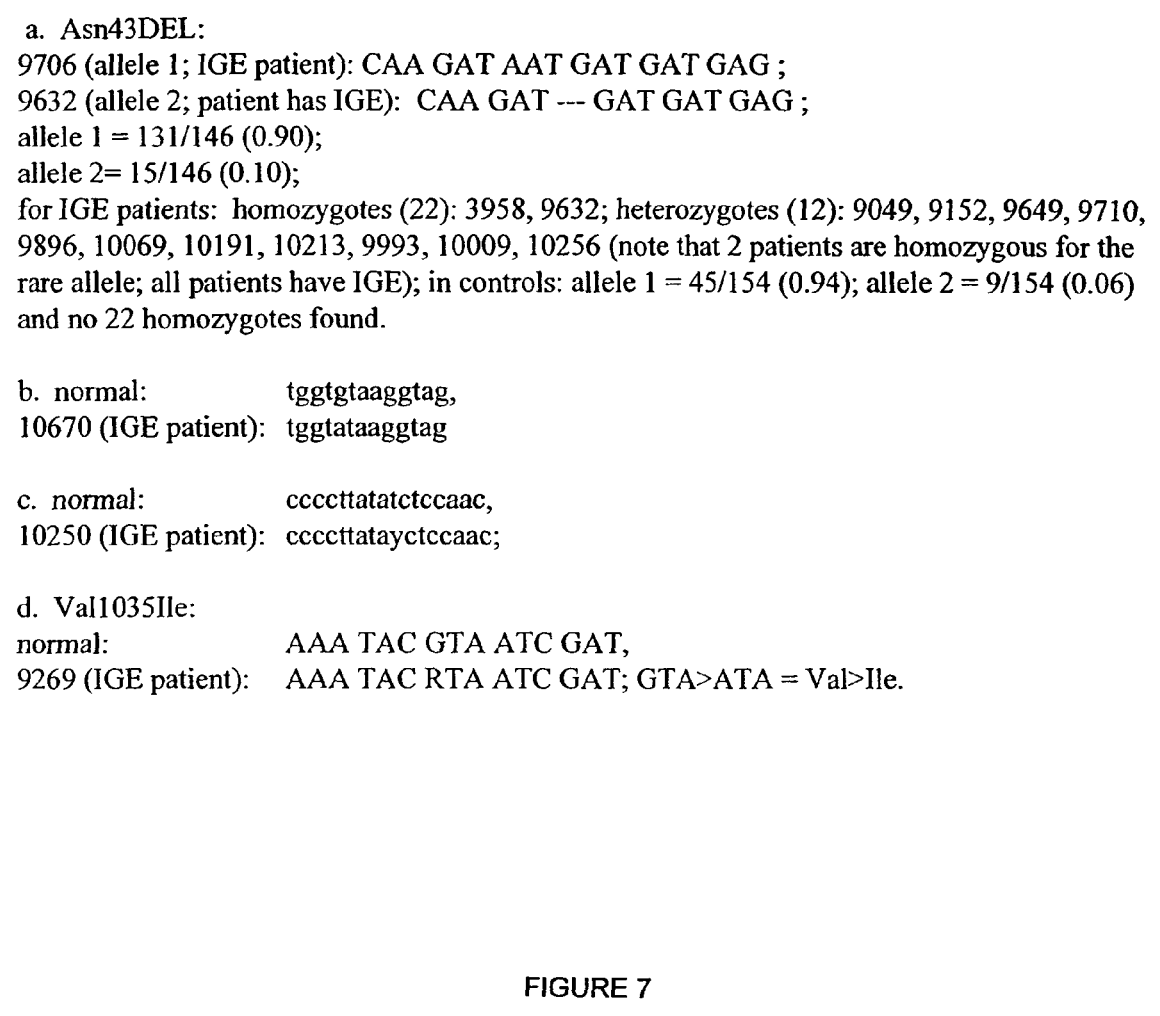

a. Asn43DEL:
9706 (allele 1; IGE patient): CAA GAT AAT GAT GAT GAG ;
9632 (allele 2; patient has IGE): CAA GAT --- GAT GAT GAG ;
allele 1 = 131/146 (0.90);
allele 2= 15/146 (0.10);
for IGE patients: homozygotes (22): 3958, 9632; heterozygotes (12): 9049, 9152, 9649, 9710, 9896, 10069, 10191, 10213, 9993, 10009, 10256 (note that 2 patients are homozygous for the rare allele; all patients have IGE); in controls: allele 1 = 45/154 (0.94); allele 2 = 9/154 (0.06) and no 22 homozygotes found.

b. normal: tggtgtaaggtag,
10670 (IGE patient): tggtataaggtag c. normal: ccccttatatctccaac,
10250 (IGE patient): ccccttatayctccaac;

d. Val1035Ile:
normal: AAA TAC GTA ATC GAT,
9269 (IGE patient): AAA TAC RTA ATC GAT; GTA>ATA = Val>Ile.

FIGURE 7

SEQUENCE LISTING

```
<160> NUMBER OF SEQ ID NOS: 411

<210> SEQ ID NO 1
<211> LENGTH: 8378
<212> TYPE: DNA
<213> ORGANISM: Homo sapiens

<400> SEQUENCE: 1

tactgcagag gtctctggtg catgtgtgta tgtgtgcgtt tgtgtgtgtt tgtgtgtctg      60

tgtgttctgc cccagtgaga ctgcagccct tgtaaatact ttgacacctt ttgcaagaag     120

gaatctgaac aattgcaact gaaggcacat tgttatcatc tcgtctttgg gtgatgctgt     180

tcctcactgc agatggataa ttttcctttt aatcaggaat ttcatatgca gaataaatgg     240

taattaaaat gtgcaggatg acaagatgga gcaaacagtg cttgtaccac caggacctga     300

cagcttcaac ttcttcacca gagaatctct tgcggctatt gaaagacgca ttgcagaaga     360

aaaggcaaag aatcccaaac cagacaaaaa agatgacgac gaaaatggcc caaagccaaa     420

tagtgacttg gaagctggaa agaaccttcc atttatttat ggagacattc ctccagagat     480

ggtgtcagag cccctggagg acctggaccc ctactatatc aataagaaaa cttttatagt     540

attgaataaa gggaaggcca tcttccggtt cagtgccacc tctgccctgt acattttaac     600

tcccttcaat cctcttagga aaatagctat taagattttg gtacattcat tattcagcat     660

gctaattatg tgcactattt tgacaaactg tgtgtttatg acaatgagta accctcctga     720
```

-continued

```
ttggacaaag aatgtagaat acaccttcac aggaatatat acttttgaat cacttataaa    780

aattattgca aggggattct gtttagaaga ttttactttc cttcgggatc catggaactg    840

gctcgatttc actgtcatta catttgcgta cgtcacagag tttgtggacc tgggcaatgt    900

ctcggcattg agaacattca gagttctccg agcattgaag acgatttcag tcattccagg    960

cctgaaaacc attgtgggag ccctgatcca gtctgtgaag aagctctcag atgtaatgat   1020

cctgactgtg ttctgtctga gcgtatttgc tctaattggg ctgcagctgt tcatgggcaa   1080

cctgaggaat aaatgtatac aatggcctcc caccaatgct tccttggagg aacatagtat   1140

agaaaagaat ataactgtga attataatgg tacacttata aatgaaactg tctttgagtt   1200

tgactggaag tcatatattc aagattcaag atatcattat ttcctggagg gtttttaga    1260

tgcactacta tgtggaaata gctctgatgc aggccaatgt ccagagggat atatgtgtgt   1320

gaaagctggt agaaatccca attatggcta cacaagcttt gataccttca gttgggcttt   1380

tttgtccttg tttcgactaa tgactcagga cttctgggaa aatctttatc aactgacatt   1440

acgtgctgct gggaaaacgt acatgatatt ttttgtattg gtcattttct tgggctcatt   1500

ctacctaata aatttgatcc tggctgtggt ggccatggcc tacgaggaac agaatcaggc   1560

caccttggaa gaagcagaac agaaagaggc cgaatttcag cagatgattg aacagcttaa   1620

aaagcaacag gaggcagctc agcaggcagc aacggcaact gcctcagaac attccagaga   1680

gcccagtgca gcaggcaggc tctcagacag ctcatctgaa gcctctaagt tgagttccaa   1740

gagtgctaag gaaagaagaa atcggaggaa gaaaagaaaa cagaaagagc agtctggtgg   1800

ggaagagaaa gatgaggatg aattccaaaa atctgaatct gaggacagca tcaggaggaa   1860

aggttttcgc ttctccattg aagggaaccg attgacatat gaaaagaggt actcctcccc   1920

acaccagtct ttgttgagca tccgtggctc cctatttca ccaaggcgaa atagcagaac    1980

aagccttttc agctttagag ggcgagcaaa ggatgtggga tctgagaacg acttcgcaga   2040

tgatgagcac agcacctttg aggataacga gagccgtaga gattccttgt ttgtgccccg   2100

acgacacgga gagagacgca acagcaacct gagtcagacc agtaggtcat cccggatgct   2160

ggcagtgttt ccagcgaatg ggaagatgca cagcactgtg gattgcaatg gtgtggtttc   2220

cttggttggt ggaccttcag ttcctacatc gcctgttgga cagcttctgc cagaggtgat   2280

aatagataag ccagctactg atgacaatgg aacaaccact gaaactgaaa tgagaaagag   2340

aaggtcaagt tctttccacg tttccatgga ctttctagaa gatccttccc aaaggcaacg   2400

agcaatgagt atagccagca ttctaacaaa tacagtagaa gaacttgaag aatccaggca   2460

gaaatgccca ccctgttggt ataaattttc caacatattc ttaatctggg actgttctcc   2520

atattggtta aaagtgaaac atgttgtcaa cctggttgtg atggacccat ttgttgacct   2580

ggccatcacc atctgtattg tcttaaatac tcttttcatg gccatggagc actatccaat   2640

gacggaccat ttcaataatg tgcttacagt aggaaacttg gttttcactg ggatctttac   2700

agcagaaatg tttctgaaaa ttattgccat ggatccttac tattatttcc aagaaggctg   2760

gaatatcttt gacggtttta ttgtgacgct tagcctggta gaacttggac tcgccaatgt   2820

ggaaggatta tctgttctcc gttcatttcg attgctgcga gttttcaagt tggcaaaatc   2880

ttggccaacg ttaaatatgc taataaagat catcggcaat tccgtggggg ctctgggaaa   2940

tttaaccctc gtcttggcca tcatcgtctt catttttgcc gtggtcggca tgcagctctt   3000

tggtaaaagc tacaaagatt gtgtctgcaa gatcgccagt gattgtcaac tcccacgctg   3060

gcacatgaat gacttcttcc actccttcct gattgtgttc cgcgtgctgt gtggggagtg   3120
```

-continued

```
gatagagacc atgtgggact gtatggaggt tgctggtcaa gccatgtgcc ttactgtctt   3180
catgatggtc atggtgattg gaaacctagt ggtcctgaat ctctttctgg ccttgcttct   3240
gagctcattt agtgcagaca accttgcagc cactgatgat gataatgaaa tgaataatct   3300
ccaaattgct gtggatagga tgcacaaagg agtagcttat gtgaaaagaa aaatatatga   3360
atttattcaa cagtccttca ttaggaaaca aaagatttta gatgaaatta aaccacttga   3420
tgatctaaac aacaagaaag acagttgtat gtccaatcat acagcagaaa ttgggaaaga   3480
tcttgactat cttaaagatg taaatggaac tacaagtggt ataggaactg gcagcagtgt   3540
tgaaaaatac attattgatg aaagtgatta catgtcattc ataaacaacc ccagtcttac   3600
tgtgactgta ccaattgctg taggagaatc tgactttgaa aatttaaaca cggaagactt   3660
tagtagtgaa tcggatctgg aagaaagcaa agagaaactg aatgaaagca gtagctcatc   3720
agaaggtagc actgtggaca tcggcgcacc tgtagaagaa cagcccgtag tggaacctga   3780
agaaactctt gaaccagaag cttgtttcac tgaaggctgt gtacaaagat tcaagtgttg   3840
tcaaatcaat gtggaagaag gcagaggaaa acaatggtgg aacctgagaa ggacgtgttt   3900
ccgaatagtt gaacataact ggtttgagac cttcattgtt ttcatgattc tccttagtag   3960
tggtgctcgg catttgaaga tatatatatt gatcagcgaa agacgattaa gacgatgttg   4020
gaatatgctg acaaggtttt cacttacatt ttcattctgg aaatgcttct aaaatgggtg   4080
gcatatggct atcaaacata tttcaccaat gcctggtgtt ggctggactt cttaattgtt   4140
gatgtttcat tggtcagttt aacagcaaat gccttgggtt actcagaact tggagccatc   4200
aaatctctca ggacactaag agctctgaga cctctaagag ccttatctcg atttgaaggg   4260
atgagggtgg ttgtgaatgc ccttttagga gcaattccat ccatcatgaa tgtgcttctg   4320
gtttgtctta tattctggct aattttcagc atcatgggcg taaatttgtt tgctggcaaa   4380
ttctaccact gtattaacac cacaactggt gacaggtttg acatcgaaga cgtgaataat   4440
catactgatt gcctaaaact aatagaaaga aatgagactg ctcgatggaa aaatgtgaaa   4500
gtaaactttg ataatgtagg atttgggtat ctctctttgc ttcaagttgc cacattcaaa   4560
ggatggatgg atataatgta tgcagcagtt gattccagaa atgtggaact ccagcctaag   4620
tatgaagaaa gtctgtacat gtatctttac tttgttattt tcatcatctt tgggtccttc   4680
ttcaccttga acctgtttat tggtgtcatc atagataatt tcaaccagca gaaaaagaag   4740
tttggaggtc aagacatctt tatgacagaa gaacagaaga aatactataa tgcaatgaaa   4800
aaattaggat cgaaaaaacc gcaaaagcct atacctcgac caggaaacaa atttcaagga   4860
atggtctttg acttcgtaac cagacaagtt tttgacataa gcatcatgat tctcatctgt   4920
cttaacatgg tcacaatgat ggtggaaaca gatgaccaga gtgaatatgt gactaccatt   4980
ttgtcacgca tcaatctggt gttcattgtg ctatttactg gagagtgtgt actgaaactc   5040
atctctctac gccattatta ttttaccatt ggatggaata tttttgattt tgtggttgtc   5100
attctctcca ttgtaggtat gtttcttgcc gagctgatag aaaagtattt cgtgtcccct   5160
accctgttcc gagtgatccg tcttgctagg attggccgaa tcctacgtct gatcaaagga   5220
gcaaagggga tccgcacgct gctctttgct ttgatgatgt cccttcctgc gttgtttaac   5280
atcggcctcc tactcttcct agtcatgttc atctacgcca tctttgggat gtccaacttt   5340
gcctatgtta agagggaagt tgggatcgat gacatgttca actttgagac ctttggcaac   5400
agcatgatct gcctattcca aattacaacc tctgctggct gggatggatt gctagcaccc   5460
```

-continued

```
attctcaaca gtaagccacc cgactgtgac cctaataaag ttaaccctgg aagctcagtt   5520
aagggagact gtgggaaccc atctgttgga attttctttt ttgtcagtta catcatcata   5580
tccttcctgg ttgtggtgaa catgtacatc gcggtcatcc tggagaactt cagtgttgct   5640
actgaagaaa gtgcagagcc tctgagtgag gatgactttg agatgttcta tgaggtttgg   5700
gagaagtttg atcccgatgc aactcagttc atggaatttg aaaaattatc tcagtttgca   5760
gctgcgcttg aaccgcctct caatctgcca caaccaaaca aactccagct cattgccatg   5820
gatttgccca tggtgagtgg tgaccggatc cactgtcttg atatcttatt tgcttttaca   5880
aagcgggttc taggagagag tggagagatg gatgctctac gaatacagat ggaagagcga   5940
ttcatggctt ccaatccttc caaggtctcc tatcagccaa tcactactac tttaaaacga   6000
aaacaagagg aagtatctgc tgtcattatt cagcgtgctt acagacgcca ccttttaaag   6060
cgaactgtaa aacaagcttc ctttacgtac aataaaaaca aaatcaaagg tggggctaat   6120
cttcttataa aagaagacat gataattgac agaataaatg aaaactctat tacagaaaaa   6180
actgatctga ccatgtccac tgcagcttgt ccaccttcct atgaccgggt gacaaagcca   6240
attgtggaaa aacatgagca agaaggcaaa gatgaaaaag ccaaagggaa ataaatgaaa   6300
ataaataaaa ataattgggt gacaaattgt ttacagcctg tgaaggtgat gtatttttat   6360
caacaggact cctttaggag gtcaatgcca aactgactgt ttttacacaa atctccttaa   6420
ggtcagtgcc tacaataaga cagtgacccc ttgtcagcaa actgtgactc tgtgtaaagg   6480
ggagatgacc ttgacaggag gttactgttc tcactaccag ctgacactgc tgaagataag   6540
atgcacaatg gctagtcaga ctgtagggac cagtttcaag ggtgcaaac ctgtgatttt   6600
ggggttgttt aacatgaaac actttagtgt agtaattgta tccactgttt gcatttcaac   6660
tgccacattt gtcacatttt tatggaatct gttagtggat tcatcttttt gttaatccat   6720
gtgtttatta tatgtgacta tttttgtaaa cgaagtttct gttgagaaat aggctaagga   6780
cctctataac aggtatgcca cctgggggt atggcaacca catggccctc ccagctacac   6840
aaagtcgtgg tttgcatgag ggcatgctgc acttagagat catgcatgag aaaaagtcac   6900
aagaaaaaca aattcttaaa tttcaccata tttctgggag ggtaattgg gtgataagtg   6960
gaggtgcttt gttgatcttg ttttgcgaaa tccagcccct agaccaagta gattatttgt   7020
gggtaggcca gtaaatctta gcaggtgcaa acttcattca aatgtttgga gtcataaatg   7080
ttatgtttct ttttgttgta ttaaaaaaaa aacctgaata gtgaatattg cccctcaccc   7140
tccaccgcca gaagactgaa ttgaccaaaa ttactcttta taaatttctg ctttttcctg   7200
cactttgttt agccatcttc ggctctcagc aaggttgaca ctgtatatgt taatgaaatg   7260
ctatttatta tgtaaatagt cattttaccc tgtggtgcac gtttgagcaa acaaataatg   7320
acctaagcac agtatttatt gcatcaaata tgtaccacaa gaaatgtaga gtgcaagctt   7380
tacacaggta ataaaatgta ttctgtacca tttatagata gtttggatgc tatcaatgca   7440
tgtttatatt accatgctgc tgtatctggt ttctctcact gctcagaatc tcatttatga   7500
gaaaccatat gtcagtggta aagtcaagga aattgttcaa cagatctcat ttatttaagt   7560
cattaagcaa tagtttgcag cactttaaca gctttttggt tatttttaca ttttaagtgg   7620
ataacatatg gtatatagcc agactgtaca gacatgttta aaaaaacaca ctgcttaacc   7680
tattaaatat gtgtttagaa ttttataagc aaatataaat actgtaaaaa gtcactttat   7740
tttatttttc agcattatgt acataaatat gaagaggaaa ttatcttcag gttgatatca   7800
caatcacttt tcttactttc tgtccatagt actttttcat gaaagaaatt tgctaaataa   7860
```

```
gacatgaaaa caagactggg tagttgtaga tttctgcttt ttaaattaca tttgctaatt   7920
ttagattatt tcacaatttt aaggagcaaa ataggttcac gattcatatc caaattatgc   7980
tttgcaattg gaaaagggtt taaaatttta tttatatttc tggtagtacc tgcactaact   8040
gaattgaagg tagtgcttat gttatttttg ttcttttttt ctgacttcgg tttatgtttt   8100
catttctttg gagtaatgct gctctagttg ttctaaatag aatgtgggct tcataatttt   8160
tttttccaca aaaacagagt agtcaactta tatagtcaat tacatcagga cattttgtgt   8220
ttcttacaga agcaaaccat aggctcctct tttccttaaa actacttaga taaactgtat   8280
tcgtgaactg catgctggaa aatgctacta ttatgctaaa taatgctaac caacatttaa   8340
aatgtgcaaa actaataaag attacatttt ttatttta                           8378
```

<210> SEQ ID NO 2
<211> LENGTH: 8378
<212> TYPE: DNA
<213> ORGANISM: Homo sapiens

<400> SEQUENCE: 2

```
tactgcagag gtctctggtg catgtgtgta tgtgtgcgtt tgtgtgtgtt tgtgtgtctg     60
tgtgttctgc cccagtgaga ctgcagccct tgtaaatact ttgacacctt ttgcaagaag    120
gaatctgaac aattgcaact gaaggcacat tgttatcatc tcgtctttgg gtgatgctgt    180
tcctcactgc agatggataa ttttcctttt aatcaggaat ttcatatgca gaataaatgg    240
taattaaaat gtgcaggatg acaagatgga gcaaacagtg cttgtaccac caggacctga    300
cagcttcaac ttcttcacca gagaatctct tgcggctatt gaaagacgca ttgcagaaga    360
aaaggcaaag aatcccaaac cagacaaaaa agatgacgac gaaaatggcc caaagccaaa    420
tagtgacttg gaagctggaa agaaccttcc atttatttat ggagacattc ctccagagat    480
ggtgtcagag cccctggagg acctggaccc ctactatatc aataagaaaa cttttatagt    540
attgaataaa gggaaggcca tcttccggtt cagtgccacc tctgccctgt acattttaac    600
tcccttcaat cctcttagga aaatagctat taagattttg gtacattcat tattcagcat    660
gctaattatg tgcactattt tgacaaactg tgtgtttatg acaatgagta accctcctga    720
ttggacaaag aatgtagaat acaccttcac aggaatatat acttttgaat cacttataaa    780
aattattgca aggggattct gtttagaaga ttttactttc cttcgggatc catggaactg    840
gctcgatttc actgtcatta catttgcgtt tgtaacagaa tttgtaaacc taggcaattt    900
ttcagctctt cgcactttca gagtcttgag agctttgaaa actatttcgg taattccagg    960
cctgaaaacc attgtgggag ccctgatcca gtctgtgaag aagctctcag atgtaatgat   1020
cctgactgtg ttctgtctga gcgtatttgc tctaattggg ctgcagctgt tcatgggcaa   1080
cctgaggaat aaatgtatac aatggcctcc caccaatgct tccttggagg aacatagtat   1140
agaaaagaat ataactgtga attataatgg tacacttata aatgaaactg tctttgagtt   1200
tgactggaag tcatatattc aagattcaag atatcattat ttcctggagg gtttttttaga   1260
tgcactacta tgtggaaata gctctgatgc aggccaatgt ccagagggat atatgtgtgt   1320
gaaagctggt agaaatccca attatggcta cacaagcttt gataccttca gttgggcttt   1380
tttgtccttg tttcgactaa tgactcagga cttctgggaa aatctttatc aactgacatt   1440
acgtgctgct gggaaaacgt acatgatatt ttttgtattg gtcattttct tgggctcatt   1500
ctacctaata aatttgatcc tggctgtggt ggccatggcc tacgaggaac agaatcaggc   1560
```

-continued

```
caccttggaa gaagcagaac agaaagaggc cgaatttcag cagatgattg aacagcttaa   1620
aaagcaacag gaggcagctc agcaggcagc aacggcaact gcctcagaac attccagaga   1680
gcccagtgca gcaggcaggc tctcagacag ctcatctgaa gcctctaagt tgagttccaa   1740
gagtgctaag gaaagaagaa atcggaggaa gaaaagaaaa cagaaagagc agtctggtgg   1800
ggaagagaaa gatgaggatg aattccaaaa atctgaatct gaggacagca tcaggaggaa   1860
aggttttcgc ttctccattg aagggaaccg attgacatat gaaaagaggt actcctcccc   1920
acaccagtct ttgttgagca tccgtggctc cctattttca ccaaggcgaa atagcagaac   1980
aagccttttc agctttagag ggcgagcaaa ggatgtggga tctgagaacg acttcgcaga   2040
tgatgagcca gcacctttga ggataacgag agccgtagag attccttgtt tgtgccccga   2100
cgacacggag agagacgcaa cagcaacctg agtcagacca gtaggtcatc ccggatgctg   2160
gcagtgtttc cagcgaatgg gaagatgcac agcactgtgg attgcaatgg tgtggtttcc   2220
ttggttggtg gaccttcagt tcctacatcg cctgttggac agcttctgcc agaggtgata   2280
atagataagc cagctactga tgacaatgga acaaccactg aaactgaaat gagaaagaga   2340
aggtcaagtt ctttccacgt ttccatggac tttctagaag atccttccca aaggcaacga   2400
gcaatgagta tagccagcat tctaacaaat acagtagaag aacttgaaga atccaggcag   2460
aaatgcccac cctgttggta taaattttcc aacatattct taatctggga ctgttctcca   2520
tattggttaa aagtgaaaca tgttgtcaac ctggttgtga tggacccatt tgttgacctg   2580
gccatcacca tctgtattgt cttaaatact cttttcatgg ccatggagca ctatccaatg   2640
acggaccatt tcaataatgt gcttacagta ggaaacttgg ttttcactgg gatctttaca   2700
gcagaaatgt ttctgaaaat tattgccatg gatccttact attatttcca agaaggctgg   2760
aatatctttg acggttttat tgtgacgctt agcctggtag aacttggact cgccaatgtg   2820
gaaggattat ctgttctccg ttcatttcga ttgctgcgag ttttcaagtt ggcaaaatct   2880
tggccaacgt taaatatgct aataaagatc atcggcaatt ccgtgggggc tctgggaaat   2940
ttaaccctcg tcttggccat catcgtcttc atttttgccg tggtcggcat gcagctcttt   3000
ggtaaaagct acaaagattg tgtctgcaag atcgccagtg attgtcaact cccacgctgg   3060
cacatgaatg acttcttcca ctccttcctg attgtgttcc gcgtgctgtg tggggagtgg   3120
atagagacca tgtgggactg tatggaggtt gctggtcaag ccatgtgcct tactgtcttc   3180
atgatggtca tggtgattgg aaacctagtg gtcctgaatc tctttctggc cttgcttctg   3240
agctcattta gtgcagacaa ccttgcagcc actgatgatg ataatgaaat gaataatctc   3300
caaattgctg tggataggat gcacaaagga gtagcttatg tgaaaagaaa aatatatgaa   3360
tttattcaac agtccttcat taggaaacaa aagattttag atgaaattaa accacttgat   3420
gatctaaaca acaagaaaga cagttgtatg tccaatcata cagcagaaat tgggaaagat   3480
cttgactatc ttaaagatgt aaatggaact acaagtggta taggaactgg cagcagtgtt   3540
gaaaaataca ttattgatga aagtgattac atgtcattca taaacaaccc cagtcttact   3600
gtgactgtac caattgctgt aggagaatct gactttgaaa atttaaacac ggaagacttt   3660
agtagtgaat cggatctgga agaaagcaaa gagaaactga atgaaagcag tagctcatca   3720
gaaggtagca ctgtggacat cggcgcacct gtagaagaac agcccgtagt ggaacctgaa   3780
gaaactcttg aaccagaagc ttgtttcact gaaggctgtg tacaaagatt caagtgttgt   3840
caaatcaatg tggaagaagg cagaggaaaa caatggtgga acctgagaag gacgtgtttc   3900
cgaatagttg aacataactg gtttgagacc ttcattgttt tcatgattct ccttagtagt   3960
```

-continued

```
ggtgctctgg catttgaaga tatatatatt gatcagcgaa agacgattaa gacgatgttg   4020
gaatatgctg acaaggtttt cacttacatt ttcattctgg aaatgcttct aaaatgggtg   4080
gcatatggct atcaaaatat ttcaccaatg cctggtgttg gctggacttc ttaattgttg   4140
atgtttcatt ggtcagttta acagcaaatg ccttgggtta ctcagaactt ggagccatca   4200
aatctctcag gacactaaga gctctgagac ctctaagagc cttatctcga tttgaaggga   4260
tgagggtggt tgtgaatgcc cttttaggag caattccatc catcatgaat gtgcttctgg   4320
tttgtcttat attctggcta attttcagca tcatgggcgt aaatttgttt gctggcaaat   4380
tctaccactg tattaacacc acaactggtg acaggtttga catcgaagac gtgaataatc   4440
atactgattg cctaaaacta atagaaagaa atgagactgc tcgatggaaa aatgtgaaag   4500
taaactttga taatgtagga tttgggtatc tctctttgct tcaagttgcc acattcaaag   4560
gatggatgga tataatgtat gcagcagttg attccagaaa tgtggaactc cagcctaagt   4620
atgaagaaag tctgtacatg tatctttact ttgttatttt catcatcttt gggtccttct   4680
tcaccttgaa cctgtttatt ggtgtcatca tagataattt caaccagcag aaaaagaagt   4740
ttggaggtca agacatcttt atgacagaag aacagaagaa atactataat gcaatgaaaa   4800
aattaggatc gaaaaaaccg caaaagccta tacctcgacc aggaaacaaa tttcaaggaa   4860
tggtctttga cttcgtaacc agacaagttt ttgacataag catcatgatt ctcatctgtc   4920
ttaacatggt cacaatgatg gtggaaacag atgaccagag tgaatatgtg actaccattt   4980
tgtcacgcat caatctggtg ttcattgtgc tatttactgg agagtgtgta ctgaaactca   5040
tctctctacg ccattattat tttaccattg gatggaatat ttttgatttt gtggttgtca   5100
ttctctccat tgtaggtatg tttcttgccg agctgataga aaagtatttc gtgtccccta   5160
ccctgttccg agtgatccgt cttgctagga ttggccgaat cctacgtctg atcaaaggag   5220
caaaggggat ccgcacgctg ctctttgctt tgatgatgtc ccttcctgcg ttgtttaaca   5280
tcggcctcct actcttccta gtcatgttca tctacgccat ctttgggatg tccaactttg   5340
cctatgttaa gagggaagtt gggatcgatg acatgttcaa ctttgagacc tttggcaaca   5400
gcatgatctg cctattccaa attacaacct ctgctggctg ggatggattg ctagcaccca   5460
ttctcaacag taagccaccc gactgtgacc ctaataaagt taaccctgga agctcagtta   5520
agggagactg tgggaaccca tctgttggaa ttttcttttt tgtcagttac atcatcatat   5580
ccttcctggt tgtggtgaac atgtacatcg cggtcatcct ggagaacttc agtgttgcta   5640
ctgaagaaag tgcagagcct ctgagtgagg atgactttga gatgttctat gaggtttggg   5700
agaagtttga tcccgatgca actcagttca tggaatttga aaaattatct cagtttgcag   5760
ctgcgcttga accgcctctc aatctgccac aaccaaacaa actccagctc attgccatgg   5820
atttgcccat ggtgagtggt gaccggatcc actgtcttga tatcttattt gcttttacaa   5880
agcgggttct aggagagagt ggagagatgg atgctctacg aatacagatg gaagagcgat   5940
tcatggcttc caatccttcc aaggtctcct atcagccaat cactactact ttaaaacgaa   6000
aacaagagga agtatctgct gtcattattc agcgtgctta cagacgccac cttttaaagc   6060
gaactgtaaa acaagcttcc tttacgtaca ataaaaacaa aatcaaaggt ggggctaatc   6120
ttcttataaa agaagacatg ataattgaca gaataaatga aaactctatt acagaaaaaa   6180
ctgatctgac catgtccact gcagcttgtc caccttccta tgaccgggtg acaaagccaa   6240
ttgtggaaaa acatgagcaa gaaggcaaag atgaaaaagc caaagggaaa taaatgaaaa   6300
```

-continued

```
taaataaaaa taattgggtg acaaattgtt tacagcctgt gaaggtgatg tatttttatc   6360

aacaggactc ctttaggagg tcaatgccaa actgactgtt tttacacaaa tctccttaag   6420

gtcagtgcct acaataagac agtgacccct tgtcagcaaa ctgtgactct gtgtaaaggg   6480

gagatgacct tgacaggagg ttactgttct cactaccagc tgacactgct gaagataaga   6540

tgcacaatgg ctagtcagac tgtagggacc agtttcaagg ggtgcaaacc tgtgattttg   6600

gggttgttta acatgaaaca ctttagtgta gtaattgtat ccactgtttg catttcaact   6660

gccacatttg tcacattttt atggaatctg ttagtggatt catctttttg ttaatccatg   6720

tgtttattat atgtgactat ttttgtaaac gaagtttctg ttgagaaata ggctaaggac   6780

ctctataaca ggtatgccac ctggggggta tggcaaccac atggccctcc cagctacaca   6840

aagtcgtggt ttgcatgagg gcatgctgca cttagagatc atgcatgaga aaaagtcaca   6900

agaaaaacaa attcttaaat ttcaccatat ttctgggagg ggtaattggg tgataagtgg   6960

aggtgctttg ttgatcttgt tttgcgaaat ccagccccta gaccaagtag attatttgtg   7020

ggtaggccag taaatcttag caggtgcaaa cttcattcaa atgtttggag tcataaatgt   7080

tatgtttctt tttgttgtat taaaaaaaaa acctgaatag tgaatattgc cctcacccct   7140

ccaccgccag aagactgaat tgaccaaaat tactctttat aaatttctgc tttttcctgc   7200

actttgttta gccatcttcg gctctcagca aggttgacac tgtatatgtt aatgaaatgc   7260

tatttattat gtaaatagtc attttaccct gtggtgcacg tttgagcaaa caaataatga   7320

cctaagcaca gtatttattg catcaaatat gtaccacaag aaatgtagag tgcaagcttt   7380

acacaggtaa taaaatgtat tctgtaccat ttatagatag tttggatgct atcaatgcat   7440

gtttatatta ccatgctgct gtatctggtt tctctcactg ctcagaatct catttatgag   7500

aaaccatatg tcagtggtaa agtcaaggaa attgttcaac agatctcatt tatttaagtc   7560

attaagcaat agtttgcagc actttaacag ctttttggtt atttttacat tttaagtgga   7620

taacatatgg tatatagcca gactgtacag acatgtttaa aaaaacacac tgcttaacct   7680

attaaatatg tgtttagaat tttataagca aatataaata ctgtaaaaag tcactttatt   7740

ttatttttca gcattatgta cataaatatg aagaggaaat tatcttcagg ttgatatcac   7800

aatcactttt cttactttct gtccatagta ctttttcatg aaagaaattt gctaaataag   7860

acatgaaaac aagactgggt agttgtagat ttctgctttt taaattacat ttgctaattt   7920

tagattattt cacaatttta aggagcaaaa taggttcacg attcatatcc aaattatgct   7980

ttgcaattgg aaaagggttt aaaattttat ttatatttct ggtagtacct gcactaactg   8040

aattgaaggt agtgcttatg ttatttttgt tctttttttc tgacttcggt ttatgttttc   8100

atttctttgg agtaatgctg ctctagattg ttctaaatag aatgtgggct tcataatttt   8160

tttttccaca aaaacagagt agtcaactta tatagtcaat tacatcagga cattttgtgt   8220

ttcttacaga agcaaaccat aggctcctct tttccttaaa actacttaga taaactgtat   8280

tcgtgaactg catgctggaa aatgctacta ttatgctaaa taatgctaac caacatttaa   8340

aatgtgcaaa actaataaag attacatttt ttatttta                           8378
```

<210> SEQ ID NO 3
<211> LENGTH: 2009
<212> TYPE: PRT
<213> ORGANISM: Homo sapiens

<400> SEQUENCE: 3

Met Glu Gln Thr Val Leu Val Pro Pro Gly Pro Asp Ser Phe Asn Phe

-continued

```
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430
```

-continued

```
Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845
```

-continued

```
Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                1015                1020

Ala Tyr  Val Lys Arg Lys Ile  Tyr Glu Phe Ile Gln  Gln Ser Phe
    1025                1030                1035

Ile Arg  Lys Gln Lys Ile Leu  Asp Glu Ile Lys Pro  Leu Asp Asp
    1040                1045                1050

Leu Asn  Asn Lys Lys Asp Ser  Cys Met Ser Asn His  Thr Ala Glu
    1055                1060                1065

Ile Gly  Lys Asp Leu Asp Tyr  Leu Lys Asp Val Asn  Gly Thr Thr
    1070                1075                1080

Ser Gly  Ile Gly Thr Gly Ser  Ser Val Glu Lys Tyr  Ile Ile Asp
    1085                1090                1095

Glu Ser  Asp Tyr Met Ser Phe  Ile Asn Asn Pro Ser  Leu Thr Val
    1100                1105                1110

Thr Val  Pro Ile Ala Val Gly  Glu Ser Asp Phe Glu  Asn Leu Asn
    1115                1120                1125

Thr Glu  Asp Phe Ser Ser Glu  Ser Asp Leu Glu Glu  Ser Lys Glu
    1130                1135                1140

Lys Leu  Asn Glu Ser Ser Ser  Ser Ser Glu Gly Ser  Thr Val Asp
    1145                1150                1155

Ile Gly  Ala Pro Val Glu Glu  Gln Pro Val Val Glu  Pro Glu Glu
    1160                1165                1170

Thr Leu  Glu Pro Glu Ala Cys  Phe Thr Glu Gly Cys  Val Gln Arg
    1175                1180                1185

Phe Lys  Cys Cys Gln Ile Asn  Val Glu Glu Gly Arg  Gly Lys Gln
    1190                1195                1200

Trp Trp  Asn Leu Arg Arg Thr  Cys Phe Arg Ile Val  Glu His Asn
    1205                1210                1215

Trp Phe  Glu Thr Phe Ile Val  Phe Met Ile Leu Leu  Ser Ser Gly
    1220                1225                1230

Ala Leu  Ala Phe Glu Asp Ile  Tyr Ile Asp Gln Arg  Lys Thr Ile
    1235                1240                1245

Lys Thr  Met Leu Glu Tyr Ala  Asp Lys Val Phe Thr  Tyr Ile Phe
```

-continued

```
    1250                1255                1260

Ile Leu  Glu Met Leu Leu Lys  Trp Val Ala Tyr Gly  Tyr Gln Thr
    1265                1270                1275

Tyr Phe  Thr Asn Ala Trp Cys  Trp Leu Asp Phe Leu  Ile Val Asp
    1280                1285                1290

Val Ser  Leu Val Ser Leu Thr  Ala Asn Ala Leu Gly  Tyr Ser Glu
    1295                1300                1305

Leu Gly  Ala Ile Lys Ser Leu  Arg Thr Leu Arg Ala  Leu Arg Pro
    1310                1315                1320

Leu Arg  Ala Leu Ser Arg Phe  Glu Gly Met Arg Val  Val Val Asn
    1325                1330                1335

Ala Leu  Leu Gly Ala Ile Pro  Ser Ile Met Asn Val  Leu Leu Val
    1340                1345                1350

Cys Leu  Ile Phe Trp Leu Ile  Phe Ser Ile Met Gly  Val Asn Leu
    1355                1360                1365

Phe Ala  Gly Lys Phe Tyr His  Cys Ile Asn Thr Thr  Thr Gly Asp
    1370                1375                1380

Arg Phe  Asp Ile Glu Asp Val  Asn Asn His Thr Asp  Cys Leu Lys
    1385                1390                1395

Leu Ile  Glu Arg Asn Glu Thr  Ala Arg Trp Lys Asn  Val Lys Val
    1400                1405                1410

Asn Phe  Asp Asn Val Gly Phe  Gly Tyr Leu Ser Leu  Leu Gln Val
    1415                1420                1425

Ala Thr  Phe Lys Gly Trp Met  Asp Ile Met Tyr Ala  Ala Val Asp
    1430                1435                1440

Ser Arg  Asn Val Glu Leu Gln  Pro Lys Tyr Glu Glu  Ser Leu Tyr
    1445                1450                1455

Met Tyr  Leu Tyr Phe Val Ile  Phe Ile Ile Phe Gly  Ser Phe Phe
    1460                1465                1470

Thr Leu  Asn Leu Phe Ile Gly  Val Ile Ile Asp Asn  Phe Asn Gln
    1475                1480                1485

Gln Lys  Lys Lys Phe Gly Gly  Gln Asp Ile Phe Met  Thr Glu Glu
    1490                1495                1500

Gln Lys  Lys Tyr Tyr Asn Ala  Met Lys Lys Leu Gly  Ser Lys Lys
    1505                1510                1515

Pro Gln  Lys Pro Ile Pro Arg  Pro Gly Asn Lys Phe  Gln Gly Met
    1520                1525                1530

Val Phe  Asp Phe Val Thr Arg  Gln Val Phe Asp Ile  Ser Ile Met
    1535                1540                1545

Ile Leu  Ile Cys Leu Asn Met  Val Thr Met Met Val  Glu Thr Asp
    1550                1555                1560

Asp Gln  Ser Glu Tyr Val Thr  Thr Ile Leu Ser Arg  Ile Asn Leu
    1565                1570                1575

Val Phe  Ile Val Leu Phe Thr  Gly Glu Cys Val Leu  Lys Leu Ile
    1580                1585                1590

Ser Leu  Arg His Tyr Tyr Phe  Thr Ile Gly Trp Asn  Ile Phe Asp
    1595                1600                1605

Phe Val  Val Val Ile Leu Ser  Ile Val Gly Met Phe  Leu Ala Glu
    1610                1615                1620

Leu Ile  Glu Lys Tyr Phe Val  Ser Pro Thr Leu Phe  Arg Val Ile
    1625                1630                1635

Arg Leu  Ala Arg Ile Gly Arg  Ile Leu Arg Leu Ile  Lys Gly Ala
    1640                1645                1650
```

```
Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005
```

<210> SEQ ID NO 4
<211> LENGTH: 2009
<212> TYPE: PRT
<213> ORGANISM: Homo sapiens

```
<400> SEQUENCE: 4

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Phe Val Thr Glu Phe Val Asn
        195                 200                 205

Leu Gly Asn Phe Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415
```

```
Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830
```

-continued

```
Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Ile Arg  Lys Gln Lys Ile Leu  Asp Glu Ile Lys Pro  Leu Asp Asp
    1040                 1045                 1050

Leu Asn  Asn Lys Lys Asp Ser  Cys Met Ser Asn His  Thr Ala Glu
    1055                 1060                 1065

Ile Gly  Lys Asp Leu Asp Tyr  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
```

-continued

```
    1235                1240                1245

Lys Thr  Met Leu Glu Tyr Ala  Asp Lys Val Phe Thr  Tyr Ile Phe
    1250                1255                1260

Ile Leu  Glu Met Leu Leu Lys  Trp Val Ala Tyr Gly  Tyr Gln Thr
    1265                1270                1275

Tyr Phe  Thr Asn Ala Trp Cys  Trp Leu Asp Phe Leu  Ile Val Asp
    1280                1285                1290

Val Ser  Leu Val Ser Leu Thr  Ala Asn Ala Leu Gly  Tyr Ser Glu
    1295                1300                1305

Leu Gly  Ala Ile Lys Ser Leu  Arg Thr Leu Arg Ala  Leu Arg Pro
    1310                1315                1320

Leu Arg  Ala Leu Ser Arg Phe  Glu Gly Met Arg Val  Val Val Asn
    1325                1330                1335

Ala Leu  Leu Gly Ala Ile Pro  Ser Ile Met Asn Val  Leu Leu Val
    1340                1345                1350

Cys Leu  Ile Phe Trp Leu Ile  Phe Ser Ile Met Gly  Val Asn Leu
    1355                1360                1365

Phe Ala  Gly Lys Phe Tyr His  Cys Ile Asn Thr Thr  Thr Gly Asp
    1370                1375                1380

Arg Phe  Asp Ile Glu Asp Val  Asn Asn His Thr Asp  Cys Leu Lys
    1385                1390                1395

Leu Ile  Glu Arg Asn Glu Thr  Ala Arg Trp Lys Asn  Val Lys Val
    1400                1405                1410

Asn Phe  Asp Asn Val Gly Phe  Gly Tyr Leu Ser Leu  Leu Gln Val
    1415                1420                1425

Ala Thr  Phe Lys Gly Trp Met  Asp Ile Met Tyr Ala  Ala Val Asp
    1430                1435                1440

Ser Arg  Asn Val Glu Leu Gln  Pro Lys Tyr Glu Glu  Ser Leu Tyr
    1445                1450                1455

Met Tyr  Leu Tyr Phe Val Ile  Phe Ile Ile Phe Gly  Ser Phe Phe
    1460                1465                1470

Thr Leu  Asn Leu Phe Ile Gly  Val Ile Ile Asp Asn  Phe Asn Gln
    1475                1480                1485

Gln Lys  Lys Lys Phe Gly Gly  Gln Asp Ile Phe Met  Thr Glu Glu
    1490                1495                1500

Gln Lys  Lys Tyr Tyr Asn Ala  Met Lys Lys Leu Gly  Ser Lys Lys
    1505                1510                1515

Pro Gln  Lys Pro Ile Pro Arg  Pro Gly Asn Lys Phe  Gln Gly Met
    1520                1525                1530

Val Phe  Asp Phe Val Thr Arg  Gln Val Phe Asp Ile  Ser Ile Met
    1535                1540                1545

Ile Leu  Ile Cys Leu Asn Met  Val Thr Met Met Val  Glu Thr Asp
    1550                1555                1560

Asp Gln  Ser Glu Tyr Val Thr  Thr Ile Leu Ser Arg  Ile Asn Leu
    1565                1570                1575

Val Phe  Ile Val Leu Phe Thr  Gly Glu Cys Val Leu  Lys Leu Ile
    1580                1585                1590

Ser Leu  Arg His Tyr Tyr Phe  Thr Ile Gly Trp Asn  Ile Phe Asp
    1595                1600                1605

Phe Val  Val Val Ile Leu Ser  Ile Val Gly Met Phe  Leu Ala Glu
    1610                1615                1620

Leu Ile  Glu Lys Tyr Phe Val  Ser Pro Thr Leu Phe  Arg Val Ile
    1625                1630                1635
```

```
Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005
```

<210> SEQ ID NO 5
<211> LENGTH: 850

-continued

<212> TYPE: DNA
<213> ORGANISM: Homo sapiens

<400> SEQUENCE: 5

```
ctaaaataat gctaaagttt ttcaagtact acttgaaaat agctatattt actttcaaac     60

cttttcctct ttgagtcatt aggttcatga tattatatag caatagggaa tgaaagagaa    120

gcaaggagaa gcaatactgg gagattacag agaagaaagg aaaaaaggct gagagaaaag    180

aggttgagga agaaatcata aatctggatt gtgagaaagt gtttaatatt tagccactag    240

atggcgatgt aatgtaaggt gctgtcttga cttttttttt ttttttttga aacaagctat    300

ttgctgattt gtattaggta ccatagagtg aggcgaggat gaagccgaga agatactgca    360

gaggtctctg gtgcatgtgt gtatgtgtgc gtttgtgtgt gtttgtgtgt ctgtgtgttc    420

tgccccagtg agactgcagc ccttgtaaat actttgacac cttttgcaag aaggaatctg    480

aacaattgca actgaaggca cattgttatc atctcgtctt tgggtgatgc tgttcctcac    540

tgcagatgga taattttcct tttaatcagg taagccatct aattgtttca tcttgatttt    600

aagtttattc attccagtta ttcctttgga aaaagagtcc atggaaattc agtttgggca    660

gagcaggaag tccatttttg tatgtgtatt cagaccaact gtccccctcc tccctctcct    720

cctcttcttg tcccctcccc cgcgccctcc tctctcaacc ttccatgaac tgaaatcagg    780

tttgttttgc agttcagcat tttgatagaa gatgggattc tttggcctga aatagcttgg    840

catctggcca                                                           850
```

<210> SEQ ID NO 6
<211> LENGTH: 483
<212> TYPE: DNA
<213> ORGANISM: Homo sapiens

<400> SEQUENCE: 6

```
acatctctta gtcctctctt aaatatctgt attcctttta ttttaggaat ttcatatgca     60

gaataaatgg taattaaaat gtgcaggatg acaagatgga gcaaacagtg cttgtaccac    120

caggacctga cagcttcaac ttcttcacca gagaatctct tgcggctatt gaaagacgca    180

ttgcagaaga aaaggcaaag aatcccaaac cagacaaaaa aagatgacga cgaaaaatgg    240

cccaaagcaa atagtgactt ggaagctgga aagaaccttc catttattta tggagacatt    300

cctccagaga tggtgtcaga gcccctggag gacctggacc cctactatat caataagaaa    360

gtgagtgttt tttttatcag gcatattttt gctgctaatt gcctactgca ttccttggac    420

tgttgtagca ccaacacatg ccaatagcac aaatctagta tctctgttag aatgaacaca    480

ttt                                                                  483
```

<210> SEQ ID NO 7
<211> LENGTH: 497
<212> TYPE: DNA
<213> ORGANISM: Homo sapiens

<400> SEQUENCE: 7

```
taagaagaga tccagtgaca gtttgttttc atggggcact ttaggaaatt gtgattgtgc     60

tggtttctca tttaacttta caataattta ttatgacaag taacagaaag tagataacag    120

agtttaagtg gtttatactt tcatacttct atgttgtgtt cctgtcttac agacttttat    180

agtattgaat aaagggaagg ccatcttccg gttcagtgcc acctctgccc tgtacatttt    240

aactcccttc aatcctctta ggaaaatagc tattaagatt ttggtacatt catatccttt    300
```

-continued

```
ttcaagtgat taatattaac tatttgtaca tgatctgtaa gcactttata gctaaatatc    360

aaattaagtt gggaaatgtc catattatat aggtttcatc actctcattt tgcatctttg    420

tcatattagc ctcattctta aagttcatta atcacataga cattactgaa acatgtactc    480

tttaacattt tatatat                                                   497
```

<210> SEQ ID NO 8
<211> LENGTH: 501
<212> TYPE: DNA
<213> ORGANISM: Homo sapiens

<400> SEQUENCE: 8

```
tcatatacat tacctcattt aatctataca aatactcagt gaaggtgata ttattaccca     60

cattttacac atgaagaaat tgaaatgtaa ggagattaga agacttgccc acaatgcatt    120

tatccctgaa ttttggctaa gctgcagttt gggcttttca atgttagctt tttgtaatat    180

aacacttgga ttttgatttt cttttgtgtg ttccttaaca ataacctaca ttattcagca    240

tgctaattat gtgcactatt ttgacaaact gtgtgtttat gacaatgagt aaccctcctg    300

attggacaaa gaatgtagag taagttcaac ttatattttt aataacatat atacattygg    360

gattytgaaa ctgtgtctta atgtagtctt aaaataaaac tgaagagcat tttattaaag    420

tcattcctag acaaaattac gcagcaagag gacaatgctc attggccctc aggcctgctg    480

gcgttatact gattatcact c                                              501
```

<210> SEQ ID NO 9
<211> LENGTH: 563
<212> TYPE: DNA
<213> ORGANISM: Homo sapiens

<400> SEQUENCE: 9

```
gctaaataga tttcatatac cttgtatttc tcacactact cttaagacac tttacgaaac     60

aactctttgt gttaggaagc tgaatttaaa tttagggcta cgtttcattt gtatgaaatt    120

aaaatccatc tgcttagttt tctttttag tatttatcta ttccactgat ggagtgataa     180

gaaattggta tgctatgaaa aaacactgtt actttatcaa attttttgga tgcttgtttt    240

cagatacacc ttcacaggaa tatatacttt tgaatcactt ataaaaatta ttgcaagggg    300

attctgttta gaagatttta ctttccttcg ggatccatgg aactggctcg atttcactgt    360

cattacattt gcgtaagtgc ctttbytgaa actttaagag agaacatagt ttggttttcc    420

atcagtgctt atgcttttaa gaataggttt gctttacctg tagaatattt ttgtgtgatt    480

tatacattca aactctggat ttcaatttag cacaacaaag gtctaagtgg aatttcacta    540

tagcatgaag gctttgcagt agt                                            563
```

<210> SEQ ID NO 10
<211> LENGTH: 253
<212> TYPE: DNA
<213> ORGANISM: Homo sapiens

<400> SEQUENCE: 10

```
cttataagcc catgcagtaa tataaatcct gctaaaatct tgaataattc tgatttaatt     60

ctacaggttt gtaacagaat ttgtaaacct aggcaatttt tcagctcttc gcactttcag    120

agtcttgaga gctttgaaaa ctatttcggt aattccaggt aagaagtgat tagagtaaag    180

gataggctct ttgtacctac agctttttct ttgtgtcctg tttttgtgtt tgtgtgtgaa    240

ctcccgctta cag                                                       253
```

<210> SEQ ID NO 11
<211> LENGTH: 340
<212> TYPE: DNA
<213> ORGANISM: Homo sapiens

<400> SEQUENCE: 11

```
gtaagaagtg attagagtaa aggataggct ctttgtacct acagcttttt ctttgtgtcc     60

tgtttttgtg tttgtgtgtg aactcccgct tacaggtacg tcacagagtt tgtggacctg    120

ggcaatgtct cggcattgag aacattcaga gttctccgag cattgaagac gatttcagtc    180

attccaggtg agagcaaggt tagataatga gacggaccca tcatgtgatt cagcatcctt    240

ctctgcttga cattcagttt tacagaaaat caggaatcat aagactaggt gttcaaagaa    300

atgattatta tgttagacat agcttatcag cctggagtta                          340
```

<210> SEQ ID NO 12
<211> LENGTH: 409
<212> TYPE: DNA
<213> ORGANISM: Homo sapiens

<400> SEQUENCE: 12

```
cacgcgtgct tagccctcat agtaatagcc tcctaccttc aggcctgaaa accattgtgg     60

gagccctgat ccagtctgtg aagaagctct cagatgtaat gatcctgact gtgttctgtc    120

tgagcgtatt tgctctaatt gggctgcagc tgttcatggg caacctgagg aataaatgta    180

tacaatggcc tcccaccaat gcttccttgg aggaacatag tatagaaaag aatataactg    240

tgaattataa tggtacactt ataaatgaaa ctgtctttga gtttgactgg aagtcatata    300

ttcaagattc aagtaagaat tattgttatg tacatttcct taaaaagtag aattggattg    360

tttgtaacac aaaggataaa tacttgaggg gctggatatc ccattttac                409
```

<210> SEQ ID NO 13
<211> LENGTH: 266
<212> TYPE: DNA
<213> ORGANISM: Homo sapiens

<400> SEQUENCE: 13

```
cgcgcaaata cttgtgcctt tgaatgaata atatatttaa aattactcaa taaacttaaa     60

agtagaacct gaccttcctg ttctctttga gtgtttttaa caatgcaaat gttcagcata    120

cgactttctt ttttcaaaca ggatatcatt atttcctgga gggtttttta gatgcactac    180

tatgtggaaa tagctctgat gcagggtaag tcaatattgt gtgcatctgt gtatattgta    240

tgtacacaat acatatgtgt atcttt                                         266
```

<210> SEQ ID NO 14
<211> LENGTH: 604
<212> TYPE: DNA
<213> ORGANISM: Homo sapiens

<400> SEQUENCE: 14

```
aggtgttgaa aatgcaaatt atcaacaaaa attattttgt aaaatattat tagaaatgct     60

gcaccatatt ttaatgatga caccaagtag ctaataagac tatatgcagt caaaagttgg    120

gaaatagatt agttacttat ttgtcaaact tttattttga aataccaaat ctttctgact    180

aggcaatatc atagcatagt atcagagtaa aaaggcagca gaacgacttg taatactttc    240

ttttacccca cttgcagcca atgtccagag ggatatatgt gtgtgacagc tggtagaaat    300
```

```
cccaattatg gctacacaag ctttgatacc ttcagttggg ctttttttgtc cttgtttcga    360

ctaatgactc aggacttctg ggaaaatctt tatcaactgg tgagaactaa agagccacac    420

tctccattta agtaaaagta tacaagaaaa ccaattgagt tatgaaatta aaaccggatg    480

ataatatagt agaaagagca gaacttgaca cgagacttga gttcctctat cctattgatt    540

ataacacata ctgagcagag tgatgccaag gattgcaatt ctctcccatt tcttcttggc    600

tcaa                                                                 604

<210> SEQ ID NO 15
<211> LENGTH: 378
<212> TYPE: DNA
<213> ORGANISM: Homo sapiens

<400> SEQUENCE: 15

ttatatctga gttttgctag ccacatgagt aaattgaaag ttgagcaccc ttagtgaata     60

atattgggaa ataattctga tatttttgtt tgcagacatt acgtgctgct gggaaaacgt    120

acatgatatt ttttgtattg gtcattttct tgggctcatt ctacctaata aatttgatcc    180

tggctgtggt ggccatggcc tacgaggaac agaatcaggc caccttggaa gaagcagaac    240

agaaagaggc cgaatttcag cagatgattg aacagcttaa aaagcaacag gaggcagctc    300

aggtaagctg ccctgctcat ggcactgacc tttatcgtct gatgtactat atgagagaag    360

tagtctagag cgtgtgat                                                  378

<210> SEQ ID NO 16
<211> LENGTH: 845
<212> TYPE: DNA
<213> ORGANISM: Homo sapiens

<400> SEQUENCE: 16

caaccctaat taaataccaa tttttaaagt aaatcaaatc ccaaaaagta atgaatttat     60

tttcttgttg atacatgttg gatatttttg aatacgtggt ctgtggagca ttaacagaga    120

cataataaat gttaccatgg agcaaactaa attatctcca aaagccttca ttaggtagaa    180

agaaaaaaaa aatctcctct tatacttgca gagaatcttc tctgtgagat gatcttcagt    240

cagttcaata tattttttaa aagccatgca aatacttcag ccctttcaaa gaaagataca    300

gtctcttcag gtgctatgtt aaaatcattt ctcttcaata tagcaggcag caacggcaac    360

tgcctcagaa cattccagag agcccagtgc agcaggcagg ctctcagaca gctcatctga    420

agcctctaag ttgagttcca agagtgctaa ggaaagaaga aatcggagga agaaaagaaa    480

acagaaagag cagtctggtg gggaagagaa agatgaggat gaattccaaa aatctgaatc    540

tgaggacagc atcaggaggw aaggttttcg cttctccatt gaagggaacc ggttgacata    600

tgaaaagagg tactcctccc cacaccaggt atggcactgc tgagtttact gatgcatggt    660

tgaaaattaa aacatgggag agagggggag atttagaaaa tggactcagg aatttttatc    720

aactgaatca accactgttg tgttatattt aaacccatcc cttcttcaca tagttatgca    780

aaaactttac tccacagata tgtaagtcta cagctcggtg tagttaagat aacaccaagt    840

tgaca                                                                845

<210> SEQ ID NO 17
<211> LENGTH: 965
<212> TYPE: DNA
<213> ORGANISM: Homo sapiens

<400> SEQUENCE: 17
```

-continued

```
cattgccata ttctaaggat gtttcccttt gaacttgaga aatggtcgtt cagggtgtgt     60

gtgtatgtgt gtgtgtgtgt gtttcaatat gttaaggttg caatctatct cctcattctt    120

taatcccaag ggctagaaac tttcttttat caaggtaatt taatttaatg tgaatgcaca    180

taaaatgaga atgataatca aaaggaatga accatattct gttatgaatg ctgaaatctc    240

cttctacata atcttgcaaa atgaaatcac attcaaatgt ccatattaat atgactctat    300

ttgtbtgctc tttcaaactt ctagtctttg ttgagcatcc gtggctccct attttcacca    360

aggcgaaata gcagaacaag ccttttcagc tttagagggc gagcaaagga tgtgggatct    420

gagaacgact tcgcagatga tgagcacagc acctttgagg ataacgagag ccgtagagat    480

tccttgtttg tgccccgacg acacggagag agacgcaaca gcaacctgag tcagaccagt    540

aggtcatccc ggatgctggc agtgtttcca gcgaatggga agatgcacag cactgtggat    600

tgcaatggtg tgggttcctt ggttggtgga ccttcagttc ctacatcgcc tgttggacag    660

cttctgccag aggtgataat agataagcca gctactgatg acaatgtaag gaagtyttaa    720

atagttcagg catggctggc tcactattgc tgcaccagcc agtgtgtcta cagaacggca    780

accttgagaa tgattcctgg ttggtcacgc tgtgaatgca cctgcatctt gtaatatctt    840

tgatagacta accaactaaa acttaaaacc ttagcagtcg cctgcacaaa cctgaatgca    900

tttacttatt aaaagtgcta aggattgatt agacacaata attactgcct ccagttggag    960

gattt                                                                965
```

```
<210> SEQ ID NO 18
<211> LENGTH: 641
<212> TYPE: DNA
<213> ORGANISM: Homo sapiens

<400> SEQUENCE: 18

aagagtttta tcaactatat taaaattatt ttgtatttta taaaattatg aaatcaggaa     60

gttaacatct tggtttttgc tgtatgacta aatggttaac agtttgaaca ttccaggcta    120

atgatacaat aagtcagaaa tatctgccat caccaattga atatgaaagt gcatgatgca    180

tgtgtttcat gaaattcact gtgtcaccat ttggttgttt gcttgtcata ttgctcaaat    240

taattgttta atgcattagc attttttttt acagggaaca accactgaaa ctgaaatgag    300

aaagagaagg tcaagttctt tccacgtttc catggacttt ctagaagatc cttcccaaag    360

gcaacgagca atgagtatag ccagcattct aacaaataca gtagaaggtt ggtaacaaat    420

tctattttcg tttcaattat tttcaccaaa cttatattgt ctcatttcaa acaaatatat    480

ttgtgagttg ggaatagtgc attctaatga aaagacagtc taattcaaga gctgttattt    540

cttatatcta ctcagatatt ctagaagcct taacaattta ttttaaaatg agtgatattg    600

ggactaagac tgttttccta actgtgtagc aactctttga a                        641
```

```
<210> SEQ ID NO 19
<211> LENGTH: 818
<212> TYPE: DNA
<213> ORGANISM: Homo sapiens

<400> SEQUENCE: 19

gtgaggcggc acatgaaaga ccacccattt aacctgaggc caagtgctga gccacaatgg     60

cagtgcataa gacaaaaaac tacccattgt tacctgggcc ctatgtgtgt gtctgatgaa    120

ataaccttgg gaggtttaga gtaaactgta atttttttaa caagtacaaa aaagggtgtc    180
```

-continued

```
tctgtaacaa aaatgtgttg attactgaaa ataagtttag tggatatgaa ataaatgtgt    240

gtgtataaag tawacctttt ggtgggtctt tttttttttt ttcttaatct agaacttgaa    300

gaatccaggc agaaatgccc accctgttgg tataaatttt ccaacatatt cttaatctgg    360

gactgttctc catattggtt aaaagtgaaa catgttgtca acctggttgt gatggaccca    420

tttgttgacc tggccatcac catctgtatt gtcttaaata ctcttttcat ggccatggag    480

cactatccaa tgacggacca tttcaataat gtgcttacag taggaaactt ggtaagcata    540

ttggaaggta aatgtgttta gtcttcaaat tttctgcttg aaaaactgtt tacatttaat    600

tgtgtatagc agtctttcaa ccatccttca tgcttcctgg cccctgcaaa atcgcaatta    660

tatttagctg gctatactct actttttgc caaaaataat caccccttaat gtgctcacaa    720

aaactgagaa aggcataggc ctacagcact acttgaaaag tcaacagcaa tatttataat    780

ttttcaggat ccagaagtag ctcatagatt aagaacat                            818
```

<210> SEQ ID NO 20
<211> LENGTH: 645
<212> TYPE: DNA
<213> ORGANISM: Homo sapiens

<400> SEQUENCE: 20

```
caagccattt cacccatctg aagacctcag tttccttatc tgtaaagtaa taattgtata     60

ttatctactt cgcgtttcca caaggataaa attaaataat gtatatgawa gtctttcatc    120

aactacaaat tgccatacaa atttaagtta gtaatagaat cattgtggga aaatagcata    180

agcattatgt tctaagagca aatcttatgt catgtatgtt attatctggt ggaattagat    240

taattttgtt ttgatcttag gttttcactg ggatctttac agcagaaatg tttctgaaaa    300

ttattgccat ggatccttac tattatttcc aagaaggctg gaatatcttt gacggtttta    360

ttgtgacgct tagcctggta gaacttggac tcgccaatgt ggaagggtta tctgttctcc    420

gttcatttcg attggtaaaa aaaaaaaaaa aaggaaccaa attcaaaaac ctttctaaca    480

ttcagggttc ttgcatagca ttgtcatagt ttttttgcca cacaaccatt aggcattgta    540

agtttttctg taacatttgc attgtcaaaa acttttccta catgggaata attctcaatt    600

attaggttac cttagttcaa gggcwaggtc ggaaaggtaa cggtt                    645
```

<210> SEQ ID NO 21
<211> LENGTH: 829
<212> TYPE: DNA
<213> ORGANISM: Homo sapiens

<400> SEQUENCE: 21

```
gaattctaat gaccatttct aggtaaagct caatatatat aatgctttta agaatcatac     60

aaatatatat taatctttca ttttccagct gcgagatttc aagttggcaa aatcttggcc    120

aacgttaaat atgctaataa agatcatcgg caattccgtg gggctctgg gaaatttaac     180

cctcgtcttg gccatcatcg tcttcatttt tgccgtggtc ggcatgcagc tctttggtaa    240

aagctacaaa gattgtgtct gcaagatcgc cagtgattgt caactcccac gctggcacat    300

gaatgacttc ttccactcck hcctgattgt gttccgcgtg ctgtgtgggg agtggataga    360

gaccatgtgg gactgtatgg aggttgctgg tcaagccatg tgccttactg tcttcatgat    420

ggtcatggtg attggaaacc tagcggtatg tacccactta agatatgcat tttggaaata    480

caccagcatg gcacatgtat acatatgtaa ctaacctgca cattgtgcac atgtacccta    540

aaacttaaag tataataaaa aaaaagagta taatttaatg gtgactgttt tgtcaaaaag    600
```

-continued

```
aaaaacaaac tatgattatt ggtttaaaag tccattacct tggatatatt atcactttaa    660

caacacagca atatabcagt gcccctgcat tttttatacc aaattctatt ttgtcagtca    720

ctttatcaca ttttttatgt gaattacaat agagtatcat attgagatga gcctaaaagg    780

atgtgctggg accattttat aaattcagag ccaaggaaga gagaagtct                829


<210> SEQ ID NO 22
<211> LENGTH: 909
<212> TYPE: DNA
<213> ORGANISM: Homo sapiens

<400> SEQUENCE: 22

gaattctcgt attgtacaca tataaatctg ttttcttcta ctcatacaat tttagagtta     60

acaaaacctt agattagctc attcaatttc actttacgaa tgggagaact tgagagcaac    120

agaaatcatg tctttgtcca aggatgtgct attgagccag tcacaaattc agatcaccca    180

tcttctaatc actatgctgt ggtgtttcct tctcatcaag ttttagaact tagagttttt    240

tccacactta aaagaaagaa taagtgattg taatctgctc ttccctacat tggtgtaaaa    300

ttataatcat gtttttgttg tttttaaggt cctgaatctc tttctggcct tgcttctgag    360

ctcatttagt gcagacaacc ttgcagccac tgatgatgat aatgaaatga ataatctcca    420

aattgctgtg gataggatgc acaaaggagt agcttatgtg aaaagaaaaa tatatgartt    480

tattcaacag tccttcatta ggaaacaaaa gattttagat gaaattaaac cacttgatga    540

tctaaacaac aagaaagaca gttgtatgtc caatcataca gcagaaattg ggaaagatct    600

tgactatctt aaagatgtaa atggaactac aagtggtata ggaactggca gcagtgttga    660

aaaatacatt attgatgaaa gtgattacat gtcattcata aacaacccca gtcttactgt    720

gactgtacca attgctgtag gagaatctga ctttgaaaat ttaaacacgg aagactttag    780

tagtgaatcg gatctggaag aaagcaaaga ggtaagattc tataggtgtg ggtaggtatg    840

aatacatata catatataca tatacacaca tacagatgay cctcagctta atgatgtttt    900

tacttaaga                                                            909


<210> SEQ ID NO 23
<211> LENGTH: 516
<212> TYPE: DNA
<213> ORGANISM: Homo sapiens
<220> FEATURE:
<221> NAME/KEY: misc_feature
<222> LOCATION: (393)..(393)
<223> OTHER INFORMATION: n = a, c, t or g
<220> FEATURE:
<221> NAME/KEY: misc_feature
<222> LOCATION: (415)..(451)
<223> OTHER INFORMATION: N = a, c, t or g
<220> FEATURE:
<221> NAME/KEY: misc_feature
<222> LOCATION: (454)..(454)
<223> OTHER INFORMATION: N = a, c, t or g
<220> FEATURE:
<221> NAME/KEY: misc_feature
<222> LOCATION: (513)..(513)
<223> OTHER INFORMATION: n = a, c, t or g

<400> SEQUENCE: 23

aagcttacat tgtgaattat ggtaaaaggg ttagcacaga caatgatttt cttatttctt     60

ccccttattc aatctctctt tttctctaaa aatatctcta cctcaagaag aataaaaaac    120

aaattcatag taataatcct tcttggcagg caacttatta ccaaaattaa ggactttact    180
```

-continued

```
ttctatgtcc atctcactta cagaaactga atgaaagcag tagctcatca gaaggtagca    240

ctgtggacat cggcgcacct gtagaagaac agcccgtagt ggaacctgaa gaaactcttg    300

aacccgaagc ttgtttcact gaaggtaaag aaaagaatcc taatgttaat ctttcatttg    360

gagtgcagct tatttagctg ttggtcagct aanataaatc acatataata aaatngcact    420

ttgtaataga tataattcaa tcacctctaa tatnttgaca gacaaaaaaa cttaaagtct    480

agtgtcatgc tttgattata tctgcccaat atntgg                              516
```

```
<210> SEQ ID NO 24
<211> LENGTH: 640
<212> TYPE: DNA
<213> ORGANISM: Homo sapiens

<400> SEQUENCE: 24

ccatttaaat gtggctgaat gtttccacaa cttcacacag ctgatgaatg tgctcttact     60

actctaggct tagagagcta tgctagcaag acagagatga gcatagtaat aaaaagacaa    120

gacaaggaca ttgctaaagg atattatgga agcagagaca ctttatctac ttttatttca    180

acactttctg caggctgtgt acaaagattc aagtgttgtc aaatcaatgt ggaagaaggc    240

agaggaaaac aatggtggaa cctgagaagg acgtgtttcc gaatagttga acataactgg    300

tttgagacct tcattgtttt catgattctc cttagtagtg gtgctctggt gagtgagatt    360

aagaaaaggt gatacagcac taatttttag aacactctaa tactgatgac ttattaatcc    420

tttgtttcat tgtcttagta tccaatgcat ttttaattat cccaccttgt atcttctata    480

gatttactct ataactctat atttctggat taacttttac tatgtatgta aatataattt    540

taagaagcta atcattaatt tttgcttact attaaatagc ccagaaagtg tagcccttca    600

gcttattcat taacaccaaa ggatgtgaat attcaattac                          640
```

```
<210> SEQ ID NO 25
<211> LENGTH: 607
<212> TYPE: DNA
<213> ORGANISM: Homo sapiens

<400> SEQUENCE: 25

ccacatcagg atacaacatc aagaactatt tcctgactaa gtcaaattaa ttcattggaa     60

tcatactttt ctttttcttc caccaatagt ctttcccctg attaaataag taaaagacct    120

ttgcgaggaa aaaaaaaaag taacagtaac tactgtttct ctgccctcct attccaatga    180

aatgtcatat gcatatgatt aattttttaa atagcttatg gagtataatt atttttgaaa    240

gctaataatg tgtaacattt tctttatagg catttgaaga tatatatatt gaycagcgaa    300

agacgattaa gacgatgttg gaatatgctg acaaggtttt cacttacatt ttcattctgg    360

aaatgcttct aaaatgggtg gcatatggct atcaaacata tttcaccaat gcctggagtt    420

ggctggactt cttaattgtt gatgtaggta tcgttcatat ttttgtctct gttcaaggta    480

gcttgtctta tttatattca aattctacaa tagtgagtct cagaccacta tgttatgttg    540

acagactata atarccacta aacgcatata tgcaatgaga gtgtcatttc tggaagacaa    600

gggctaa                                                              607
```

```
<210> SEQ ID NO 26
<211> LENGTH: 336
<212> TYPE: DNA
<213> ORGANISM: Homo sapiens

<400> SEQUENCE: 26
```

-continued

```
aaaaattata cttgtcgtat tatatagcaa ctacacattg aatgatgatt ctgtttatta     60

attgttatta ttcytgtgtg tgcaggtttc attggtcagt ttaacagcaa atgccttggg    120

ttactcagaa cttggagcct atcaatctct caggacacta agagctctga gacctctaag    180

agccttatct cgatttgaag ggatgagggt aagaaaaatg aaagaacctg aagtattgta    240

tatagccaaa attaaactaa attaaattta gaaaaaagga aaaatgtatg catgcaaaag    300

gaatggcaaa ttcttgcaaa atgctcttta ttgttt                              336
```

<210> SEQ ID NO 27
<211> LENGTH: 677
<212> TYPE: DNA
<213> ORGANISM: Homo sapiens

<400> SEQUENCE: 27

```
cttggttata ttgcctatag ttgttttcct aagtgtattg cttaagaaaa aaaaatgaat     60

tttaagattt ttttgaacct tgcttttaca tatcctagaa taaatagcat tgatagaaaa    120

aaagaatgga aagaccagag attactaggg gaattttttt tctttattaa cagataagaa    180

ttctgacttt tcttttttttc catttgtgta ttaggtggtt gtgaatgccc ttttaggagc    240

aattccatcc atcatgaatg tgcttctggt ttgtcttata ttctggctaa ttttcagcat    300

catgggcgta aatttgtttg ctggcaaatt ctaccactgt attaacacca caactggtga    360

caggtttgac atcgaagacg tgaataatca tactgattgc ctaaaactaa tagaaagaaa    420

tgagactgct cgatggaaaa atgtgaaagt aaactttgat aatgtaggat ttgggtatct    480

ctctttgctt caagttgtaa gtgaacacta ttttctctga atatttttat tgtttggaat    540

aataacaaaa taatgacata catctattat ttagttccta agaaaaagta tatatttctt    600

tctatttaaa aaatttcaat ttgttagtac aagtttatga gcccagatgg gtgaaaactt    660

tattacatgt aaggact                                                   677
```

<210> SEQ ID NO 28
<211> LENGTH: 457
<212> TYPE: DNA
<213> ORGANISM: Homo sapiens

<400> SEQUENCE: 28

```
aatggccatt ttgttcaata tgtgttctag aaatgaaaag ccatactaaa atactgtctt     60

ggtccaaaat ctgtgtaaaa tttgttttga aatgtctttc aaaaatattc ccttttgaaa    120

attatatcag taagaatatt tattaaacat caggtctaaa ttatttttac tccaaagtaa    180

aacatgcatg tccttcttaa taggccacat tcaaaggatg gatggatata atgtatgcag    240

cagttgattc cagaaatgta agtattcctt gtattctaag tctttttaca atattgatca    300

ggtggtaaaa ttaatcgaat aaagcataaa cgaccaaatg aaatgattct atcttgattt    360

aaaatatttg ggaaaaagtg tgacaggtaa atattcaagc atagcaatgt ttatcagaaa    420

gatcttacta agataattca acacatgaat tattttg                             457
```

<210> SEQ ID NO 29
<211> LENGTH: 379
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n = a, c, t or g

<400> SEQUENCE: 29

```
cagaaaaaaa aaaaatgctg acatattagt aagaataatt ttntctattg ttatgaaaaa     60

gcaccagtga cgatttccag cactaaaatg tatggtaata ttttacaaaa tattcccctt    120

tggtaggtgg aactccagcc taagtatgaa gaaagtctgt acatgtatct ttactttgtt    180

attttcatca tctttgggtc cttcttcacc ttgaacctgt ttattggtgt catcatagat    240

aatttcaacc agcagaaaaa gaagataagt atttctaata ttttctctcc cactgagata    300

gaaaaattat tccttggagt gttttctctg ccaaatgagt acttgaattt agaacaaatg    360

ggagtatata ttataactg                                                 379
```

<210> SEQ ID NO 30
<211> LENGTH: 393
<212> TYPE: DNA
<213> ORGANISM: Homo sapiens

<400> SEQUENCE: 30

```
gtcattttga attatttagg gaattaaaat attatcatac ctaaagagta caattttttt     60

tacattttaa atcccagata taattatact aatcagttga attttgtatt tcttttttta    120

gccatccatt ttctatttta acattgaaaa aaatgtacaa aaggacacag ttttaaccag    180

tttgattttt cttttctata ctttggaggt caagacatct ttatgacaga agaacagaag    240

aaatactata atgcaatgaa aaaattagga tcgaaaaaac cgcaaaagcc tatacctcga    300

ccaggagtaa gaagtatcaa atgatatggg ggaaaataca aaaacaaaaa ctgcatgctt    360

gtctcacaaa aaagaaaagt aagctaaaca ttt                                 393
```

<210> SEQ ID NO 31
<211> LENGTH: 539
<212> TYPE: DNA
<213> ORGANISM: Homo sapiens

<400> SEQUENCE: 31

```
ttttaacaat taattatgct ataaattcat tcttacaaaa atcatttgga atgactactt     60

tgcaagaaac tagaaagtca attaatgcag aaagtactta atgctaatgc acatgagaaa    120

aactcctttg ttgttaaaag catttctatt tctctacaga acaaatttca aggaatggtc    180

tttgacttcg taaccagaca agtttttgac ataagcatca tgattctcat ctgtcttaac    240

atggtcacaa tgatggtgga aacagatgac cagagtgaat atgtgactac cattttgtca    300

cgcatcaatc tggtgttcat tgtgctattt actggagagt gtgtactgaa actcatctct    360

ctacgccatt attattttac cattggatgg aatatttttg attttgtggt tgtcattctc    420

tccattgtag gtaagaaata tttaaagttc ttaaattcag ttaaataaaa gtgaaagctg    480

aaacaatcaa gattagattc aagatcatcc cagcaatcag agataatcac tgtaaatat     539
```

<210> SEQ ID NO 32
<211> LENGTH: 3403
<212> TYPE: DNA
<213> ORGANISM: Homo sapiens

<400> SEQUENCE: 32

```
agtatatatt atatatagtt gtcatattta atataactgg gttcaggact ctgaacctta     60

ccttggagct ttagaagaaa catatgttta ttttaacgca tgatttcttc actggttggt    120

attctcattg tttattcata ggtatgtttc ttgccgagct gatagaaaag tatttcgtgt    180

cccctaccct gttccgagtg atccgtcttg ctaggattgg ccgaatccta cgtctgatca    240
```

-continued

```
aaggagcaaa ggggatccgc acgctgctct ttgctttgat gatgtccctt cctgcgttgt    300
ttaacatcgg cctcctactc ttcctagtca tgttcatcta cgccatcttt gggatgtcca    360
actttgccta tgttaagagg gaagttggga tcgatgacat gttcaacttt gagacctttg    420
gcaacagcat gatctgccta ttccaaatta caacctctgc tggctgggat ggattgctag    480
cacccattct caacagtaag ccacccgact gtgaccctaa taaagttaac cctggaagct    540
cagttaaggg agactgtggg aacccatctg ttggaatttt ctttttgtc agttacatca     600
tcatatcctt cctggttgtg gtgaacatgt acatcgcggt catcctggag aacttcagtg    660
ttgctactga agaaagtgca gagcctctga gtgaggatga ctttgagatg ttctatgagg    720
tttgggagaa gtttgatccc gatgcaactc agttcatgga atttgaaaaa ttatctcagt    780
ttgcagtgcg cttgaaccgc ctctcaatct gccacaacca aacaaactcc agctcattgc    840
catggatttg cccatggtga gtggtgaccg gatccactgt cttgatatct tatttgcttt    900
tacaaagcgg gttctaggag agagtggaga gatggatgct ctacgaatac agatggaaga    960
gcgattcatg gcttccaatc cttccaaggt ctcctatcag ccaatcacta ctactttaaa   1020
acgaaaacaa gaggaagtat ctgctgtcat tattcagcgt gcttacagac gccacctttt   1080
aaagcgaact gtaaaacaag cttcctttac gtacaataaa aacaaaatca aaggtggggc   1140
taatcttctt ataaaagaag acatgataat tgacagaata aatgaaaact ctattacaga   1200
aaaaactgat ctgaccatgt ccactgcagc ttgtccacct tcctatgacc gggtgacaaa   1260
gccaattgtg gaaaaacatg agcaagaagg caaagatgaa aaagccaaag ggaaataaat   1320
gaaaataaat aaaaataatt gggtgacaaa ttgtttacag cctgtgaagg tgatgtattt   1380
ttatcaacag gactccttta ggaggtcaat gccaaactga ctgtttttac acaaatctcc   1440
ttaaggtcag tgcctacaat aagacagtga ccccttgtca gcaaactgtg actctgtgta   1500
aaggggagat gaccttgaca ggaggttact gttctcacta ccagctgaca ctgctgaaga   1560
taagatgcac aatggctagt cagactgtag ggaccagttt caaggggtgc aaacctgtga   1620
ttttggggtt gtttaacatg aaacacttta gtgtagtaat tgtatccact gtttgcattt   1680
caactgccac atttgtcaca tttttatgga atctgttagt ggattcatct ttttgttaat   1740
ccatgtgttt attatatgtg actatttttg taaacgaagt ttctgttgag aaataggcta   1800
aggacctcta taacaggtat gccacctggg ggtatggca accacatggc cctcccagct    1860
acacaaagtc gtggtttgca tgagggcatg ctgcacttag agatcatgca tgagaaaaag   1920
tcacaagaaa aacaaattct taaatttcac catatttctg ggaggggtaa ttgggtgata   1980
agtggaggtg ctttgttgat cttgttttgc gaaatccagc ccctagacca agtagattat   2040
ttgtgggtag gccagtaaat cttagcaggt gcaaacttca ttcaaatgtt tggagtcata   2100
aatgttatgt ttcttttgt tgtattaaaa aaaaaacctg aatagtgaat attgcccctc    2160
accctccacc gccagaagac tgaattgacc aaaattactc tttataaatt tctgcttttt   2220
cctgcacttt gtttagccat cttcggctct cagcaaggtt gacactgtat atgttaatga   2280
aatgctattt attatgtaaa tagtcatttt accctgtggt gcacgtttga gcaaacaaat   2340
aatgacctaa gcacagtatt tattgcatca aatatgtacc acaagaaatg tagagtgcaa   2400
gctttacaca ggtaataaaa tgtattctgt accatttata gatagtttgg atgctatcaa   2460
tgcatgttta tattaccatg ctgctgtatc tggtttctct cactgctcag aatctcattt   2520
atgagaaacc atatgtcagt ggtaaagtca aggaaattgt tcaacagatc tcatttattt   2580
```

-continued

```
aagtcattaa gcaatagttt gcagcacttt aacagctttt tggttatttt tacattttaa   2640
gtggataaca tatggtatat agccagactg tacagacatg tttaaaaaaa cacactgctt   2700
aacctattaa atatgtgttt agaattttat aagcaaatat aaatactgta aaaagtcact   2760
ttattttatt tttcagcatt atgtacataa atatgaagag gaaattatct tcaggttgat   2820
atcacaatca cttttcttac tttctgtcca tagtactttt tcatgaaaga aatttgctaa   2880
ataagacatg aaaacaagac tgggtagttg tagatttctg ctttttaaat tacatttgct   2940
aattttagat tatttcacaa ttttaaggag caaaataggt tcacgattca tatccaaatt   3000
atgctttgca attggaaaag ggtttaaaat tttatttata tttctggtag tacctgcact   3060
aactgaattg aaggtagtgc ttatgttatt tttgttcttt ttttctgact tcggtttatg   3120
ttttcatttc tttggagtaa tgctgctcta gattgttcta aatagaatgt gggcttcata   3180
attttttttt ccacaaaaac agagtagtca acttatatag tcaattacat caggacattt   3240
tgtgtttctt acagaagcaa accataggct cctcttttcc ttaaaactac ttagataaac   3300
tgtattcgtg aactgcatgc tggaaaatgc tactattatg ctaaataatg ctaaccaaca   3360
tttaaaatgt gcaaaactaa taaagattac atttttttatt tta                     3403
```

```
<210> SEQ ID NO 33
<211> LENGTH: 8349
<212> TYPE: DNA
<213> ORGANISM: Homo sapiens

<400> SEQUENCE: 33

ttcttggtgc cagcttatca atcccaaact ctgggtgtaa aagattctac agggcacttt     60
cttatgcaag gagctaaaca gtgattaaag gagcaggatg aaaagatggc acagtcagtg    120
ctggtaccgc caggacctga cagcttccgc ttctttacca gggaatccct tgctgctatt    180
gaacaacgca ttgcagaaga gaaagctaag agacccaaac aggaacgcaa ggatgaggat    240
gatgaaaatg gcccaaagcc aaacagtgac ttggaagcag gaaaatctct tccatttatt    300
tatggagaca ttcctccaga gatggtgtca gtgcccctgg aggatctgga cccctactat    360
atcaataaga aaacgtttat agtattgaat aaagggaaag caatctctcg attcagtgcc    420
acccctgccc tttacatttt aactcccttc aaccctatta gaaaattagc tattaagatt    480
ttggtacatt ctttattcaa tatgctcatt atgtgcacga ttcttaccaa ctgtgtattt    540
atgaccatga gtaaccctcc agactggaca aagaatgtgg agtatacctt tacaggaatt    600
tatacttttg aatcacttat taaaatactt gcaaggggct ttgtttaga agatttcaca    660
tttttacggg atccatggaa ttggttggat ttcacagtca ttacttttgc atatgtgaca    720
gagtttgtgg acctgggcaa tgtctcagcg ttgagaacat tcagagttct ccgagcattg    780
aaaacaattt cagtcattcc aggcctgaag accattgtgg gggccctgat ccagtcagtg    840
aagaagcttt ctgatgtcat gatcttgact gtgttctgtc taagcgtgtt tgcgctaata    900
ggattgcagt tgttcatggg caacctacga aataaatgtt tgcaatggcc tccagataat    960
tcttcctttg aaataaatat cacttccttc tttaacaatt cattggatgg gaatggtact   1020
actttcaata ggacagtgag catatttaac tgggatgaat atattgagga taaaagtcac   1080
ttttattttt tagaggggca aaatgatgct ctgctttgtg gcaacagctc agatgcaggc   1140
cagtgtcctg aaggatacat ctgtgtgaag gctggtagaa accccaacta tggctacacg   1200
agctttgaca cctttagttg ggcctttttg tccttatttc gtctcatgac tcaagacttc   1260
tgggaaaacc tttatcaact gacactacgt gctgctggga aaacgtacat gatatttttt   1320
```

-continued

```
gtgctggtca ttttcttggg ctcattctat ctaataaatt tgatcttggc tgtggtggcc   1380
atggcctatg aggaacagaa tcaggccaca ttggaagagg ctgaacagaa ggaagctgaa   1440
tttcagcaga tgctcgaaca gttgaaaaag caacaagaag aagctcaggc ggcagctgca   1500
gccgcatctg ctgaatcaag agacttcagt ggtgctggtg ggataggagt tttttcagag   1560
agttcttcag tagcatctaa gttgagctcc aaaagtgaaa aagagctgaa aaacagaaga   1620
aagaaaaaga aacagaaaga acagtctgga gaagaagaga aaaatgacag agtcctaaaa   1680
tcggaatctg aagacagcat aagaagaaaa ggtttccgtt tttccttgga aggaagtagg   1740
ctgacatatg aaaagagatt ttcttctcca caccagtcct tactgagcat ccgtggctcc   1800
cttttctctc caagacgcaa cagtagggcg agccttttca gcttcagagg tcgagcaaag   1860
gacattggct ctgagaatga ctttgctgat gatgagcaca gcacctttga ggacaatgac   1920
agccgaagag actctctgtt cgtgccgcac agacatggag aacggcgcca cagcaatgtc   1980
agccaggcca gccgtgcctc cagggtgctc cccatcctgc ccatgaatgg gaagatgcat   2040
agcgctgtgg actgcaatgg tgtggtctcc ctggtcgggg gcccttctac cctcacatct   2100
gctgggcagc tcctaccaga gggcacaact actgaaacag aaataagaaa gagacggtcc   2160
agttcttatc atgtttccat ggatttattg gaagatccta catcaaggca aagagcaatg   2220
agtatagcca gtattttgac caacaccatg gaagaacttg aagaatccag acagaaatgc   2280
ccaccatgct ggtataaatt tgctaatatg tgtttgattt gggactgttg taaaccatgg   2340
ttaaaggtga aacaccttgt caacctggtt gtaatggacc catttgttga cctggccatc   2400
accatctgca ttgtcttaaa tacactcttc atggctatgg agcactatcc catgacggag   2460
cagttcagca gtgtactgtc tgttggaaac ctggtcttca cagggatctt cacagcagaa   2520
atgtttctca agataattgc catggatcca tattattact ttcaagaagg ctggaatatt   2580
tttgatggtt ttattgtgag ccttagttta atggaacttg gtttggcaaa tgtggaagga   2640
ttgtcagttc tccgatcatt ccggctgctc cgagttttca agttggcaaa atcttggcca   2700
actctaaata tgctaattaa gatcattggc aattctgtgg gggctctagg aaacctcacc   2760
ttggtattgg ccatcatcgt cttcattttt gctgtggtcg gcatgcagct ctttggtaag   2820
agctacaaag aatgtgtctg caagatttcc aatgattgtg aactcccacg ctggcacatg   2880
catgactttt tccactcctt cctgatcgtg ttccgcgtgc tgtgtggaga gtggatagag   2940
accatgtggg actgtatgga ggtcgctggc caaaccatgt gccttactgt cttcatgatg   3000
gtcatggtga ttggaaatct agtggttctg aacctcttct tggccttgct tttgagttcc   3060
ttcagttctg acaatcttgc tgccactgat gatgataacg aaatgaataa tctccagatt   3120
gctgtgggaa ggatgcagaa aggaatcgat tttgttaaaa gaaaaatacg tgaatttatt   3180
cagaaagcct ttgttaggaa gcagaaagct ttagatgaaa ttaaaccgct tgaagatcta   3240
aataataaaa aagacagctg tatttccaac cataccacca tagaaatagg caaagacctc   3300
aattatctca aagacggaaa tggaactact agtggcatag gcagcagtgt agaaaaatat   3360
gtcgtggatg aaagtgatta catgtcattt ataaacaacc ctagcctcac tgtgacagta   3420
ccaattgctg ttggagaatc tgactttgaa aatttaaata ctgaagaatt cagcagcgag   3480
tcagatatgg aggaaagcaa agagaagcta aatgcaacta gttcatctga aggcagcacg   3540
gttgatattg gagctcccgc cgagggagaa cagcctgagg ttgaacctga ggaatccctt   3600
gaacctgaag cctgttttac agaagactgt gtacggaagt tcaagtgttg tcagataagc   3660
```

-continued

```
atagaagaag gcaaagggaa actctggtgg aatttgagga aaacatgcta taagatagtg   3720
gagcacaatt ggttcgaaac cttcattgtc ttcatgattc tgctgagcag tggggctctg   3780
gcctttgaag atatatacat tgagcagcga aaaaccatta agaccatgtt agaatatgct   3840
gacaaggttt tcacttacat attcattctg gaaatgctgc taaagtgggt tgcatatggt   3900
tttcaagtgt attttaccaa tgcctggtgc tggctagact tcctgattgt tgatgtctca   3960
ctggttagct taactgcaaa tgccttgggt tactcagaac ttggtgccat caaatccctc   4020
agaacactaa gagctctgag gccactgaga gctttgtccc ggtttgaagg aatgagggct   4080
gttgtaaatg ctcttttagg agccattcca tctatcatga atgtacttct ggtttgtctg   4140
atcttttggc taatattcag tatcatggga gtgaatctct ttgctggcaa gttttaccat   4200
tgtattaatt acaccactgg agagatgttt gatgtaagcg tggtcaacaa ctacagtgag   4260
tgcaaagctc tcattgagag caatcaaact gccaggtgga aaaatgtgaa agtaaacttt   4320
gataacgtag gacttggata tctgtctcta cttcaagtag ccacgtttaa gggatggatg   4380
gatattatgt atgcagctgt tgattcacga aatgtagaat tacaacccaa gtatgaagac   4440
aacctgtaca tgtatcttta ttttgtcatc tttattattt ttggttcatt ctttaccttg   4500
aatcttttca ttggtgtcat catagataac ttcaaccaac agaaaaagaa gtttggaggt   4560
caagacattt ttatgacaga agaacagaag aaatactaca atgcaatgaa aaaactgggt   4620
tcaaagaaac cacaaaaacc catacctcga cctgctaaca aattccaagg aatggtcttt   4680
gattttgtaa ccaaacaagt ctttgatatc agcatcatga tcctcatctg ccttaacatg   4740
gtcaccatga tggtggaaac cgatgaccag agtcaagaaa tgacaaacat tctgtactgg   4800
attaatctgg tgtttattgt tctgttcact ggagaatgtg tgctgaaact gatctctctt   4860
cgttactact atttcactat tggatggaat atttttgatt ttgtggtggt cattctctcc   4920
attgtaggaa tgtttctggc tgaactgata gaaaagtatt ttgtgtcccc taccctgttc   4980
cgagtgatcc gtcttgccag gattggccga atcctacgtc tgatcaaagg agcaaagggg   5040
atccgcacgc tgctctttgc tttgatgatg tcccttcctg cgttgtttaa catcggcctc   5100
cttcttttcc tggtcatgtt catctacgcc atctttggga tgtccaattt tgcctatgtt   5160
aagagggaag ttgggatcga tgacatgttc aactttgaga cctttggcaa cagcatgatc   5220
tgcctgttcc aaattacaac ctctgctggc tgggatggat tgctagcacc tattcttaat   5280
agtggacctc cagactgtga ccctgacaaa gatcaccctg gaagctcagt taaaggagac   5340
tgtgggaacc catctgttgg gattttcttt tttgtcagtt acatcatcat atccttcctg   5400
gttgtggtga acatgtacat cgcggtcatc ctggagaact tcagtgttgc tactgaagaa   5460
agtgcagagc ctctgagtga ggatgacttt gagatgttct atgaggtttg ggagaagttt   5520
gatcccgatg cgacccagtt tatagagttt gccaaacttt ctgattttgc agatgccctg   5580
gatcctcctc ttctcatagc aaaacccaac aaagtccagc tcattgccat ggatctgccc   5640
atggtgagtg gtgaccggat ccactgtctt gacatcttat ttgcttttac aaagcgtgtt   5700
ttgggtgaga gtggagagat ggatgccctt cgaatacaga tggaagagcg attcatggca   5760
tcaaacccct ccaaagtctc ttatgagccc attacgacca cgttgaaacg caaacaagag   5820
gaggtgtctg ctattattat ccagagggct tacagacgct acctcttgaa gcaaaaagtt   5880
aaaaaggtat caagtatata caagaaagac aaaggcaaag aatgtgatgg aacacccatc   5940
aaagaagata ctctcattga taaactgaat gagaattcaa ctccagagaa aaccgatatg   6000
acgccttcca ccacgtctcc accctcgtat gatagtgtga ccaaaccaga aaaagaaaaa   6060
```

-continued

```
tttgaaaaag acaaatcaga aaaggaagac aaagggaaag atatcaggga aagtaaaaag   6120
taaaaagaaa ccaagaattt tccattttgt gatcaattgt ttacagcccg tgatggtgat   6180
gtgtttgtgt caacaggact cccacaggag gtctatgcca aactgactgt ttttacaaat   6240
gtatacttaa ggtcagtgcc tataacaaga cagagacctc tggtcagcaa actggaactc   6300
agtaaactgg agaaatagta tcgatgggag gtttctattt tcacaaccag ctgacactgc   6360
tgaagagcag aggcgtaatg gctactcaga cgataggaac caatttaaag gggggaggga   6420
agttaaattt ttatgtaaat tcaacatgtg acacttgata atagtaattg tcaccagtgt   6480
ttatgtttta actgccacac ctgccatatt tttacaaaac gtgtgctgtg aatttatcac   6540
ttttcttttt aattcacagg ttgtttacta ttatatgtga ctatttttgt aaatgggttt   6600
gtgtttgggg agagggatta aagggaggga attctacatt tctctattgt attgtataac   6660
tggatatatt ttaaatggag gcatgctgca attctcattc acacataaaa aaatcacatc   6720
acaaaaggga agagtttact tcttgtttca ggatgttttt agatttttga ggtgcttaaa   6780
tagctattcg tatttttaag gtgtctcatc cagaaaaaat ttaatgtgcc tgtaaatgtt   6840
ccatagaatc acaagcatta aagagttgtt ttatttttac ataacccatt aaatgtacat   6900
gtatatatgt atatatgtat atgtgcgtgt atatacatat atatgtatac acacatgcac   6960
acacagagat atacacatac cattacattg tcattcacag tcccagcagc atgactatca   7020
catttttgat aagtgtcctt tggcataaaa taaaaatatc ctatcagtcc tttctaagaa   7080
gcctgaattg accaaaaaac atccccacca ccactttata aagttgattc tgctttatcc   7140
tgcagtattg tttagccatc ttctgctctt ggtaaggttg acatagtata tgtcaattta   7200
aaaaataaaa gtctgctttg taaatagtaa ttttacccag tggtgcatgt ttgagcaaac   7260
aaaaatgatg atttaagcac actacttatt gcatcaaata tgtaccacag taagtatagt   7320
ttgcaagctt tcaacaggta atatgatgta attggttcca ttatagtttg aagctgtcac   7380
tgctgcatgt ttatcttgcc tatgctgctg tatcttattc cttccactgt tcagaagtct   7440
aatatgggaa gccatatatc agtggtaaag tgaagcaaat tgttctacca agacctcatt   7500
cttcatgtca ttaagcaata ggttgcagca aacaaggaag agcttcttgc tttttattct   7560
tccaacctta attgaacact caatgatgaa aagcccgact gtacaaacat gttgcaagct   7620
gcttaaatct gtttaaaata tatggttaga gttttctaag aaaatataaa tactgtaaaa   7680
agttcatttt attttatttt tcagcctttt gtacgtaaaa tgagaaatta aaagtatctt   7740
caggtggatg tcacagtcac tattgttagt ttctgttcct agcactttta aattgaagca   7800
cttcacaaaa taagaagcaa ggactaggat gcagtgtagg tttctgcttt tttattagta   7860
ctgtaaactt gcacacattt caatgtgaaa caaatctcaa actgagttca atgtttattt   7920
gctttcaata gtaatgcctt atcattgaaa gaggcttaaa gaaaaaaaaa atcagctgat   7980
actcttggca ttgcttgaat ccaatgtttc cacctagtct ttttattcag taatcatcag   8040
tcttttccaa tgtttgttta cacagataga tcttattgac ccatatggca ctagaactgt   8100
atcagatata atatgggatc ccagcttttt ttcctctccc acaaaaccag gtagtgaagt   8160
tatattacca gttacagcaa aatactttgt gtttcacaag caacaataaa tgtagattct   8220
ttatactgaa gctattgact tgtagtgtgt tggtgaatgc atgcaggaag atgctgttac   8280
cataaagaac ggtaaaccac attacaatca agccaaagaa taaaggttcg cttatgtata   8340
tgtatttaa                                                           8349
```

-continued

<210> SEQ ID NO 34
<211> LENGTH: 8349
<212> TYPE: DNA
<213> ORGANISM: Homo sapiens

<400> SEQUENCE: 34

```
ttcttggtgc cagcttatca atcccaaact ctgggtgtaa aagattctac agggcacttt     60
cttatgcaag gagctaaaca gtgattaaag gagcaggatg aaaagatggc acagtcagtg    120
ctggtaccgc caggacctga cagcttccgc ttctttacca gggaatccct tgctgctatt    180
gaacaacgca ttgcagaaga gaaagctaag agacccaaac aggaacgcaa ggatgaggat    240
gatgaaaatg gcccaaagcc aaacagtgac ttggaagcag gaaaatctct tccatttatt    300
tatggagaca ttcctccaga gatggtgtca gtgcccctgg aggatctgga cccctactat    360
atcaataaga aaacgtttat agtattgaat aaagggaaag caatctctcg attcagtgcc    420
acccctgccc tttacatttt aactcccttc aaccctatta gaaaattagc tattaagatt    480
ttggtacatt ctttattcaa tatgctcatt atgtgcacga ttcttaccaa ctgtgtattt    540
atgaccatga gtaaccctcc agactggaca aagaatgtgg agtatacctt tacaggaatt    600
tatacttttg aatcacttat taaaatactt gcaaggggct tttgtttaga agatttcaca    660
tttttacggg atccatggaa ttggttggat ttcacagtca ttacttttgc atatgtgaca    720
gagtttgtgg acctgggcaa tgtctcagcg ttgagaacat tcagagttct ccgagcattg    780
aaaacaattt cagtcattcc aggcctgaag accattgtgg gggccctgat ccagtcagtg    840
aagaagcttt ctgatgtcat gatcttgact gtgttctgtc taagcgtgtt tgcgctaata    900
ggattgcagt tgttcatggg caacctacga aataaatgtt tgcaatggcc tccagataat    960
tcttcctttg aaataaatat cacttccttc tttaacaatt cattggatgg gaatggtact   1020
actttcaata ggacagtgag catatttaac tgggatgaat atattgagga taaaagtcac   1080
ttttattttt tagaggggca aaatgatgct ctgctttgtg gcaacagctc agatgcaggc   1140
cagtgtcctg aaggatacat ctgtgtgaag gctggtagaa accccaacta tggctacacg   1200
agctttgaca cctttagttg ggcctttttg tccttatttc gtctcatgac tcaagacttc   1260
tgggaaaacc tttatcaact gacactacgt gctgctggga aaacgtacat gatatttttt   1320
gtgctggtca ttttcttggg ctcattctat ctaataaatt tgatcttggc tgtggtggcc   1380
atggcctatg aggaacagaa tcaggccaca ttggaagagg ctgaacagaa ggaagctgaa   1440
tttcagcaga tgctcgaaca gttgaaaaag caacaagaag aagctcaggc ggcagctgca   1500
gccgcatctg ctgaatcaag agacttcagt ggtgctggtg ggataggagt tttttcagag   1560
agttcttcag tagcatctaa gttgagctcc aaaagtgaaa aagagctgaa aaacagaaga   1620
aagaaaaaga aacagaaaga acagtctgga gaagaagaga aaaatgacag agtcctaaaa   1680
tcggaatctg aagacagcat aagaagaaaa ggtttccgtt tttccttgga aggaagtagg   1740
ctgacatatg aaaagagatt ttcttctcca caccagtcct tactgagcat ccgtggctcc   1800
cttttctctc caagacgcaa cagtagggcg agccttttca gcttcagagg tcgagcaaag   1860
gacattggct ctgagaatga ctttgctgat gatgagcaca gcacctttga ggacaatgac   1920
agccgaagag actctctgtt cgtgccgcac agacatggag aacggcgcca cagcaatgtc   1980
agccaggcca gccgtgcctc cagggtgctc cccatcctgc ccatgaatgg gaagatgcat   2040
agcgctgtgg actgcaatgg tgtggtctcc ctggtcgggg gcccttctac cctcacatct   2100
gctgggcagc tcctaccaga gggcacaact actgaaacag aaataagaaa gagacggtcc   2160
```

-continued

```
agttcttatc atgtttccat ggatttattg gaagatccta catcaaggca aagagcaatg   2220
agtatagcca gtattttgac caacaccatg gaagaacttg aagaatccag acagaaatgc   2280
ccaccatgct ggtataaatt tgctaatatg tgtttgattt gggactgttg taaaccatgg   2340
ttaaaggtga aacaccttgt caacctggtt gtaatggacc catttgttga cctggccatc   2400
accatctgca ttgtcttaaa tacactcttc atggctatgg agcactatcc catgacggag   2460
cagttcagca gtgtactgtc tgttggaaac ctggtcttca cagggatctt cacagcagaa   2520
atgtttctca agataattgc catggatcca tattattact ttcaagaagg ctggaatatt   2580
tttgatggtt ttattgtgag ccttagttta atggaacttg gtttggcaaa tgtggaagga   2640
ttgtcagttc tccgatcatt ccggctgctc cgagttttca agttggcaaa atcttggcca   2700
actctaaata tgctaattaa gatcattggc aattctgtgg gggctctagg aaacctcacc   2760
ttggtattgg ccatcatcgt cttcattttt gctgtggtcg gcatgcagct ctttggtaag   2820
agctacaaag aatgtgtctg caagatttcc aatgattgtg aactcccacg ctggcacatg   2880
catgactttt tccactcctt cctgatcgtg ttccgcgtgc tgtgtggaga gtggatagag   2940
accatgtggg actgtatgga ggtcgctggc caaaccatgt gccttactgt cttcatgatg   3000
gtcatggtga ttggaaatct agtggttctg aacctcttct tggccttgct tttgagttcc   3060
ttcagttctg acaatcttgc tgccactgat gatgataacg aaatgaataa tctccagatt   3120
gctgtgggaa ggatgcagaa aggaatcgat tttgttaaaa gaaaaatacg tgaatttatt   3180
cagaaagcct ttgttaggaa gcagaaagct ttagatgaaa ttaaaccgct tgaagatcta   3240
aataataaaa aagacagctg tatttccaac cataccacca tagaaatagg caaagacctc   3300
aattatctca aagacggaaa tggaactact agtggcatag gcagcagtgt agaaaaatat   3360
gtcgtggatg aaagtgatta catgtcattt ataaacaacc ctagcctcac tgtgacagta   3420
ccaattgctg ttggagaatc tgactttgaa aatttaaata ctgaagaatt cagcagcgag   3480
tcagatatgg aggaaagcaa agagaagcta aatgcaacta gttcatctga aggcagcacg   3540
gttgatattg gagctcccgc cgagggagaa cagcctgagg ttgaacctga ggaatccctt   3600
gaacctgaag cctgttttac agaagactgt gtacggaagt tcaagtgttg tcagataagc   3660
atagaagaag gcaaagggaa actctggtgg aatttgagga aaacatgcta taagatagtg   3720
gagcacaatt ggttcgaaac cttcattgtc ttcatgattc tgctgagcag tggggctctg   3780
gcctttgaag atatatacat tgagcagcga aaaaccatta agaccatgtt agaatatgct   3840
gacaaggttt tcacttacat attcattctg gaaatgctgc taaagtgggt tgcatatggt   3900
tttcaagtgt attttaccaa tgcctggtgc tggctagact tcctgattgt tgatgtctca   3960
ctggttagct taactgcaaa tgccttgggt tactcagaac ttggtgccat caaatccctc   4020
agaacactaa gagctctgag gccactgaga gctttgtccc ggtttgaagg aatgagggct   4080
gttgtaaatg ctcttttagg agccattcca tctatcatga atgtacttct ggtttgtctg   4140
atcttttggc taatattcag tatcatggga gtgaatctct ttgctggcaa gttttaccat   4200
tgtattaatt acaccactgg agagatgttt gatgtaagcg tggtcaacaa ctacagtgag   4260
tgcaaagctc tcattgagag caatcaaact gccaggtgga aaaatgtgaa agtaaacttt   4320
gataacgtag gacttggata tctgtctcta cttcaagtag ccacgtttaa gggatggatg   4380
gatattatgt atgcagctgt tgattcacga aatgtagaat tacaacccaa gtatgaagac   4440
aacctgtaca tgtatcttta ttttgtcatc tttattattt ttggttcatt ctttaccttg   4500
```

-continued

```
aatcttttca ttggtgtcat catagataac ttcaaccaac agaaaaagaa gtttggaggt   4560
caagacattt ttatgacaga agaacagaag aaatactaca atgcaatgaa aaaactgggt   4620
tcaaagaaac cacaaaaacc catacctcga cctgctaaca aattccaagg aatggtcttt   4680
gattttgtaa ccaaacaagt ctttgatatc agcatcatga tcctcatctg ccttaacatg   4740
gtcaccatga tggtggaaac cgatgaccag agtcaagaaa tgacaaacat tctgtactgg   4800
attaatctgg tgtttattgt tctgttcact ggagaatgtg tgctgaaact gatctctctt   4860
cgttactact atttcactat tggatggaat atttttgatt ttgtggtggt cattctctcc   4920
attgtaggaa tgtttctggc tgaactgata gaaaagtatt ttgtgtcccc taccctgttc   4980
cgagtgatcc gtcttgccag gattggccga atcctacgtc tgatcaaagg agcaaagggg   5040
atccgcacgc tgctctttgc tttgatgatg tcccttcctg cgttgtttaa catcggcctc   5100
cttcttttcc tggtcatgtt catctacgcc atctttggga tgtccaattt tgcctatgtt   5160
aagagggaag ttgggatcga tgacatgttc aactttgaga cctttggcaa cagcatgatc   5220
tgcctgttcc aaattacaac ctctgctggc tgggatggat tgctagcacc tattcttaat   5280
agtggacctc cagactgtga ccctgacaaa gatcaccctg gaagctcagt taaaggagac   5340
tgtgggaacc catctgttgg gattttcttt tttgtcagtt acatcatcat atccttcctg   5400
gttgtggtga acatgtacat cgcggtcatc ctggagaact tcagtgttgc tactgaagaa   5460
agtgcagagc ctctgagtga ggatgacttt gagatgttct atgaggtttg ggagaagttt   5520
gatcccgatg cgacccagtt tatagagttt gccaaacttt ctgattttgc agatgccctg   5580
gatcctcctc ttctcatagc aaaacccaac aaagtccagc tcattgccat ggatctgccc   5640
atggtgagtg gtgaccggat ccactgtctt gacatcttat ttgcttttac aaagcgtgtt   5700
ttgggtgaga gtggagagat ggatgccctt cgaatacaga tggaagagcg attcatggca   5760
tcaaacccct ccaaagtctc ttatgagccc attacgacca cgttgaaacg caaacaagag   5820
gaggtgtctg ctattattat ccagagggct tacagacgct acctcttgaa gcaaaaagtt   5880
aaaaaggtat caagtatata caagaaagac aaaggcaaag aatgtgatgg aacacccatc   5940
aaagaagata ctctcattga taaactgaat gagaattcaa ctccagagaa aaccgatatg   6000
acgccttcca ccacgtctcc accctcgtat gatagtgtga ccaaaccaga aaaagaaaaa   6060
tttgaaaaag acaaatcaga aaaggaagac aaagggaaag atatcaggga aagtaaaaag   6120
taaaaagaaa ccaagaattt tccattttgt gatcaattgt ttacagcccg tgatggtgat   6180
gtgtttgtgt caacaggact cccacaggag gtctatgcca aactgactgt ttttacaaat   6240
gtatacttaa ggtcagtgcc tataacaaga cagagacctc tggtcagcaa actggaactc   6300
agtaaactgg agaaatagta tcgatgggag gtttctattt tcacaaccag ctgacactgc   6360
tgaagagcag aggcgtaatg gctactcaga cgataggaac caatttaaag gggggaggga   6420
agttaaattt ttatgtaaat tcaacatgtg acacttgata atagtaattg tcaccagtgt   6480
ttatgtttta actgccacac ctgccatatt tttacaaaac gtgtgctgtg aatttatcac   6540
ttttcttttt aattcacagg ttgtttacta ttatatgtga ctatttttgt aaatgggttt   6600
gtgtttgggg agagggatta aagggaggga attctacatt tctctattgt attgtataac   6660
tggatatatt ttaaatggag gcatgctgca attctcattc acacataaaa aaatcacatc   6720
acaaaaggga agagtttact tcttgtttca ggatgttttt agatttttga ggtgcttaaa   6780
tagctattcg tatttttaag gtgtctcatc cagaaaaaat ttaatgtgcc tgtaaatgtt   6840
ccatagaatc acaagcatta aagagttgtt ttatttttac ataacccatt aaatgtacat   6900
```

-continued

```
gtatatatgt atatatgtat atgtgcgtgt atatacatat atatgtatac acacatgcac   6960

acacagagat atacacatac cattacattg tcattcacag tcccagcagc atgactatca   7020

catttttgat aagtgtcctt tggcataaaa taaaaatatc ctatcagtcc tttctaagaa   7080

gcctgaattg accaaaaaac atccccacca ccactttata aagttgattc tgctttatcc   7140

tgcagtattg tttagccatc ttctgctctt ggtaaggttg acatagtata tgtcaattta   7200

aaaaataaaa gtctgctttg taaatagtaa ttttacccag tggtgcatgt ttgagcaaac   7260

aaaaatgatg atttaagcac actacttatt gcatcaaata tgtaccacag taagtatagt   7320

ttgcaagctt tcaacaggta atatgatgta attggttcca ttatagtttg aagctgtcac   7380

tgctgcatgt ttatcttgcc tatgctgctg tatcttattc cttccactgt tcagaagtct   7440

aatatgggaa gccatatatc agtggtaaag tgaagcaaat tgttctacca agacctcatt   7500

cttcatgtca ttaagcaata ggttgcagca aacaaggaag agcttcttgc tttttattct   7560

tccaacctta attgaacact caatgatgaa aagcccgact gtacaaacat gttgcaagct   7620

gcttaaatct gtttaaaata tatggttaga gttttctaag aaaatataaa tactgtaaaa   7680

agttcatttt attttatttt tcagcctttt gtacgtaaaa tgagaaatta aaagtatctt   7740

caggtggatg tcacagtcac tattgttagt ttctgttcct agcactttta aattgaagca   7800

cttcacaaaa taagaagcaa ggactaggat gcagtgtagg tttctgcttt tttattagta   7860

ctgtaaactt gcacacattt caatgtgaaa caaatctcaa actgagttca atgtttattt   7920

gctttcaata gtaatgcctt atcattgaaa gaggcttaaa gaaaaaaaaa atcagctgat   7980

actcttggca ttgcttgaat ccaatgtttc cacctagtct ttttattcag taatcatcag   8040

tcttttccaa tgtttgttta cacagataga tcttattgac ccatatggca ctagaactgt   8100

atcagatata atatgggatc ccagcttttt ttcctctccc acaaaaccag gtagtgaagt   8160

tatattacca gttacagcaa aatactttgt gtttcacaag caacaataaa tgtagattct   8220

ttatactgaa gctattgact tgtagtgtgt tggtgaatgc atgcaggaag atgctgttac   8280

cataaagaac ggtaaaccac attacaatca agccaaagaa taaaggttcg cttatgtata   8340

tgtatttaa                                                           8349
```

<210> SEQ ID NO 35
<211> LENGTH: 2005
<212> TYPE: PRT
<213> ORGANISM: Homo sapiens

<400> SEQUENCE: 35

```
Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110
```

-continued

```
Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asp Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
        275                 280                 285

Glu Ile Asn Ile Thr Ser Phe Phe Asn Asn Ser Leu Asp Gly Asn Gly
    290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
        355                 360                 365

Thr Phe Ser Trp Ala Phe Leu Ser Leu Phe Arg Leu Met Thr Gln Asp
    370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
        435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Lys Gln Lys Glu
            500                 505                 510

Gln Ser Gly Glu Glu Glu Lys Asn Asp Arg Val Leu Lys Ser Glu Ser
        515                 520                 525
```

-continued

```
Glu Asp Ser Ile Arg Arg Lys Gly Phe Arg Phe Ser Leu Glu Gly Ser
    530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg His Ser Asn
    610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
        675                 680                 685

His Val Ser Met Asp Leu Leu Glu Asp Pro Thr Ser Arg Gln Arg Ala
    690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
        755                 760                 765

Ile Val Leu Asn Thr Leu Phe Met Ala Met Glu His Tyr Pro Met Thr
    770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
    850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
        915                 920                 925

Phe His Ser Phe Leu Ile Val Phe Arg Val Leu Cys Gly Glu Trp Ile
    930                 935                 940

Glu Thr Met Trp Asp Cys Met Glu Val Ala Gly Gln Thr Met Cys Leu
```

-continued

```
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990

Ala Thr Asp Asp Asp Asn Glu Met  Asn Asn Leu Gln Ile  Ala Val Gly
        995                 1000                1005

Arg Met  Gln Lys Gly Ile Asp  Phe Val Lys Arg Lys  Ile Arg Glu
    1010                1015                1020

Phe Ile  Gln Lys Ala Phe Val  Arg Lys Gln Lys Ala  Leu Asp Glu
    1025                1030                1035

Ile Lys  Pro Leu Glu Asp Leu  Asn Asn Lys Lys Asp  Ser Cys Ile
    1040                1045                1050

Ser Asn  His Thr Thr Ile Glu  Ile Gly Lys Asp Leu  Asn Tyr Leu
    1055                1060                1065

Lys Asp  Gly Asn Gly Thr Thr  Ser Gly Ile Gly Ser  Ser Val Glu
    1070                1075                1080

Lys Tyr  Val Val Asp Glu Ser  Asp Tyr Met Ser Phe  Ile Asn Asn
    1085                1090                1095

Pro Ser  Leu Thr Val Thr Val  Pro Ile Ala Val Gly  Glu Ser Asp
    1100                1105                1110

Phe Glu  Asn Leu Asn Thr Glu  Glu Phe Ser Ser Glu  Ser Asp Met
    1115                1120                1125

Glu Glu  Ser Lys Glu Lys Leu  Asn Ala Thr Ser Ser  Ser Glu Gly
    1130                1135                1140

Ser Thr  Val Asp Ile Gly Ala  Pro Ala Glu Gly Glu  Gln Pro Glu
    1145                1150                1155

Val Glu  Pro Glu Glu Ser Leu  Glu Pro Glu Ala Cys  Phe Thr Glu
    1160                1165                1170

Asp Cys  Val Arg Lys Phe Lys  Cys Cys Gln Ile Ser  Ile Glu Glu
    1175                1180                1185

Gly Lys  Gly Lys Leu Trp Trp  Asn Leu Arg Lys Thr  Cys Tyr Lys
    1190                1195                1200

Ile Val  Glu His Asn Trp Phe  Glu Thr Phe Ile Val  Phe Met Ile
    1205                1210                1215

Leu Leu  Ser Ser Gly Ala Leu  Ala Phe Glu Asp Ile  Tyr Ile Glu
    1220                1225                1230

Gln Arg  Lys Thr Ile Lys Thr  Met Leu Glu Tyr Ala  Asp Lys Val
    1235                1240                1245

Phe Thr  Tyr Ile Phe Ile Leu  Glu Met Leu Leu Lys  Trp Val Ala
    1250                1255                1260

Tyr Gly  Phe Gln Val Tyr Phe  Thr Asn Ala Trp Cys  Trp Leu Asp
    1265                1270                1275

Phe Leu  Ile Val Asp Val Ser  Leu Val Ser Leu Thr  Ala Asn Ala
    1280                1285                1290

Leu Gly  Tyr Ser Glu Leu Gly  Ala Ile Lys Ser Leu  Arg Thr Leu
    1295                1300                1305

Arg Ala  Leu Arg Pro Leu Arg  Ala Leu Ser Arg Phe  Glu Gly Met
    1310                1315                1320

Arg Ala  Val Val Asn Ala Leu  Leu Gly Ala Ile Pro  Ser Ile Met
    1325                1330                1335

Asn Val  Leu Leu Val Cys Leu  Ile Phe Trp Leu Ile  Phe Ser Ile
    1340                1345                1350
```

```
Met Gly Val Asn Leu Phe Ala Gly Lys Phe Tyr His Cys Ile Asn
    1355                1360                1365

Tyr Thr Thr Gly Glu Met Phe Asp Val Ser Val Val Asn Asn Tyr
    1370                1375                1380

Ser Glu Cys Lys Ala Leu Ile Glu Ser Asn Gln Thr Ala Arg Trp
    1385                1390                1395

Lys Asn Val Lys Val Asn Phe Asp Asn Val Gly Leu Gly Tyr Leu
    1400                1405                1410

Ser Leu Leu Gln Val Ala Thr Phe Lys Gly Trp Met Asp Ile Met
    1415                1420                1425

Tyr Ala Ala Val Asp Ser Arg Asn Val Glu Leu Gln Pro Lys Tyr
    1430                1435                1440

Glu Asp Asn Leu Tyr Met Tyr Leu Tyr Phe Val Ile Phe Ile Ile
    1445                1450                1455

Phe Gly Ser Phe Phe Thr Leu Asn Leu Phe Ile Gly Val Ile Ile
    1460                1465                1470

Asp Asn Phe Asn Gln Gln Lys Lys Lys Phe Gly Gly Gln Asp Ile
    1475                1480                1485

Phe Met Thr Glu Glu Gln Lys Lys Tyr Tyr Asn Ala Met Lys Lys
    1490                1495                1500

Leu Gly Ser Lys Lys Pro Gln Lys Pro Ile Pro Arg Pro Ala Asn
    1505                1510                1515

Lys Phe Gln Gly Met Val Phe Asp Phe Val Thr Lys Gln Val Phe
    1520                1525                1530

Asp Ile Ser Ile Met Ile Leu Ile Cys Leu Asn Met Val Thr Met
    1535                1540                1545

Met Val Glu Thr Asp Asp Gln Ser Gln Glu Met Thr Asn Ile Leu
    1550                1555                1560

Tyr Trp Ile Asn Leu Val Phe Ile Val Leu Phe Thr Gly Glu Cys
    1565                1570                1575

Val Leu Lys Leu Ile Ser Leu Arg Tyr Tyr Tyr Phe Thr Ile Gly
    1580                1585                1590

Trp Asn Ile Phe Asp Phe Val Val Val Ile Leu Ser Ile Val Gly
    1595                1600                1605

Met Phe Leu Ala Glu Leu Ile Glu Lys Tyr Phe Val Ser Pro Thr
    1610                1615                1620

Leu Phe Arg Val Ile Arg Leu Ala Arg Ile Gly Arg Ile Leu Arg
    1625                1630                1635

Leu Ile Lys Gly Ala Lys Gly Ile Arg Thr Leu Leu Phe Ala Leu
    1640                1645                1650

Met Met Ser Leu Pro Ala Leu Phe Asn Ile Gly Leu Leu Leu Phe
    1655                1660                1665

Leu Val Met Phe Ile Tyr Ala Ile Phe Gly Met Ser Asn Phe Ala
    1670                1675                1680

Tyr Val Lys Arg Glu Val Gly Ile Asp Asp Met Phe Asn Phe Glu
    1685                1690                1695

Thr Phe Gly Asn Ser Met Ile Cys Leu Phe Gln Ile Thr Thr Ser
    1700                1705                1710

Ala Gly Trp Asp Gly Leu Leu Ala Pro Ile Leu Asn Ser Gly Pro
    1715                1720                1725

Pro Asp Cys Asp Pro Asp Lys Asp His Pro Gly Ser Ser Val Lys
    1730                1735                1740
```

-continued

Gly Asp Cys Gly Asn Pro Ser Val Gly Ile Phe Phe Phe Val Ser
1745 1750 1755

Tyr Ile Ile Ile Ser Phe Leu Val Val Val Asn Met Tyr Ile Ala
1760 1765 1770

Val Ile Leu Glu Asn Phe Ser Val Ala Thr Glu Glu Ser Ala Glu
1775 1780 1785

Pro Leu Ser Glu Asp Asp Phe Glu Met Phe Tyr Glu Val Trp Glu
1790 1795 1800

Lys Phe Asp Pro Asp Ala Thr Gln Phe Ile Glu Phe Ala Lys Leu
1805 1810 1815

Ser Asp Phe Ala Asp Ala Leu Asp Pro Pro Leu Leu Ile Ala Lys
1820 1825 1830

Pro Asn Lys Val Gln Leu Ile Ala Met Asp Leu Pro Met Val Ser
1835 1840 1845

Gly Asp Arg Ile His Cys Leu Asp Ile Leu Phe Ala Phe Thr Lys
1850 1855 1860

Arg Val Leu Gly Glu Ser Gly Glu Met Asp Ala Leu Arg Ile Gln
1865 1870 1875

Met Glu Glu Arg Phe Met Ala Ser Asn Pro Ser Lys Val Ser Tyr
1880 1885 1890

Glu Pro Ile Thr Thr Thr Leu Lys Arg Lys Gln Glu Glu Val Ser
1895 1900 1905

Ala Ile Ile Ile Gln Arg Ala Tyr Arg Arg Tyr Leu Leu Lys Gln
1910 1915 1920

Lys Val Lys Lys Val Ser Ser Ile Tyr Lys Lys Asp Lys Gly Lys
1925 1930 1935

Glu Cys Asp Gly Thr Pro Ile Lys Glu Asp Thr Leu Ile Asp Lys
1940 1945 1950

Leu Asn Glu Asn Ser Thr Pro Glu Lys Thr Asp Met Thr Pro Ser
1955 1960 1965

Thr Thr Ser Pro Pro Ser Tyr Asp Ser Val Thr Lys Pro Glu Lys
1970 1975 1980

Glu Lys Phe Glu Lys Asp Lys Ser Glu Lys Glu Asp Lys Gly Lys
1985 1990 1995

Asp Ile Arg Glu Ser Lys Lys
2000 2005

<210> SEQ ID NO 36
<211> LENGTH: 2005
<212> TYPE: PRT
<213> ORGANISM: Homo sapiens

<400> SEQUENCE: 36

Met Ala Gln Ser Val Leu Val Pro Pro Gly Pro Asp Ser Phe Arg Phe
1 5 10 15

Phe Thr Arg Glu Ser Leu Ala Ala Ile Glu Gln Arg Ile Ala Glu Glu
20 25 30

Lys Ala Lys Arg Pro Lys Gln Glu Arg Lys Asp Glu Asp Asp Glu Asn
35 40 45

Gly Pro Lys Pro Asn Ser Asp Leu Glu Ala Gly Lys Ser Leu Pro Phe
50 55 60

Ile Tyr Gly Asp Ile Pro Pro Glu Met Val Ser Val Pro Leu Glu Asp
65 70 75 80

Leu Asp Pro Tyr Tyr Ile Asn Lys Lys Thr Phe Ile Val Leu Asn Lys
85 90 95

```
Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asn Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
        275                 280                 285

Glu Ile Asn Ile Thr Ser Phe Phe Asn Asn Ser Leu Asp Gly Asn Gly
    290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
        355                 360                 365

Thr Phe Ser Trp Ala Phe Leu Ser Leu Phe Arg Leu Met Thr Gln Asp
    370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
        435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Lys Gln Lys Glu
            500                 505                 510
```

-continued

```
Gln Ser Gly Glu Glu Glu Lys Asn Asp Arg Val Leu Lys Ser Glu Ser
        515                 520                 525

Glu Asp Ser Ile Arg Arg Lys Gly Phe Arg Phe Ser Leu Glu Gly Ser
    530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg His Ser Asn
    610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
        675                 680                 685

His Val Ser Met Asp Leu Leu Glu Asp Pro Thr Ser Arg Gln Arg Ala
    690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
        755                 760                 765

Ile Val Leu Asn Thr Leu Phe Met Ala Met Glu His Tyr Pro Met Thr
    770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
    850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
        915                 920                 925

Phe His Ser Phe Leu Ile Val Phe Arg Val Leu Cys Gly Glu Trp Ile
```

-continued

```
    930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990

Ala Thr Asp Asp Asp Asn Glu Met  Asn Asn Leu Gln Ile  Ala Val Gly
        995                 1000                 1005

Arg Met  Gln Lys Gly Ile Asp  Phe Val Lys Arg Lys  Ile Arg Glu
    1010                 1015                 1020

Phe Ile  Gln Lys Ala Phe Val  Arg Lys Gln Lys Ala  Leu Asp Glu
    1025                 1030                 1035

Ile Lys  Pro Leu Glu Asp Leu  Asn Asn Lys Lys Asp  Ser Cys Ile
    1040                 1045                 1050

Ser Asn  His Thr Thr Ile Glu  Ile Gly Lys Asp Leu  Asn Tyr Leu
    1055                 1060                 1065

Lys Asp  Gly Asn Gly Thr Thr  Ser Gly Ile Gly Ser  Ser Val Glu
    1070                 1075                 1080

Lys Tyr  Val Val Asp Glu Ser  Asp Tyr Met Ser Phe  Ile Asn Asn
    1085                 1090                 1095

Pro Ser  Leu Thr Val Thr Val  Pro Ile Ala Val Gly  Glu Ser Asp
    1100                 1105                 1110

Phe Glu  Asn Leu Asn Thr Glu  Glu Phe Ser Ser Glu  Ser Asp Met
    1115                 1120                 1125

Glu Glu  Ser Lys Glu Lys Leu  Asn Ala Thr Ser Ser  Ser Glu Gly
    1130                 1135                 1140

Ser Thr  Val Asp Ile Gly Ala  Pro Ala Glu Gly Glu  Gln Pro Glu
    1145                 1150                 1155

Val Glu  Pro Glu Glu Ser Leu  Glu Pro Glu Ala Cys  Phe Thr Glu
    1160                 1165                 1170

Asp Cys  Val Arg Lys Phe Lys  Cys Cys Gln Ile Ser  Ile Glu Glu
    1175                 1180                 1185

Gly Lys  Gly Lys Leu Trp Trp  Asn Leu Arg Lys Thr  Cys Tyr Lys
    1190                 1195                 1200

Ile Val  Glu His Asn Trp Phe  Glu Thr Phe Ile Val  Phe Met Ile
    1205                 1210                 1215

Leu Leu  Ser Ser Gly Ala Leu  Ala Phe Glu Asp Ile  Tyr Ile Glu
    1220                 1225                 1230

Gln Arg  Lys Thr Ile Lys Thr  Met Leu Glu Tyr Ala  Asp Lys Val
    1235                 1240                 1245

Phe Thr  Tyr Ile Phe Ile Leu  Glu Met Leu Leu Lys  Trp Val Ala
    1250                 1255                 1260

Tyr Gly  Phe Gln Val Tyr Phe  Thr Asn Ala Trp Cys  Trp Leu Asp
    1265                 1270                 1275

Phe Leu  Ile Val Asp Val Ser  Leu Val Ser Leu Thr  Ala Asn Ala
    1280                 1285                 1290

Leu Gly  Tyr Ser Glu Leu Gly  Ala Ile Lys Ser Leu  Arg Thr Leu
    1295                 1300                 1305

Arg Ala  Leu Arg Pro Leu Arg  Ala Leu Ser Arg Phe  Glu Gly Met
    1310                 1315                 1320

Arg Ala  Val Val Asn Ala Leu  Leu Gly Ala Ile Pro  Ser Ile Met
    1325                 1330                 1335
```

-continued

```
Asn Val  Leu Leu Val Cys Leu  Ile Phe Trp Leu Ile  Phe Ser Ile
    1340                 1345                 1350

Met Gly  Val Asn Leu Phe Ala  Gly Lys Phe Tyr His  Cys Ile Asn
    1355                 1360                 1365

Tyr Thr  Thr Gly Glu Met Phe  Asp Val Ser Val Val  Asn Asn Tyr
    1370                 1375                 1380

Ser Glu  Cys Lys Ala Leu Ile  Glu Ser Asn Gln Thr  Ala Arg Trp
    1385                 1390                 1395

Lys Asn  Val Lys Val Asn Phe  Asp Asn Val Gly Leu  Gly Tyr Leu
    1400                 1405                 1410

Ser Leu  Leu Gln Val Ala Thr  Phe Lys Gly Trp Met  Asp Ile Met
    1415                 1420                 1425

Tyr Ala  Ala Val Asp Ser Arg  Asn Val Glu Leu Gln  Pro Lys Tyr
    1430                 1435                 1440

Glu Asp  Asn Leu Tyr Met Tyr  Leu Tyr Phe Val Ile  Phe Ile Ile
    1445                 1450                 1455

Phe Gly  Ser Phe Phe Thr Leu  Asn Leu Phe Ile Gly  Val Ile Ile
    1460                 1465                 1470

Asp Asn  Phe Asn Gln Gln Lys  Lys Lys Phe Gly Gly  Gln Asp Ile
    1475                 1480                 1485

Phe Met  Thr Glu Glu Gln Lys  Lys Tyr Tyr Asn Ala  Met Lys Lys
    1490                 1495                 1500

Leu Gly  Ser Lys Lys Pro Gln  Lys Pro Ile Pro Arg  Pro Ala Asn
    1505                 1510                 1515

Lys Phe  Gln Gly Met Val Phe  Asp Phe Val Thr Lys  Gln Val Phe
    1520                 1525                 1530

Asp Ile  Ser Ile Met Ile Leu  Ile Cys Leu Asn Met  Val Thr Met
    1535                 1540                 1545

Met Val  Glu Thr Asp Asp Gln  Ser Gln Glu Met Thr  Asn Ile Leu
    1550                 1555                 1560

Tyr Trp  Ile Asn Leu Val Phe  Ile Val Leu Phe Thr  Gly Glu Cys
    1565                 1570                 1575

Val Leu  Lys Leu Ile Ser Leu  Arg Tyr Tyr Tyr Phe  Thr Ile Gly
    1580                 1585                 1590

Trp Asn  Ile Phe Asp Phe Val  Val Val Ile Leu Ser  Ile Val Gly
    1595                 1600                 1605

Met Phe  Leu Ala Glu Leu Ile  Glu Lys Tyr Phe Val  Ser Pro Thr
    1610                 1615                 1620

Leu Phe  Arg Val Ile Arg Leu  Ala Arg Ile Gly Arg  Ile Leu Arg
    1625                 1630                 1635

Leu Ile  Lys Gly Ala Lys Gly  Ile Arg Thr Leu Leu  Phe Ala Leu
    1640                 1645                 1650

Met Met  Ser Leu Pro Ala Leu  Phe Asn Ile Gly Leu  Leu Leu Phe
    1655                 1660                 1665

Leu Val  Met Phe Ile Tyr Ala  Ile Phe Gly Met Ser  Asn Phe Ala
    1670                 1675                 1680

Tyr Val  Lys Arg Glu Val Gly  Ile Asp Asp Met Phe  Asn Phe Glu
    1685                 1690                 1695

Thr Phe  Gly Asn Ser Met Ile  Cys Leu Phe Gln Ile  Thr Thr Ser
    1700                 1705                 1710

Ala Gly  Trp Asp Gly Leu Leu  Ala Pro Ile Leu Asn  Ser Gly Pro
    1715                 1720                 1725
```

-continued

```
Pro Asp  Cys Asp Pro Asp Lys  Asp His Pro Gly Ser  Ser Val Lys
    1730                 1735                 1740

Gly Asp  Cys Gly Asn Pro Ser  Val Gly Ile Phe Phe  Phe Val Ser
    1745                 1750                 1755

Tyr Ile  Ile Ile Ser Phe Leu  Val Val Val Asn Met  Tyr Ile Ala
    1760                 1765                 1770

Val Ile  Leu Glu Asn Phe Ser  Val Ala Thr Glu Glu  Ser Ala Glu
    1775                 1780                 1785

Pro Leu  Ser Glu Asp Asp Phe  Glu Met Phe Tyr Glu  Val Trp Glu
    1790                 1795                 1800

Lys Phe  Asp Pro Asp Ala Thr  Gln Phe Ile Glu Phe  Ala Lys Leu
    1805                 1810                 1815

Ser Asp  Phe Ala Asp Ala Leu  Asp Pro Pro Leu Leu  Ile Ala Lys
    1820                 1825                 1830

Pro Asn  Lys Val Gln Leu Ile  Ala Met Asp Leu Pro  Met Val Ser
    1835                 1840                 1845

Gly Asp  Arg Ile His Cys Leu  Asp Ile Leu Phe Ala  Phe Thr Lys
    1850                 1855                 1860

Arg Val  Leu Gly Glu Ser Gly  Glu Met Asp Ala Leu  Arg Ile Gln
    1865                 1870                 1875

Met Glu  Glu Arg Phe Met Ala  Ser Asn Pro Ser Lys  Val Ser Tyr
    1880                 1885                 1890

Glu Pro  Ile Thr Thr Thr Leu  Lys Arg Lys Gln Glu  Glu Val Ser
    1895                 1900                 1905

Ala Ile  Ile Ile Gln Arg Ala  Tyr Arg Arg Tyr Leu  Leu Lys Gln
    1910                 1915                 1920

Lys Val  Lys Lys Val Ser Ser  Ile Tyr Lys Lys Asp  Lys Gly Lys
    1925                 1930                 1935

Glu Cys  Asp Gly Thr Pro Ile  Lys Glu Asp Thr Leu  Ile Asp Lys
    1940                 1945                 1950

Leu Asn  Glu Asn Ser Thr Pro  Glu Lys Thr Asp Met  Thr Pro Ser
    1955                 1960                 1965

Thr Thr  Ser Pro Pro Ser Tyr  Asp Ser Val Thr Lys  Pro Glu Lys
    1970                 1975                 1980

Glu Lys  Phe Glu Lys Asp Lys  Ser Glu Lys Glu Asp  Lys Gly Lys
    1985                 1990                 1995

Asp Ile  Arg Glu Ser Lys Lys
    2000                 2005


<210> SEQ ID NO 37
<211> LENGTH: 912
<212> TYPE: DNA
<213> ORGANISM: Homo sapiens

<400> SEQUENCE: 37

gaattcttta tatgggttga atgactttct gacatagcaa ataaaaagca tgaggagaag     60

cattatctgt taacaaaatt aacacttaaa atcaacaaag ttttaatgtt tcgttccaag    120

aaaagcctgt ggaagatcag ttccacaact gagagctttg ggctgcttca gacatatgtc    180

tgtgtgtacg ctgtgaaggt gtttctcttc acagttcccc gccctctagt ggtagttaca    240

ataatgccat tttgtagtcc ctgtacagga aatgcctctt cttacttcag ttaccagaat    300

ccttttacag gaagttaggt gtggtctttg aaggagaatt aaaaaaaaaa aaaaaaaaaa    360

aaaaaagatt ttttttttt taaagcatga tggaatttta gctgcagtct tcttggggcc    420
```

-continued

```
agcttatcaa tcccaaactc tgggggtaaa agattctaca ggggtaatgt tttattattc    480

ttattatgct tattctctgt gatgcttctc tacctttaca gtagtagaat ccttggggaa    540

atctgcagag ggaccacttt cattttgaag ctgctggctg catgttttag catgtctctt    600

ctattagaga atccaggcat ggcagtttcc tcccccagtg tgcaaggacc atcttcatgc    660

ctatgtctgt cgctaggcat gagggtctct aggaatgggt gaaaaaaatg agggatgttt    720

tggaggcact ataatactgg ggagggcagt ctgctagctg gtagctgaaa ggtcctggtt    780

tacttcaaca ttttttttaa ataaaactgt gcagtagttt ttgttatttt agggttccct    840

ctgttttatc tggtgtatgc tgcagaagtg aactgcataa cacatttcac tcttagaaat    900

gcattccata ta                                                          912
```

<210> SEQ ID NO 38
<211> LENGTH: 722
<212> TYPE: DNA
<213> ORGANISM: Homo sapiens

<400> SEQUENCE: 38

```
ctcagtgcat gtaactgaca caatcacctc tatctaatgg tcatgcttct tacctcctgt     60

tctgtagcac tttcttatgc aaggagctaa acagtgatta aaggagcagg atgaaaagat    120

ggcacagtca gtgctggtac cgccaggacc tgacagcttc cgcttcttta ccagggaatc    180

ccttgctgct attgaacaac gcattgcaga agagaaagct aagagaccca aacaggaacg    240

caaggatgag gatgatgaaa atggcccaaa gccaaacagt gacttggaag cagsaaaatc    300

tcttccattt atttatggag acattcctcc agagatggtg tcagtgcccc tggaggatct    360

ggacccctac tatatcaata agaaagtgag ttcttagtca agttgccttc actgcctatt    420

tactaattgg ttctgggcta gtcccaggga tgatggtgaa gaaggctggc ctccttccct    480

ctgtctaaag tatcactaag atgctggatg ggcctgaccg tgtaatggac caatgatcct    540

agaagtcttt tggaagcact catttgaacc tgcatttgtg agacaggcag agaactggtg    600

aggcatcctc cagcgcggga attaaggaag gacaaaagcc tattcacctt cttgaataca    660

aattatatgc ttaaaccagt gtaaattgac cctgattccc taataatgtt gagaagcaaa    720

aa                                                                     722
```

<210> SEQ ID NO 39
<211> LENGTH: 561
<212> TYPE: DNA
<213> ORGANISM: Homo sapiens

<400> SEQUENCE: 39

```
cctatggcat tgatcacaaa ttttcttaat aatcctcatg tcatttatca aatttaggaa     60

agtttatagt gctcagaaaa aaaaagcatc tatcttcatg tcatatgatg gtaattatta    120

tgttatacac tattttacag ggcaatattt ataaataatg gttttacttt tctcttaaaa    180

tattcttaat atatattcta agttttgttt tatgtgttgt gttttctttt tcagacgttt    240

atagtattga ataaagggaa agcaatctct cgattcagtg ccacccctgc cctttacatt    300

ttaactccct tcaaccctat tagaaaatta gctattaaga ttttggtaca ttcatatcct    360

ttttcaaatc gtcacttaat atgattttct tctttgacca agttattgag ctacacattt    420

tccaaaatat ctgtggttgg caatgttatg tgttctttct ttttctttcc ttttactcaa    480

tcgttagcat gttgcaaaat gagatcacag gtaagtgaat tactttcccc cgtcttctaa    540

gtgtttcttc tctacccaac t                                               561
```

```
<210> SEQ ID NO 40
<211> LENGTH: 510
<212> TYPE: DNA
<213> ORGANISM: Homo sapiens

<400> SEQUENCE: 40

acctaaatag cctcaaaata gttgatggct tggcctgaag acaagatcta aatatgaggt     60

tgctgagtta tagaaatggc aaaaaaaagg gtcaataata gaataataag caacaaaata    120

atagtaagca ctaaagtttt aaacttcatg gtggtgaagg catggtagtg cataaaagta    180

agatttttcc attgaacttt gtcttccttg acgatattct actttattca atatgctcat    240

tatgtgcacg attcttacca actgtgtatt tatgaccatg agtaaccctc cagactggac    300

aaagaatgtg gagtaagtat aaatattttt caatattgac ctccctttat gtttcatatt    360

gtgcttttaa caccttgaga cctcctcaat ttctttaaca aatcatgcta gctactgtta    420

accagaccct gattcaaatt catttctgtc actaaatgtc ttctaggaca aagcttgtag    480

tgggctcact tagttgtgta aattactgca                                     510


<210> SEQ ID NO 41
<211> LENGTH: 370
<212> TYPE: DNA
<213> ORGANISM: Homo sapiens
<220> FEATURE:
<221> NAME/KEY: misc_feature
<222> LOCATION: (293)..(293)
<223> OTHER INFORMATION: n= a, c, t or g

<400> SEQUENCE: 41

taagatatgt acttgtaaat taaccactag atttttaatg tgagcttggc tattgtctct     60

caggtatacc tttacaggaa tttatacttt tgaatcactt attaaaatac ttgcaagggg    120

cttttgttta gaagatttca catttttacg ggatccatgg aattggttgg atttcacagt    180

cattactttt gcgtaagtat cttaatacat tttctatcct ggaagagtaa atcactggtg    240

ggagcctata ctatattttc cttggtggct tgccttgaca gaccaagcat ttntcttagt    300

aatcatagtt ttcttccaat caaattatcc agtttggaga aattaggaac tatcatagta    360

aattacatgg                                                           370


<210> SEQ ID NO 42
<211> LENGTH: 370
<212> TYPE: DNA
<213> ORGANISM: Homo sapiens
<220> FEATURE:
<221> NAME/KEY: misc_feature
<222> LOCATION: (133)..(133)
<223> OTHER INFORMATION: n = a, c, t or g

<400> SEQUENCE: 42

caattagcac tgtaaagtaa taaagtttcc caaataacag agattatgat tgatgacaat     60

gccattttcc tcttaattgg gaaagctgat ggcgacactc atgaaattaa aaaggtcttg    120

atgaaagacc aangaagacg tagatttccc taaattctga ataactctga tttaattcta    180

caggtatgta acagaatttg taaacctagg caatgtttca gctcttcgaa ctttcagagt    240

cttgagagct ttgaaaacta tttctgtaat tccaggtaag aagaaaatgg tataaggtgg    300

taggcccctt atatctccaa ctgtttcttg tgttctgtca ttgtgtttgt gtgtgaaccc    360

cctattacag                                                           370
```

<210> SEQ ID NO 43
<211> LENGTH: 410
<212> TYPE: DNA
<213> ORGANISM: Homo sapiens

<400> SEQUENCE: 43

```
gtaagaagaa aatggtataa ggtggtaggc cccttatatc tccaactgtt tcttgtgttc     60

tgtcattgtg tttgtgtgtg aaccccctat tacagatatg tgacagagtt tgtggacctg    120

ggcaatgtct cagcgttgag aacattcaga gttctccgag cattgaaaac aatttcagtc    180

attccaggtg agagctaggt taaacaccga ggctgacttt agctacagtg gtgctacaat    240

cacagctttt gtgcagaagc cttgttgcta gttgcatatt gcaaataaat atgtaaaaaa    300

gcaagaattg gtacatcatt ttttggatgg atttgattct ttgcttttta cccgttgctt    360

tctttaaaac tattctaaat cagcctttga gtttaacaag tgttgcatga               410
```

<210> SEQ ID NO 44
<211> LENGTH: 1066
<212> TYPE: DNA
<213> ORGANISM: Homo sapiens
<220> FEATURE:
<221> NAME/KEY: misc_feature
<222> LOCATION: (229)..(229)
<223> OTHER INFORMATION: n = a, c, t or g

<400> SEQUENCE: 44

```
aaagagtgtt tggaaataca catttggttc atttccattc acagttttct aatgaacata     60

caagttctgc tttcattcat tttcaccagc tagtaggctt ttcatgaaaa tgttattcaa    120

tcacaaacat taaactaata ttgttggcat tctgcatgac atttttattt tccaggccaa    180

gctcatgata tttttgccgg taaaatagct gttgagtagt atatttaant tccccccttct    240

gattttgttt gtaggcctga agaccattgt gggggccctg atccagtcag tgaagaagct    300

ttctgatgtc atgatcttga ctgtgttctg tctaagcgtg tttgcgctaa taggattgca    360

gttgttcatg ggcaacctac gaaataaatg tttgcaatgg cctccagata attcttcctt    420

tgaaataaat atcacttcct tctttaacaa ttcattggat gggaatggta ctactttcaa    480

taggacagtg agcatattta actgggatga atatattgag gataaaagta agatatactc    540

tataaaccat taagttgttt agttctctaa atattaaata ttatatataa tggaaattat    600

ctcaatttag atgtgaatca agtgacttag actaatttaa gatgatttaa tacatataaa    660

agagatatca aaggatacct tattctattt ttsttatctg tccattgata tagtaaaagt    720

tctcatttga aaatgtgttg tcttatactc atgttgaaag taatttcata ttatgccata    780

ttaaaaaagg tttatttggt agacattaat caggttttc agtcatttta ataaataagt    840

cagtagtttg aactattcmg cgtattccac tgaaatgtcg ttaagaagac tgaggggaaa    900

taatttggcc ctatttggtt gatgcaacat atgtattgag tacatatgct atatctgaaa    960

ctagagaaac catttatcaa gatgaaataa gaatttgtgt gctcctcaga aggttaagta   1020

accctgattt agccattcac ttcatccata ttctaattag tccctt                  1066
```

<210> SEQ ID NO 45
<211> LENGTH: 385
<212> TYPE: DNA
<213> ORGANISM: Homo sapiens

<400> SEQUENCE: 45

```
gttcaattat tgtgaaaaat cttctttagc catatatatt tattagttta tccatctcat     60
```

```
tatgattgaa aacatttgtg agctttgcca cctaaacagg gtggctgaag tgttttacag    120

gattttaatg attctttcta ttcctttctc tttaaatagg tcacttttat tttttacagg    180

ggcaaaatga tgctctgctt tgtggcaaca gctcagatgc agggtaagtg tatgcttcct    240

actgagtttc agtccacact gctccatcag tgtcaataac ctgccacctc ccactcatcc    300

agtcccacca ctcctcactc aaaaccctcc ataaattcta cttcacggtg actctcagaa    360

tgaccaggat aagtgtagat tctca                                          385
```

<210> SEQ ID NO 46
<211> LENGTH: 430
<212> TYPE: DNA
<213> ORGANISM: Homo sapiens

<400> SEQUENCE: 46

```
tataataatg acaattatga atcacagagg aatccacaaa gtagacctta tagattctgt     60

cattatataa atcagtccac ttagtgctga gttaagtact gggtaaggtg agagaaatcg    120

gctttttctt agtgcctgta taaaacagac attggcatat attaaaacag gaaaaccaat    180

tagcagactt gccgttattg actycctctc tttcctctaa cctaattaca gccagtgtcc    240

tgaaggatac atctgtgtga aggctggtag aaaccccaac tatggctaca cgagctttga    300

cacctttagt tgggcctttt tgtccttatt tcgtctcatg actcaagact tctgggaaaa    360

cctttatcaa ctggtgagaa cagataaaat catttttctg agaatcataa aacaccgaac    420

tcaagagaat                                                           430
```

<210> SEQ ID NO 47
<211> LENGTH: 646
<212> TYPE: DNA
<213> ORGANISM: Homo sapiens

<400> SEQUENCE: 47

```
tgctgtagaa tattttatta cttagagtgt aagtttgtaa catcctatat aaaatttatt     60

aaaatctctc ttccattttg cagacactac gtgctgctgg gaaaacgtac atgatatttt    120

ttgtgctggt cattttcttg ggctcattct atctaataaa tttgatcttg gctgtggtgg    180

ccatggccta tgaggaacag aatcaggcca cattggaaga ggctgaacag aaggaagctg    240

aatttcagca gatgctcgaa cagttgaaaa agcaacaaga agaagctcag gtatagtgaa    300

caagcatacg gtcctttgtt tttctgtatc taaattcttt aacctaaatg ttgaggtcag    360

tggcaaggta gttgacatta gaaataggtc atatgtgttt ggtaagtgct aggagcctgt    420

ttggttatta agaagttatt actttattgc aatgatctct gtcaatagtg tcaatagtaa    480

tggcatcaaa aaatggataa ttataattgc tttactgaca tttttttctc ccttgtgact    540

ccttgaggaa attaatgatt aacaaaggcc tcatgtactc aaacttgcag agtagataaa    600

cctacatgtc ctcagttgaa gtattttctt aggggaagag gaattc                   646
```

<210> SEQ ID NO 48
<211> LENGTH: 711
<212> TYPE: DNA
<213> ORGANISM: Homo sapiens
<220> FEATURE:
<221> NAME/KEY: misc_feature
<222> LOCATION: (164)..(164)
<223> OTHER INFORMATION: n = a, c, t or g

<400> SEQUENCE: 48

-continued

```
tatgtatcat cttccatatg aatgcgcatt ttactctttg attggtctaa taacagtgta     60

ctgtgttcta aaacacagaa taaaatggag aattgttttt caagattatc ttcatgatat    120

tgaagctcaa ttaagcagta acatgataat tattttttaa gatnatatgc aacttcccac    180

atactttgcg cccttctagg cggcagctgc agccgcatct gctgaatcaa gagacttcag    240

tggtgctggt gggataggag tttttcaga gagttcttca gtagcatcta agttgagctc    300

caaaagtgaa aaagagctga aaaacagaag aaagaaaaag aaacagaaag aacagtctgg    360

agaagaagag aaaaatgaca gagtcctaaa atcggaatct gaagacagca taagaagaaa    420

aggtttccgt ttttccttgg aaggaagtag gctgacatat gaaaagagat tttcttctcc    480

acaccaggta aaaatattaa attacatgaa ttgtgttctc ataaattttt taaaagaata    540

tgccagaatt taatggagag aaaaccgcct tccacctgga tggcacaatg ctttcagagt    600

agtgatgatt atcaagtgtt ttggctatca cttcagagaa tttgtgagtt ttgcaacttt    660

ttggaatccc aggaaggaaa ttttagatcc ctctgggttt ggaaaaattt g             711
```

<210> SEQ ID NO 49
<211> LENGTH: 1026
<212> TYPE: DNA
<213> ORGANISM: Homo sapiens

<400> SEQUENCE: 49

```
ttatggggac acttctgact atgttgaggt gtgggtaaag taggagaaaa gagagcagaa     60

gatggaaaat ggaggaagga gaaaaagcga gagtgaaata gaaaaggtga accttgtaga    120

aagtgccaaa atgccaccag cagtcatcag aggggtgctt tcttccacat gtccaatgac    180

ttatccttga gtaagtcaat gactatgaca caatgaatca aattctgttt ttcagaatgc    240

cagctcttaa ctctcttcat ctcatttttg tttcttttct tgttattcat agtccttact    300

gagcatccgt ggctcccttt tctctccaag acgcaacagt agggcgagcc ttttcagctt    360

cagaggtcga gcaaaggaca ttggctctga gaatgacttt gctgatgatg agcacagcac    420

ctttgaggac aatgacagcc gaagagactc tctgttcgtg ccgcacagac atggagaacg    480

gcgccacagc aatgtcagcc aggccagccg tgcctccagg gtgctcccca tcctgcccat    540

gaatgggaag atgcatagcg ctgtggactg caatggtgtg gtctccctgg tcgggggccc    600

ttctaccctc acatctgctg ggcagctcct accagaggtg aggccaacyy magattgcag    660

ctgatgtgaa gagagttgtg actggtgcag gcaggagtgy ttttccattt mcacatctaa    720

gaatttkttg agtttsttgc ccaaaggctg ggagtttgtt caatcaagct gttaactgtc    780

ttgtgaaact sttctattca gactttycta caaagtaatt aaaaacctag gttggctgtc    840

agagaatata attagamgtm atctttcatc ayyattacta tggtatgaaa ctcgccaaaa    900

agcaaagcaa caatttatca agcataatgt tygaytaata tagttaaatt aaatccaagg    960

aaattaatgc tcacaaatta aataaatact taaggatttt gtgattgttg ttcatttaaa   1020

aggaga                                                              1026
```

<210> SEQ ID NO 50
<211> LENGTH: 601
<212> TYPE: DNA
<213> ORGANISM: Homo sapiens

<400> SEQUENCE: 50

```
ataggaaagc ccaccttgac aaacccaggg ctccccaaaa gctgaaaatc tgacagactt     60

taaacaaccc ccaaataatt atcattccaa caatatctta gtgagctttt tacatctgag    120
```

```
aaagcatggt gtatatttag ttaaataaca cctgttgtag gaatgctttg ggctttgctg    180

ctttcaaaaa tagtggttat ttcatctgaa attctacttc tagggcacaa ctactgaaac    240

agaaataaga aagagacggt ccagttctta tcatgtttcc atggatttat tggaagatcc    300

tacatcaagg caaagagcaa tgagtatagc cagtattttg accaacacca tggaaggtat    360

gttaaaagtc ctgcgtcaca gttacttggt gctttcctaa tgatgaaaaa cacttcataa    420

atttcaataa aatacttcct gacttgatat tgtatcatta ttacacattt tactaaataa    480

cagtaaaatc cgtgcataac tcatggattc atatattcca cagatttttt tttttttatat    540

ttagcctgta gaaagctgct gcaaatgtaa ggtatatttg aacaccactt tcataactta    600

a                                                                    601
```

```
<210> SEQ ID NO 51
<211> LENGTH: 645
<212> TYPE: DNA
<213> ORGANISM: Homo sapiens

<400> SEQUENCE: 51

gcttactagc ctttctgtac tgatcctttc tatgacagca aacccattgt aaaattttcc     60

ctgttcctcc agcagattaa cccataatat cttttaacaa ctttagattt tttaaattcc    120

ttttaattta aaccaaatct gcttaataga aagtaagcag ttttcatgag gattctaact    180

ttttttcttc cagaacttga agaatccaga cagaaatgcc caccatgctg gtataaattt    240

gctaatatgt gtttgatttg ggactgttgt aaaccatggt taaaggtgaa acaccttgtc    300

aacctggttg taatggaccc atttgttgac ctggccatca ccatctgcat tgtcttaaat    360

acactcttca tggctatgga gcactatccc atgacggagc agttcagcag tgtactgtct    420

gttggaaacc tggtaagcct cactgagagt ttctcttcct cttgaaagag tttataattg    480

ccttagtgaa ttttacatat tgctctcaaa ttaaatatca actaattggc catgtatatc    540

ttgacatcaa atgtttagca tcccttttaa ataacaaaaa aatgttgcta ccatagtgca    600

aaagagtcaa agaatttatg tacaatttga tttagaattg aattt                    645
```

```
<210> SEQ ID NO 52
<211> LENGTH: 485
<212> TYPE: DNA
<213> ORGANISM: Homo sapiens

<400> SEQUENCE: 52

tggcccaaac caatttttaa atcaggaatt taatttwtat attgttggga gttaaattaa     60

gttgctcaat aattattcgt gtttcaakas tatttgctca tataatgaac tacacttctc    120

atttaggtct tcacagggat cttcacagca gaaatgtttc tcaagataat tgccatggat    180

ccatattatt actttcaaga aggctggaat atttttgatg gttttattgt gagccttagt    240

ttaatggaac ttggtttggc aaatgtggaa ggattgtcag ttctccgatc attccggctg    300

gtaaattaac tgggagtgtt cataaaatgt actttrtaat taattagtct tcattctcat    360

ctagtaaaaa tggcaagatt tcccatcatt ataatatatt tgaatacctt ctaaaacaga    420

ttggattgcc ataccaccaa atggtagttt cttcttcatc atagctttaa taaagttcac    480

ttaaa                                                                485
```

```
<210> SEQ ID NO 53
<211> LENGTH: 602
<212> TYPE: DNA
```

<213> ORGANISM: Homo sapiens

<400> SEQUENCE: 53

```
acagatttcc tcctgtgtcc atgtgactaa cccattgtgc acatgtaccc taaaaattag     60

tatataataa taaaataaaa taaaaataaa aataaaaaaa taaaaataaa ataaaattgc    120

agattttttt agaaatgcag agattaacac tgttcttgct tttatttcca gctccgagtt    180

ttcaagttgg caaaatcttg gccaactcta aatatgctaa ttaagatcat tggcaattct    240

gtgggggctc taggaaacct caccttggta ttggccatca tcgtcttcat tttgctgtg     300

gtcggcatgc agctctttgg taagagctac aaagaatgtg tctgcaagat ttccaatgat    360

tgtgaactcc cacgctggca catgcatgac tttttccact ccttcctgat cgtgttccgc    420

gtgctgtgtg gagagtggat agagaccatg tgggactgta tggaggtcgc tggccaaacc    480

atgtgcctta ctgtcttcat gatggtcatg gtgattggaa atctagtggt atgtagcaaa    540

aacattttcc tcattttcat taaaaataat gtaatcatta aaaagtgttc aactgaagaa    600

ta                                                                   602
```

<210> SEQ ID NO 54
<211> LENGTH: 803
<212> TYPE: DNA
<213> ORGANISM: Homo sapiens

<400> SEQUENCE: 54

```
gtttcattta gcaatgattt cagtattttc tgcaatgact aataagcaaa tagtgataat     60

agtattattt tatattgacc aagcattttt atttcattca cttttttca gaatagtgta     120

tcatgaatta gcagaaatgc atgttagaat aaaataaggt gtcaagaaca atcttagaaa    180

actaatgatg gaaagcaatt gaagcaatag aatgttttga tcacctgttt ttcctgctgt    240

gtttcaggtt ctgaacctct tcttggcctt gcttttgagt tccttcagtt ctgacaatct    300

tgctgccact gatgatgata acgaaatgaa taatctccag attgctgtgg gaaggatgca    360

gaaaggaatc gattttgtta aaagaaaaat acgtgaattt attcagaaag cctttgttag    420

gaagcagaaa gctttagatg aaattaaacc gcttgaagat ctaaataata aaaaagacag    480

ctgtatttcc aaccatacca ccatagaaat aggcaaagac ctcaattatc tcaaagacgg    540

aaatggaact actagtggca taggcagcag tgtagaaaaa tatgtcgtgg atgaaagtga    600

ttacatgtca tttataaaca accctagcct cactgtgaca gtaccaattg ctgttggaga    660

atctgacttt gaaaatttaa atactgaaga attcagcagc gagtcagata tggaggaaag    720

caaagaggta aaatgttaaa taaggagata ttttggtgta tataatctgt gttaaatatc    780

aggtgtttaa tgcgtgtctc tgt                                            803
```

<210> SEQ ID NO 55
<211> LENGTH: 615
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n = a, c, t or g
<220> FEATURE:
<221> NAME/KEY: misc_feature
<222> LOCATION: (378)..(386)
<223> OTHER INFORMATION: n = a, c, t or g

<400> SEQUENCE: 55

```
atctctatac taggctcaaa cagaagttat ttccgttgtt agcaccatat ttttaaaaga     60
```

```
aaaaaaaata ctatggtgtt gtatctaatn ttgtgacccc tgacctttac caaagcggat    120

tggcattatg tttaagttct taattacaga tcaagaaaaa tgcatacaga agatgggggg    180

gggcacacct aattaatttt tatatttaga ttaaagaaaa taattaaatg tgtttttttg    240

tgggattgat tttcagaagc taaatgcaac tagttcatct gaaggcagca cggttgatat    300

tggagctccc gccgagggag aacagcctga ggttgaacct gaggaatccc ttgaacctga    360

agcctgtttt acagaagnnn nnnnnnaagc aaaacaataa catatgtggt cttgagtatc    420

ctcttttcta cccatttttt cctatttatt taaatgtctg tttatttgtc taccatctag    480

ttcatctatc tatctgtatc tatctatcta tctatctatc tagtaatcat ctatacctat    540

ccaacaactg tacatttatt tgtttttttt ttttgcattt gctgtttgaa aaaaaatgca    600

acgttttaaa ggcaa                                                     615
```

<210> SEQ ID NO 56
<211> LENGTH: 400
<212> TYPE: DNA
<213> ORGANISM: Homo sapiens

<400> SEQUENCE: 56

```
gatagctttt gtaagcggaa gctatcttaa aaattaatgt tatttacaat gtattatcag     60

gtaataatgt aaatgaatct cccaccaaca caaatatacc taatcaaaga gtaatttttt    120

gtcttcattt ttttcccaca tattttagac tgtgtacgga agttcaagtg ttgtcagata    180

agcatagaag aaggcaaagg gaaactctgg tggaatttga ggaaaacatg ctataagata    240

gtggagcaca attggttcga aaccttcatt gtcttcatga ttctgctgag cagtggggct    300

ctggtaggtg atgcatgatc cactccttca cctttcatct gaaatctttt ccctttccct    360

tcaatcaact catattaccc acttttaaat taaggtgttt                          400
```

<210> SEQ ID NO 57
<211> LENGTH: 560
<212> TYPE: DNA
<213> ORGANISM: Homo sapiens

<400> SEQUENCE: 57

```
aaattactga aacccttggt tgactgaaat gcccagtcag cagtcattta tgatcagata     60

atgataaagt aaaattcagc catgggaaac attaaacctt ccagccttag gcacctgata    120

agagcttgca tcgtttcctt ttttaagaaa tcatcaatta gagactgttt ctgatcataa    180

aatttaatag aattttttga cttacaggcc tttgaagata tatacattga gcagcgaaaa    240

accattaaga ccatgttaga atatgctgac aaggttttca cttacatatt cattctggaa    300

atgctgctaa agtgggttgc atatggtttt caagtgtatt ttaccaatgc ctggtgctgg    360

ctagacttcc tgattgttga tgtgagtatg ctgcactttg ctgctttatt cattggcata    420

tatgtaatag ttctagcaat ggtgcctgac acagtgtagg cactcagtaa cactgtatca    480

gcccaaatat aaattatgtt tctcatttca cagtgagagg atgcctcaaa acatttttta    540

ccaatttaaa tacatataca                                                560
```

<210> SEQ ID NO 58
<211> LENGTH: 480
<212> TYPE: DNA
<213> ORGANISM: Homo sapiens

<400> SEQUENCE: 58

-continued

```
aaattcttag gcctttcccc aaacttacta agtcagactc tgctattggt gtttttaaca     60

agacccctgg gtgattttga aactcatgaa agttcgagaa ttactgattc attgcataga    120

gcaaggctga actgtgtaga catttttata tgtaaataag aaaattgtgt tgctttttct    180

gtataggtct cactggttag cttaactgca aatgccttgg gttactcaga acttggtgcc    240

atcaaatccc tcagaacact aagagctctg aggccactga gagctttgtc ccggtttgaa    300

ggaatgaggg taagactgaa tgccttagag tttgtcagaa ttattattga gagcagactg    360

acactttgta ccatggaaat gtcaaattta tggagaattt gtgtcttaca cattcatact    420

gacatagcta atcaatcaaa aataatattt accagatgcc cataatactt ggcactgctg    480
```

<210> SEQ ID NO 59
<211> LENGTH: 640
<212> TYPE: DNA
<213> ORGANISM: Homo sapiens

<400> SEQUENCE: 59

```
taattttaaa attcttagtt ggagctacca gagtctagtt tctacccaat attcaacttt     60

gaaacagatt tttttaatca tttgactgtt cttttaataa tgtttaaaaa taagtaaata    120

tttgttgttg gcttttcact tatttttcct tctcatcctg tgccaggttg ttgtaaatgc    180

tcttttagga gccattccat ctatcatgaa tgtacttctg gtttgtctga tcttttggct    240

aatattcagt atcatgggag tgaatctctt tgctggcaag ttttaccatt gtattaatta    300

caccactgga gagatgtttg atgtaagcgt ggtcaacaac tacagtgagt gcaaagctct    360

cattgagagc aatcaaactg ccaggtggaa aaatgtgaaa gtaaactttg ataacgtagg    420

acttggatat ctgtctctac ttcaagtagt aagtaatcac tttattattt tccatgatgt    480

gtaattaaaa tgagtctaaa gtttttcttc ctcataatga gatatccacc tgttagaatg    540

gctattatca aacagataaa tgacaataaa tgctggcaag aatgtgaaga aaagggaacc    600

cttgtacatt gttggcaggg atgtaaatta gtatagcttt                          640
```

<210> SEQ ID NO 60
<211> LENGTH: 480
<212> TYPE: DNA
<213> ORGANISM: Homo sapiens

<400> SEQUENCE: 60

```
atttgaagta ttttcaatgc atatcgcaaa acattgcccc aaaagtgaat acaaatttca     60

agcttattta tatgcctgta ttgaatacat gtcaaataga attttgatca attattcaat    120

ttattttcta aaattataat tttgggaaaa aagaaaatga tatgactttt cttacaggcc    180

acgtttaagg gatggatgga tattatgtat gcagctgttg attcacgaaa tgtaagtcta    240

gttagaggga aattgtttag tttgattaaa tgtatatttc tacaatattg taatttagtg    300

atattgtcaa taaaataaaa ttatgtgctt aatttataaa acccatctat attataagga    360

taaaatattt aatcatacta tttctttcaa aattatcata ggatgatttt ctctaatcac    420

tctgtatctt ttaacatatc ttttctagta tttagcaagg cacctgacac aaaactttat    480
```

<210> SEQ ID NO 61
<211> LENGTH: 366
<212> TYPE: DNA
<213> ORGANISM: Homo sapiens

<400> SEQUENCE: 61

```
taaaacatgc ttagataatt aaaaactcac tgatgtactt tttgtgaaac aagtactaga     60
```

```
tataatggtt acaattcttc atattcttta ggtagaatta caacccaagt atgaagacaa    120

cctgtacatg tatctttatt ttgtcatctt tattattttt ggttcattct ttaccttgaa    180

tcttttcatt ggtgtcatca tagataactt caaccaacag aaaaagaaga taagtatatt    240

aaaacttcat ccttgctctg aaatatgaac taaatatttc atactctttc ctttagcctc    300

caaaatgcaa tcaccaaaaa aagaatataa aattcagaaa ttattttgag acatttgata    360

atcgat                                                               366
```

<210> SEQ ID NO 62
<211> LENGTH: 560
<212> TYPE: DNA
<213> ORGANISM: Homo sapiens

<400> SEQUENCE: 62

```
tcgataagct tttaagcaat taataattca gatagcatgt ttttgatatt tttagtctag     60

aaatatgact aatatggcat aatttatata ttgaataaag gcatctctat aaatacagat    120

attagtaaca atagaatgaa atgtgggagc caattttcac atgattacta aggtggattt    180

tatagccagc aaagaacaca attttaacaa gtgttgcttt catttcttta ctttggaggt    240

caagacattt ttatgacaga agaacagaag aaatactaca atgcaatgaa aaaactgggt    300

tcaaagaaac cacaaaaacc catacctcga cctgctgtaa gaataacata ttttcattgc    360

ctgttaaaac tatattacct aaccgtttca cagcccgaat ttctagaaac tagttatttt    420

tgtggatttg taacacaaag ttttttacct taacaatggg actagctagc ctaaatagct    480

tgaaaaatgt actttacata tataatatgt ataaattata taatgcataa catattttat    540

atgtaaacat ataaaataca                                                560
```

<210> SEQ ID NO 63
<211> LENGTH: 650
<212> TYPE: DNA
<213> ORGANISM: Homo sapiens

<400> SEQUENCE: 63

```
gttttgcaag gaattttttt ttttgtaaaa tgttgtgagg attaaagatg tgtttttata     60

aaagctacat tttttgttgc tttcttaaaa tcagaagaat tgaattcgat ttttttttaag    120

gtttctaatg gaacttttac atattatttg ttccagaaca aattccaagg aatggtcttt    180

gattttgtaa ccaaacaagt ctttgatatc agcatcatga tcctcatctg ccttaacatg    240

gtcaccatga tggtggaaac cgatgaccag agtcaagaaa tgacaaacat tctgtactgg    300

attaatctgg tgtttattgt tctgttcact ggagaatgtg tgctgaaact gatctctctt    360

cgttactact atttcactat tggatggaat atttttgatt ttgtggtggt cattctctcc    420

attgtaggta agaagaggtg cttttattca gttaaggaat atagtggtaa aaatatgtgt    480

tttaaaactt tagaggtgtt tttcactaat ctttctcatt catcccaaac tcccaaataa    540

aaatctaata gtccattgtt ttagttttag tttgccattt ctctaattgc atgctgtgct    600

tgaaatgatg agtggaatac aaggaattta tattttcagc tttcatttat                650
```

<210> SEQ ID NO 64
<211> LENGTH: 3700
<212> TYPE: DNA
<213> ORGANISM: Homo sapiens

<400> SEQUENCE: 64

-continued

```
aatgttataa caccaaacat accagtttca ttttgctcaa caaacattgc agattatttg      60
catatataca tgtacctaac tgtcctgttc acattttgta aaactaatgt acttatgtaa     120
actttcattt gctactatta agtataacaa tatttttgtt atttgttgat tttctacagg     180
aatgtttctg gctgaactga tagaaaagta ttttgtgtcc cctaccctgt tccgagtgat     240
ccgtcttgcc aggattggcc gaatcctacg tctgatcaaa ggagcaaagg ggatccgcac     300
gctgctcttt gctttgatga tgtcccttcc tgcgttgttt aacatcggcc tccttctttt     360
cctggtcatg ttcatctacg ccatctttgg gatgtccaat tttgcctatg ttaagaggga     420
agttgggatc gatgacatgt tcaactttga gacctttggc aacagcatga tctgcctgtt     480
ccaaattaca acctctgctg gctgggatgg attgctagca cctattctta atagtggacc     540
tccagactgt gaccctgaca aagatcaccc tggaagctca gttaaaggag actgtgggaa     600
cccatctgtt gggattttct tttttgtcag ttacatcatc atatccttcc tggttgtggt     660
gaacatgtac atcgcggtca tcctggagaa cttcagtgtt gctactgaag aaagtgcaga     720
gcctctgagt gaggatgact ttgagatgtt ctatgaggtt tgggagaagt ttgatcccga     780
tgcgacccag tttatagagt ttgccaaact ttctgatttt gcagatgccc tggatcctcc     840
tcttctcata gcaaaaccca acaaagtcca gctcattgcc atggatctgc ccatggtgag     900
tggtgaccgg atccactgtc ttgacatctt atttgctttt acaaagcgtg ttttgggtga     960
gagtggagag atggatgccc ttcgaataca gatggaagag cgattcatgg catcaaaccc    1020
ctccaaagtc tcttatgagc ccattacgac cacgttgaaa cgcaaacaag aggaggtgtc    1080
tgctattatt atccagaggg cttacagacg ctacctcttg aagcaaaaag ttaaaaaggt    1140
atcaagtata tacaagaaag acaaaggcaa agaatgtgat ggaacaccca tcaaagaaga    1200
tactctcatt gataaactga atgagaattc aactccagag aaaaccgata tgacgccttc    1260
caccacgtct ccaccctcgt atgatagtgt gaccaaacca gaaaaagaaa aatttgaaaa    1320
agacaaatca gaaaaggaag acaaagggaa agatatcagg gaaagtaaaa agtaaaaaga    1380
aaccaagaat tttccatttt gtgatcaatt gtttacagcc cgtgatggtg atgtgtttgt    1440
gtcaacagga ctcccacagg aggtctatgc caaactgact gtttttacaa atgtatactt    1500
aaggtcagtg cctataacaa gacagagacc tctggtcagc aaactggaac tcagtaaact    1560
ggagaaatag tatcgatggg aggtttctat tttcacaacc agctgacact gctgaagagc    1620
agaggcgtaa tggctactca gacgatagga accaatttaa agggggggagg gaagttaaat    1680
ttttatgtaa attcaacatg tgacacttga taatagtaat tgtcaccagt gtttatgttt    1740
taactgccac acctgccata tttttacaaa acgtgtgctg tgaatttatc acttttcttt    1800
ttaattcaca ggttgtttac tattatatgt gactattttt gtaaatgggt ttgtgtttgg    1860
ggagagggat taaagggagg gaattctaca tttctctatt gtattgtata actggatata    1920
ttttaaatgg aggcatgctg caattctcat tcacacataa aaaaatcaca tcacaaaagg    1980
gaagagttta cttcttgttt caggatgttt ttagattttt gaggtgctta aatagctatt    2040
cgtattttta aggtgtctca tccagaaaaa atttaatgtg cctgtaaatg ttccatagaa    2100
tcacaagcat taaagagttg ttttattttt acataaccca ttaaatgtac atgtatatat    2160
gtatatatgt atatgtgcgt gtatatacat atatatgtat acacacatgc acacacagag    2220
atatacacat accattacat tgtcattcac agtcccagca gcatgactat cacatttttg    2280
ataagtgtcc tttggcataa aataaaaata tcctatcagt cctttctaag aagcctgaat    2340
tgaccaaaaa acatccccac caccacttta taaagttgat tctgctttat cctgcagtat    2400
```

-continued

```
tgtttagcca tcttctgctc ttggtaaggt tgacatagta tatgtcaatt taaaaaataa   2460

aagtctgctt tgtaaatagt aattttaccc agtggtgcat gtttgagcaa acaaaaatga   2520

tgatttaagc acactactta ttgcatcaaa tatgtaccac agtaagtata gtttgcaagc   2580

tttcaacagg taatatgatg taattggttc cattatagtt tgaagctgtc actgctgcat   2640

gtttatcttg cctatgctgc tgtatcttat tccttccact gttcagaagt ctaatatggg   2700

aagccatata tcagtggtaa agtgaagcaa attgttctac caagacctca ttcttcatgt   2760

cattaagcaa taggttgcag caaacaagga agagcttctt gctttttatt cttccaacct   2820

taattgaaca ctcaatgatg aaaagcccga ctgtacaaac atgttgcaag ctgcttaaat   2880

ctgtttaaaa tatatggtta gagttttcta agaaaatata aatactgtaa aaagttcatt   2940

ttattttatt tttcagcctt ttgtacgtaa aatgagaaat taaaagtatc ttcaggtgga   3000

tgtcacagtc actattgtta gtttctgttc ctagcacttt taaattgaag cacttcacaa   3060

aataagaagc aaggactagg atgcagtgta ggtttctgct tttttattag tactgtaaac   3120

ttgcacacat ttcaatgtga aacaaatctc aaactgagtt caatgtttat ttgctttcaa   3180

tagtaatgcc ttatcattga aagaggctta aagaaaaaaa aaatcagctg atactcttgg   3240

cattgcttga atccaatgtt tccacctagt ctttttattc agtaatcatc agtcttttcc   3300

aatgtttgtt tacacagata gatcttattg acccatatgg cactagaact gtatcagata   3360

taatatggga tcccagcttt ttttcctctc ccacaaaacc aggtagtgaa gttatattac   3420

cagttacagc aaaatacttt gtgtttcaca agcaacaata aatgtagatt ctttatactg   3480

aagctattga cttgtagtgt gttggtgaat gcatgcagga agatgctgtt accataaaga   3540

acggtaaacc acattacaat caagccaaag aataaaggtt cgcttatgta tatgtattta   3600

attgttgtct ttgtttctat ctttgaaatg ccatttaaag gtagatttct atcatgtaaa   3660

aataatctat ctgaaaaaca aatgtaaaga acacacatta                         3700
```

<210> SEQ ID NO 65
<211> LENGTH: 9112
<212> TYPE: DNA
<213> ORGANISM: Homo sapiens

<400> SEQUENCE: 65

```
accatagagt gaatctcaga acaggaagcg gaggcataag cagagaggat tctggaaagg     60

tctctttgtt ttcttatcca cagagaaaga aagaaaaaaa attgtaacta atttgtaaac    120

ctctgtggtc aaaaaaaaaa aaaaaaaaaa aagctgaaca gctgcagagg aagacacgtt    180

ataccctaac catcttggat gctgggcttt gttatgctgt aattcataag gctctgtttt    240

atcagagatt atggagcaag aaaactgaag ccaagccaca tcaaggtttg acagggatga    300

gatacctgtc aaggattcat agtagagtgg cttactggga aaggagcaaa gaatctcttc    360

tagggatatt gtaagaataa atgagataat tcacagaagg gacctggagc ttttccggaa    420

aaaggtgctg tgactatcta aggggaaaag ctgagagtct ggaactagcc tatcttccga    480

ggacttagag acaacagtat gggaatttca acgagacgtt tttactttct tttgaccaag    540

attcaaattc tttattccag cccttgataa gtaaataaga aggtaattcg tatgcaagaa    600

gctacacgta attaaatgtg caggatgaaa agatggcaca ggcactgttg gtacccccag    660

gacctgaaag cttccgcctt tttactagag aatctcttgc tgctatcgaa aaacgtgctg    720

cagaagagaa agccaagaag cccaaaaagg aacaagataa tgatgatgag aacaaaccaa    780
```

-continued

```
agccaaatag tgacttggaa gctggaaaga accttccatt tatttatgga gacattcctc    840
cagagatggt gtcagagccc ctggaggacc tggatcccta ctatatcaat aagaaaactt    900
ttatagtaat gaataaagga aaggcaattt cccgattcag tgccacctct gccttgtata    960
ttttaactcc actaaaccct gttaggaaaa ttgctabsaa gattttggta cattctttat   1020
tcagcatgct tatcatgtgc actattttga ccaactgtgt atttatgacc ttgagcaacc   1080
ctcctgactg gacaaagaat gtagagtaca cattcactgg aatctatacc tttgagtcac   1140
ttataaaaat cttggcaaga gggttttgct tagaagattt tacgtttctt cgtgatccat   1200
ggaactggct ggatttcagt gtcattgtga tggcatatgt gacagagttt gtggacctgg   1260
gcaatgtctc agcgttgaga acattcagag ttctccgagc actgaaaaca atttcagtca   1320
ttccaggttt aaagaccatt gtgggggccc tgatccagtc ggtaaagaag ctttctgatg   1380
tgatgatcct gactgtgttc tgtctgagcg tgtttgctct cattgggctg cagctgttca   1440
tgggcaatct gaggaataaa tgtttgcagt ggcccccaag cgattctgct tttgaaacca   1500
acaccacttc ctactttaat ggcacaatgg attcaaatgg gacatttgtt aatgtaacaa   1560
tgagcacatt taactggaag gattacattg gagatgacag tcacttttat gttttggatg   1620
ggcaaaaaga ccctttactc tgtggaaatg gctcagatgc aggccagtgt ccagaaggat   1680
acatctgtgt gaaggctggt cgaaacccca actatggcta cacaagcttt gacaccttta   1740
gctgggcttt cctgtctcta tttcgactca tgactcaaga ctactgggaa aatctttacc   1800
agttgacatt acgtgctgct gggaaaacat acatgatatt ttttgtcctg gtcattttct   1860
tgggctcatt ttatttggtg aatttgatcc tggctgtggt ggccatggcc tatgaggggc   1920
agaatcaggc caccttggaa gaagcagaac aaaaagaggc cgaatttcag cagatgctcg   1980
aacagcttaa aaagcaacag gaagaagctc aggcagttgc ggcagcatca gctgcttcaa   2040
gagatttcag tggaataggt gggttaggag agctgttgga aagttcttca gaagcatcaa   2100
agttgagttc caaaagtgct aaagaatgga ggaaccgaag gaagaaaaga agacagagag   2160
agcaccttga aggaaacaac aaaggagaga gagacagctt tcccaaatcc gaatctgaag   2220
acagcgtcaa aagaagcagc ttccttttct ccatggatgg aaacagactg accagtgaca   2280
aaaaattctg ctcccctcat cagtctctct tgagtatccg tggctccctg ttttccccaa   2340
gacgcaatag caaaacaagc attttcagtt tcagaggtcg ggcaaaggat gttggatctg   2400
aaaatgactt tgctgatgat gaacacagca catttgaaga cagcgaaagc aggagagact   2460
cactgtttgt gccgcacaga catggagagc gacgcaacag taacggcacc accactgaaa   2520
cggaagtcag aaagagaagg ttaagctctt accagatttc aatggagatg ctggaggatt   2580
cctctggaag gcaaagagcc gtgagcatag ccagcattct gaccaacaca atggaagaac   2640
ttgaagaatc tagacagaaa tgtccgccat gctggtatag atttgccaat gtgttcttga   2700
tctgggactg ctgtgatgca tggttaaaag taaaacatct tgtgaattta attgttatgg   2760
atccatttgt tgatcttgcc atcactattt gcattgtctt aaataccctc tttatggcca   2820
tggagcacta ccccatgact gagcaattca gtagtgtgtt gactgtagga aacctggtct   2880
ttactgggat ttttacagca gaaatggttc tcaagatcat tgccatggat ccttattact   2940
atttccaaga aggctggaat atctttgatg gaattattgt cagcctcagt ttaatggagc   3000
ttggtctgtc aaatgtggag ggattgtctg tactgcgatc attcagactg cttagagttt   3060
tcaagttggc aaaatcctgg cccacactaa atatgctaat taagatcatt ggcaattctg   3120
tgggggctct aggaaacctc accttggtgt tggccatcat cgtcttcatt tttgctgtgg   3180
```

-continued

```
tcggcatgca gctctttggt aagagctaca aagaatgtgt ctgcaagatc aatgatgact   3240
gtacgctccc acggtggcac atgaacgact tcttccactc cttcctgatt gtgttccgcg   3300
tgctgtgtgg agagtggata gagaccatgt gggactgtat ggaggtcgct ggccaaacca   3360
tgtgccttat tgttttcatg ttggtcatgg tcattggaaa ccttgtggtt ctgaacctct   3420
ttctggcctt attgttgagt tcatttagct cagacaacct tgctgctact gatgatgaca   3480
atgaaatgaa taatctgcag attgcagtag gaagaatgca aaagggaatt gattatgtga   3540
aaaataagat gcgggagtgt ttccaaaaag cctttttttag aaagccaaaa gttatagaaa   3600
tccatgaagg caataagata gacagctgca tgtccaataa tactggaatt gaaataagca   3660
aagagcttaa ttatcttaga gatgggaatg gaaccaccag tggtgtaggt actggaagca   3720
gtgttgaaaa atacgtaatc gatgaaaatg attatatgtc attcataaac aaccccagcc   3780
tcaccgtcac agtgccaatt gctgttggag agtctgactt tgaaaactta aatactgaag   3840
agttcagcag tgagtcagaa ctagaagaaa gcaaggagaa attaaatgca accagctcat   3900
ctgaaggaag cacagttgat gttgttctac cccgagaagg tgaacaagct gaaactgaac   3960
ccgaagaaga ccttaaaccg gaagcttgtt ttactgaagg atgtattaaa aagtttccat   4020
tctgtcaagt aagtacagaa gaaggcaaag ggaagatctg gtggaatctt cgaaaaacct   4080
gctacagtat tgttgagcac aactggtttg agactttcat tgtgttcatg atccttctca   4140
gtagtggtgc attggccttt gaagatatat acattgaaca gcgaaagact atcaaaacca   4200
tgctagaata tgctgacaaa gtctttacct atatattcat tctggaaatg cttctcaaat   4260
gggttgctta tggatttcaa acatatttca ctaatgcctg gtgctggcta gatttcttga   4320
tcgttgatgt ttctttggtt agcctggtag ccaatgctct tggctactca gaactcggtg   4380
ccatcaaatc attacggaca ttaagagctt taagacctct aagagcctta tcccggtttg   4440
aaggcatgag ggtggttgtg aatgctcttg ttggagcaat tccctctatc atgaatgtgc   4500
tgttggtctg tctcatcttc tggttgatct ttagcatcat gggtgtgaat ttgtttgctg   4560
gcaagttcta ccactgtgtt aacatgacaa cgggtaacat gtttgacatt agtgatgtta   4620
acaatttgag tgactgtcag gctcttggca agcaagctcg gtggaaaaac gtgaaagtaa   4680
actttgataa tgttggcgct ggctatcttg cactgcttca agtggccaca tttaaaggct   4740
ggatggatat tatgtatgca gctgttgatt cacgagatgt taaacttcag cctgtatatg   4800
aagaaaatct gtacatgtat ttatactttg tcatctttat catctttggg tcattcttca   4860
ctctgaatct attcattggt gtcatcatag ataacttcaa ccagcagaaa aagaagtttg   4920
gaggtcaaga catctttatg acagaggaac agaaaaaata ttacaatgca atgaagaaac   4980
ttggatccaa gaaacctcag aaacccatac ctcgcccagc aaacaaattc caaggaatgg   5040
tctttgattt tgtaaccaga caagtctttg atatcagcat catgatcctc atctgcctca   5100
acatggtcac catgatggtg gaaacggatg accagggcaa atacatgacc ctagttttgt   5160
cccggatcaa cctagtgttc attgttctgt tcactggaga atttgtgctg aagctcgtct   5220
ccctcagaca ctactacttc actataggct ggaacatctt tgactttgtg gtggtgattc   5280
tctccattgt aggtatgttt ctggctgaga tgatagaaaa gtattttgtg tcccctacct   5340
tgttccgagt gatccgtctt gccaggattg gccgaatcct acgtctgatc aaaggagcaa   5400
aggggatccg cacgctgctc tttgctttga tgatgtccct tcctgcgttg tttaacatcg   5460
gcctcctgct cttcctggtc atgtttatct atgccatctt tgggatgtcc aactttgcct   5520
```

-continued

```
atgttaaaaa ggaagctgga attgatgaca tgttcaactt tgagaccttt ggcaacagca   5580
tgatctgctt gttccaaatt acaacctctg ctggatggga tggattgcta gcacctattc   5640
ttaatagtgc accacccgac tgtgaccctg acacaattca ccctggcagc tcagttaagg   5700
gagactgtgg gaacccatct gttgggattt tctttttgt cagttacatc atcatatcct   5760
tcctggtggt ggtgaacagt tacatcgcgg tcatcctgga gaacttcagt gttgctactg   5820
aagaaagtgc agagcccctg agtgaggatg actttgagat gttctatgag gtttgggaaa   5880
agtttgatcc cgatgcgacc cagtttatag agttctctaa actctctgat tttgcagctg   5940
ccctggatcc tcctcttctc atagcaaaac ccaacaaagt ccagcttatt gccatggatc   6000
tgcccatggt cagtggtgac cggatccact gtcttgatat tttatttgcc tttacaaagc   6060
gtgttttggg tgagagtgga gagatggatg cccttcgaat acagatggaa gacaggttta   6120
tggcatcaaa cccctccaaa gtctcttatg agcctattac aaccactttg aaacgtaaac   6180
aagaggaggt gtctgccgct atcattcagc gtaatttcag atgttatctt ttaaagcaaa   6240
ggttaaaaaa tatatcaagt aactataaca aagaggcaat aaaggggagg attgacttac   6300
ctataaaaca agacatgatt attgacaaac tgaatgggaa ctccactcca gaaaaaacag   6360
atgggagttc ctctaccacc tctcctcctt cctatgatag tgtaacaaaa ccagacaagg   6420
aaaagtttga gaaagacaaa ccagaaaaag aaagcaaagg aaaagaggtc agagaaaatc   6480
aaaagtaaaa agaaacaaag aattatcttt gtgatcaatt gtttacagcc tatgaaggta   6540
aagtatatgt gtcaactgga cttcaagagg aggtccatgc caaactgact gttttaacaa   6600
atactcatag tcagtgccta tacaagacag tgaagtgacc tctctgtcac tgcaactctg   6660
tgaagcaggg tatcaacatt gacaagaggt tgctgttttt attaccagct gacactgctg   6720
aggagaaacc caatggctac ctagactata gggatagttg tgcaaagtga acattgtaac   6780
tacaccaaac acctttagta cagtccttgc atccattcta tttttaactt ccatatctgc   6840
catattttta caaaatttgt tctagtgcat ttccatggtc cccaattcat agtttattca   6900
taatgctatg tcactatttt tgtaaatgag gtttacgttg aagaaacagt atacaagaac   6960
cctgtctctc aaatgatcag acaaaggtgt tttgccagag agataaaatt tttgctcaaa   7020
accagaaaaa gaattgtaat ggctacagtt tcagttactt ccattttcta gatggcttta   7080
attttgaaag tattttagtc tgttatgttt gtttctatct gaacagttat gtgcctgtaa   7140
agtctcctct aatatttaaa ggattatttt tatgcaaagt attctgtttc agcaagtgca   7200
aattttattc taagtttcag agctctatat ttaatttagg tcaaatgctt tccaaaaagt   7260
aatctaataa atccattcta gaaaaatata tctaaagtat tgctttagaa tagttgttcc   7320
actttctgct gcagtattgc tttgccatct tctgctctca gcaaagctga tagtctatgt   7380
caattaaata ccctatgtta tgtaaatagt tattttatcc tgtggtgcat gtttgggcaa   7440
atatatatat agcctgataa acaacttcta ttaaatcaaa tatgtaccac agtgtatgtg   7500
tcttttgcaa gcttccaaca gggatgtatc ctgtatcatt cattaaacat agtttaaagg   7560
ctatcactaa tgcatgttaa tattgcctat gctgctctat tttactcaat ccattcttca   7620
caagtcttgg ttaaagaatg tcacatattg gtgatagaat gaattcaacc tgctctgtcc   7680
attatgtcaa gcagaataat ttgaagctat ttacaaacac ctttactttt gcacttttaa   7740
ttcaacatga gtatcatatg gtatctctct agatttcaag gaaacacact ggatactgcc   7800
tactgacaaa acctattctt catattttgc taaaaatatg tctaaaactt gcgcaaatat   7860
aaataatgta aaaatataat caactttatt tgtcagcatt ttgtacataa gaaaattatt   7920
```

```
ttcaggttga tgacatcaca atttatttta ctttatgctt ttgcttttga tttttaatca   7980

caattccaaa cttttgaatc cataagattt ttcaatggat aatttcctaa aataaaagtt   8040

agataatggg ttttatggat ttctttgtta taatatattt tctaccattc caataggaga   8100

tacattggtc aaacactcaa acctagatca ttttctacca actatggttg cctcaatata   8160

accttttatt catagatgtt ttttttattt caacttttgt agtatttacg tatgcagact   8220

agtcttattt ttttaattcc tgctgcacta aagctattac aaatataaca tggactttgt   8280

tctttttagc catgaacaaa gtggcaaagt tgtgcaatta cctaacatga tataaatttt   8340

tgtttttttgc acaaaccaaa agtttaatgt taattctttt tacaaaacta tttactgtag   8400

tgtattgaag aactgcatgc agggaattgc tattgctaaa aagaatggtg agctacgtca   8460

ttattgagcc aaaagaataa atttcatttt ttattgcatt tcacttattg gcctctgggg   8520

tttttgttt ttgtttttg ctgttggcag tttaaaatat atataattaa taaaacctgt   8580

gcttgatctg acatttgtat acataaaagt ttacatgaat tttacaacag actagtgcat   8640

gattcaccaa gcagtactac agaacaaagg caaatgaaaa gcagctttgt gcacttttat   8700

gtgtgcaaag gatcaagttc acatgttcca actttcaggt ttgataataa tagtagtaac   8760

cacctacaat agctttcaat ttcaattaac tcccttggct ataagcatct aaactcatct   8820

tctttcaata taattgatgc tatctcctaa ttacttggtg gctaataaat gttacattct   8880

ttgttactta aatgcattat ataaactcct atgtatacat aaggtattaa tgatatagtt   8940

attgagaatt tatattaact ttttttcaa gaacccttgg atttatgtga ggtcaaaacc   9000

aaactcttat tctcagtgga aaactccagt tgtaatgcat atttttaaag acaatttgga   9060

tctaaatatg tatttcataa ttctcccata ataaattata taaggtggct aa           9112
```

<210> SEQ ID NO 66
<211> LENGTH: 9112
<212> TYPE: DNA
<213> ORGANISM: Homo sapiens

<400> SEQUENCE: 66

```
accatagagt gaatctcaga acaggaagcg gaggcataag cagagaggat tctggaaagg     60

tctctttgtt ttcttatcca cagagaaaga aagaaaaaaa attgtaacta atttgtaaac    120

ctctgtggtc aaaaaaaaaa aaaaaaaaaa aagctgaaca gctgcagagg aagacacgtt    180

ataccctaac catcttggat gctgggcttt gttatgctgt aattcataag gctctgtttt    240

atcagagatt atggagcaag aaaactgaag ccaagccaca tcaaggtttg acagggatga    300

gatacctgtc aaggattcat agtagagtgg cttactggga aaggagcaaa gaatctcttc    360

tagggatatt gtaagaataa atgagataat tcacagaagg gacctggagc ttttccggaa    420

aaaggtgctg tgactatcta aggggaaaag ctgagagtct ggaactagcc tatcttccga    480

ggacttagag acaacagtat gggaatttca acgagacgtt tttactttct tttgaccaag    540

attcaaattc tttattccag cccttgataa gtaaataaga aggtaattcg tatgcaagaa    600

gctacacgta attaaatgtg caggatgaaa agatggcaca ggcactgttg gtaccccag     660

gacctgaaag cttccgcctt tttactagag aatctcttgc tgctatcgaa aaacgtgctg    720

cagaagagaa agccaagaag cccaaaaagg aacaagataa tgatgatgag aacaaaccaa    780

agccaaatag tgacttggaa gctggaaaga accttccatt tatttatgga gacattcctc    840

cagagatggt gtcagagccc ctggaggacc tggatcccta ctatatcaat aagaaaactt    900
```

-continued

```
ttatagtaat gaataaagga aaggcaattt cccgattcag tgccacctct gccttgtata     960
ttttaactcc actaaaccct gttaggaaaa ttgctabsaa gattttggta cattctttat    1020
tcagcatgct tatcatgtgc actattttga ccaactgtgt atttatgacc ttgagcaacc    1080
ctcctgactg gacaaagaat gtagagtaca cattcactgg aatctatacc tttgagtcac    1140
ttataaaaat cttggcaaga gggttttgct tagaagattt tacgtttctt cgtgatccat    1200
ggaactggct ggatttcagt gtcattgtga tggcgtatgt aacagaattt gtaagcctag    1260
gcaatgtttc agcccttcga actttcagag tcttgagagc tctgaaaact atttctgtaa    1320
tcccaggttt aaagaccatt gtgggggccc tgatccagtc ggtaaagaag ctttctgatg    1380
tgatgatcct gactgtgttc tgtctgagcg tgtttgctct cattgggctg cagctgttca    1440
tgggcaatct gaggaataaa tgtttgcagt ggcccccaag cgattctgct tttgaaacca    1500
acaccacttc ctactttaat ggcacaatgg attcaaatgg gacatttgtt aatgtaacaa    1560
tgagcacatt taactggaag gattacattg gagatgacag tcacttttat gttttggatg    1620
ggcaaaaaga ccctttactc tgtggaaatg gctcagatgc aggccagtgt ccagaaggat    1680
acatctgtgt gaaggctggt cgaaacccca actatggcta cacaagcttt gacaccttta    1740
gctgggcttt cctgtctcta tttcgactca tgactcaaga ctactgggaa aatctttacc    1800
agttgacatt acgtgctgct gggaaaacat acatgatatt ttttgtcctg gtcattttct    1860
tgggctcatt ttatttggtg aatttgatcc tggctgtggt ggccatggcc tatgaggggc    1920
agaatcaggc caccttggaa gaagcagaac aaaaagaggc cgaatttcag cagatgctcg    1980
aacagcttaa aaagcaacag gaagaagctc aggcagttgc ggcagcatca gctgcttcaa    2040
gagatttcag tggaataggt gggttaggag agctgttgga aagttcttca gaagcatcaa    2100
agttgagttc caaaagtgct aaagaatgga ggaaccgaag gaagaaaaga agacagagag    2160
agcaccttga aggaaacaac aaaggagaga gagacagctt tcccaaatcc gaatctgaag    2220
acagcgtcaa aagaagcagc ttccttttct ccatggatgg aaacagactg accagtgaca    2280
aaaaattctg ctcccctcat cagtctctct tgagtatccg tggctccctg ttttccccaa    2340
gacgcaatag caaaacaagc attttcagtt tcagaggtcg ggcaaaggat gttggatctg    2400
aaaatgactt tgctgatgat gaacacagca catttgaaga cagcgaaagc aggagagact    2460
cactgtttgt gccgcacaga catggagagc gacgcaacag taacggcacc accactgaaa    2520
cggaagtcag aaagagaagg ttaagctctt accagatttc aatggagatg ctggaggatt    2580
cctctggaag gcaaagagcc gtgagcatag ccagcattct gaccaacaca atggaagaac    2640
ttgaagaatc tagacagaaa tgtccgccat gctggtatag atttgccaat gtgttcttga    2700
tctgggactg ctgtgatgca tggttaaaag taaaacatct tgtgaattta attgttatgg    2760
atccatttgt tgatcttgcc atcactattt gcattgtctt aaataccctc tttatggcca    2820
tggagcacta ccccatgact gagcaattca gtagtgtgtt gactgtagga aacctggtct    2880
ttactgggat tttttacagca gaaatggttc tcaagatcat tgccatggat ccttattact    2940
atttccaaga aggctggaat atctttgatg gaattattgt cagcctcagt ttaatggagc    3000
ttggtctgtc aaatgtggag ggattgtctg tactgcgatc attcagactg cttagagttt    3060
tcaagttggc aaaatcctgg cccacactaa atatgctaat taagatcatt ggcaattctg    3120
tgggggctct aggaaacctc accttggtgt tggccatcat cgtcttcatt tttgctgtgg    3180
tcggcatgca gctctttggt aagagctaca aagaatgtgt ctgcaagatc aatgatgact    3240
gtacgctccc acggtggcac atgaacgact tcttccactc cttcctgatt gtgttccgcg    3300
```

-continued

```
tgctgtgtgg agagtggata gagaccatgt gggactgtat ggaggtcgct ggccaaacca   3360
tgtgccttat tgttttcatg ttggtcatgg tcattggaaa ccttgtggtt ctgaacctct   3420
ttctggcctt attgttgagt tcatttagct cagacaacct tgctgctact gatgatgaca   3480
atgaaatgaa taatctgcag attgcagtag gaagaatgca aaagggaatt gattatgtga   3540
aaaataagat gcgggagtgt ttccaaaaag cctttttttag aaagccaaaa gttatagaaa   3600
tccatgaagg caataagata gacagctgca tgtccaataa tactggaatt gaaataagca   3660
aagagcttaa ttatcttaga gatgggaatg gaaccaccag tggtgtaggt actggaagca   3720
gtgttgaaaa atacgtaatc gatgaaaatg attatatgtc attcataaac aaccccagcc   3780
tcaccgtcac agtgccaatt gctgttggag agtctgactt tgaaaactta aatactgaag   3840
agttcagcag tgagtcagaa ctagaagaaa gcaaggagaa attaaatgca accagctcat   3900
ctgaaggaag cacagttgat gttgttctac cccgagaagg tgaacaagct gaaactgaac   3960
ccgaagaaga ccttaaaccg gaagcttgtt ttactgaagg atgtattaaa aagtttccat   4020
tctgtcaagt aagtacagaa gaaggcaaag ggaagatctg gtggaatctt cgaaaaacct   4080
gctacagtat tgttgagcac aactggtttg agactttcat tgtgttcatg atccttctca   4140
gtagtggtgc attggccttt gaagatatat acattgaaca gcgaaagact atcaaaacca   4200
tgctagaata tgctgacaaa gtctttacct atatattcat tctggaaatg cttctcaaat   4260
gggttgctta tggatttcaa acatatttca ctaatgcctg gtgctggcta gatttcttga   4320
tcgttgatgt ttctttggtt agcctggtag ccaatgctct tggctactca gaactcggtg   4380
ccatcaaatc attacggaca ttaagagctt taagacctct aagagcctta tcccggtttg   4440
aaggcatgag ggtggttgtg aatgctcttg ttggagcaat tccctctatc atgaatgtgc   4500
tgttggtctg tctcatcttc tggttgatct ttagcatcat gggtgtgaat ttgtttgctg   4560
gcaagttcta ccactgtgtt aacatgacaa cgggtaacat gtttgacatt agtgatgtta   4620
acaatttgag tgactgtcag gctcttggca agcaagctcg gtggaaaaac gtgaaagtaa   4680
actttgataa tgttggcgct ggctatcttg cactgcttca agtggccaca tttaaaggct   4740
ggatggatat tatgtatgca gctgttgatt cacgagatgt taaacttcag cctgtatatg   4800
aagaaaatct gtacatgtat ttatactttg tcatctttat catctttggg tcattcttca   4860
ctctgaatct attcattggt gtcatcatag ataacttcaa ccagcagaaa aagaagtttg   4920
gaggtcaaga catctttatg acagaggaac agaaaaaata ttacaatgca atgaagaaac   4980
ttggatccaa gaaacctcag aaacccatac ctcgcccagc aaacaaattc caaggaatgg   5040
tctttgattt tgtaaccaga caagtctttg atatcagcat catgatcctc atctgcctca   5100
acatggtcac catgatggtg gaaacggatg accagggcaa atacatgacc ctagttttgt   5160
cccggatcaa cctagtgttc attgttctgt tcactggaga atttgtgctg aagctcgtct   5220
ccctcagaca ctactacttc actataggct ggaacatctt tgactttgtg gtggtgattc   5280
tctccattgt aggtatgttt ctggctgaga tgatagaaaa gtattttgtg tcccctacct   5340
tgttccgagt gatccgtctt gccaggattg gccgaatcct acgtctgatc aaaggagcaa   5400
aggggatccg cacgctgctc tttgctttga tgatgtccct tcctgcgttg tttaacatcg   5460
gcctcctgct cttcctggtc atgtttatct atgccatctt tgggatgtcc aactttgcct   5520
atgttaaaaa ggaagctgga attgatgaca tgttcaactt tgagaccttt ggcaacagca   5580
tgatctgctt gttccaaatt acaacctctg ctggatggga tggattgcta gcacctattc   5640
```

-continued

```
ttaatagtgc accacccgac tgtgaccctg acacaattca ccctggcagc tcagttaagg   5700
gagactgtgg gaacccatct gttgggattt tctttttgt cagttacatc atcatatcct   5760
tcctggtggt ggtgaacagt tacatcgcgg tcatcctgga gaacttcagt gttgctactg   5820
aagaaagtgc agagcccctg agtgaggatg actttgagat gttctatgag gtttgggaaa   5880
agtttgatcc cgatgcgacc cagtttatag agttctctaa actctctgat tttgcagctg   5940
ccctggatcc tcctcttctc atagcaaaac ccaacaaagt ccagcttatt gccatggatc   6000
tgcccatggt cagtggtgac cggatccact gtcttgatat tttatttgcc tttacaaagc   6060
gtgttttggg tgagagtgga gagatggatg cccttcgaat acagatggaa gacaggttta   6120
tggcatcaaa cccctccaaa gtctcttatg agcctattac aaccactttg aaacgtaaac   6180
aagaggaggt gtctgccgct atcattcagc gtaatttcag atgttatctt ttaaagcaaa   6240
ggttaaaaaa tatatcaagt aactataaca aagaggcaat aaaggggagg attgacttac   6300
ctataaaaca agacatgatt attgacaaac tgaatgggaa ctccactcca gaaaaaacag   6360
atgggagttc ctctaccacc tctcctcctt cctatgatag tgtaacaaaa ccagacaagg   6420
aaaagtttga gaaagacaaa ccagaaaaag aaagcaaagg aaaagaggtc agagaaaatc   6480
aaaagtaaaa agaaacaaag aattatcttt gtgatcaatt gtttacagcc tatgaaggta   6540
aagtatatgt gtcaactgga cttcaagagg aggtccatgc caaactgact gttttaacaa   6600
atactcatag tcagtgccta tacaagacag tgaagtgacc tctctgtcac tgcaactctg   6660
tgaagcaggg tatcaacatt gacaagaggt tgctgttttt attaccagct gacactgctg   6720
aggagaaacc caatggctac ctagactata gggatagttg tgcaaagtga acattgtaac   6780
tacaccaaac acctttagta cagtccttgc atccattcta tttttaactt ccatatctgc   6840
catattttta caaaatttgt tctagtgcat ttccatggtc cccaattcat agtttattca   6900
taatgctatg tcactatttt tgtaaatgag gtttacgttg aagaaacagt atacaagaac   6960
cctgtctctc aaatgatcag acaaaggtgt tttgccagag agataaaatt tttgctcaaa   7020
accagaaaaa gaattgtaat ggctacagtt tcagttactt ccatttctca gatggcttta   7080
attttgaaag tattttagtc tgttatgttt gtttctatct gaacagttat gtgcctgtaa   7140
agtctcctct aatatttaaa ggattatttt tatgcaaagt attctgtttc agcaagtgca   7200
aattttattc taagtttcag agctctatat ttaatttagg tcaaatgctt tccaaaaagt   7260
aatctaataa atccattcta gaaaaatata tctaaagtat tgctttagaa tagttgttcc   7320
actttctgct gcagtattgc tttgccatct tctgctctca gcaaagctga tagtctatgt   7380
caattaaata ccctatgtta tgtaaatagt tattttatcc tgtggtgcat gtttgggcaa   7440
atatatatat agcctgataa acaacttcta ttaaatcaaa tatgtaccac agtgtatgtg   7500
tcttttgcaa gcttccaaca gggatgtatc ctgtatcatt cattaaacat agtttaaagg   7560
ctatcactaa tgcatgttaa tattgcctat gctgctctat tttactcaat ccattcttca   7620
caagtcttgg ttaaagaatg tcacatattg gtgatagaat gaattcaacc tgctctgtcc   7680
attatgtcaa gcagaataat ttgaagctat ttacaaacac ctttactttt gcacttttaa   7740
ttcaacatga gtatcatatg gtatctctct agatttcaag gaaacacact ggatactgcc   7800
tactgacaaa acctattctt catattttgc taaaaatatg tctaaaactt gcgcaaatat   7860
aaataatgta aaaatataat caactttatt tgtcagcatt ttgtacataa gaaaattatt   7920
ttcaggttga tgacatcaca atttatttta ctttatgctt ttgcttttga tttttaatca   7980
caattccaaa cttttgaatc cataagattt ttcaatggat aatttcctaa aataaaagtt   8040
```

```
agataatggg ttttatggat ttctttgtta taatatattt tctaccattc caataggaga   8100

tacattggtc aaacactcaa acctagatca ttttctacca actatggttg cctcaatata   8160

accttttatt catagatgtt ttttttattt caacttttgt agtatttacg tatgcagact   8220

agtcttattt ttttaattcc tgctgcacta aagctattac aaatataaca tggactttgt   8280

tctttttagc catgaacaaa gtggcaaagt tgtgcaatta cctaacatga tataaatttt   8340

tgtttttgc acaaaccaaa agtttaatgt taattctttt tacaaaacta tttactgtag   8400

tgtattgaag aactgcatgc agggaattgc tattgctaaa aagaatggtg agctacgtca   8460

ttattgagcc aaaagaataa atttcatttt ttattgcatt tcacttattg gcctctgggg   8520

tttttgttt ttgtttttg ctgttggcag tttaaaatat atataattaa taaaacctgt   8580

gcttgatctg acatttgtat acataaaagt ttacatgaat tttacaacag actagtgcat   8640

gattcaccaa gcagtactac agaacaaagg caaatgaaaa gcagctttgt gcacttttat   8700

gtgtgcaaag gatcaagttc acatgttcca actttcaggt ttgataataa tagtagtaac   8760

cacctacaat agctttcaat ttcaattaac tcccttggct ataagcatct aaactcatct   8820

tctttcaata taattgatgc tatctcctaa ttacttggtg gctaataaat gttacattct   8880

ttgttactta aatgcattat ataaactcct atgtatacat aaggtattaa tgatatagtt   8940

attgagaatt tatattaact tttttttcaa gaacccttgg atttatgtga ggtcaaaacc   9000

aaactcttat tctcagtgga aaactccagt tgtaatgcat atttttaaag acaatttgga   9060

tctaaatatg tatttcataa ttctcccata ataaattata taaggtggct aa           9112
```

<210> SEQ ID NO 67
<211> LENGTH: 1951
<212> TYPE: PRT
<213> ORGANISM: Homo sapiens
<220> FEATURE:
<221> NAME/KEY: MISC_FEATURE
<222> LOCATION: (122)..(122)
<223> OTHER INFORMATION: Xaa = any amino acid

<400> SEQUENCE: 67

```
Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Met Asn Lys Gly
                85                  90                  95

Lys Ala Ile Ser Arg Phe Ser Ala Thr Ser Ala Leu Tyr Ile Leu Thr
            100                 105                 110

Pro Leu Asn Pro Val Arg Lys Ile Ala Xaa Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160
```

-continued

```
Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190

Leu Asp Phe Ser Val Ile Val Met Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
        275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
        355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Gly Gln Asn Gln
            420                 425                 430

Ala Thr Leu Glu Glu Ala Glu Gln Lys Glu Ala Glu Phe Gln Gln Met
        435                 440                 445

Leu Glu Gln Leu Lys Lys Gln Gln Glu Glu Ala Gln Ala Val Ala Ala
    450                 455                 460

Ala Ser Ala Ala Ser Arg Asp Phe Ser Gly Ile Gly Gly Leu Gly Glu
465                 470                 475                 480

Leu Leu Glu Ser Ser Ser Glu Ala Ser Lys Leu Ser Ser Lys Ser Ala
                485                 490                 495

Lys Glu Trp Arg Asn Arg Arg Lys Lys Arg Arg Gln Arg Glu His Leu
            500                 505                 510

Glu Gly Asn Asn Lys Gly Glu Arg Asp Ser Phe Pro Lys Ser Glu Ser
        515                 520                 525

Glu Asp Ser Val Lys Arg Ser Ser Phe Leu Phe Ser Met Asp Gly Asn
    530                 535                 540

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Arg Asn Ser Lys Thr Ser
                565                 570                 575

Ile Phe Ser Phe Arg Gly Arg Ala Lys Asp Val Gly Ser Glu Asn Asp
```

-continued

```
            580                 585                 590

Phe Ala Asp Asp Glu His Ser Thr Phe Glu Asp Ser Glu Ser Arg Arg
        595                 600                 605

Asp Ser Leu Phe Val Pro His Arg His Gly Glu Arg Arg Asn Ser Asn
    610                 615                 620

Gly Thr Thr Thr Glu Thr Glu Val Arg Lys Arg Arg Leu Ser Ser Tyr
625                 630                 635                 640

Gln Ile Ser Met Glu Met Leu Glu Asp Ser Ser Gly Arg Gln Arg Ala
                645                 650                 655

Val Ser Ile Ala Ser Ile Leu Thr Asn Thr Met Glu Glu Leu Glu Glu
            660                 665                 670

Ser Arg Gln Lys Cys Pro Pro Cys Trp Tyr Arg Phe Ala Asn Val Phe
        675                 680                 685

Leu Ile Trp Asp Cys Cys Asp Ala Trp Leu Lys Val Lys His Leu Val
    690                 695                 700

Asn Leu Ile Val Met Asp Pro Phe Val Asp Leu Ala Ile Thr Ile Cys
705                 710                 715                 720

Ile Val Leu Asn Thr Leu Phe Met Ala Met Glu His Tyr Pro Met Thr
                725                 730                 735

Glu Gln Phe Ser Ser Val Leu Thr Val Gly Asn Leu Val Phe Thr Gly
            740                 745                 750

Ile Phe Thr Ala Glu Met Val Leu Lys Ile Ile Ala Met Asp Pro Tyr
        755                 760                 765

Tyr Tyr Phe Gln Glu Gly Trp Asn Ile Phe Asp Gly Ile Ile Val Ser
    770                 775                 780

Leu Ser Leu Met Glu Leu Gly Leu Ser Asn Val Glu Gly Leu Ser Val
785                 790                 795                 800

Leu Arg Ser Phe Arg Leu Leu Arg Val Phe Lys Leu Ala Lys Ser Trp
                805                 810                 815

Pro Thr Leu Asn Met Leu Ile Lys Ile Ile Gly Asn Ser Val Gly Ala
            820                 825                 830

Leu Gly Asn Leu Thr Leu Val Leu Ala Ile Ile Val Phe Ile Phe Ala
        835                 840                 845

Val Val Gly Met Gln Leu Phe Gly Lys Ser Tyr Lys Glu Cys Val Cys
    850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
            900                 905                 910

Ile Val Phe Met Leu Val Met Val Ile Gly Asn Leu Val Val Leu Asn
        915                 920                 925

Leu Phe Leu Ala Leu Leu Leu Ser Ser Phe Ser Ser Asp Asn Leu Ala
    930                 935                 940

Ala Thr Asp Asp Asp Asn Glu Met Asn Asn Leu Gln Ile Ala Val Gly
945                 950                 955                 960

Arg Met Gln Lys Gly Ile Asp Tyr Val Lys Asn Lys Met Arg Glu Cys
                965                 970                 975

Phe Gln Lys Ala Phe Phe Arg Lys Pro Lys Val Ile Glu Ile His Glu
            980                 985                 990

Gly Asn Lys Ile Asp Ser Cys Met  Ser Asn Asn Thr Gly  Ile Glu Ile
        995                 1000                 1005
```

```
Ser Lys  Glu Leu Asn Tyr Leu  Arg Asp Gly Asn Gly  Thr Thr Ser
    1010                 1015                 1020

Gly Val  Gly Thr Gly Ser Ser  Val Glu Lys Tyr Val  Ile Asp Glu
    1025                 1030                 1035

Asn Asp  Tyr Met Ser Phe Ile  Asn Asn Pro Ser Leu  Thr Val Thr
    1040                 1045                 1050

Val Pro  Ile Ala Val Gly Glu  Ser Asp Phe Glu Asn  Leu Asn Thr
    1055                 1060                 1065

Glu Glu  Phe Ser Ser Glu Ser  Glu Leu Glu Glu Ser  Lys Glu Lys
    1070                 1075                 1080

Leu Asn  Ala Thr Ser Ser Ser  Glu Gly Ser Thr Val  Asp Val Val
    1085                 1090                 1095

Leu Pro  Arg Glu Gly Glu Gln  Ala Glu Thr Glu Pro  Glu Glu Asp
    1100                 1105                 1110

Leu Lys  Pro Glu Ala Cys Phe  Thr Glu Gly Cys Ile  Lys Lys Phe
    1115                 1120                 1125

Pro Phe  Cys Gln Val Ser Thr  Glu Glu Gly Lys Gly  Lys Ile Trp
    1130                 1135                 1140

Trp Asn  Leu Arg Lys Thr Cys  Tyr Ser Ile Val Glu  His Asn Trp
    1145                 1150                 1155

Phe Glu  Thr Phe Ile Val Phe  Met Ile Leu Leu Ser  Ser Gly Ala
    1160                 1165                 1170

Leu Ala  Phe Glu Asp Ile Tyr  Ile Glu Gln Arg Lys  Thr Ile Lys
    1175                 1180                 1185

Thr Met  Leu Glu Tyr Ala Asp  Lys Val Phe Thr Tyr  Ile Phe Ile
    1190                 1195                 1200

Leu Glu  Met Leu Leu Lys Trp  Val Ala Tyr Gly Phe  Gln Thr Tyr
    1205                 1210                 1215

Phe Thr  Asn Ala Trp Cys Trp  Leu Asp Phe Leu Ile  Val Asp Val
    1220                 1225                 1230

Ser Leu  Val Ser Leu Val Ala  Asn Ala Leu Gly Tyr  Ser Glu Leu
    1235                 1240                 1245

Gly Ala  Ile Lys Ser Leu Arg  Thr Leu Arg Ala Leu  Arg Pro Leu
    1250                 1255                 1260

Arg Ala  Leu Ser Arg Phe Glu  Gly Met Arg Val Val  Val Asn Ala
    1265                 1270                 1275

Leu Val  Gly Ala Ile Pro Ser  Ile Met Asn Val Leu  Leu Val Cys
    1280                 1285                 1290

Leu Ile  Phe Trp Leu Ile Phe  Ser Ile Met Gly Val  Asn Leu Phe
    1295                 1300                 1305

Ala Gly  Lys Phe Tyr His Cys  Val Asn Met Thr Thr  Gly Asn Met
    1310                 1315                 1320

Phe Asp  Ile Ser Asp Val Asn  Asn Leu Ser Asp Cys  Gln Ala Leu
    1325                 1330                 1335

Gly Lys  Gln Ala Arg Trp Lys  Asn Val Lys Val Asn  Phe Asp Asn
    1340                 1345                 1350

Val Gly  Ala Gly Tyr Leu Ala  Leu Leu Gln Val Ala  Thr Phe Lys
    1355                 1360                 1365

Gly Trp  Met Asp Ile Met Tyr  Ala Ala Val Asp Ser  Arg Asp Val
    1370                 1375                 1380

Lys Leu  Gln Pro Val Tyr Glu  Glu Asn Leu Tyr Met  Tyr Leu Tyr
    1385                 1390                 1395
```

-continued

```
Phe Val  Ile Phe Ile Ile Phe  Gly Ser Phe Phe Thr  Leu Asn Leu
    1400                 1405                 1410

Phe Ile  Gly Val Ile Ile Asp  Asn Phe Asn Gln Gln  Lys Lys Lys
    1415                 1420                 1425

Phe Gly  Gly Gln Asp Ile Phe  Met Thr Glu Glu Gln  Lys Lys Tyr
    1430                 1435                 1440

Tyr Asn  Ala Met Lys Lys Leu  Gly Ser Lys Lys Pro  Gln Lys Pro
    1445                 1450                 1455

Ile Pro  Arg Pro Ala Asn Lys  Phe Gln Gly Met Val  Phe Asp Phe
    1460                 1465                 1470

Val Thr  Arg Gln Val Phe Asp  Ile Ser Ile Met Ile  Leu Ile Cys
    1475                 1480                 1485

Leu Asn  Met Val Thr Met Met  Val Glu Thr Asp Asp  Gln Gly Lys
    1490                 1495                 1500

Tyr Met  Thr Leu Val Leu Ser  Arg Ile Asn Leu Val  Phe Ile Val
    1505                 1510                 1515

Leu Phe  Thr Gly Glu Phe Val  Leu Lys Leu Val Ser  Leu Arg His
    1520                 1525                 1530

Tyr Tyr  Phe Thr Ile Gly Trp  Asn Ile Phe Asp Phe  Val Val Val
    1535                 1540                 1545

Ile Leu  Ser Ile Val Gly Met  Phe Leu Ala Glu Met  Ile Glu Lys
    1550                 1555                 1560

Tyr Phe  Val Ser Pro Thr Leu  Phe Arg Val Ile Arg  Leu Ala Arg
    1565                 1570                 1575

Ile Gly  Arg Ile Leu Arg Leu  Ile Lys Gly Ala Lys  Gly Ile Arg
    1580                 1585                 1590

Thr Leu  Leu Phe Ala Leu Met  Met Ser Leu Pro Ala  Leu Phe Asn
    1595                 1600                 1605

Ile Gly  Leu Leu Leu Phe Leu  Val Met Phe Ile Tyr  Ala Ile Phe
    1610                 1615                 1620

Gly Met  Ser Asn Phe Ala Tyr  Val Lys Lys Glu Ala  Gly Ile Asp
    1625                 1630                 1635

Asp Met  Phe Asn Phe Glu Thr  Phe Gly Asn Ser Met  Ile Cys Leu
    1640                 1645                 1650

Phe Gln  Ile Thr Thr Ser Ala  Gly Trp Asp Gly Leu  Leu Ala Pro
    1655                 1660                 1665

Ile Leu  Asn Ser Ala Pro Pro  Asp Cys Asp Pro Asp  Thr Ile His
    1670                 1675                 1680

Pro Gly  Ser Ser Val Lys Gly  Asp Cys Gly Asn Pro  Ser Val Gly
    1685                 1690                 1695

Ile Phe  Phe Phe Val Ser Tyr  Ile Ile Ile Ser Phe  Leu Val Val
    1700                 1705                 1710

Val Asn  Ser Tyr Ile Ala Val  Ile Leu Glu Asn Phe  Ser Val Ala
    1715                 1720                 1725

Thr Glu  Glu Ser Ala Glu Pro  Leu Ser Glu Asp Asp  Phe Glu Met
    1730                 1735                 1740

Phe Tyr  Glu Val Trp Glu Lys  Phe Asp Pro Asp Ala  Thr Gln Phe
    1745                 1750                 1755

Ile Glu  Phe Ser Lys Leu Ser  Asp Phe Ala Ala Ala  Leu Asp Pro
    1760                 1765                 1770

Pro Leu  Leu Ile Ala Lys Pro  Asn Lys Val Gln Leu  Ile Ala Met
    1775                 1780                 1785

Asp Leu  Pro Met Val Ser Gly  Asp Arg Ile His Cys  Leu Asp Ile
```

```
    1790                1795                1800

Leu Phe  Ala Phe Thr Lys Arg  Val Leu Gly Glu Ser  Gly Glu Met
    1805                1810                1815

Asp Ala  Leu Arg Ile Gln Met  Glu Asp Arg Phe Met  Ala Ser Asn
    1820                1825                1830

Pro Ser  Lys Val Ser Tyr Glu  Pro Ile Thr Thr Thr  Leu Lys Arg
    1835                1840                1845

Lys Gln  Glu Glu Val Ser Ala  Ala Ile Ile Gln Arg  Asn Phe Arg
    1850                1855                1860

Cys Tyr  Leu Leu Lys Gln Arg  Leu Lys Asn Ile Ser  Ser Asn Tyr
    1865                1870                1875

Asn Lys  Glu Ala Ile Lys Gly  Arg Ile Asp Leu Pro  Ile Lys Gln
    1880                1885                1890

Asp Met  Ile Ile Asp Lys Leu  Asn Gly Asn Ser Thr  Pro Glu Lys
    1895                1900                1905

Thr Asp  Gly Ser Ser Ser Thr  Thr Ser Pro Pro Ser  Tyr Asp Ser
    1910                1915                1920

Val Thr  Lys Pro Asp Lys Glu  Lys Phe Glu Lys Asp  Lys Pro Glu
    1925                1930                1935

Lys Glu  Ser Lys Gly Lys Glu  Val Arg Glu Asn Gln  Lys
    1940                1945                1950


<210> SEQ ID NO 68
<211> LENGTH: 1951
<212> TYPE: PRT
<213> ORGANISM: Homo sapiens
<220> FEATURE:
<221> NAME/KEY: MISC_FEATURE
<222> LOCATION: (122)..(122)
<223> OTHER INFORMATION: Xaa = any amino acid

<400> SEQUENCE: 68

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Met Asn Lys Gly
                85                  90                  95

Lys Ala Ile Ser Arg Phe Ser Ala Thr Ser Ala Leu Tyr Ile Leu Thr
            100                 105                 110

Pro Leu Asn Pro Val Arg Lys Ile Ala Xaa Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190
```

-continued

```
Leu Asp Phe Ser Val Ile Val Met Ala Tyr Val Thr Glu Phe Val Ser
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
        275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
        355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Gly Gln Asn Gln
            420                 425                 430

Ala Thr Leu Glu Glu Ala Glu Gln Lys Glu Ala Glu Phe Gln Gln Met
        435                 440                 445

Leu Glu Gln Leu Lys Lys Gln Gln Glu Glu Ala Gln Ala Val Ala Ala
    450                 455                 460

Ala Ser Ala Ala Ser Arg Asp Phe Ser Gly Ile Gly Gly Leu Gly Glu
465                 470                 475                 480

Leu Leu Glu Ser Ser Ser Glu Ala Ser Lys Leu Ser Ser Lys Ser Ala
                485                 490                 495

Lys Glu Trp Arg Asn Arg Arg Lys Lys Arg Arg Gln Arg Glu His Leu
            500                 505                 510

Glu Gly Asn Asn Lys Gly Glu Arg Asp Ser Phe Pro Lys Ser Glu Ser
        515                 520                 525

Glu Asp Ser Val Lys Arg Ser Ser Phe Leu Phe Ser Met Asp Gly Asn
    530                 535                 540

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Arg Asn Ser Lys Thr Ser
                565                 570                 575

Ile Phe Ser Phe Arg Gly Arg Ala Lys Asp Val Gly Ser Glu Asn Asp
            580                 585                 590

Phe Ala Asp Asp Glu His Ser Thr Phe Glu Asp Ser Glu Ser Arg Arg
        595                 600                 605
```

-continued

```
Asp Ser Leu Phe Val Pro His Arg His Gly Glu Arg Arg Asn Ser Asn
    610                 615                 620

Gly Thr Thr Thr Glu Thr Glu Val Arg Lys Arg Arg Leu Ser Ser Tyr
625                 630                 635                 640

Gln Ile Ser Met Glu Met Leu Glu Asp Ser Ser Gly Arg Gln Arg Ala
                645                 650                 655

Val Ser Ile Ala Ser Ile Leu Thr Asn Thr Met Glu Glu Leu Glu Glu
            660                 665                 670

Ser Arg Gln Lys Cys Pro Pro Cys Trp Tyr Arg Phe Ala Asn Val Phe
        675                 680                 685

Leu Ile Trp Asp Cys Cys Asp Ala Trp Leu Lys Val Lys His Leu Val
    690                 695                 700

Asn Leu Ile Val Met Asp Pro Phe Val Asp Leu Ala Ile Thr Ile Cys
705                 710                 715                 720

Ile Val Leu Asn Thr Leu Phe Met Ala Met Glu His Tyr Pro Met Thr
                725                 730                 735

Glu Gln Phe Ser Ser Val Leu Thr Val Gly Asn Leu Val Phe Thr Gly
            740                 745                 750

Ile Phe Thr Ala Glu Met Val Leu Lys Ile Ile Ala Met Asp Pro Tyr
        755                 760                 765

Tyr Tyr Phe Gln Glu Gly Trp Asn Ile Phe Asp Gly Ile Ile Val Ser
    770                 775                 780

Leu Ser Leu Met Glu Leu Gly Leu Ser Asn Val Glu Gly Leu Ser Val
785                 790                 795                 800

Leu Arg Ser Phe Arg Leu Leu Arg Val Phe Lys Leu Ala Lys Ser Trp
                805                 810                 815

Pro Thr Leu Asn Met Leu Ile Lys Ile Ile Gly Asn Ser Val Gly Ala
            820                 825                 830

Leu Gly Asn Leu Thr Leu Val Leu Ala Ile Ile Val Phe Ile Phe Ala
        835                 840                 845

Val Val Gly Met Gln Leu Phe Gly Lys Ser Tyr Lys Glu Cys Val Cys
    850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
            900                 905                 910

Ile Val Phe Met Leu Val Met Val Ile Gly Asn Leu Val Val Leu Asn
        915                 920                 925

Leu Phe Leu Ala Leu Leu Leu Ser Ser Phe Ser Ser Asp Asn Leu Ala
    930                 935                 940

Ala Thr Asp Asp Asp Asn Glu Met Asn Asn Leu Gln Ile Ala Val Gly
945                 950                 955                 960

Arg Met Gln Lys Gly Ile Asp Tyr Val Lys Asn Lys Met Arg Glu Cys
                965                 970                 975

Phe Gln Lys Ala Phe Phe Arg Lys Pro Lys Val Ile Glu Ile His Glu
            980                 985                 990

Gly Asn Lys Ile Asp Ser Cys Met  Ser Asn Asn Thr Gly  Ile Glu Ile
        995                 1000                1005

Ser Lys  Glu Leu Asn Tyr Leu  Arg Asp Gly Asn Gly  Thr Thr Ser
    1010                1015                1020

Gly Val  Gly Thr Gly Ser Ser  Val Glu Lys Tyr Val  Ile Asp Glu
```

-continued

```
    1025                1030                1035

Asn Asp  Tyr Met Ser Phe Ile  Asn Asn Pro Ser Leu  Thr Val Thr
    1040                1045                1050

Val Pro  Ile Ala Val Gly Glu  Ser Asp Phe Glu Asn  Leu Asn Thr
    1055                1060                1065

Glu Glu  Phe Ser Ser Glu Ser  Glu Leu Glu Glu Ser  Lys Glu Lys
    1070                1075                1080

Leu Asn  Ala Thr Ser Ser Ser  Glu Gly Ser Thr Val  Asp Val Val
    1085                1090                1095

Leu Pro  Arg Glu Gly Glu Gln  Ala Glu Thr Glu Pro  Glu Glu Asp
    1100                1105                1110

Leu Lys  Pro Glu Ala Cys Phe  Thr Glu Gly Cys Ile  Lys Lys Phe
    1115                1120                1125

Pro Phe  Cys Gln Val Ser Thr  Glu Glu Gly Lys Gly  Lys Ile Trp
    1130                1135                1140

Trp Asn  Leu Arg Lys Thr Cys  Tyr Ser Ile Val Glu  His Asn Trp
    1145                1150                1155

Phe Glu  Thr Phe Ile Val Phe  Met Ile Leu Leu Ser  Ser Gly Ala
    1160                1165                1170

Leu Ala  Phe Glu Asp Ile Tyr  Ile Glu Gln Arg Lys  Thr Ile Lys
    1175                1180                1185

Thr Met  Leu Glu Tyr Ala Asp  Lys Val Phe Thr Tyr  Ile Phe Ile
    1190                1195                1200

Leu Glu  Met Leu Leu Lys Trp  Val Ala Tyr Gly Phe  Gln Thr Tyr
    1205                1210                1215

Phe Thr  Asn Ala Trp Cys Trp  Leu Asp Phe Leu Ile  Val Asp Val
    1220                1225                1230

Ser Leu  Val Ser Leu Val Ala  Asn Ala Leu Gly Tyr  Ser Glu Leu
    1235                1240                1245

Gly Ala  Ile Lys Ser Leu Arg  Thr Leu Arg Ala Leu  Arg Pro Leu
    1250                1255                1260

Arg Ala  Leu Ser Arg Phe Glu  Gly Met Arg Val Val  Val Asn Ala
    1265                1270                1275

Leu Val  Gly Ala Ile Pro Ser  Ile Met Asn Val Leu  Leu Val Cys
    1280                1285                1290

Leu Ile  Phe Trp Leu Ile Phe  Ser Ile Met Gly Val  Asn Leu Phe
    1295                1300                1305

Ala Gly  Lys Phe Tyr His Cys  Val Asn Met Thr Thr  Gly Asn Met
    1310                1315                1320

Phe Asp  Ile Ser Asp Val Asn  Asn Leu Ser Asp Cys  Gln Ala Leu
    1325                1330                1335

Gly Lys  Gln Ala Arg Trp Lys  Asn Val Lys Val Asn  Phe Asp Asn
    1340                1345                1350

Val Gly  Ala Gly Tyr Leu Ala  Leu Leu Gln Val Ala  Thr Phe Lys
    1355                1360                1365

Gly Trp  Met Asp Ile Met Tyr  Ala Ala Val Asp Ser  Arg Asp Val
    1370                1375                1380

Lys Leu  Gln Pro Val Tyr Glu  Glu Asn Leu Tyr Met  Tyr Leu Tyr
    1385                1390                1395

Phe Val  Ile Phe Ile Ile Phe  Gly Ser Phe Phe Thr  Leu Asn Leu
    1400                1405                1410

Phe Ile  Gly Val Ile Ile Asp  Asn Phe Asn Gln Gln  Lys Lys Lys
    1415                1420                1425
```

-continued

```
Phe Gly Gly Gln Asp Ile Phe Met Thr Glu Glu Gln Lys Lys Tyr
    1430                1435                1440

Tyr Asn Ala Met Lys Lys Leu Gly Ser Lys Lys Pro Gln Lys Pro
    1445                1450                1455

Ile Pro Arg Pro Ala Asn Lys Phe Gln Gly Met Val Phe Asp Phe
    1460                1465                1470

Val Thr Arg Gln Val Phe Asp Ile Ser Ile Met Ile Leu Ile Cys
    1475                1480                1485

Leu Asn Met Val Thr Met Met Val Glu Thr Asp Asp Gln Gly Lys
    1490                1495                1500

Tyr Met Thr Leu Val Leu Ser Arg Ile Asn Leu Val Phe Ile Val
    1505                1510                1515

Leu Phe Thr Gly Glu Phe Val Leu Lys Leu Val Ser Leu Arg His
    1520                1525                1530

Tyr Tyr Phe Thr Ile Gly Trp Asn Ile Phe Asp Phe Val Val Val
    1535                1540                1545

Ile Leu Ser Ile Val Gly Met Phe Leu Ala Glu Met Ile Glu Lys
    1550                1555                1560

Tyr Phe Val Ser Pro Thr Leu Phe Arg Val Ile Arg Leu Ala Arg
    1565                1570                1575

Ile Gly Arg Ile Leu Arg Leu Ile Lys Gly Ala Lys Gly Ile Arg
    1580                1585                1590

Thr Leu Leu Phe Ala Leu Met Met Ser Leu Pro Ala Leu Phe Asn
    1595                1600                1605

Ile Gly Leu Leu Leu Phe Leu Val Met Phe Ile Tyr Ala Ile Phe
    1610                1615                1620

Gly Met Ser Asn Phe Ala Tyr Val Lys Lys Glu Ala Gly Ile Asp
    1625                1630                1635

Asp Met Phe Asn Phe Glu Thr Phe Gly Asn Ser Met Ile Cys Leu
    1640                1645                1650

Phe Gln Ile Thr Thr Ser Ala Gly Trp Asp Gly Leu Leu Ala Pro
    1655                1660                1665

Ile Leu Asn Ser Ala Pro Pro Asp Cys Asp Pro Asp Thr Ile His
    1670                1675                1680

Pro Gly Ser Ser Val Lys Gly Asp Cys Gly Asn Pro Ser Val Gly
    1685                1690                1695

Ile Phe Phe Phe Val Ser Tyr Ile Ile Ile Ser Phe Leu Val Val
    1700                1705                1710

Val Asn Ser Tyr Ile Ala Val Ile Leu Glu Asn Phe Ser Val Ala
    1715                1720                1725

Thr Glu Glu Ser Ala Glu Pro Leu Ser Glu Asp Asp Phe Glu Met
    1730                1735                1740

Phe Tyr Glu Val Trp Glu Lys Phe Asp Pro Asp Ala Thr Gln Phe
    1745                1750                1755

Ile Glu Phe Ser Lys Leu Ser Asp Phe Ala Ala Ala Leu Asp Pro
    1760                1765                1770

Pro Leu Leu Ile Ala Lys Pro Asn Lys Val Gln Leu Ile Ala Met
    1775                1780                1785

Asp Leu Pro Met Val Ser Gly Asp Arg Ile His Cys Leu Asp Ile
    1790                1795                1800

Leu Phe Ala Phe Thr Lys Arg Val Leu Gly Glu Ser Gly Glu Met
    1805                1810                1815
```

-continued

```
Asp Ala  Leu Arg Ile Gln Met  Glu Asp Arg Phe Met  Ala Ser Asn
    1820                 1825                 1830

Pro Ser  Lys Val Ser Tyr Glu  Pro Ile Thr Thr Thr  Leu Lys Arg
    1835                 1840                 1845

Lys Gln  Glu Glu Val Ser Ala  Ala Ile Ile Gln Arg  Asn Phe Arg
    1850                 1855                 1860

Cys Tyr  Leu Leu Lys Gln Arg  Leu Lys Asn Ile Ser  Ser Asn Tyr
    1865                 1870                 1875

Asn Lys  Glu Ala Ile Lys Gly  Arg Ile Asp Leu Pro  Ile Lys Gln
    1880                 1885                 1890

Asp Met  Ile Ile Asp Lys Leu  Asn Gly Asn Ser Thr  Pro Glu Lys
    1895                 1900                 1905

Thr Asp  Gly Ser Ser Ser Thr  Thr Ser Pro Pro Ser  Tyr Asp Ser
    1910                 1915                 1920

Val Thr  Lys Pro Asp Lys Glu  Lys Phe Glu Lys Asp  Lys Pro Glu
    1925                 1930                 1935

Lys Glu  Ser Lys Gly Lys Glu  Val Arg Glu Asn Gln  Lys
    1940                 1945                 1950
```

<210> SEQ ID NO 69
<211> LENGTH: 1380
<212> TYPE: DNA
<213> ORGANISM: Homo sapiens

<400> SEQUENCE: 69

```
aatgtattta tttaattgat gataaactgt aataaaatca tagttgtttg ctctaaagta     60

gatatgaaag gtcagatgaa acaataacat acatctggat tgagaaatat cttaataact    120

gatggattat ttttattttc tttatgtatt gtgtgcttca atatcctaat aaataatatt    180

agctaggttc actgatgtat agaatctttt tctacattta gatatttctt gcaaatgttt    240

taccagaaag caacacaaaa atactatcag tgagtatgtg tttacactgt tctctaagga    300

gtcaaattcc tcaccttgaa aataattcat cccaggaaga gaaaaggttt tcaaaagact    360

agagcaggcc acaagggagc tttcgcaaaa ctctacacgt aaagggtaat gtaaacttaa    420

aacctatttt tcaaacagta atttatatat cttttaattt tagtagttta tgtgtgaaac    480

aatcatgcaa aacaacaaag tgataaaatt ttttaaaaaa attagtgaga tgcaaataac    540

tgaatatgta aaaggtctca tacatattta tatgtagtag ataagttaca ttttttttagt    600

gtgttgggaa attttagctc acatcacctc tctactgtca tcttggggca ctttcatgac    660

tacccatgct tcatgcaggt ttactttcct ccctgtgaca gaggataatg ggaatgtttt    720

ttctttggct caattttgtg tgtgtccgcc agtagatggc gtaccacttt gagtgcgatc    780

ggcctttttt tctttctttt ttttttccct caaagctgtt ttctgatata tgttgggtac    840

catagagtga atctcagaac aggaagcgga ggcataagca gagaggattc tggaaaggtc    900

tctttgtttt cttatccaca gagaaagaaa gaaaaaaaat tgtaactaat ttgtaaacct    960

ctgtggtcaa aaaaaaaaaa aaaaaaaaaa gctgaacagc tgcagaggaa gacacgttat   1020

accctaacca tcttggatgc tgggctttgt tatgctgtaa ttcataaggc tctgttttat   1080

caggtaagct gacaaaacat ttcattatct gcaccataga acctagctac caggtcattt   1140

tccttacttt aaaatcatct tcatgctgct atttttaacc cagtgttgtt taaatgtaaa   1200

ttacaggaac caaaggcatc gtttgatgtg taaactgctt actatttctt tatctttcaa   1260

agaaaataga gcctgtctgg aaatggtgat ttatggtaca tactaggcat caatggtctt   1320
```

gtgtttttgt agatgcttat gattaattgt attcagaaaa aatatttttt attatactta 1380

<210> SEQ ID NO 70
<211> LENGTH: 840
<212> TYPE: DNA
<213> ORGANISM: Homo sapiens

<400> SEQUENCE: 70
agggaagaac agaaggatgc tcaggagtgc cagcatgcct tcagaaagac taaatggatc 60
aaggctgcca aagaaggggg agcacccctg tcccaaccct aggatcctgg cagtggttcc 120
tggtcccatt cttcctaaat catgctaggg catgctttta acaagggtca aatatcttgc 180
tttgcatcat ccttgctttc tcgatccagg gccataaaaa aaaaaggaat aaaacccaga 240
cacagagcca gagcacccct atgccaaatg tcaaagatta taggctaatt tcacctgtat 300
tctctttcta cagagattat ggagcaagaa aactgaagcc aagccacatc aaggtttgac 360
agggatgaga tacctgtcaa ggattcatag tagagtggct tactgggaaa ggagcaaaga 420
atctcttcta gggatattgt aagaataaat gagataattc acagaaggga cctggagctt 480
ttccggaaaa aggtgctgtg actatctaag gtaactaaac aacttctggg tataagtttg 540
tttttgtgga aaataaacta aaatctctac tatttaacaa ggacagctgt atcaggacca 600
aaagaaggca gaggggtgtt ttcttccttc ctctaccagt ttgttcttcc aaagaggcaa 660
atacatacag ggagacatag cacagatgac cttagggaat ggaatgatgc caaaggctgt 720
tgatgtaaga aagagagatt aactcagttt ttttttgtt tttgtttttt tgttgttgtt 780
gttgttgttt tgagacagag tctctctctg tcgcccaggc tggagtgcag tggcatgaac 840

<210> SEQ ID NO 71
<211> LENGTH: 780
<212> TYPE: DNA
<213> ORGANISM: Homo sapiens

<400> SEQUENCE: 71
gatatattaa attttatgta ttttaataaa ttataatgtg catataatca ttaataatat 60
atatattcca caccaaggca tcagtaagaa ttaattttta aagtctgctc taatgtgaat 120
ataaaattat gtaagaactc tgtataataa gctcacagag tacaagaaag gagaggaaaa 180
aagtaaaaga gaactgcgaa agaactatga gggatttcca aacagcaaaa ttgtcattga 240
agccatgaga aactctactc actaaattct ttaatttctc agcctaccca aatattgggc 300
aaaccctaat tctcttgcag gggaaaagct gagagtctgg aactagccta tcttccgagg 360
acttagagac aacagtatgg gaatttcaac gagacgtttt tactttcttt tgaccaagat 420
tcaaattctt tattccagcc cttgataagt aaataagaag gtaaaggact atttatttgt 480
aaaaagtttt tcatgatttt gtgatggcac cttgttccat atcatctcag ataaatcaga 540
ataatttgtg aaaattactc ggtgatttcc acattagata ttttaaacct aatgttattt 600
ctaaaacaaa aaccaaccag gagaatccaa ttaagtaaaa tgtatgtatt aatataaatt 660
agctattccc atctggaaaa gggcagccat ttctgtgttg aggtgcctca atgatactga 720
ggctgagaca ggttagatga tacaggcata ccattagcag cagactcaat actaacccag 780

<210> SEQ ID NO 72
<211> LENGTH: 1025
<212> TYPE: DNA
<213> ORGANISM: Homo sapiens

<400> SEQUENCE: 72

```
acaaagttat gaaaaggcgg ggggcaggat gcagaataat taagcaattt tattgacaaa     60

ctttactggc attactcttt tgctgaaagt atactatatt ttggcttaca gtgtcaaaac    120

agaatttttt aaatgctttt aaaaaatgga caaaattata gatattcttg agtttaaata    180

taatgtttat atattatata tactgtacat tgtagaatgg ctaaatcaaa ctaattaaca    240

ttaagtacag acttttgata gatttatgaa cttggcttat tgagaatgag gttgaatgat    300

gatgttttca agttcaaatg tgtagtgcag tactaaaagc atgacttaat gtttatagct    360

ttaaaaagtt actaaagaat gacattttgg ttgatgttct tatgcccaat cgcttgcttt    420

cctaactctt gtgcaatttt tctttttatt gcaggtaatt cgtatgcaag aagctacacg    480

taattaaatg tgcaggatga aaagatggca caggcactgt tggtaccccc aggacctgaa    540

agcttccgcc tttttactag agaatctctt gctgctatcg aaaaacgtgc tgcagaagag    600

aaagccaaga agcccaaaaa ggaacaagat aatgatgatg agaacaaacc aaagccaaat    660

agtgacttgg aagctggaaa gaaccttcca tttatttatg gagacattcc tccagagatg    720

gtgtcagagc ccctggagga cctggatccc tactatatca ataagaaagt gagtattgat    780

tttagacttc taataaatct ttaatgaaac tcttaactgt aatatacttt tctgggcctt    840

atatacagca tcacaatttt tcttctgtta aagattttat aatactcttc actgtcactt    900

atttttatca caatataata aaacaaacat ttataagaaa tgaagtcaag agttggttac    960

agtcaggaaa tatgaataga tgaatgattt ctacaatttc acagtgataa ttcagatagt   1020

caaaa                                                               1025
```

<210> SEQ ID NO 73
<211> LENGTH: 433
<212> TYPE: DNA
<213> ORGANISM: Homo sapiens

<400> SEQUENCE: 73

```
tgtaacyata tgttaattta aacatctaac atgtttgtag ttatgatata tcaactggtt     60

taaacaaacc agtttgaaca aacaaattcy atttttttaaa aaggtcctca tgtatgtaag    120

ctccttaaat aagcccatgt ctaatttagt aattttactc gtattttctg tttcagactt    180

ttatagtaat gaataaagga aaggcaattt cccgattcag tgccacctct gccttgtata    240

ttttaactcc actaaaccct gttaggaaaa ttgctabsaa gattttggta cattcatatc    300

cttttaatgt gaattgccta aatgctattt ctaacagttg attttaaaga aaatgtcagt    360

tatattttca agtatctgta aaatttcttt gagattaatg gtaacattgt tagtttaatt    420

catttatttg cat                                                       433
```

<210> SEQ ID NO 74
<211> LENGTH: 450
<212> TYPE: DNA
<213> ORGANISM: Homo sapiens

<400> SEQUENCE: 74

```
gagtgcacca aggccatatc acaggctttg aagtttctta ttattttatc attgttttaa     60

aacaaataat attaatttca cagtttttgc atcgataaac ttttttgtgt gttttggatc    120

atttataaat ggccatggta acctactaac atttattcct taactataat ctactttatt    180

cagcatgctt atcatgtgca ctattttgac caactgtgta tttatgacct tgagcaaccc    240

tcctgactgg acaaagaatg tagagtaagt aggaataact tctgggaatg agaaatgcac    300
```

-continued

```
actcaaattc tctagcaatc tccttgtggg tatagcctga cttatggttt ccacttctgt    360

ctaagaaaag ttattttcat aatatgcagc cggtaaggga ggtctttcgg gggagctatt    420

cttctacgag gtaagtattt tcccacaaaa                                     450


<210> SEQ ID NO 75
<211> LENGTH: 701
<212> TYPE: DNA
<213> ORGANISM: Homo sapiens

<400> SEQUENCE: 75

aaaatttacc atttgyggct ttccattaca tttctatcag ataactctgc gctagtaggt     60

caaactagat gattatccat aagatacatg aaactattat tctaaaaccc aaatagttaa    120

accagattag attcctaaag aatatatttt ctcttcagtt taactctttg ctcaggcttg    180

taaaactaac taaatgaata gattatttgg taaatagaag taaggaacaa tattttaatg    240

aattgaaaaa ccacaaaagg ataggatttg ctatgattga aaacatttat tttaacagtt    300

caagcaaaat tgttaatttt ggcttggatg tttttcctag gtacacattc actggaatct    360

atacctttga gtcacttata aaaatcttgg caagagggtt ttgcttagaa gattttacgt    420

ttcttcgtga tccatggaac tggctggatt tcagtgtcat tgtgatggcg tgagtaactt    480

tgaaaatttg ataagcgcaa aggagtgaaa atagtcatag tacaaacaag gtctttgtgt    540

catatattaa atgtagagct ttcttgttag tcaagttaac tatatgggtt gtgtattttc    600

agaatacata ttagaataca tattgcaatg taaatatatc cagtaaatga tcaataaatg    660

gggttatctt catgtcatat agtctttctc ttcatcaaaa t                        701


<210> SEQ ID NO 76
<211> LENGTH: 286
<212> TYPE: DNA
<213> ORGANISM: Homo sapiens

<400> SEQUENCE: 76

atttgttaaa ctcacagggc tctatgtgcc aaacccagca ttaagtcctt atttagtata     60

aactttgcca aaactatcag taactctgat ttaattctgc aggtatgtaa cagaatttgt    120

aagcctaggc aatgtttcag cccttcgaac tttcagagtc ttgagagctc tgaaaactat    180

ttctgtaatc ccaggtaaga agaaactggt gtaaggtagt aggcccctta tatctccaac    240

ttttcttgtg tgttattgtg tttgtgtgtg aactccccta ttacag                   286


<210> SEQ ID NO 77
<211> LENGTH: 515
<212> TYPE: DNA
<213> ORGANISM: Homo sapiens

<400> SEQUENCE: 77

gtaagaagaa actggtgtaa ggtagtaggc cccttatatc tccaactttt cttgtgtgtt     60

attgtgtttg tgtgtgaact cccctattac agatatgtga cagagtttgt ggacctgggc    120

aatgtctcag cgttgagaac attcagagtt ctccgagcac tgaaaacaat ttcagtcatt    180

ccaggtgaga gctaggttaa acaccgaggt tgactttaat tattgagttt gaaatcaatt    240

tatatgactt acagcattag ccttgttgct tattattaca gttcatcccg gtaaataatg    300

ccaaatgatg tttcaatgtc agtttagctc ctaaaatttt ataaattaca tgcgtattta    360

taaagtcagc ctttgagttt aacagaaaat tgcatgagac atcttcaaaa aatgctaatt    420

tgggcctctt gcgctctctc tctctctttt tcactaccat ggctttacta acagatttgg    480
```

```
attttaccat tcgctgcaga tgtagttcaa aaatg                              515


<210> SEQ ID NO 78
<211> LENGTH: 564
<212> TYPE: DNA
<213> ORGANISM: Homo sapiens

<400> SEQUENCE: 78

aaacttcctg actagatatt taaaccttca tattgaattt ccagcaagca cactgttcat    60

gtgtaaaatc tgctgttcat ctatttccca aatcatcagg ctatccatac agctttggtg   120

tctaaatagt caagcaatca tttatggggg aaagagaatg tgtgtgacta ttaagaaatc   180

atgatttctg gcactcttcc tcaggtaacc tatagttctc tctctgcagg tttaaagacc   240

attgtggggg ccctgatcca gtcggtaaag aagctttctg atgtgatgat cctgactgtg   300

ttctgtctga gcgtgtttgc tctcattggg ctgcagctgt tcatgggcaa tctgaggaat   360

aaatgtttgc agtggccccc aagcgattct gcttttgaaa ccaacaccac ttcctacttt   420

aatggcacaa tggattcaaa tgggacattt gttaatgtaa caatgagcac atttaactgg   480

aaggataaca ttggagatga cagtaagaag tattacatta tgttaacctt agtgttgctg   540

aatgaatttt caactataaa tagt                                          564


<210> SEQ ID NO 79
<211> LENGTH: 497
<212> TYPE: DNA
<213> ORGANISM: Homo sapiens

<400> SEQUENCE: 79

tgagactgtg ggtgtacagc cacctttgta aataactgaa atagtccaac tctgatttat    60

tactaatact aatgtgaata ggattaatat gaaataaaat gggttttttt ttgtattaac   120

aggtcacttt tatgttttgg atgggcaaaa agacccttta ctctgtggaa atggttcaga   180

tgcagggtaa gaaacataat atatattttt aagatataga actctttgcg aaaaaaaaaa   240

gtaggtagga aaacaactac atggttatat gtgtagcctt accatgtatg caataaagag   300

cagtgctgct cccctaggaa gtgccttgtc tgccttaccg gattgccact ggtcctaaac   360

tcacagcaat taaaaattat ccctttgtga agacctttcc ccaaaatttc acagttaaga   420

tgttcttaaa ttgatgctcc aatgtgtgaa ggcccagagt ctgtctttgc tgtacatcta   480

tcagagctgt taggaaa                                                  497


<210> SEQ ID NO 80
<211> LENGTH: 501
<212> TYPE: DNA
<213> ORGANISM: Homo sapiens

<400> SEQUENCE: 80

aaagagtaaa aatatggtaa ggtcagagcc aaaagtgtgt ggttgctagc tttctgccat    60

tctaaatgtc trwaaawatt tatttgcatc taaattttct atcggtcttc ctagtgaatt   120

tcatctgata agtttcacgg tggcaatca cctaaagtgt tctggaaatt aaagcaagat   180

aattcgtcac agatagcagc tttgggtttt gaaaattcct ataagtcaaa taaattgaaa   240

ttgctgtaat ttctaaactg accctacctc catttctctc tcttatagcc agtgtccaga   300

aggatacatc tgtgtgaagg ctggtcgaaa ccccaactat ggctacacaa gctttgacac   360

ctttagctgg gctttcctgt ctctatttcg actcatgact caagactact gggaaaatct   420
```

```
ttaccagttg gtaaggtcca aatgagcatg cataacattt atttttatag acatgtatga    480

aatgaaaagc ataggctgag t                                             501


<210> SEQ ID NO 81
<211> LENGTH: 432
<212> TYPE: DNA
<213> ORGANISM: Homo sapiens

<400> SEQUENCE: 81

agctaattag tctactgact atctaactgt ggtaatcaga tatttatttg ggacattat     60

actaaaatac tgatggaatt atccccccatt tcccctagac attacgtgct gctgggaaaa  120

catacatgat attttttgtc ctggtcattt tcttgggctc attttatttg gtgaatttga   180

tcctggctgt ggtggccatg gcctatgagg ggcagaatca ggccaccttg gaagaagcag   240

aacaaaaaga ggccgaattt cagcagatgc tcgaacagct taaaaagcaa caggaagaag   300

ctcaggtact gagtgataaa mgcaaagatt tatcattatt attmttagtt tctaagtaga   360

aatagtgtta tactatagag ggtagattgg aactgctttt tcattttata tatmggcatt   420

gtcattagac ac                                                       432


<210> SEQ ID NO 82
<211> LENGTH: 489
<212> TYPE: DNA
<213> ORGANISM: Homo sapiens

<400> SEQUENCE: 82

tgcaaactgt tttcaaagct ctgtgttcta aatagtgcct ggctttgttt tatgacaggc    60

agttgcggca gcatcagctg cttcaagaga tttcagtgga ataggtgggt taggagagct   120

gttggaaagt tcttcagaag catcaaagtt gagttccaaa agtgctaaag aatggaggaa   180

ccgaaggaag aaaagaagac agagagagca ccttgaagga aacaacaaag gagagagaga   240

cagctttccc aaatccgaat ctgaagacag cgtcaaaaga agcagcttcc ttttctccat   300

ggatggaaac agactgacca gtgacaaaaa attctgctcc cctcatcagg tatgattttc   360

tactaagtgc tctggtttct ttgtcattgc tattgctttt tagtttttgt attttgtttt   420

ggtacacttt tgtactatct gtacttcagt tgagggacag ggaactaaca tttaatatag   480

ttgtttaaa                                                           489


<210> SEQ ID NO 83
<211> LENGTH: 653
<212> TYPE: DNA
<213> ORGANISM: Homo sapiens

<400> SEQUENCE: 83

gtgaagacta aatgaagtgg ttgtatactt agtaaattgc aaatcagtat tgttagtcag    60

aaaaacactc tttgtactta aatttgcttt aataaaaata tcaaaatata tgtgtcctct   120

ataaatttga ttatccatgt ttaagggcaa gagtatacta actccaaaga aaacagatcc   180

tttaatatta atatttatta aataattgcg ttcttcccct acccccatcc cattcctttc   240

ctttttgctt tctctgcagt ctctcttgag tatccgtggc tccctgtttt ccccaagacg   300

caatagcaaa acaagcattt tcagtttcag aggtcgggca aaggatgttg gatctgaaaa   360

tgactttgct gatgatgaac acagcacatt tgaagacagc gaaagcagga gagactcact   420

gtttgtgccg cacagacatg gagagcgacg caacagtaac gttagtcagg ccagtatgtc   480

atccaggatg gtgccagggc ttccagcaaa tggggaagat gcacagcact gtggattgca   540
```

atggtgtggt ttccttggtg ggtggacctt cagctctaac gtcacctact gggcaacttc 600
cccagaggtg ataatagatg acctagctgc tactgacatt attcaccaat ttg 653

<210> SEQ ID NO 84
<211> LENGTH: 566
<212> TYPE: DNA
<213> ORGANISM: Homo sapiens
<220> FEATURE:
<221> NAME/KEY: misc_feature
<222> LOCATION: (477)..(477)
<223> OTHER INFORMATION: n = a, c, t or g

<400> SEQUENCE: 84
gaattctctt aaaggtacta cctgtgatac tttttttaaa aaaaaactgt ttataactta 60
gcaataattc aatattttat tcttgaaatt cttacctgga aaattgcatg tagcatgatt 120
tgcaaagaaa tgctatgtgg tgttgtatta cttattggga agagtggttt gagccatcag 180
tatttggttt gcagggcacc accactgaaa cggaagtcag aaagagaagg ttaagctctt 240
accagatttc aatggagatg ctggaggatt cctctggaag gcaaagagcc gtgagcatag 300
ccagcattct gaccaacaca atggaaggta agagcaggtc atggaacagc caactttctg 360
tgattatgtg ctttgtgaac tattccttct tttcatagaa ttactgaagt ctgttaccca 420
gatcgaacta tatattagac ctaagaatgt gatatatggt gtacattatc acattgntta 480
caaaactaat attggcctta ttctttttga cttgggtcct taccttactt gcagagtgat 540
atttcaacac ttgatattat atcaat 566

<210> SEQ ID NO 85
<211> LENGTH: 748
<212> TYPE: DNA
<213> ORGANISM: Homo sapiens

<400> SEQUENCE: 85
tagtcatttt aaaagcaaaa tattaaattc aaagtgctta ttttctgtat tcaaaagaga 60
aaaaagtcga tctatatgac attttaatta acattttctg aaaatattta atgggattgt 120
cttctcaagt ttcttaagta atatgaactt ctattttcaa atataagcat caattttgtt 180
aaataatgta aaatctacta gcaataataa ctcatttttg ttgttattta ctactcttcc 240
ttgttattgt ccctccagaa cttgaagaat ctagacagaa atgtccgcca tgctggtata 300
gatttgccaa tgtgttcttg atctgggact gctgtgatgc atggttaaaa gtaaaacatc 360
ttgtgaattt aattgttatg gatccatttg ttgatcttgc catcactatt tgcattgtct 420
taaataccct ctttatggcc atggagcact accccatgac tgagcaattc agtagtgtgt 480
tgactgtagg aaacctggta agtacatttg aagtttactt atttactttg gtagatgtgg 540
gagagataga ccaaagggaa agatgtattt gtgctgtgtt gaacccaaaa attatatcct 600
ctttcctcat agaaagaaat atctaaggaa tattacaggg aatctcagag atacagccta 660
aaactcaact ggtatgaatg ctgattgttt aggccaatgt ctgtgctgat tgatcatggt 720
gtcttaccag ttgtaaacgt ctcaaaat 748

<210> SEQ ID NO 86
<211> LENGTH: 664
<212> TYPE: DNA
<213> ORGANISM: Homo sapiens

<400> SEQUENCE: 86

-continued

```
ctaagacttg aattgatttg tcactattct ctcactttaa attttagata tttttattcc      60

tgtctaatgt tcttctttat aaattcgtgt agcatcagtg ttttcagtgc tcttgatagt     120

agtgctgatc tctaattttt taggtcttta ctgggatttt tacagcagaa atggttctca     180

agatcattgc catggatcct tattactatt tccaagaagg ctggaatatc tttgatggaa     240

ttattgtcag cctcagttta atggagcttg gtctgtcaaa tgtggaggga ttgtctgtac     300

tgcgatcatt cagactggta tctatttata tatatccctg tcgctcattg gcacaacatt     360

tattttgaaa ttgaatcaat gtatatttat ataattatta attttaattt taaatttaca     420

tcaatatgtg acattctaag aaaacatgta aacatccyct ttaaagctaa accattttct     480

aagaatgatg aaagcattca aaatactcta taatgattag gtatgtaggg cacattagaa     540

aacctacaag tactttctaa aactgtgttt taagtttatg aagctttttt ggccttacag     600

tctgtaaaga tacgcaaata aaaatttaga ccccagttaa ttttagcttt ttattaaccc     660

tact                                                                  664
```

<210> SEQ ID NO 87
<211> LENGTH: 750
<212> TYPE: DNA
<213> ORGANISM: Homo sapiens

<400> SEQUENCE: 87

```
tatttttatt tttgcactta aatgatatta tgaccagatt tacaattcta atattgttaa      60

cactattttt tctggatttg aaattgaatc agttcagtat attttgagtt tttacatcta     120

ccacgtgtgg ttctatgata ccacatacta ataaaataat gtctaaaatt atattatgat     180

tactactaac agcatctttt cacttgatta cagcttagag ttttcaagtt ggcaaaatcc     240

tggcccacac taaatatgct aattaagatc attggcaatt ctgtgggggc tctaggaaac     300

ctcaccttgg tgttggccat catcgtcttc atttttgctg tggtcggcat gcagctcttt     360

ggtaagagct acaaagaatg tgtctgcaag atcaatgatg actgtacgct cccacggtgg     420

cacatgaacg acttcttcca ctccttcctg attgtgttcc gcgtgctgtg tggagagtgg     480

atagagacca tgtgggactg tatggaggtc gctggccaaa ccatgtgcct tattgttttc     540

atgttggtca tggtcattgg aaaccttgtg gtatgtatgt agtacaaatg ctcataaatt     600

agaacaagag cagacagtag ctaggaacgt ggccagatgt agtaaacata tctctggttt     660

atagtaagtg gcctagactg aaatccccct attagcactc agagaataag caagttattt     720

aacttctcct gggctctggt ttcccatttt                                      750
```

<210> SEQ ID NO 88
<211> LENGTH: 768
<212> TYPE: DNA
<213> ORGANISM: Homo sapiens

<400> SEQUENCE: 88

```
ccttagagca ggatattagg tcctttaaag agtgtgtgac ttagacatgg catctgaaat      60

atagtaagca ttcaataaac atttgttgaa ataattttag caaagatcta tgagttccct     120

ttttaggctg ttatttaaat gcatatttca atattaarat aggcattttt cttttttttct     180

tttaggttct gaacctcttt ctggccttat tgttgagttc atttagctca gacaaccttg     240

ctgctactga tgatgacaat gaaatgaata atctgcagat tgcagtagga agaatgcaaa     300

agggaattga ttatgtgaaa aataagatgc gggagtgttt ccaaaaagcc tttttttagaa     360

agccaaaagt tatagaaatc catgaaggca ataagataga cagctgcatg tccaataata     420
```

```
ctggaattga aataagcaaa gagcttaatt atcttagaga tgggaatgga accaccagtg    480

gtgtaggtac tggaagcagt gttgaaaaat acgtaatcga tgaaaatgat tatatgtcat    540

tcataaacaa ccccagcctc accgtcacag tgccaattgc tgttggagag tctgactttg    600

aaaacttaaa tactgaagag ttcagcagtg agtcagaact agaagaaagc aaggaggtaa    660

ggaatgcttt taaatttttt gttccatttc ctatgataac catgtactac agttatttac    720

tattttcatt gtgcttatat gcattatcga aaagcaatga ttgtaagt                 768
```

<210> SEQ ID NO 89
<211> LENGTH: 471
<212> TYPE: DNA
<213> ORGANISM: Homo sapiens

<400> SEQUENCE: 89

```
taattattag tacataatga tcagtaatgc taatagagtt aaatgctatc actacatttt     60

ttttcacaca atgacacagt atttcccagt tagttaaata aaagggggaa aatcacatct    120

ttgaaatggg attttgtttc cagaaattaa atgcaaccag ctcatctgaa ggaagcacag    180

ttgatgttgt tctaccccga gaaggtgaac aagctgaaac tgaacccgaa gaagacctta    240

aaccggaagc ttgttttact gaaggtaaac aagctctgat gtgattaaat acaatctccc    300

cttgttcttt acggagactg aatatgcctc atttaaaaaa aaaaatttag caaacgaggt    360

gtggtggctt atgcctgtaa ccccaaaatt ttgggaggct acggtaggag gattgcttga    420

ccccaggagt ttgagaccac cctgggaaat gtagtaaggc tttgcctcta c             471
```

<210> SEQ ID NO 90
<211> LENGTH: 623
<212> TYPE: DNA
<213> ORGANISM: Homo sapiens

<400> SEQUENCE: 90

```
gaattctaag tagctggctg agtatataag tctgagaata attcattata caggagggat     60

gctgacgata actaggaaat gaaggagatg gttaccctat gaaatgatta cctggaagtg    120

gagtggggaa ggggcaagaa agtttatttt ttcctattta agattaaaat atattttta     180

attaactata tttsattttt aggatgtatt aaaaagtttc cattctgtca agtaagtaca    240

gaagaaggca aagggaagat ctggtggaat cttcgaaaaa cctgctacag tattgttgag    300

cacaactggt ttgagacttt cattgtgttc atgatccttc tcagtagtgg tgcattggta    360

agtgaaatgc atattggcaa gaatcagatt ctggtgaaat agtttattct ccaaaattac    420

cagatgcaaa cactgagctt cagaatcaaa agaaaaggca tatctgtgtc ttgcagagct    480

tggcacccaa ggtttaacga tgcaaaattc agttctgaac aaatcagcac catgaaacag    540

ccagatggaa tttctcatct ggtgtttatc taacagatgt tttcctcact gagacaacca    600

tttgcagaga cattctgtaa cca                                            623
```

<210> SEQ ID NO 91
<211> LENGTH: 520
<212> TYPE: DNA
<213> ORGANISM: Homo sapiens

<400> SEQUENCE: 91

```
ctagttagtc tttagatttg tctcatgttc aatgtttatg taaaatatca ataatcaaaa     60

ttattctttt gtactcacta ttatactaag caattttttc aaatatttag aagaagcaag    120
```

-continued

```
ccatttaagt aaaataaaat atttttgatt cataggcctt tgaagatata tacattgaac    180

agcgaaagac tatcaaaacc atgctagaat atgctgacaa agtctttacc tatatattca    240

ttctggaaat gcttctcaaa tgggttgctt atggatttca aacatatttc actaatgcct    300

ggtgctggct agatttcttg atcgttgatg taagtatttt aagtgatttt tataaaattg    360

tttttaaaag aggcaagttt gacatttcat atgtttctgt tattaaaact ttcactaata    420

atgacataat tatgcagtta tttaaacaaa actgtaacat atgcaacaat gaggaatatc    480

tcatgggaaa gagtagagga ggtcctaaac atgggcagtg                          520
```

<210> SEQ ID NO 92
<211> LENGTH: 595
<212> TYPE: DNA
<213> ORGANISM: Homo sapiens

<400> SEQUENCE: 92

```
ctaactaata atttaagcac acatccatga aggatctggc attgaactca atcctgaatt     60

atcagtggta tatgcacaag ttgaaaaggg gtccatggta taaaatatct aactggagat    120

attgacacgt gttgataaat atgggcaagt attctggttt cattggttaa aaaaaagcaa    180

tagtatgaga tgagactggc aatataagat gaccccacta tgtggaagat gaaagttgcc    240

aaggtatgtc caaattagta tttagtctgc attaaataga taccacaccc tataccttca    300

gtcaacagtt tatttcttgg tgaactaatt aatttttttt tccttttgta ggtttctttg    360

gttagcctgg tagccaatgc tcttggctac tcagaactcg gtgccatcaa atcattacgg    420

acattaagag ctttaagacc tctaagagcc ttatcccggt ttgaaggcat gagggtaaga    480

agaatagaca ctctaattat tcatgtcaaa aattacatgt aggtaatgat ttagatagaa    540

aagggtgcca tactcttctg atatttattt caatagaaat tacagaatta gaagc         595
```

<210> SEQ ID NO 93
<211> LENGTH: 787
<212> TYPE: DNA
<213> ORGANISM: Homo sapiens

<400> SEQUENCE: 93

```
ccagcataca aacattttct gactccatct tactatacca ggtttttaat gatttctttt     60

catactgtag catattttgc tttccttaaa accttagctc tttagttgtg tcattgtttg    120

ttttccttca aatatgtgct agaaaaatta gaagaaacaa cttgtccacc tagattttta    180

tttaactctt ttcaagcaca tattaatact aaacaaatac attgaaggaa tggtttccat    240

tcaaaaggtt tgtaagctat gttcccctcg ctgtctcttc taggtggttg tgaatgctct    300

tgttggagca attccctcta tcatgaatgt gctgttggtc tgtctcatct tctggttgat    360

ctttagcatc atgggtgtga atttgtttgc tggcaagttc taccactgtg ttaacatgac    420

aacgggtaac atgtttgaca ttagtgatgt taacaatttg agtgactgtc aggctcttgg    480

caagcaagct cggtggaaaa acgtgaaagt aaactttgat aatgttggcg ctggctatct    540

tgcactgctt caagtggtaa gtggctactg tacgagtttt gaaaaagttt tcaagatgtt    600

tcaaggaaga ttatttccct gatgttcttc gtttgaatga ctaacatttg acagcatgaa    660

aaaaagttaa tgataacacc tataatatca gcttgaattg atcataaaaa agatgttaca    720

attattttat aatgtatttt ccttagtgtt aagcttttag tatgttttaa tgtgatttta    780

tatttct                                                              787
```

-continued

<210> SEQ ID NO 94
<211> LENGTH: 438
<212> TYPE: DNA
<213> ORGANISM: Homo sapiens

<400> SEQUENCE: 94
aaaggaaaca agttccagac tttaaataca aatgtttttc tatttcaatt ttatttcaat 60
ctcttgatat gaaatttcac aatattgtac aaaaagttat ttgttataat actgtcagat 120
tttcatctgg ttaaatgtca ttgttaggtg aaatttttat gaacaattca aatatatgtt 180
atttacaggc cacatttaaa ggctggatgg atattatgta tgcagctgtt gattcacgag 240
atgtaagtat cactcaaata ttatttatag gttctagatt tcttatggtg aatattggtg 300
gtaatttaaa cactgataca tccaaaattc tatattagaa catttaatat tgcatataaa 360
aaatgaacag tctgcttcaa tatagatgat gcttgattaa tgtgtgccta atatacaata 420
tgtagctaat atgaaacg 438

<210> SEQ ID NO 95
<211> LENGTH: 637
<212> TYPE: DNA
<213> ORGANISM: Homo sapiens

<400> SEQUENCE: 95
gtaaggcaca atgggaaaag agaatcaaga acaatcataa aacttgcaaa ccttcatttt 60
actagatcat actagtttta aaaaattgtt tttgtagaac aatatctcag ggtaaggcaa 120
aagtagcact gtattaagta acagcactca ataaattact gatttagtgt aagtatttat 180
agtatttttc atattattta atattttcaa tatcatttag gttaaacttc agcctgtata 240
tgaagaaaat ctgtacatgt atttatactt tgtcatcttt atcatctttg ggtcattctt 300
cactctgaat ctattcattg gtgtcatcat agataacttc aaccagcaga aaaagaagat 360
aagtattctt tagcttttac ctttcttcat tctggggttc tgtctgttaa tacagccaaa 420
taaccagaat acctgtggtc atgacagact taaatcatgt ttatattatt ttcagttgcc 480
catgtggtta tttaagctgc agggattcca gcctctagtc agtggctcct ctcaaagttt 540
atctattgga tagctttctg acccaaaaat gtgtccactc cttcggaccc atccaacggg 600
tctccagtgc tttagcttgg cttacagagc ctttcag 637

<210> SEQ ID NO 96
<211> LENGTH: 637
<212> TYPE: DNA
<213> ORGANISM: Homo sapiens

<400> SEQUENCE: 96
acccttgtgc ctacttttaa acatagtata atcaaattag gatcctgtag cgatcagagt 60
tttatgtacg taaggatttt gcataatatt aagatattca gaatttcaca taaatgggaa 120
aagcaggata aatgtatatg taggaggata atatccactt aaaaattaga aaagattaaa 180
ggaaagacaa atatttttttg tgaaagtact attggaacac agaattgtaa ccagttttat 240
actatgtctt tactttggag gtcaagacat ctttatgaca gaggaacaga aaaaatatta 300
caatgcaatg aagaaacttg gatccaagaa acctcagaaa cccatacctc gcccagcagt 360
aagaattact tgtctccttt aatgttccaa agccatgcgt ccatatggtc aaattgagca 420
atgctctgga gcagaacata ttaggtgata tcaccaatat tgagccctaa ttataaagtt 480
catattttgc atcataattc acaacttctg cactcattag gagttaccac attccaaaaa 540

-continued

```
aaggaggtaa tgttctttat aatttgtgag ttgaaaactt ctagctcagg gttcctaata    600

aatacttcca aagcaaggtt cactttcctg ctaccaa                             637
```

<210> SEQ ID NO 97
<211> LENGTH: 759
<212> TYPE: DNA
<213> ORGANISM: Homo sapiens

<400> SEQUENCE: 97

```
tatataaacc aaatatgctt tgtttagcta tataaatttt ttttccattt tttttaacat     60

gaagagaaaa aaagcacaca aaattgtttg gggtaatatg aggagggtgc acatccatcc    120

cgtatgtgga agggctttat ctacaatttt actgcattat tctttatgaa atatatatag    180

taaccttatt tctcttctct cactttctag aacaaattcc aaggaatggt ctttgatttt    240

gtaaccagac aagtctttga tatcagcatc atgatcctca tctgcctcaa catggtcacc    300

atgatggtgg aaacggatga ccagggcaaa tacatgaccc tagttttgtc ccggatcaac    360

ctagtgttca ttgttctgtt cactggagaa tttgtgctga agctcgtctc cctcagacac    420

tactacttca ctataggctg gaacatcttt gactttgtgg tggtgattct ctccattgta    480

ggtaagaaca gcttaattac caagaggtat agttacagag aaacagttgc cccaggacct    540

tctagctgat taacatggaa attaggtctg agaataataa tgcatataga tgtaaagttc    600

aacactagca tatttgaata aaaactctga aacctgggtt tattcacaaa gctaactagt    660

tagaaaccat gttaggaata ccagatttgg gaaagaggtg aagaagacag gaaataaaca    720

ttatcaggta ctctcctaat cttaaaccaa ggtcacagg                           759
```

<210> SEQ ID NO 98
<211> LENGTH: 3975
<212> TYPE: DNA
<213> ORGANISM: Homo sapiens

<400> SEQUENCE: 98

```
aatctgtaat gctaatgcag ggagtggatc caaatattta ataaaggctc atattcataa     60

caagtttgtt gtgttcatag accttaaaaa agataaagcc atcatgtaaa gtgaaaagat    120

attatctgtt tagctgtgtt ctatgttttc cataggtatg tttctggctg agatgataga    180

aaagtatttt gtgtccccta ccttgttccg agtgatccgt cttgccagga ttggccgaat    240

cctacgtctg atcaaaggag caaaggggat ccgcacgctg ctctttgctt tgatgatgtc    300

ccttcctgcg ttgtttaaca tcggcctcct gctcttcctg gtcatgttta tctatgccat    360

ctttgggatg tccaactttg cctatgttaa aaaggaagct ggaattgatg acatgttcaa    420

ctttgagacc tttggcaaca gcatgatctg cttgttccaa attacaacct ctgctggatg    480

ggatggattg ctagcaccta ttcttaatag tgcaccaccc gactgtgacc ctgacacaat    540

tcaccctggc agctcagtta agggagactg tgggaaccca tctgttggga ttttcttttt    600

tgtcagttac atcatcatat ccttcctggt ggtggtgaac agttacatcg cggtcatcct    660

ggagaacttc agtgttgcta ctgaagaaag tgcagagccc ctgagtgagg atgactttga    720

gatgttctat gaggtttggg aaaagtttga tcccgatgcg acccagttta tagagttctc    780

taaactctct gattttgcag ctgccctgga tcctcctctt ctcatagcaa aacccaacaa    840

agtccagctt attgccatgg atctgcccat ggtcagtggt gaccggatcc actgtcttga    900

tattttattt gcctttacaa agcgtgtttt gggtgagagt ggagagatgg atgcccttcg    960

aatacagatg gaagacaggt ttatggcatc aaacccctcc aaagtctctt atgagcctat   1020
```

-continued

```
tacaaccact ttgaaacgta aacaagagga ggtgtctgcc gctatcattc agcgtaattt   1080
cagatgttat cttttaaagc aaaggttaaa aaatatatca agtaactata acaaagaggc   1140
aataaagggg aggattgact tacctataaa acaagacatg attattgaca aactgaatgg   1200
gaactccact ccagaaaaaa cagatgggag ttcctctacc acctctcctc cttcctatga   1260
tagtgtaaca aaaccagaca aggaaaagtt tgagaaagac aaaccagaaa aagaaagcaa   1320
aggaaaagag gtcagagaaa atcaaaagta aaaagaaaca aagaattatc tttgtgatca   1380
attgtttaca gcctatgaag gtaaagtata tgtgtcaact ggacttcaag aggaggtcca   1440
tgccaaactg actgttttaa caaatactca tagtcagtgc ctatacaaga cagtgaagtg   1500
acctctctgt cactgcaact ctgtgaagca gggtatcaac attgacaaga ggttgctgtt   1560
tttattacca gctgacactg ctgaggagaa acccaatggc tacctagact atagggatag   1620
ttgtgcaaag tgaacattgt aactacacca aacaccttta gtacagtcct tgcatccatt   1680
ctatttttaa cttccatatc tgccatattt ttacaaaatt tgttctagtg catttccatg   1740
gtccccaatt catagtttat tcataatgct atgtcactat tttgtaaat gaggtttacg    1800
ttgaagaaac agtatacaag aaccctgtct ctcaaatgat cagacaaagg tgttttgcca   1860
gagagataaa atttttgctc aaaaccagaa aaagaattgt aatggctaca gtttcagtta   1920
cttccatttt ctagatggct ttaattttga aagtatttta gtctgttatg tttgtttcta   1980
tctgaacagt tatgtgcctg taaagtctcc tctaatattt aaaggattat ttttatgcaa   2040
agtattctgt ttcagcaagt gcaaatttta ttctaagttt cagagctcta tatttaattt   2100
aggtcaaatg ctttccaaaa agtaatctaa taaatccatt ctagaaaaat atatctaaag   2160
tattgcttta gaatagttgt tccactttct gctgcagtat tgctttgcca tcttctgctc   2220
tcagcaaagc tgatagtcta tgtcaattaa ataccctatg ttatgtaaat agttatttta   2280
tcctgtggtg catgtttggg caaatatata tatagcctga taaacaactt ctattaaatc   2340
aaatatgtac cacagtgtat gtgtcttttg caagcttcca acagggatgt atcctgtatc   2400
attcattaaa catagtttaa aggctatcac taatgcatgt taatattgcc tatgctgctc   2460
tattttactc aatccattct tcacaagtct tggttaaaga atgtcacata ttggtgatag   2520
aatgaattca acctgctctg tccattatgt caagcagaat aatttgaagc tatttacaaa   2580
cacctttact tttgcacttt taattcaaca tgagtatcat atggtatctc tctagatttc   2640
aaggaaacac actggatact gcctactgac aaaacctatt cttcatattt tgctaaaaat   2700
atgtctaaaa cttgcgcaaa tataaataat gtaaaaatat aatcaacttt atttgtcagc   2760
atttgtaca taagaaaatt attttcaggt tgatgacatc acaatttatt ttactttatg    2820
cttttgcttt tgatttttaa tcacaattcc aaacttttga atccataaga tttttcaatg   2880
gataatttcc taaaataaaa gttagataat gggttttatg gatttctttg ttataatata   2940
ttttctacca ttccaatagg agatacattg gtcaaacact caaacctaga tcattttcta   3000
ccaactatgg ttgcctcaat ataacctttt attcatagat gttttttttt attcaacttt   3060
tgtagtattt acgtatgcag actagtctta ttttttttaat tcctgctgca ctaaagctat  3120
tacaaatata acatggactt tgttcttttt agccatgaac aaagtggcaa agttgtgcaa   3180
ttacctaaca tgatataaat ttttgttttt tgcacaaacc aaaagtttaa tgttaattct   3240
ttttacaaaa ctatttactg tagtgtattg aagaactgca tgcagggaat tgctattgct   3300
aaaaagaatg gtgagctacg tcattattga gccaaaagaa taaatttcat tttttattgc   3360
```

-continued

```
atttcactta ttggcctctg gggtttttttg tttttgtttt ttgctgttgg cagtttaaaa   3420

tatatataat taataaaacc tgtgcttgat ctgacatttg tatacataaa agtttacatg   3480

aattttacaa cagactagtg catgattcac caagcagtac tacagaacaa aggcaaatga   3540

aaagcagctt tgtgcacttt tatgtgtgca aaggatcaag ttcacatgtt ccaactttca   3600

ggtttgataa taatagtagt aaccacctac aatagctttc aatttcaatt aactcccttg   3660

gctataagca tctaaactca tcttctttca atataattga tgctatctcc taattacttg   3720

gtggctaata aatgttacat tctttgttac ttaaatgcat tatataaact cctatgtata   3780

cataaggtat taatgatata gttattgaga atttatatta actttttttt caagaaccct   3840

tggatttatg tgaggtcaaa accaaactct tattctcagt ggaaaactcc agttgtaatg   3900

catattttta aagacaattt ggatctaaat atgtatttca taattctccc ataataaatt   3960

atataaggtg gctaa                                                     3975
```

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 99

```
tgtgttctgc cccagtgaga ct                                              22
```

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 100

```
cttcctgctc tgcccaaact gaat                                            24
```

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 101

```
ggcgatgtaa tgtaaggtgc tgtc                                            24
```

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 102

```
gtgccttcag ttgcaattgt tcag                                            24
```

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 103
ttaggaattt catatgcaga ataa 24

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 104
tgggccattt ttcgtcgtc 19

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 105
gaaagacgca ttgcagaaga aaagg 25

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 106
ctattggcat gtgttggtgc taca 24

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 107
gtgctggttt ctcatttaac tttac 25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 108
ttcccaactt aatttgatat ttagc 25

<210> SEQ ID NO 109
<211> LENGTH: 24
<212> TYPE: DNA
<213> ORGANISM: Artificial Sequence
<220> FEATURE:

-continued

<223> OTHER INFORMATION: Description of Artificial Sequence: synthetic oligonucleotide

<400> SEQUENCE: 109
gcagtttggg cttttcaatg ttag 24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 110
gacacagttt caraatcccr aatg 24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 111
ttagggctac gtttcatttg tatg 24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 112
agcactgatg gaaaaccaaa ctat 24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 113
agcccatgca gtaatataaa tcct 24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 114
tccaggctga taagctatgt ctaa 24

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 115
ctgtggcctg cctgagcgta tt 22

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 116
ccaattctac tttttaagga aatg 24

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 117
aaatacttgt gcctttgaa 19

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 118
gtacatacaa tatacacaga tgc 23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 119
aggcagcaga acgacttgta ata 23

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 120
atccggtttt aatttcataa ctca 24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide -continued

<400> SEQUENCE: 121
gttgagcacc cttagtgaat aata 24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 122
tcacacgctc tagactactt ctct 24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 123
tgcaaatact tcagcccttt caaa 24

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 124
ttccccacca gactgctctt tc 22

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 125
gcagcaggca ggctctca 18

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 126
tctcccatgt tttaattttc aacc 24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 127
ataatcttgc aaaatgaaat caca 24

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 128
atccgggatg acctactgg 19

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 129
gataacgaga gccgtagaga ttcc 24

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 130
agccagccat gcctgaacta 20

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 131
tgtttgcttg tcatattgct caa 23

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 132
tgcactattc ccaactcaca aa 22

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 133
aagggtgtct ctgtaacaaa aatg 24

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 134
gtgatggcca ggtcaacaaa 20

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 135
ctgggactgt tctccatatt ggtt 24

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 136
tttgcagggg ccaggaag 18

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 137
cattgtggga aaatagcata agc 23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 138
gcaagaaccc tgaatgttag aaa 23

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 139
taatgctttt aagaatcata caaa 24

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 140
ccagcgtggg agttgacaat c 21

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 141
cggcatgcag ctctttggta 20

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 142
atgtgccatg ctggtgtatt tc 22

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 143
cacccatctt ctaatcacta tgc 23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 144
cagcaatttg gagattattc att 23

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 145
gcagccactg atgatgataa 20

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 146
ctgccagttc ctataccact t 21

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 147
tacagcagaa attgggaaag at 22

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 148
gtattcatac ctacccacac ctat 24

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 149
ttcttggcag gcaacttatt acc 23

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 150
taagctgcac tccaaatgaa agat 24

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 151
ggctgaatgt ttccacaact 20

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 152
gttcaactat tcggaaacac g 21

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 153
aggcagagga aaacaatgg 19

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 154
acaaggtggg ataattaaaa atg 23

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 155
gtttctctgc cctcctattc c 21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 156
aagctacctt gaacagagac a 21

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 157
aatgatgatt ctgtttatta 20

-continued

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 158
aatttgccat tccttttg 18

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 159
ttgacatcga agacgtgaat aatc 24

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 160
ccatctgggc tcataaactt gta 23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 161
ccctttgaaa attatatcag taa 23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 162
atttggtcgt ttatgcttta ttc 23

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 163
tccagcacta aaatgtatgg taat 24

<210> SEQ ID NO 164

<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 164
atttggcaga gaaaacactc c 21

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 165
ttttagccat ccattttcta tttt 24

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 166
tattttcccc catatcattt ga 22

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 167
tttgcaagaa actagaaagt c 21

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 168
ttgatgcgtg acaaaatgg 19

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 169
gaccagagtg aatatgtgac tacc 24

<210> SEQ ID NO 170
<211> LENGTH: 23

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 170

ctgggatgat cttgaatcta atc                                           23


<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 171

gcaactcagt tcatggaatt tgaa                                          24


<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 172

cttgttttcg ttttaaagta gta                                           23


<210> SEQ ID NO 173
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 173

caaagatcac cctggaagct cagtt                                         25


<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 174

ttcaagcgca gctgcaaact gagat                                         25


<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 175

acatcggcct cctactcttc cta                                           23


<210> SEQ ID NO 176
<211> LENGTH: 21
<212> TYPE: DNA
```

<213> ORGANISM: Artificial Sequence
<220> FEATURE:
<223> OTHER INFORMATION: Description of Artificial Sequence: synthetic
      oligonucleotide

<400> SEQUENCE: 176
acagatgggt tcccacagtc c 21

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 177
taacgcatga tttcttcact ggtt 24

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 178
atcccaaaga tggcgtagat ga 22

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 179
tgagaaatag gctaaggacc tcta 24

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 180
cctaggggct ggattcc 17

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 181
aaggggtgca aacctgtgat ttt 23

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 182
agggccatgt ggttgccata c 21

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 183
cttccggttt atgttttcat ttct 24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 184
tctttattag ttttgcacat ttta 24

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 185
caatccttcc aaggtctcct atc 23

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 186
tttcatcttt gccttcttgc tcat 24

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 187
catgtccact gcagcttgtc ca 22

<210> SEQ ID NO 188
<211> LENGTH: 24
<212> TYPE: DNA
<213> ORGANISM: Artificial Sequence
<220> FEATURE:

```
<223> OTHER INFORMATION: Description of Artificial Sequence: synthetic
      oligonucleotide

<400> SEQUENCE: 188

tcccctttac acagagtcac agtt                                            24


<210> SEQ ID NO 189
<211> LENGTH: 15
<212> TYPE: DNA
<213> ORGANISM: Homo sapiens

<400> SEQUENCE: 189

gcatttgaag atata                                                      15


<210> SEQ ID NO 190
<211> LENGTH: 15
<212> TYPE: DNA
<213> ORGANISM: Homo sapiens

<400> SEQUENCE: 190

gcatttgacg atata                                                      15


<210> SEQ ID NO 191
<211> LENGTH: 15
<212> TYPE: DNA
<213> ORGANISM: Homo sapiens

<400> SEQUENCE: 191

atcatatcct tcctg                                                      15


<210> SEQ ID NO 192
<211> LENGTH: 15
<212> TYPE: DNA
<213> ORGANISM: Homo sapiens

<400> SEQUENCE: 192

atcatatmct tcctg                                                      15


<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 193

atgggttgaa tgactttctg acat                                            24


<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 194

aggcatttcc tgtacaggga ctac                                            24


<210> SEQ ID NO 195
<211> LENGTH: 24
<212> TYPE: DNA
<213> ORGANISM: Artificial Sequence
<220> FEATURE:
```

<223> OTHER INFORMATION: Description of Artificial Sequence: synthetic
oligonucleotide

<400> SEQUENCE: 195
acaggaaatg cctcttctta cttc 24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 196
tttccccaag gattctacta ctgt 24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 197
agtgcatgta actgacacaa tcac 24

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 198
cttgcgttcc tgtttgggtc tct 23

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 199
tccgcttctt taccagggaa tc 22

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 200
aggcagtgaa ggcaacttga ctaa 24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 201
cagggcaata tttataaata atgg 24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 202
tttggaaaat gtgtagctca ataa 24

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 203
aaggcatggt agtgcataaa ag 22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 204
atgaaacata aagggaggtc aa 22

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 205
aatgtgagct tggctattgt ctct 24

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 206
ataggctccc accagtgatt tac 23

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 207
aggcccctta tatctccaac tg 22

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 208
caacaaggct tctgcacaaa ag 22

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 209
cttggtggct tgccttgac 19

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 210
tcatgagtgt cgccatcagc 20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 211
ggaaagctga tggcgacact 20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 212
ctgagacatt gcccaggtcc 20

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 213
tttttacccg ttgctttctt ta 22

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 214
tatcccttgc tctttcattt atct 24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 215
gccggtaaaa tagctgttga gtag 24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 216
gccattgcaa acatttattt cgta 24

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 217
gcgtgtttgc gctaatag 18

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 218
ctaagtcact tgattcacat ctaa 24

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 219
acagggtggc tgaagtgttt ta 22

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 220
gtgggaggtg gcaggttatt 20

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 221
caattagcag acttgccgtt att 23

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 222
tctcttgagt tcggtgtttt atga 24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 223
accgaactca agagaattgc tgta 24

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 224
aaaggaccgt atgcttgttc acta 24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 225
tatgaatgcg cattttactc tttg 24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 226
tggagctcaa cttagatgct actg 24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 227
ggtgctggtg ggataggagt tttt 24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 228
tccattaaat tctggcatat tctt 24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 229
tcagaggggt gctttcttcc acat 24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 230
cttcggctgt cattgtcctc aaag 24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 231
gcaaaggaca ttggctctga gaat 24

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 232
ctgcctgcac cagtcacaac tct 23

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 233
tgggctttgc tgctttcaa 19

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 234
agtaactgtg acgcaggact ttta 24

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 235
ccctgttcct ccagcagatt a 21

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 236
gtgatggcca ggtcaacaaa 20

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 237
tttgatttgg gactgttgta aac 23

```
<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 238

aaggcaatta taaactcttt caag                                              24


<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 239

tgggagttaa attaagttgc tcaa                                              24


<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 240

acattttatg aacactccca gtta                                              24


<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 241

attaacactg ttcttgcttt tat                                               23


<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 242

gtgccagcgt gggagttc                                                     18


<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 243

gtgggggctc taggaaacct                                                   20
```

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 244
tttaatgaaa atgaggaaaa tgtt 24

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 245
gaccaagcat ttttatttca ttc 23

<210> SEQ ID NO 246
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 246
agtggcagca agattgtca 19

<210> SEQ ID NO 247
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 247
ggccttgctt ttgagttcc 19

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 248
ggtctttgcc tatttctatg gtg 23

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 249
ttaaaccgct tgaagatcta aata 24

<210> SEQ ID NO 250

<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 250
tatacaccaa aatatctcct tat 23

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 251
ggggcacacc taattaattt ttat 24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 252
aaagaggata ctcaagacca cata 24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 253
cccaccaaca caaatatacc taat 24

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 254
tgaagggaaa gggaaaagat tt 22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 255
tccagcctta ggcacctgat aa 22

<210> SEQ ID NO 256
<211> LENGTH: 24

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 256

ataaagcagc aaagtgcagc atac                                            24


<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 257

aaggctgaac tgtgtagaca tttt                                            24


<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 258

tgacatttcc atggtacaaa gtgt                                            24


<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 259

tttgttgttg gcttttcact tat                                             23


<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 260

ccacctggca gtttgattg                                                  19


<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 261

taagcgtggt caacaactac agt                                             23


<210> SEQ ID NO 262
<211> LENGTH: 22
<212> TYPE: DNA
```

<213> ORGANISM: Artificial Sequence
<220> FEATURE:
<223> OTHER INFORMATION: Description of Artificial Sequence: synthetic
      oligonucleotide

<400> SEQUENCE: 262
attcttgcca gcatttattg tc                                               22

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 263
caaaacattg ccccaaaag                                                   19

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 264
tcaaactaaa caatttccct ctaa                                             24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 265
gataattaaa aactcactga tgta                                             24

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 266
ggaggctaaa ggaaagagta tg                                               22

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 267
attttatagc cagcaaagaa cac                                              23

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 268
ctagaaattc gggctgtgaa 20

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 269
ctgctttgtg acctaaggca agtt 24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 270
gtgaccatgt taaggcagat gagg 24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 271
ggaatggtct ttgattttgt aacc 24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 272
tccttaactg aataaaagca cctc 24

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 273
tggaacaccc atcaaagaag atact 25

<210> SEQ ID NO 274
<211> LENGTH: 23
<212> TYPE: DNA
<213> ORGANISM: Artificial Sequence
<220> FEATURE:

<223> OTHER INFORMATION: Description of Artificial Sequence: synthetic
oligonucleotide

<400> SEQUENCE: 274
gtgggagtcc tgttgacaca aac 23

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 275
agcgattcat ggcatcaaac 20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 276
acgtggtgga aggcgtcata 20

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 277
gcgacccagt ttatagagtt tgcc 24

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 278
cttgtttgcg tttcaacgtg gtc 23

<210> SEQ ID NO 279
<211> LENGTH: 25
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 279
caaagatcac cctggaagct cagtt 25

<210> SEQ ID NO 280
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 280
atccagggca tctgcaaaat cagaa 25

<210> SEQ ID NO 281
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 281
tgcctatgtt aagagggaag ttggg 25

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 282
atgaccgcga tgtacatgtt cag 23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 283
tcaattgttt acagcccgtg atg 23

<210> SEQ ID NO 284
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 284
tttatacaaa ggcagacaac at 22

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 285
aggcgtaatg gctactcaga cga 23

<210> SEQ ID NO 286
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 286
gtaatccctc tccccgaaca taaac 25

<210> SEQ ID NO 287
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 287
tttgattcac gggttgttta ctctta 26

<210> SEQ ID NO 288
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 288
ttctatggaa catttacagg cacatt 26

<210> SEQ ID NO 289
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 289
taatgtgcct gtaaatgttc cataga 26

<210> SEQ ID NO 290
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 290
caggcttctt agaaaggact gatagg 26

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 291
gtcccagcag catgactatc 20

<210> SEQ ID NO 292
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 292
cccactgggt aaaattacta ac 22

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 293
tagccatctt ctgctcttgg t 21

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 294
tggcttccca tattagactt ctg 23

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 295
tcttgcctat gctgctgtat ctta 24

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 296
agtcgggctt ttcatcattg ag 22

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 297
ttcttcatgt cattaagcaa tagg 24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 298
ttcaatttaa aagtgctagg aaca 24

<210> SEQ ID NO 299
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 299
cttcaggtgg atgtcacagt cacta 25

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 300
attcaagcaa tgccaagagt atca 24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 301
ctttcaatag taatgcctta tcat 24

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 302
tcctgcatgc atttcaccaa c 21

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 303
ctgttcacat tttgtaaaac taat 24

<210> SEQ ID NO 304
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 304

-continued atcccaaaga tggcgtagat ga 22

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 305
cacgctgctc tttgctttga 20

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 306
gatctttgtc agggtcacag tct 23

<210> SEQ ID NO 307
<211> LENGTH: 9
<212> TYPE: DNA
<213> ORGANISM: Homo sapiens

<400> SEQUENCE: 307 tacaaagaa 9

<210> SEQ ID NO 308
<211> LENGTH: 9
<212> TYPE: DNA
<213> ORGANISM: Homo sapiens

<400> SEQUENCE: 308 tacagagaa 9

<210> SEQ ID NO 309
<211> LENGTH: 9
<212> TYPE: DNA
<213> ORGANISM: Homo sapiens

<400> SEQUENCE: 309 tacagagaa 9

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 310
tgtgtccgcc agtagatgg 19

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 311
tttttgacca cagaggttta caa 23

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 312
gaagcggagg cataagcaga 20

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 313
ggtgcagata atgaaatgtt ttgt 24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 314 caccccctatg ccaaatgtca aaga 24

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 315
caaaaacaaa cttataccca gaag 24

<210> SEQ ID NO 316
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 316
caaatattgg gcaaacccta at 22

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 317
aaggtgccat cacaaaatca t 21

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 318
atcgcttgct ttcctaactc ttgt 24

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 319
aagtcactat ttggctttgg ttg 23

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 320
agaagcccaa aaaggaacaa gata 24

<210> SEQ ID NO 321
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 321
ggcccagaaa agtatattac agtt 24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 322
tccttaaata agcccatgtc taat 24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 323
tctcaaagaa attttacaga tact 24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 324
aatggccatg gtaacctact aaca 24

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 325
caggctatac ccacaaggag att 23

<210> SEQ ID NO 326
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 326
tgttaatttt ggcttggatg tt 22

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 327
tcactccttt gcgcttatca a 21

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 328
agggctctat gtgccaaacc 20

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 329
aggggcctac taccttacac cag 23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 330
tgtaatccca ggtaagaaga aac 23

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 331
taccgggatg aactgtaata ataa 24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 332
ttctggcact cttcctcagg taac 24

<210> SEQ ID NO 333
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 333
gtcccatttg aatccattgt gc 22

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 334
ggcccccaag cgattctg 18

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 335
tgtacaccca cagtctcaac tatt 24

```
<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 336

acagccacct ttgtaaataa                                                20


<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 337

tttttcgcaa agagttctat                                                20


<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 338

aaactgaccc tacctccatt tctc                                           24


<210> SEQ ID NO 339
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 339

actcagccta tgcttttcat ttca                                           24


<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 340

cagatattta tttggggaca ttat                                           24


<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 341

aaatctttgc ktttatcact cagt                                           24
```

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 342
tagtgcctgg ctttgtttta tgac 24

<210> SEQ ID NO 343
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 343
cggatttggg aaagctgtct ct 22

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 344
agagcacctt gaaggaaaca acaa 24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 345
tccctcaact gaagtacaga tagt 24

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 346
ataattgcgt tcttccccta ccc 23

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 347
aagccctggc accatcctg 19

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 348
tttgcaaaga aatgctatgt 20

<210> SEQ ID NO 349
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 349
ctgggtaaca gacttcagta at 22

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 350
atgggattgt cttctcaagt ttct 24

<210> SEQ ID NO 351
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 351
gatggcaaga tcaacaaatg ga 22

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 352
cttgatctgg gactgctgtg atg 23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 353
aggatataat ttttggttca aca 23

<210> SEQ ID NO 354

-continued

<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 354
ttttcagtgc tcttgatagt agtg 24

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 355
gtgccaatga gcgacagg 18

<210> SEQ ID NO 356
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 356
ccacgtgtgg ttctatgata cc 22

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 357
accgtgggag cgtacagtca 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 358
cggcatgcag ctctttggta 20

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 359
tggccacgtt cctagctact gtc 23

<210> SEQ ID NO 360
<211> LENGTH: 24

<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 360
gagttccctt tttaggctgt tatt 24

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 361
tcttattgcc ttcatggatt tcta 24

<210> SEQ ID NO 362
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 362
tgaaaaataa gatgcgggag tg 22

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 363
gtgaggctgg ggttgtttat g 21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 364
gagatgggaa tggaaccacc a 21

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 365
ttcgataatg catataagca caa 23

<210> SEQ ID NO 366
<211> LENGTH: 21
<212> TYPE: DNA

<213> ORGANISM: Artificial Sequence
<220> FEATURE:
<223> OTHER INFORMATION: Description of Artificial Sequence: synthetic oligonucleotide

<400> SEQUENCE: 366
aagggggaaa atcacatctt t 21

<210> SEQ ID NO 367
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 367
ttaaatgagg catattcagt ctcc 24

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 368
ggaagtggag tggggaagg 19

<210> SEQ ID NO 369
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 369
attcttgcca atatgcattt cact 24

<210> SEQ ID NO 370
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 370
ttcttttgta ctcactatta tactaa 26

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 371
aaacttgcct cttttaaaaa caat 24

<210> SEQ ID NO 372
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 372
taccacaccc tataccttca gtca 24

<210> SEQ ID NO 373
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 373
gagtatggca cccttttcta tcta 24

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 374
gctatgttcc cctcgctgtc t 21

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 375
tgcttgccaa gagcctgac 19

<210> SEQ ID NO 376
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 376
gctggcaagt tctaccactg tg 22

<210> SEQ ID NO 377
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 377
caaacgaaga acatcaggga aata 24

<210> SEQ ID NO 378
<211> LENGTH: 24
<212> TYPE: DNA
<213> ORGANISM: Artificial Sequence
<220> FEATURE:

-continued

<223> OTHER INFORMATION: Description of Artificial Sequence: synthetic
      oligonucleotide

<400> SEQUENCE: 378
ttcacaatat tgtacaaaaa gtta 24

<210> SEQ ID NO 379
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 379
attaccacca atattcacca taag 24

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 380
tcagggtaag gcaaaagtag cac 23

<210> SEQ ID NO 381
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 381
gaaccccaga atgaagaaag gtaa 24

<210> SEQ ID NO 382
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 382
tttgtgaaag tactattgga acac 24

<210> SEQ ID NO 383
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 383
acgcatggct ttggaacat 19

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 384
cccgtatgtg gaagggcttt at 22

<210> SEQ ID NO 385
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 385
ctaggttgat ccgggacaaa acta 24

<210> SEQ ID NO 386
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 386
aacggatgac cagggcaaat ac 22

<210> SEQ ID NO 387
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 387
ctagaaggtc ctggggcaac tg 22

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 388
aagccatcat gtaaagtgaa aag 23

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 389
atcccaaaga tggcatagat a 21

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 390
cacgctgctc tttgctttga 20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 391
tgagctgcca gggtgaattg 20

<210> SEQ ID NO 392
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 392
ttgctagcac ctattcttaa tagtgc 26

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 393
ccagggcagc tgcaaaatca gag 23

<210> SEQ ID NO 394
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 394
cccgatgcga cccagttta 19

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 395
tggaggggtt tgatgccata 20

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 396
gatggatgcc cttcgaatac aga 23

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 397
ttcccattta gtttgtcaat aatc 24

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 398
aaggggagga ttgacttacc tat 23

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 399
ttggcatgga cctcctcttg a 21

<210> SEQ ID NO 400
<211> LENGTH: 13
<212> TYPE: DNA
<213> ORGANISM: Homo sapiens

<400> SEQUENCE: 400
tggtataagg tag 13

<210> SEQ ID NO 401
<211> LENGTH: 18
<212> TYPE: DNA
<213> ORGANISM: Homo sapiens

<400> SEQUENCE: 401
caagataatg atgatgag 18

<210> SEQ ID NO 402
<211> LENGTH: 15
<212> TYPE: DNA
<213> ORGANISM: Homo sapiens

<400> SEQUENCE: 402
caagatgatg atgag 15

<210> SEQ ID NO 403
<211> LENGTH: 13
<212> TYPE: DNA
<213> ORGANISM: Homo sapiens

<400> SEQUENCE: 403
tggtgtaagg tag 13

<210> SEQ ID NO 404
<211> LENGTH: 17
<212> TYPE: DNA
<213> ORGANISM: Homo sapiens

<400> SEQUENCE: 404
ccccttatat ctccaac 17

<210> SEQ ID NO 405
<211> LENGTH: 17
<212> TYPE: DNA
<213> ORGANISM: Homo sapiens

<400> SEQUENCE: 405
ccccttatay ctccaac 17

<210> SEQ ID NO 406
<211> LENGTH: 15
<212> TYPE: DNA
<213> ORGANISM: Homo sapiens

<400> SEQUENCE: 406
aaatacgtaa tcgat 15

<210> SEQ ID NO 407
<211> LENGTH: 15
<212> TYPE: DNA
<213> ORGANISM: Homo sapiens

<400> SEQUENCE: 407
aaatacataa tcgat 15

<210> SEQ ID NO 408
<211> LENGTH: 15
<212> TYPE: DNA
<213> ORGANISM: Homo sapiens

<400> SEQUENCE: 408
aaatacrtaa tcgat 15

<210> SEQ ID NO 409
<211> LENGTH: 2009
<212> TYPE: PRT
<213> ORGANISM: Homo sapiens

<400> SEQUENCE: 409

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95
```

-continued

```
Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Val Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510
```

-continued

```
Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
```

-continued

```
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                 1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Ile Arg  Lys Gln Lys Ile Leu  Asp Glu Ile Lys Pro  Leu Asp Asp
    1040                 1045                 1050

Leu Asn  Asn Lys Lys Asp Ser  Cys Met Ser Asn His  Thr Ala Glu
    1055                 1060                 1065

Ile Gly  Lys Asp Leu Asp Tyr  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335
```

```
Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725
```

-continued

```
Leu Leu  Ala Pro Ile Leu Asn  Ser Lys Pro Pro Asp  Cys Asp Pro
    1730                 1735                 1740

Asn Lys  Val Asn Pro Gly Ser  Ser Val Lys Gly Asp  Cys Gly Asn
    1745                 1750                 1755

Pro Ser  Val Gly Ile Phe Phe  Phe Val Ser Tyr Ile  Ile Ile Ser
    1760                 1765                 1770

Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Ile Lys Gly Gly  Ala Asn Leu
    1940                 1945                 1950

Leu Ile  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
    1985                 1990                 1995

Gln Glu  Gly Lys Asp Glu Lys  Ala Lys Gly Lys
    2000                 2005


<210> SEQ ID NO 410
<211> LENGTH: 2009
<212> TYPE: PRT
<213> ORGANISM: Homo sapiens

<400> SEQUENCE: 410

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80
```

```
Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495
```

-continued

```
Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
```

-continued

```
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                 1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Ile Arg  Lys Gln Lys Ile Leu  Asp Glu Ile Lys Pro  Leu Asp Asp
    1040                 1045                 1050

Leu Asn  Asn Lys Lys Asp Ser  Cys Met Ser Asn His  Thr Ala Glu
    1055                 1060                 1065

Ile Gly  Lys Asp Leu Asp Tyr  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Asp Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320
```

-continued

```
Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710
```

-continued

```
Met Ile  Cys Leu Phe Gln Ile  Thr Thr Ser Ala Gly  Trp Asp Gly
    1715                 1720                 1725

Leu Leu  Ala Pro Ile Leu Asn  Ser Lys Pro Pro Asp  Cys Asp Pro
    1730                 1735                 1740

Asn Lys  Val Asn Pro Gly Ser  Ser Val Lys Gly Asp  Cys Gly Asn
    1745                 1750                 1755

Pro Ser  Val Gly Ile Phe Phe  Phe Val Ser Tyr Ile  Ile Ile Ser
    1760                 1765                 1770

Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Ile Lys Gly Gly  Ala Asn Leu
    1940                 1945                 1950

Leu Ile  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
    1985                 1990                 1995

Gln Glu  Gly Lys Asp Glu Lys  Ala Lys Gly Lys
    2000                 2005


<210> SEQ ID NO 411
<211> LENGTH: 2009
<212> TYPE: PRT
<213> ORGANISM: Homo sapiens

<400> SEQUENCE: 411

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60
```

```
Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480
```

```
Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
```

-continued

```
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                1015                1020

Ala Tyr  Val Lys Arg Lys Ile  Tyr Glu Phe Ile Gln  Gln Ser Phe
    1025                1030                1035

Ile Arg  Lys Gln Lys Ile Leu  Asp Glu Ile Lys Pro  Leu Asp Asp
    1040                1045                1050

Leu Asn  Asn Lys Lys Asp Ser  Cys Met Ser Asn His  Thr Ala Glu
    1055                1060                1065

Ile Gly  Lys Asp Leu Asp Tyr  Leu Lys Asp Val Asn  Gly Thr Thr
    1070                1075                1080

Ser Gly  Ile Gly Thr Gly Ser  Ser Val Glu Lys Tyr  Ile Ile Asp
    1085                1090                1095

Glu Ser  Asp Tyr Met Ser Phe  Ile Asn Asn Pro Ser  Leu Thr Val
    1100                1105                1110

Thr Val  Pro Ile Ala Val Gly  Glu Ser Asp Phe Glu  Asn Leu Asn
    1115                1120                1125

Thr Glu  Asp Phe Ser Ser Glu  Ser Asp Leu Glu Glu  Ser Lys Glu
    1130                1135                1140

Lys Leu  Asn Glu Ser Ser Ser  Ser Ser Glu Gly Ser  Thr Val Asp
    1145                1150                1155

Ile Gly  Ala Pro Val Glu Glu  Gln Pro Val Val Glu  Pro Glu Glu
    1160                1165                1170

Thr Leu  Glu Pro Glu Ala Cys  Phe Thr Glu Gly Cys  Val Gln Arg
    1175                1180                1185

Phe Lys  Cys Cys Gln Ile Asn  Val Glu Glu Gly Arg  Gly Lys Gln
    1190                1195                1200

Trp Trp  Asn Leu Arg Arg Thr  Cys Phe Arg Ile Val  Glu His Asn
    1205                1210                1215

Trp Phe  Glu Thr Phe Ile Val  Phe Met Ile Leu Leu  Ser Ser Gly
    1220                1225                1230

Ala Leu  Ala Phe Glu Asp Ile  Tyr Ile Asp Gln Arg  Lys Thr Ile
    1235                1240                1245

Lys Thr  Met Leu Glu Tyr Ala  Asp Lys Val Phe Thr  Tyr Ile Phe
    1250                1255                1260

Ile Leu  Glu Met Leu Leu Lys  Trp Val Ala Tyr Gly  Tyr Gln Thr
    1265                1270                1275

Tyr Phe  Thr Asn Ala Trp Cys  Trp Leu Asp Phe Leu  Ile Val Asp
    1280                1285                1290

Val Ser  Leu Val Ser Leu Thr  Ala Asn Ala Leu Gly  Tyr Ser Glu
    1295                1300                1305
```

-continued

```
Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
    1385                 1390                 1395

Leu Ile  Glu Arg Asn Glu Thr  Ala Arg Trp Lys Asn  Val Lys Val
    1400                 1405                 1410

Asn Phe  Asp Asn Val Gly Phe  Gly Tyr Leu Ser Leu  Leu Gln Val
    1415                 1420                 1425

Ala Thr  Phe Lys Gly Trp Met  Asp Ile Met Tyr Ala  Ala Val Asp
    1430                 1435                 1440

Ser Arg  Asn Val Glu Leu Gln  Pro Lys Tyr Glu Glu  Ser Leu Tyr
    1445                 1450                 1455

Met Tyr  Leu Tyr Phe Val Ile  Phe Ile Ile Phe Gly  Ser Phe Phe
    1460                 1465                 1470

Thr Leu  Asn Leu Phe Ile Gly  Val Ile Ile Asp Asn  Phe Asn Gln
    1475                 1480                 1485

Gln Lys  Lys Lys Phe Gly Gly  Gln Asp Ile Phe Met  Thr Glu Glu
    1490                 1495                 1500

Gln Lys  Lys Tyr Tyr Asn Ala  Met Lys Lys Leu Gly  Ser Lys Lys
    1505                 1510                 1515

Pro Gln  Lys Pro Ile Pro Arg  Pro Gly Asn Lys Phe  Gln Gly Met
    1520                 1525                 1530

Val Phe  Asp Phe Val Thr Arg  Gln Val Phe Asp Ile  Ser Ile Met
    1535                 1540                 1545

Ile Leu  Ile Cys Leu Asn Met  Val Thr Met Met Val  Glu Thr Asp
    1550                 1555                 1560

Asp Gln  Ser Glu Tyr Val Thr  Thr Ile Leu Ser Arg  Ile Asn Leu
    1565                 1570                 1575

Val Phe  Ile Val Leu Phe Thr  Gly Glu Cys Val Leu  Lys Leu Ile
    1580                 1585                 1590

Ser Leu  Arg His Tyr Tyr Phe  Thr Ile Gly Trp Asn  Ile Phe Asp
    1595                 1600                 1605

Phe Val  Val Val Ile Leu Ser  Ile Val Gly Met Phe  Leu Ala Glu
    1610                 1615                 1620

Leu Ile  Glu Lys Tyr Phe Val  Ser Pro Thr Leu Phe  Arg Val Ile
    1625                 1630                 1635

Arg Leu  Ala Arg Ile Gly Arg  Ile Leu Arg Leu Ile  Lys Gly Ala
    1640                 1645                 1650

Lys Gly  Ile Arg Thr Leu Leu  Phe Ala Leu Met Met  Ser Leu Pro
    1655                 1660                 1665

Ala Leu  Phe Asn Ile Gly Leu  Leu Leu Phe Leu Val  Met Phe Ile
    1670                 1675                 1680

Tyr Ala  Ile Phe Gly Met Ser  Asn Phe Ala Tyr Val  Lys Arg Glu
    1685                 1690                 1695
```

-continued

```
Val Gly  Ile Asp Asp Met Phe  Asn Phe Glu Thr Phe  Gly Asn Ser
    1700                 1705                 1710

Met Ile  Cys Leu Phe Gln Ile  Thr Thr Ser Ala Gly  Trp Asp Gly
    1715                 1720                 1725

Leu Leu  Ala Pro Ile Leu Asn  Ser Lys Pro Pro Asp  Cys Asp Pro
    1730                 1735                 1740

Asn Lys  Val Asn Pro Gly Ser  Ser Val Lys Gly Asp  Cys Gly Asn
    1745                 1750                 1755

Pro Ser  Val Gly Ile Phe Phe  Phe Val Ser Tyr Ile  Ile Ile Tyr
    1760                 1765                 1770

Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Ile Lys Gly Gly  Ala Asn Leu
    1940                 1945                 1950

Leu Ile  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
    1985                 1990                 1995

Gln Glu  Gly Lys Asp Glu Lys  Ala Lys Gly Lys
    2000                 2005
```

NUCLEIC ACIDS ENCODING SODIUM CHANNEL SCN1A ALPHA SUBUNIT PROTEINS WITH MUTATIONS ASSOCIATED WITH EPILEPSY

This application is a Divisional Application of, and claims priority to, co-pending U.S. application Ser. No. 09/718,355 filed Nov. 24, 2000, which claims priority to U.S. Provisional Application No. 60/167,623 filed on Nov. 26, 1999.

FIELD OF THE INVENTION

The present invention relates to epilepsy. More particularly, the present invention relates to idiopathic generalized epilepsy (IGE) and to the identification of three loci mapping to chromosome 2, which show a linkage with epilepsy in patients. The invention further relates to nucleic acid sequences, and protein sequences of these loci (SCNA), to variations and mutations in these sequences and to the use thereof to assess, diagnose, prognose or treat epilepsy.

BACKGROUND OF THE INVENTION

Epilepsy is one of the most common neurological conditions, occurring in about 1.0% of the general population. The disease is characterised by paroxysmal abnormal electrical discharges in the brain, which lead to transient cerebral dysfunction in the form of a seizure. A seizure is considered partial when the epileptic discharge is limited to part of one brain hemisphere, or generalised when it involves both cerebral hemispheres at the onset. The current classification of the epileptic syndromes rests on two criteria: 1) seizure type which may be generalised or partial at the onset, according to clinical and EEG features; and 2) etiology, which may be idiopathic, cryptogenic and symptomatic. Symptomatic epilepsies have multiple and heterogeneous causes including brain injury, CNS infection, migrational and metabolic disorders. In the majority (65%) of the patients with either generalised or partial epilepsy, there is no underlying cause (idiopathic) or the cause is though to be hidden or occult (cryptogenic). Also, in the idiopathic epileptic syndromes, there is no evidence of cerebral dysfunction other than the seizure, and the neurological examination is normal. There is now increasing evidence that in this latter group, genetic factors are important, especially for the idiopathic generalised epilepsy (IGE). In a recent study, Berkovic et al (1998) showed a 62% concordance rate in monozygotic twins overall for epilepsy. In this study, a higher concordance rate has been found in the generalised compared to the partial epilepsies, with 76% concordance rate for IGE. Recent studies using molecular genetic approaches have shown that many susceptibility genes for the epilepsies in human involve membrane ion channel and related proteins. These studies include the syndrome of benign familial neonatal convulsions where two loci have been identified [EBN1 on chromosome 20, the KCNQ2 gene (a potassium channel); and EBN2 on chromosome 8, the KCNQ3 gene (also a potassium channel)] (Bievert et al, 1998; Charlier et al, 1998; Singh et al, 1998), as well as autosomal dominant nocturnal frontal lobe epilepsy [ADNFLE—chromosome 20, and the CHRNA4 gene (the neuronal nicotinic acetylcholine receptor alpha 4 subunit)] (Steinlein et al, 1995). More recently, there was a clinical description of a new syndrome (GEFS), which consisted of generalised epilepsy with febrile seizures. According to the current classification of epileptic syndrome, this syndrome would fall in the category of IGE, based on the seizure and electroencaphalographic features. However, febrile seizures were present in all probants with GEFS, and the pattern of inheritance was clearly autosomal dominant, which are not part of the usual IGE phenotype. This unique GEFS syndrome has been shown to be associated with a mutation on the beta-1 subunit of brain voltage-gated sodium channel (SCN1B) gene (Wallace et al, 1998). In addition, three different groups, including the group of the present inventors, have identified another locus on chromosome 2 in large kindred with this specific syndrome (GEFS). This region contains many candidate genes, including a cluster of alpha subunits of sodium channels (SCNA). Voltage-gated sodium channels play an important role in the generation of action potential in nerve cells and muscle. The alpha subunit (SCNA) is the main component of the channel, and would be sufficient to generate an efficient channel when expressed in cells in vitro. In turn, the beta-1 and 2 subunits need an alpha subunit to give an effective channel. The role of these subunits would be to modify the kinetic properties of the channel, mainly by fast inactivation of the sodium currents. The mutation found in the GEFS syndrome on the SCN1B gene was shown to reduce the fast inactivation of the sodium channels as compared to a normal SCNB1, when co-expressed with an alpha subunit. It is probable that this could be the mechanism by which the mutation induce an hyperexcitability state in the brain, leading to seizure in humans. Interestingly, the mechanism of action of most of the anticonvulsant drugs is through a reduction of the repetitive firing of neurons, which is also known to be dependent on fast inactivation. These finding make it likely that additional epilepsy genes will be identified by mutations in ion channels.

There thus remains a need to identify whether IGE is caused by a mutation in a sodium channel (SCNA). There also remains a need to assess whether a mutation(s) in SCNA is associated with GEFs. There also remains a need to determine whether a mutation that affects the fast inactivation of a sodium channel, given the particular phenotype of GEFS or IGE, could be linked to a region which includes SCNA genes.

The present invention seeks to meet these and other needs.

The present description refers to a number of documents, the content of which is herein incorporated by reference in their entirety.

SUMMARY OF THE INVENTION

In one embodiment, the present invention relates to a genetic assay for determining predisposition to epilepsy.

In another embodiment, the present invention relates to a use of at least one of the loci of the present invention or an equivalent thereof (e.g. a loci in linkage disequilibrium therewith) as a marker for epilepsy and to determine the optimal treatment thereof (e.g. to guide the treatment modalities, thereby optimizing treatment to a particular clinical situation).

Yet in another embodiment, the present invention relates to an assay to screen for drugs for the treatment and/or prevention of epilepsy. In a particular embodiment, such assays can be designed using cells from patients having a known genotype at one of the loci of the present invention. These cells harboring recombinant vectors can enable an assessment of the functionality of the SCN1A, and/or SCN2A and/or SCN3A and a combination thereof. Non-limiting examples of assays that could be used in accordance with the present invention include cis-trans assays similar to those described in U.S. Pat. No. 4,981,784.

It shall be understood that the determination of allelic variations in at least one of the loci of the present invention can be combined to the determination of allelic variation in other gene/markers linked to a predisposition to epilepsy. This combination, of genotype analyses could lead to better diagnosis programs and/or treatment of epilepsy. Non-limiting examples of such markers include SCN1B, EBN1, KCNQ2, EBN2, KCNQ3, ADNFLE and CHRNA4.

In accordance with the present invention, there is therefore provided a method of determining an individual's predisposition to epilepsy, which comprises determining the genotype of at least one locus selected from the group consisting of SCN1A, SCN2A and SCN3A. In one particular embodiment, the present invention provides a method of determining an individual's predisposition to epilepsy, which comprises determining a polymorphism (directly or indirectly by linkage disequilibrium) in a biological sample of an individual and analyzing the allelic variation in at least one of the loci selected from SCN1A, SCN2A and SCN3A, thereby determining an individual's predisposition to epilepsy.

In accordance with the present invention, there is also provided a method for identifying, from a library of compounds, a compound with therapeutic effect on epilepsy or other neurological disorders comprising providing a screening assay comprising a measurable biological activity of SCN1A, SCN2A or SCN3A protein or gene; contacting the screening assay with a test compound; and detecting if the test compound modulates the biological activity of SCN1A, SCN2A or SCN3A protein or gene; wherein a test compound which modulates the biological activity is a compound with this therapeutic effect.

Also provided within the present invention is a compound having therapeutic effect on epilepsy or other neurological disorders, identified by a method comprising: providing a screening assay comprising a measurable biological activity of SCN1A, SCN2A or SCN3A protein or gene; contacting the screening assay with a test compound; and detecting if the test compound modulates the biological activity of SCN1A, SCN2A or SCN3A protein or gene, wherein a test compound which modulates the biological activity is a compound with this therapeutic effect.

SCN1A, SCN2A and SCN3A refers to genes and proteins for Sodium Channel, Neuronal Type I, Alpha Subunit isoforms, and are described at OMIM # 182389 (Online Mendelian Inheritance in Man). These genes are structurally distinct sodium channel alpha-subunit isoforms in brain, also known as brain types I, II and III, respectively. Gene, cDNA and protein sequences for the various isoforms are shown in SEQ ID NOS:1-98.

Numerous methods for determining a genotype are known and available to the skilled artisan. All these genotype determination methods are within the scope of the present invention. In a particular embodiment of a method of the present invention, the determination of the genotype comprises an amplification of a segment of one of the loci selected from the group consisting of SCN1A, SCN2A and SCN3A and in a particularly preferred embodiment, the amplification is carried out using polymerase chain reaction.

In a particular embodiment, a pair of primers is designed to specifically amplify a segment of one of the markers of the present invention. This pair of primers is preferably derived from a nucleic acid sequence of SCN1A, SCN2A or SCN3A or from sequences flanking these genes, to amplify a segment of SCN1A, SCN2A or SCN3A (or to amplify a segment of a loci in linkage disequilibrium with at least one of the loci of the present invention). While a number of primers are exemplified herein, other primer pairs can be designed, using the sequences of the SCN1A, SCN2A and SCN3A nucleic acids molecules described hereinbelow. The same would apply to primer pairs from loci in linkage disequilibrium with the markers of the present invention.

Restriction fragment length polymorphisms can be used to determine polymorphisms at the SCN1A, SCN2A and SCN3A loci (and equivalent loci).

While human SCN1A, SCN2A and SCN3A are preferred sequences (nucleic acid and proteins) in accordance with the present invention, the invention should not be so limited. Indeed, in view of the significant conservation of these genes throughout evolution, sequences from different species, and preferably mammalian species, could be used in the assays of the present invention. One non-limiting example is the rat SCN1A ortholog gene which shows 95% identity with the human SCN1A gene. The significant conservation of the mouse SCN1A gene can also be observed in OMIM (see above).

In order to provide a clear and consistent understanding of terms used in the present description, a number of definitions are provided hereinbelow.

As used herein the term "RFLP" refers to restriction fragment length polymorphism.

The terms "polymorphism", "DNA polymorphism" and the like, refer to any sequence in the human genome which exists in more than one version or variant in the population.

The term "linkage disequilibrium" refers to any degree of non-random genetic association between one or more allele(s) of two different polymorphic DNA sequences, that is due to the physical proximity of the two loci. Linkage disequilibrium is present when two DNA segments that are very close to each other on a given chromosome will tend to remain unseparated for several generations with the consequence that alleles of a DNA polymorphism (or marker) in one segment will show a non-random association with the alleles of a different DNA polymorphism (or marker) located in the other DNA segment nearby. Hence, testing of a marker in linkage desiquilibrium with the polymorphisms of the present invention at the SCN1A, SCN2A and/or SCN3A genes (indirect testing), will give almost the same information as testing for the SCN1A, SCN2A and SCN3A polymorphisms directly. This situation is encountered throughout the human genome when two DNA polymorphisms that are very close to each other are studied. Linkage disequilibriums are well known in the art and various degrees of linkage disequilibrium can be encountered between two genetic markers so that some are more closely associated than others.

It shall be recognized by the person skilled in the art to which the present invention pertains, that since some of the polymorphisms or mutations herein identified in the SCN1A, SCN2A and/or SCN3A genes can be within the coding region of the genes and therefore expressed, that the present invention should not be limited to the identification of the polymorphisms/mutations at the DNA level (whether on genomic DNA, amplified DNA, cDNA, or the like). Indeed, the herein-identified polymorphisms and/or mutations could be detected at the mRNA or protein level. Such detections of polymorphism identification on mRNA or protein are known in the art. Non-limiting examples include detection based on oligos designed to hybridize to mRNA or ligands such as antibodies which are specific to the encoded polymorphism (i.e. specific to the protein fragment encoded by the distinct polymorphisms).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (i.e. genomic DNA, cDNA, RNA molecules (i.e. mRNA) and chimeras of DNA and RNA. The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (i.e. DNA, RNA or chimeras thereof) for practicing the present invention may be obtained according to well known methods.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hydrizidation thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

The term "DNA" molecule or sequence (as well as sometimes the term "oligonucleotide") refers to a molecule comprised of the deoxyribonucleotides adenine (A), guanine (G), thymine (T) and/or cytosine (C). Sometimes, in a double-stranded form, it can comprise or include a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. Of course, as very well-known, DNA molecules or sequences are often in single stranded form.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred to above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 μg/ml denatured carrier DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 1989, supra).

Probes of the invention can be utilized with naturally occurring sugar-phosphate backbones as well as modified backbones including phosphorothioates, dithionates, alkyl phosphonates and "-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. More recently, PNAs have been described (Nielsen et al. 1999, Current Opin. Biotechnol. 10:71-75). PNAs could also be used to detect the polymorphisms of the present invention. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^{3}H$, $^{14}C$, $^{32}P$, and $^{35}S$. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods.

Non-limiting examples thereof include kinasing the 5' ends of the probes using gamma $^{32}P$ ATP and polynucleotide kinase, using the Klenow fragment of Pol I of *E. coli* in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthetised chemically or derived by cloning according to well known methods.

As used herein, a "primer" defines an oligonucleotide which is capable of annealing to a target sequence, thereby creating a double stranded region which can serve as an initiation point for nucleic acid synthesis under suitable conditions.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Q$ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise to a specific polypeptide or protein. It will be readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boses and "CCAT" boxes. Prokaryotic promoters contain Shine-Dalgarno sequences in addition to the −10 and −35 consensus sequences.

In accordance with one embodiment of the present invention, an expression vector can be constructed to assess the functionality of specific alleles of the SCN1A, SCN2A and SCN3A sodium channels. Non-limiting examples of such expression vectors include a vector comprising the nucleic acid sequence encoding one of the sodium channels (or part thereof) according to the present invention. These vectors can be transfected in cells. The sequences of the alpha subunit of the sodium channels in accordance with the present invention and their structure-function relationship could be assessed by a number of methods known to the skilled artisan. One non-limiting example includes the use of cells expressing the β-1 and β-2 subunits and the sequence of an alpha subunit in accordance with the present invention. For example, an alpha subunit having a mutation, which is linked to epilepsy, could be compared to a sequence devoid of that mutation, as a control. In such cells, the functionality of the sodium channel could be tested as known to the skilled artisan and these cells could be used to screen for agents which could modulate the activity of the sodium channel. For example, agents could be tested and selected, which would reduce the hyperexcitability state of the sodium channel (e.g. their reduction in fast inactivation). Agents known to the person of ordinary skill as affecting other sodium channels could be tested, for example, separately or in batches. Of course, it will be understood that the SCN1A, SCN2A and/or SCN3A genes expressed by these cells can be modified at will (e.g. by in vitro mutagenesis or the like).

As used herein, the designation "functional derivative" denotes, in the context of a functional derivative of a sequence whether a nucleic acid or amino acid sequence, a molecule that retains a biological activity (either function or structural; e.g. sodium channel function or structure) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include, similarities in charge, bulkiness, hydrophobicity, hydrophylicity and the like. The term "functional derivatives" is intended to include "fragments", "segments", "variants", "analogs" or "chemical derivatives" of the subject matter of the present invention. The genetic code, the chemico-physical characteristics of amino acids and teachings relating to conservative vs. non-conservative mutations are well-known in the art. Non-limiting examples of textbooks teaching such information are Stryer, Biochemistry, 3rd ed.; and Lehninger, Biochemistry, 3rd ed. The functional derivatives of the present invention can be synthesized chemically or produced through recombinant DNA technology all these methods are well known in the art.

The term "variant" refers herein to a protein or nucleic acid molecule which is substantially similar in structure and biological activity to the protein or nucleic acid of the present invention.

As used herein, "chemical derivatives" is meant to cover additional chemical moieties not normally part of the subject matter of the invention. Such moieties could affect the physico-chemical characteristic of the derivative (i.e. solubility, absorption, half life, decrease of toxicity and the like). Such moieties are exemplified in Remington's Pharmaceutical Sciences (1980). Methods of coupling these chemical-physical moieties to a polypeptide or nucleic acid sequence are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

As used herein, "SCNA biological activity" refers to any detectable biological activity of SCN1A, SCN2A or SCN3A gene or protein (herein sometimes collectively called SCNA genes or SCNA proteins). This includes any physiological function attributable to an SCNA gene or protein. It can include the specific biological activity of SCNA proteins which is efflux of sodium or related ions. This includes measurement of channel properties such as, but not limited to: 1) the voltage-dependence of activation, a measure of the strength of membrane depolarization necessary to open the channels, 2) the voltage-dependence of steady state inactivation, a measure of the fraction of channels available to open at the resting membrane potential; and 3) the time course of inactivation. At a larger scale, SCNA biological activity includes transmission of impulses through cells, wherein changes in transmission characteristics caused by modulators of SCNA proteins can be identified. Non-limiting examples of such measurements of these biological activities may be made directly or indirectly, such as through the transient accumulation of ions in a cell, dynamics of membrane depolarization, etc. SCNA biological activity is not limited, however, to these most important biological activities herein identified. Biological activities may also include simple binding or pKa analysis of SCNA with compounds, substrates, interacting proteins, and the like. For example, by measuring the effect of a test compound on its ability to increase or inhibit such SCNA binding or interaction is measuring a biological activity of SCNA according to this invention. SCNA biological activity includes any standard biochemical measurement of SCNA such as conformational changes, phosphorylation status or any other feature of the protein that can be measured with techniques known in the art. Finally, SCNA biological activity also includes activities related to SCNA gene transcription or translation, or any biological activities of such transcripts or translation products.

As used herein, the terms “molecule”, “compound”, “agent” or “ligand” are used interchangeably and broadly to refer to natural, synthetic or semi-synthetic molecules or compounds. The term “molecule” therefore denotes for example chemicals, macromolecules, cell or tissue extracts (from plants or animals) and the like. Non limiting examples of molecules include nucleic acid molecules, peptides, ligands (including, for example, antibodies and carbohydrates) and pharmaceutical agents. The agents can be selected and screened by a variety of means including random screening, rational selection and by rational design using for example protein or ligand modelling methods such as computer modelling. The terms “rationally selected” or “rationally designed” are meant to define compounds which have been chosen based on the configuration of the interacting domains of the present invention. As will be understood by the person of ordinary skill, macromolecules having non-naturally occurring modifications are also within the scope of the term “molecule”. For example, peptidomimetics, well known in the pharmaceutical industry and generally referred to as peptide analogs can be generated by modelling as mentioned above. Similarly, in a preferred embodiment, the polypeptides of the present invention are modified to enhance their stability. It should be understood that in most cases this modification should not alter the biological activity of the protein. The molecules identified in accordance with the teachings of the present invention have a therapeutic value in diseases or conditions in which sodium transport through the sodium channels is compromised by a mutation (or combination thereof in one of the genes identified in accordance with the present invention. Alternatively, the molecules identified in accordance with the teachings of the present invention find utility in the development of compounds which can modulate the activity of the alpha subunit sodium channels and/or the action potential in nerve cells and muscles cells (e.g. restore the fast inactivation of the sodium channel to normal levels).

As used herein, agonists and antagonists also include potentiators of known compounds with such agonist or antagonist properties. In one embodiment, modulators of the fast inactivation of the sodium channel in accordance with the present invention can be identified and selected by contacting the indicator cell with a compound or mixture or library of molecules for a fixed period of time.

As used herein the recitation “indicator cells” refers to cells that express at least one sodium channel α subunit (SCNA) according to the present invention. As alluded to above, such indicator cells can be used in the screening assays of the present invention. In certain embodiments, the indicator cells have been engineered so as to express a chosen derivative, fragment, homolog, or mutant of the combination of genotypes of the present invention. The cells can be yeast cells or higher eukaryotic cells such as mammalian cells. In one particular embodiment, the indicator cell would be a yeast cell harboring vectors enabling the use of the two hybrid system technology, as well known in the art (Ausubel et al., 1994, supra) and can be used to test a compound or a library thereof. In another embodiment, the cis-trans assay as described in U.S. Pat. No. 4,981,784, can be adapted and used in accordance with the present invention. Such an indicator cell could be used to rapidly screen at high-throughput a vast array of test molecules. In a particular embodiment, the reporter gene is luciferase or β-Gal.

It shall be understood that the “in vivo” experimental model can also be used to carry out an “in vitro” assay. For example, cellular extracts from the indicator cells can be prepared and used in an “in vitro” test. A non-limiting example thereof include binding assays.

In some embodiments, it might be beneficial to express a fusion protein. The design of constructs therefor and the expression and production of fusion proteins and are well known in the art (Sambrook et al., 1989, supra; and Ausubel et al., 1994, supra).

Non-limiting examples of such fusion proteins include hemaglutinin fusions and Gluthione-S-transferase (GST) fusions and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the protein of the present invention to signal peptide sequences enabling a secretion of the fusion protein from the host cell. Signal peptides from diverse organisms are well known in the art. Bacterial OmpA and yeast Suc2 are two non-limiting examples of proteins containing signal sequences. In certain embodiments, it might also be beneficial to introduce a linker (commonly known) between the interaction domain and the heterologous polypeptide portion. Such fusion protein find utility in the assays of the present invention as well as for purification purposes, detection purposes and the like.

For certainty, the sequences and polypeptides useful to practice the invention include without being limited thereto mutants, homologs, subtypes, alleles and the like. It shall be understood that generally, the sequences of the present invention should encode a functional (albeit defective) alpha subunit of sodium channels (SCNA). It will be clear to the person of ordinary skill that whether the SCNA sequence of the present invention, variant, derivative, or fragment thereof retains its function, can be determined by using the teachings and assays of the present invention and the general teachings of the art.

It should be understood that the SCNA protein of the present invention can be modified, for example by in vitro mutagenesis, to dissect the structure-function relationship thereof and permit a better design and identification of modulating compounds. However, some derivative or analogs having lost their biological function may still find utility, for example for raising antibodies. These antibodies could be used for detection or purification purposes. In addition, these antibodies could also act as competitive or non-competitive inhibitor and be found to be modulators of the activity of the SCNA proteins of the present invention.

A host cell or indicator cell has been “transfected” by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra). The use of a mammalian cell as indicator can provide the advantage of furnishing an intermediate factor, which permits for example the interaction of two polypeptides which are tested, that might not be present in lower eukaryotes or prokaryotes. It will be understood that extracts from mammalian cells for example could be used in certain embodiments, to compensate for the lack of certain factors.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody—A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents. Further, the DNA segments or proteins according to the present invention could be introduced into individuals in a number of ways. For example, cells can be isolated from the afflicted individual, transformed with a DNA construct according to the invention and reintroduced to the afflicted individual in a number of ways. Alternatively, the DNA construct can be administered directly to the afflicted individual. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e. DNA construct, protein, cells), the response and condition of the patient as well as the severity of the disease.

Composition within the scope of the present invention should contain the active agent (i.e. molecule, hormone) in an amount effective to achieve the desired therapeutic effect while avoiding adverse side effects. Typically, the nucleic acids in accordance with the present invention can be administered to mammals (i.e. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

The present invention also relates to a kit for diagnosing and/or prognosing epilepsy, and/or predicting response to a medication comprising an assessment of a genotype at SCNA loci of the present invention (or loci in linkage disequilibrium therewith) using a nucleic acid fragment, a protein or a ligand, a restriction enzyme or the like, in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include in one particular embodiment a container which will accept the test sample (DNA protein or cells), a container which contains the primers used in the assay, containers which contain enzymes, containers which contain wash reagents, and containers which contain the reagents used to detect the extension products.

BRIEF DESCRIPTION OF THE DRAWINGS

Having thus generally described the invention, reference will now be made to the accompanying drawings, showing by way of illustration a preferred embodiment thereof, and in which:

FIG. 1 shows the IGE candidate region on ch 2q23-q31. Order and distance between markers are according to Gyapay et al., 1994.

FIG. 2 shows the PCR primers used for genomic PCR-SSCP of SCN1A (SEQ ID NOs: 99-188);

FIG. 3 shows the sequence of the SCN1A mutations found in epilepsy patients (SEQ ID NOs: 189-192 and 309);

FIG. 4 shows the PCR primers used for genomic PCR-SSCP of SCN2A (SEQ ID NOs: 193-306);

FIG. 5 shows the mutation found in epilepsy patients in SCN2A (SEQ ID NOs: 307 and 308);

FIG. 6 shows the PCR primers used for genomic PCR-SSCP of SCN3A (SEQ ID NOs: 310-399); and FIG. 7 shows the mutation found in epilepsy patients in SCN3A (SEQ ID NOs: 400-408).

Sequences are also shown in the Sequence Listing. For example, SEQ ID NO.:1 shows the nucleic acid sequence of the adult form of SCN1A; SEQ ID NO.:2 shows the nucleic acid sequence of the neonatal form of SCN1A; SEQ ID NO.:3 shows the protein sequence of the adult form of SCN1A; SEQ ID NO.:4 shows the protein sequence of the neonatal form of SCN1A; SEQ ID NOS.:5-32 show the genomic sequence of SCN1A; SEQ ID NO.:33 shows the cDNA sequence of the adult form of SCN2A; SEQ ID NO.:34 shows the cDNA sequence of the neonatal form of SCN2A; SEQ ID NO.:35 shows the protein sequence of the adult form of SCN2A; SEQ ID NO.:36 shows the protein sequence of the neonatal form of SCN2A; SEQ ID NOS.:37-64 show the genomic sequence of SCN2A; SEQ ID NO.:65 shows the cDNA sequence of the adult form of SCN3A; SEQ ID NO.:66 shows the cDNA sequence of the neonatal form of SCN3A; SEQ ID NO.:67 shows the protein sequence of the adult form of SCN3A; SEQ ID NO.:68 shows the protein sequence of the neonatal form of SCN3A; and SEQ ID NOS.:69-98 show the genomic sequence of SCN3A. Rat SCNA1 sequences can be found in GenBank under accession numbers M22253 and X03638.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

Epilepsy is one of the most common neurological conditions, affecting 1-2% of the general population. Familial aggregation studies have shown an increased risk for epilepsy in relatives of probands with different types of epilepsy, and especially for the idiopathic generalized epilepsies (IGEs). The epilepsy genes identified to date account for a very small proportion of all the epilepsies. In addition, they have been identified in rare syndromes where the pattern of inheritance was clearly Mendelian. This is not the case for the vast majority of epileptic patients, however, where the pattern of inheritance is not compatible with a simple Mendelian model. In fact, most authors consider epilepsy to be the result of a combination of many different genetic and environmental factors, features of a complex trait. While the pattern of inheritance is not mendelian, sporadic IGE cases may be caused by specific mutations in the same genes. Based on this assumption, a large cohort of IGE patients was tested for mutation in the SCNA genes.

In order to localize the gene causing epilepsy in a large family segregating an autosomal dominant form of IGE, 41 family members, including 21 affected individuals, were genotyped. A detailed clinical description of this family has been reported elsewhere (Scheffer and Berkovic 1997). The majority of patients in this family present a benign epilepsy syndrome occurring in childhood and characterized by frequent generalized tonic-clonic seizures not always associated with fever: a syndrome called febrile seizures plus (FS+). However, several patients presented other types of generalized seizures (GTCS) as well, such as myoclonic seizures and absences (Scheffer and Berkovic 1997). Mean age at onset was 2.2 years and offset was 11.7 years. Neurological examination and intellect were normal in all individuals except one, who had moderate intellectual disability. EEG recordings were normal in most patients. However, in three individuals generalized epileptiform activity was found and four patients had mild or moderate diffuse background slowing. Table 1 shows the different types of seizures found in the 21 patients included in this study.

TABLE 1

Different types of generalized seizures found in the 21 patients included in the linkage analysis.

| Type of seizures | n |
|---|---|
| Febrile convulsions alone | 9 |
| GTCSs[a] + absence seizures | 4 |
| GTCSs + myoclonic seizures | 1 |
| GTCSs + atonic seizures | 1 |
| Solitary afebril GTCS | 1 |
| Secondary epilepsy + mental retardation | 1 |
| Unwitnessed events | 4 |

[a]GTCS: generalized tonic clonic seizure

A genome wide search examining 190 markers identified linkage of IGE to chromosome (ch) 2 based on an initial positive lod score for marker D2S294 (Z=4.4, (=0). A total of 24 markers were tested on ch 2q in order to define the smallest IGE candidate region. Table 2 shows the two-point lod scores for 17 markers spanning the IGE candidate region. The highest lod score (Zmax=5.29; (=0) was obtained with marker D2S324. Critical recombination events mapped the IGE gene to a 29 cM region flanked by markers D2S156 and D2S311, assigning the IGE locus to ch 2q23-q31 (FIG. 1). Although the relationship of FS+ with other IGE phenotypes remains unclear, the observation that in this family, several affected individuals have different types of generalized seizures, suggests that seizure predisposition determined by the ch 2q-IGE gene could be modified by other genes and/or environmental factors, to produce different seizure types.

TABLE 2

Two-point lod-scores for 17 markers localized on ch 2q23-q31.

| | Recombination fractions | | | | | | | | |
|---|---|---|---|---|---|---|---|---|---|
| Locus | 0 | 0.05 | 0.1 | 0.15 | 0.2 | 0.3 | 0.4 | Zmax | max |
| D2S142 | 0.99 | 1.94 | 1.97 | 1.85 | 1.68 | 1.22 | 0.66 | 1.98 | 0.078 |
| D2S284 | 1.3 | 1.18 | 1.06 | 0.94 | 0.82 | 0.57 | 0.3 | 1.3 | 0 |
| D2S306 | 1.9 | 2.82 | 2.74 | 2.52 | 2.25 | 1.6 | 0.85 | 2.82 | 0.057 |
| D2S156 | 2.15 | 3.05 | 2.96 | 2.73 | 2.43 | 1.73 | 0.93 | 3.05 | 0.056 |
| D2S354 | 4.72 | 4.26 | 3.82 | 3.4 | 2.97 | 2.1 | 1.13 | 4.72 | 0 |
| D2S111 | 5.15 | 4.71 | 4.26 | 3.78 | 3.29 | 2.26 | 1.17 | 5.15 | 0 |
| D2S124 | 3.5 | 3.2 | 2.89 | 2.58 | 2.26 | 1.58 | 0.84 | 3.5 | 0 |
| D2S382 | 4.31 | 3.93 | 3.54 | 3.14 | 2.74 | 1.91 | 1.02 | 4.31 | 0 |
| D2S399 | 0.48 | 0.4 | 0.33 | 0.27 | 0.22 | 0.14 | 0.08 | 0.48 | 0 |
| D2S294 | 4.4 | 4.04 | 3.65 | 3.25 | 2.84 | 2 | 1.07 | 4.4 | 0 |
| D2S335 | 4.76 | 4.32 | 3.91 | 3.51 | 3.1 | 2.22 | 1.21 | 4.76 | 0 |
| D2S333 | 1.42 | 1.23 | 1.04 | 0.87 | 0.72 | 0.45 | 0.22 | 1.4 | 0 |
| D2S324 | 5.29 | 4.72 | 4.16 | 3.63 | 3.13 | 2.15 | 1.14 | 5.29 | 0 |
| D2S384 | 3.85 | 3.52 | 3.17 | 2.82 | 2.45 | 1.69 | 0.89 | 3.85 | 0 |
| D2S152 | 1.9 | 1.7 | 1.52 | 1.36 | 1.2 | 0.87 | 0.48 | 1.9 | 0 |
| D2S311 | −0.81 | 1.62 | 1.66 | 1.58 | 1.46 | 1.11 | 0.63 | 1.66 | 0.085 |
| D2S155 | −5.21 | 0.57 | 1.12 | 1.29 | 1.29 | 1.04 | 0.59 | 1.3 | 0.17 |

Haplotypes using 17 markers spanning the IGE candidate region were constructed (data not shown). The centromeric boundary was defined by a recombination event between the markers D2S156 and D2S354; whereas a recombination between the markers D2S152 and D2S311 set the telomeric boundary. These critical recombination events localized the IGE gene to a 29 cM region flanked by markers D2S156 and D2S311 (FIG. 1).

Over the last four decades, family studies provided two important pieces of evidence supporting the role of genetic factors in determining susceptibility to seizures: 1) familial aggregation studies have shown evidence for an increased risk for epilepsy in relatives of probands with different types of epilepsy. In two studies standardized morbidity ratios for unprovoked seizures in relatives of individuals with idiopathic childhood-onset epilepsy varied from 2.5 to 3.4 in siblings and 6.7 in offspring (Anneger et al. 1982; Ottman et al. 1989); and 2) the presence of higher concordance rates for epilepsy in monozygotic than in dizygotic twins. Different studies showed concordance rates varying from 54 to 11% in monozygotic twins and 10 to 5% in dizygotic pairs (Inouye 1960; Lennox, 1960; Harvald and Hauge 1965; Corey et al. 1991; Silanpaa et al 1991).

It is now generally accepted that seizure susceptibility probably reflects complex interactions of multiple factors affecting neuronal excitability and that most common genetic epilepsies display familial aggregation patterns that are not explained by segregation of a single autosomal gene (Andermann 1982; Ottman et al. 1995). This of course significantly makes more complex one's ability to isolate genes which predispose or induce epilepsy. However, some specific epileptic syndromes, which aggregate in families, may result from definable monogenic abnormalities. These families present a unique opportunity to rapidly map genes that play a role in determining predisposition to seizures.

To date, there are a total of six loci (Greenberg et al. 1988; Leppert et al 1989; Lewis et al. 1993; Elmslie et al. 1997; Guipponi et al. 1997; Wallace et al. 1998), for which three genes have been identified in specific IGE syndromes (Bievert et al. 1998; Singh et al. 1998; Wallace et al. 1998). Interestingly, all three genes are ion channels, including a mutation found in the Na+-channel (1 in a Tasmania family with febrile seizures and generalized epilepsy (Wallace et al. 1998). While the candidate interval identified in our kindred remains large, a number of interesting genes map to the region. These include a cluster of Na+ channel genes and K+ channel genes (electronic data base search), as well as the GAD1 gene, which encodes for glutamate decarboxylase, an enzyme involved in the syntheses of γ-aminobutyric acid (GABA) (Bu and Tobin 1994). GABA is one of the major neurotransmitters involved in synaptic inhibition in the central nervous system (Barnard et al. 1987). However, the large size of the candidate interval will require further refinement of the locus prior to the identification of the gene responsible for IGE in the kindred studied herein.

Fifty-three % (9/17) of affected individuals in the large IGE family described herein, who had their seizures classified, had only febrile convulsions. However, 41% of patients (7/17) presented with different types of generalized seizures. These findings may indicate that, although the predisposition to IGE in this family is determined by a single gene localized on ch2q23-q31, the different types of generalized seizures occurring in the same family may have resulted from interactions among genetic and/or environmental modifiers.

In conclusion, a locus for IGE was mapped on ch 2q23-q31. This locus seems to be associated with a specific IGE syndrome, FS+. However, the relationship of FS+ with other IGE phenotypes, and the role of the ch 2q locus in other FS+ families and in other forms of IGE are still undetermined.

Having identified a locus for IGE on chromosome 2q23-q31, it was next verified whether mutations and/or polymorphisms could be linked to epilepsy. Public data bases were screened to identify potential genes in that chromosome region. The blasts of the data bases were also oriented to identify more specifically, membrane channels since seizures in mice and human are known to be associated with membrane channels. Having identified membrane channel coding sequences or parts thereof by the computer searches, the candidate genes, potentially involved in epilepsy, had to be validated as susceptibility genes for the disease. Two approaches were used. The first one was to test the candidate genes for mutations in a family comprising members having the disease (data not shown). The second approach was as follows. Since it is known that epilepsy results from a lower seizure threshold, and that generalized epilepsy results, in many instances, from a generalized lowering of the seizure threshold, the following hypothesis was formulated. The gene which results in epilepsy in the large family (that enabled the focusing chromosome 2q23-q31) should have other, less severe, mutations that would cause epilepsy in people who have only a weak family history of epilepsy. The sodium channel genes were chosen because they are involved in key electrical functions and could thus be good candidates. To formally test the hypothesis, many (60 to 70) unrelated cases of epilepsy were tested for mutations in these candidate genes. Surprisingly, mutations were found in all three candidate genes.

In order to assess whether mutations/polymorphisms could be identified and correlated to epilepsy, a panel of 70 to 80 epileptic patients (IGE) were tested for mutations in SCN1A, SCN2A and SCN3A, using Single-strand conformation polymorphism (SSCP). SSCP analysis enables the detection of mutations as small as single-base substitutions. Indeed, such substitutions, by altering the conformations of single-strand DNA molecules, affect the electrophoretic mobilities thereof in non-denaturing gels. Thus, one can distinguish among sequences by comparing the mobilities of wild type (wt), mutant DNA, or different alleles of a given locus. The identification of single base substitutions of genes using SSCP is well known in the art, and numerous protocols are available therefor. A non-limiting example thereof includes fluorescence-based SSCP analysis, following PCR carried out using fluorescent-labeled primers specific for the DNA regions one wishes to amplify.

Upon the identification of differences between normal and epileptic mobilities for one of the SCNA loci of the present invention, the amplified fragments were sequenced and the nucleic acid sequences between a normal patient and an epileptic patient (IGE) compared. This comparison enabled the identification of mutations in SCN1A, SCN2A, and SCN3A. To assess, whether this difference in sequence or mutation was significantly associated with the disease, SSCP analysis was performed once again using a large cohort of normal patients. This analysis enabled to show that the mutations identified by SSCP and confirmed by sequence analysis were not present in the large cohort of normal patients tested, thereby showing that the mutaions identified correlated with IGE, for the population tested.

Taken together, these results show that SCN1A, SCN2A and SCN3A are validated genes associated with epilepsy and more specifically with IGE.

This invention now establishes, for the first time, that SCN1A, SCN2A, and SCN3A, is directly responsible for idiopathic generalized epilepsy (IGE) in certain human populations. Further, this discovery suggests that compounds which modulate the activity of SCN1A, SCN2A and SCN3A may have application far beyond the small groups of families with IGE, and may have applicability for treating many or all forms of epilepsy and related neurological disorders. It is therefore an object of this invention to provide screening assays using SCN1A, SCN2A and/or SCN3A which can identify compounds which have therapeutic benefit for epilepsy and related neurological disorders. This invention also claims those compounds, the use of these compounds in treating epilepsy and related neurological disorders, and any use of any compounds identified using such a screening assay in treating epilepsy and related neurological disorders.

Generally, high throughput screens for one or more SCN1A, SCN2A or SCN3A (herein collectively called SCNA) sodium channels modulators i.e. candidate or test compounds or agents (e.g., peptides, peptidomimetics, small molecules or other drugs) may be based on assays which measure biological activity of SCNA. The invention therefore provides a method (also referred to herein as a "screening assay") for identifying modulators, which have a stimulatory or inhibitory effect on, for example, SCNA biological activity or expression, or which bind to or interact with SCNA proteins, or which have a stimulatory or inhibitory effect on, for example, the expression or activity of SCNA interacting proteins (targets) or substrates.

Examples of methods available for cell-based assays and instrumentation for screening ion-channel targets are described in the review by Gonzalez et al. (Drug Discov. Today 4:431-439, 1999), and high-throughput screens for ion-channel drugs are described in review by Denyer et al. (Drug Discov. Today 3:323-332, 1998). Such assays include efflux of sodium or related ions that can be measured in a cell line (recombinant or non-recombinant) using fluorescence-based assays using both sodium indicator dyes and voltage sensing dyes. Preferred assays employ $^{14}C$ guanidine flux and/or sodium indicator dyes such as SBFI and voltage sensing dyes such as DiBAC. Oxonal dyes such as $DiBAC_4$ are responsive to membrane depolarization. Hyper-polarization results in removal of the dye from the cell by passive diffusion, while depolarization results in concentration of the dye within the cell.

In one embodiment, the invention provides assays for screening candidate or test compounds which interact with substrates of a SCNA protein or biologically active portion thereof.

In another embodiment, the invention provides assays for screening candidate or test compounds which bind to or modulate the activity of a SCNA protein or polypeptide or biologically active portion thereof.

In one embodiment, an assay is a cell-based assay in which a cell which expresses a SCNA protein or biologically active portion thereof, either natural or recombinant in origin, is contacted with a test compound and the ability of the test compound to modulate SCNA biological activity, e.g., modulation of sodium efflux activity, or binding to a sodium channel or a portion thereof, or any other measurable biological activity of SCNA is determined. Determining the ability of the test compound to modulate SCNA activity can be accomplished by monitoring, for example, the release of a neurotransmitter or other compound, from a cell which expresses SCNA such as a neuronal cell, e.g. a substantia nigra neuronal cell, or a cardiac cell upon exposure of the test compound to the cell. Furthermore, determining the ability of the test compound to modulate SCNA activity can be accomplished by monitoring, for example, the change in current or the change in release of a neurotransmitter from a cell which expresses SCNA upon exposure to a test compound. Currents in cells can be measured using the patch-clamp technique as described in the Examples below using the techniques described in, for example, Hamill et al. 1981 Pfluegers Arch. 391:85-100. Alternatively, changes in current can be measured by dye based fluorescence assays described below.

Determining the ability of the test compound to modulate binding of SCNA to a substrate can be accomplished, for example, by coupling the SCNA agent or substrate with a radioisotope or enzymatic label such that binding of the SCNA substrate to SCNA can be determined by detecting the labeled SCNA substrate in a complex. For example, compounds (e.g., SCNA agents or substrates) can be labeled with $^{125}$I, $^{35}$S, $^{14}$C, or $^{3}$H, either directly or indirectly, and the radioisotope detected by direct counting radio-emission or by scintillation counting. Alternatively, compounds can be enzymatically labeled with, for example, horseradish peroxidase or alkaline phosphatase. In these assays, compounds which inhibit or increase substrate binding to SCNA are useful for the therapeutic objectives of the invention.

It is also within the scope of this invention to determine the ability of a compound (e.g. SCNA substrate) to interact with SCNA without the labeling of any of the interactants. For example, a microphysiometer can be used to detect the interaction of a compound with SCNA without the labeling of either the compound or the SCNA (McConnell H. M. et al. (1992), Science 257:1906-1912). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between a compound and SCNA.

Modulators of SCNA can also be identified through the changes they induce in membrane potential. A suitable instrument for measuring such changes is the VIPR™ (voltage ion probe reader) from Aurora Biosciences. This instrument works together with a series of voltage-sensing ion probe assays. The probes sense changes in transmembrane electrical potential through a voltage-sensitive FRET mechanism for which the ratio donor fluorescence emission to acceptor fluorescence emission reveals the extent of cell depolarization for both sodium and potassium channels. Depolarization results from transport of a quencher across the membrane and far enough away from a membrane-boundfluorescence emitter to relieve the initial quenching and produce light at the emission wavelength of the emitter. The system follows fluorescence at two wavelengths, both the intensities and ratios change during cell depolarization. The reader permits detection of sub-second, real-time optical signals from living cells in a microplate format. The system is amenable to manual operation for assay development or automation via robots for high-throughput screening.

In another embodiment, the assay is a cell-based assay comprising a contacting of a cell containing a target molecule (e.g. another molecule, substrate or protein that interacts with or binds to SCNA) with a test compound and determining the ability of the test compound to indirectly modulate (e.g. stimulate or inhibit) the biological activity of SCNA by binding or interacting with the target molecule. Determining the ability of the test compound to indirectly modulate the activity of SCNA can be accomplished, for example, by determining the ability of the test compound to bind to or interact with the target molecule and thereby to indirectly modulate SCNA, to modulate sodium efflux, or to modulate other biological activities of SCNA. Determining the ability of the SCNA protein or a biologically active fragment thereof, to bind to or interact with the target molecule can be accomplished by one of the methods described above or known in the art for determining direct binding. In a preferred embodiment, determining the ability of the test compound's ability to bind to or interact with the target molecule and thereby to modulate the SCNA protein can be accomplished by determining a secondary activity of the target molecule. For example, the activity of the target molecule can be determined by detecting induction of a cellular second messenger of the target (e.g. intracellular Ca2+, diacylglycerol, IP3, and the like), detecting catalytic/enzymatic activity of the target on an appropriate substrate, detecting the induction of a reporter gene (comprising a target-responsive regulatory element operatively linked to a nucleic acid encoding a detectable marker, such as luciferase), or detecting a target-regulated cellular response such as the release of a neurotransmitter. Alternatively, recombinant cell lines may employ recombinant reporter proteins which respond, either directly or indirectly to sodium efflux or secondary messengers all as known in the art.

In yet another embodiment, an assay of the present invention is a cell-free assay in which a SCNA protein or biologically active portion thereof, either naturally occurring or recombinant in origin, is contacted with a test compound and the ability of the test compound to bind to, or otherwise modulate the biological activity of, the SCNA protein or biologically active portion thereof is determined. Preferred biologically active portions of the SCNA proteins to be used in assays of the present invention include fragments which participate in interactions with non-SCNA molecules, (e.g. other channels for sodium, potassium or Ca+ or fragments thereof, or fragments with high surface probability scores for protein-protein or protein-substrate interactions). Binding of the test compound to the SCNA protein can be determined either directly or indirectly as described above. In a preferred embodiment, the assay includes contacting the SCNA protein or biologically active portion thereof with a known compound which binds SCNA to form an assay mixture, contacting the assay mixture with a test compound, and determining the ability of the test compound to interact with a SCNA protein, wherein determining the ability of the test compound to interact with a SCNA protein comprises determining the ability of the test compound to preferentially bind to SCNA or biologically active portion thereof as compared to the known compound.

In another embodiment, the assay is a cell-free assay in which a SCNA protein or biologically active portion thereof is contacted with a test compound and the ability of the test compound to modulate (e.g., stimulate or inhibit) the activity of the SCNA protein or biologically active portion thereof is determined. Determining the ability of the test compound to modulate the activity of a SCNA protein can be accomplished, for example, by determining the ability of the SCNA protein to bind to a SCNA target molecule by one of the methods described above for determining direct binding. Determining the ability of the SCNA protein to bind to a SCNA target molecule can also be accomplished using a technology such as real-time Biomolecular Interaction Analysis (BIA, Sjolander, S. and Urbaniczky, C. (1991) Anal. Chem. 63:2338-2345 and Szabo et al. (1995) Curr. Opin. Struct. Biol. 5:699-705). As used herein, "BIA" refers to a technology for studying biospecific interactions in real time, without labeling any of the interactants (e.g. BIA core). Changes in the optical phenomenon of surface plasmon resonance (SPR) can be used as an indication of real-time reactions between biological molecules.

In an alternative embodiment, determining the ability of the test compound to modulate the activity of a SCNA protein can be accomplished by determining the ability of the test compound to modulate the activity of an upstream or downstream effector of a SCNA target molecule. For example, the activity of the test compound on the effector molecule can be determined or the binding of the effector to SCNA can be determined as previously described.

The cell-free assays of the present invention are amenable to use of both soluble and/or membrane-bound forms of isolated proteins. In the case of cell-free assays in which a membrane-bound form of an isolated protein is used (e.g. a sodium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-IOO, Triton®X-114, Thesit®, Isotridecypoly(ethylene glycol ether)n. 3-[(3-cholamidopropyl)dimethy-amino]-I-propane sulfonate (CHAPS), 3-[(3-cholamidopropyl)dimethylamino]-2-hydroxy-I-propane sulfonate (CHAPSO), or N-dodecyl-N,N-dimethyl-3-ammnonio-I-propane sulfonate.

In more than one embodiment of the above assay methods of the present invention, it may be desirable to immobilize either SCNA or its target molecule to facilitate separation of complexed from uncomplexed forms of one or both of the proteins, as well as to accommodate automation of the assay. Binding of a test compound to a SCNA protein or interaction of a SCNA protein with a target molecule in the presence and absence of a candidate compound, can be accomplished in any vessel suitable for containing the reactants. Examples of such vessels include microtitre plates, test tubes and microcentrifuge tubes. In one embodiment a fusion protein can be provided which adds a domain that allows one or both of the proteins to be bound to a matrix. For example, glutathione-S-transferase/SCNA fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or SCNA protein and the mixture incubated under conditions conducive to complex formation (e.g. at physiological conditions for salt and pH). Following incubation the beads or microtitre plate wells are washed to remove any unbound components, the matrix immobilized in the case of beads, complex determined either directly or indirectly, for example, as described above. Alternatively, the complexes can be dissociated from the matrix, and the level of SCNA binding or activity determined using standard techniques.

Other techniques for immobilizing proteins on matrices (and well-known in the art) can also be used in the screening assays of the invention. For example, either a SCNA protein or a SCNA target molecule can be immobilized utilizing conjugation of biotin and streptavidin. Biotinylated SCNA protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with SCNA protein or target molecules but which do not interfere with binding of the SCNA protein to its target molecule can be derivatized to the wells of the plate, and unbound target or SCNA protein trapped in the wells by antibody conjugation. Methods for detecting such complexes, in addition to those described above for the GST-immobilized complexes, include immunodetection of complexes using antibodies reactive with the SCNA protein or target molecule, as well as enzyme-linked assays which rely on detecting an enzymatic activity associated with the SCNA protein or target molecule.

In a preferred embodiment, candidate or test compounds or agents are tested for their ability to inhibit or stimulate a SCNA molecule's ability to modulate vesicular traffic and protein transport in a cell, e.g. a neuronal or cardiac cell using the assays described in for example Komada M. et al. (1999) Genes Dev. 13(11):1475-85, and Roth M. G. et al. (1999) Chem. Phys. Lipids. 98(12):141-52.

In another preferred embodiment candidate, or test compounds or agents are tested for their ability to inhibit or stimulate or regulate the phosphorylation state of a SCNA channel protein or portion thereof, or an upstream or downstream target protein, using for example an in vitro kinase assay. Briefly, a SCNA target molecule (e.g. an immunoprecipitated sodium channel from a cell line expressing such a molecule), can be incubated with radioactive ATP, e.g., [gamma-32P]-ATP, in a buffer containing MgCl2 and MnCl2, e.g., 10 mM MgCl2 and 5 mM MnCl2. Following the incubation, the immunoprecipitated SCNA target molecule (e.g. the sodium channel), can be separated by SDS-polyacrylamide gel electrophoresis under reducing conditions, transferred to a membrane, e.g., a PVDF membrane, and autoradiographed. The appearance of detectable bands on the auto radiograph indicates that the SCNA substrate, e.g., the sodium channel, has been phosphorylated. Phosphoaminoacid analysis of the phosphorylated substrate can also be performed in order to determine which residues on the SCNA substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards. Assays such as those described in, for example, Tamaskovic R. et al. (1999) Biol. Chem. 380(5):569-78.

In another preferred embodiment, candidate or test compounds or agents are tested for their ability to inhibit or stimulate a SCNA molecule's ability to associate with (e.g.

bind) calcium, using for example, the assays described in Liu L. (1999) Cell Signal. 11(5):317-24 and Kawai T. et al. (1999) Oncogene 18(23):3471-80.

In another preferred embodiment, candidate or test compounds or agents are tested for their ability to inhibit or stimulate a SCNA molecule's ability to modulate chromatin formation in a cell using for example the assays described in Okuwaki M. et al. (1998) J. Biol. Chem. 273(51):34511-8 and Miyaji-Yamaguchi M. (1999) J. Mol. Biol. 290(2): 547-557.

In yet another preferred embodiment candidate or test compounds or agents are tested for their ability to inhibit or stimulate a SCNA molecule's ability to modulate cellular proliferation, using for example, the assays described in Baker F. L. et al. (1995) Cell Prolif. 28(1):1-15, Cheviron N. et al. (1996) Cell Prolif. 29(8):437-46. Hu Z. W. et al. (1999) J: Pharmacol. Exp. Ther. 290(1):28-37 and Elliott K. et al. (1999) Oncogene 18(24):3564-73.

In a preferred embodiment, candidate or test compounds or agents are tested for their ability to inhibit or stimulate a SCNA molecule's ability to regulate it's association with the cellular cytoskeleton. Using for example, the assays similar to those described in Gonzalez C. et al. (1998) Cell Mol. Biol. 44(7):1117-27 and Chia C. P. et al. (1998) Exp. Cell Res. 244(1):340-8.

In another preferred embodiment, candidate or test compounds or agents are tested for their ability to inhibit or stimulate a SCNA molecule's ability to modulate membrane excitability, using for example, the assays described in Bar-Sagi D. et al. (1985) J. Biol. Chem. 260(8):4740-4 and Barker J. L. et al. (1984) Neurosci. Lett. 47(3):313-8.

In another preferred embodiment, candidate or test compounds or agents are tested for their ability to inhibit or stimulate a SCNA molecule's ability to modulate cytokine signaling in a cell, (e.g., a neuronal or cardiac cell), the assays described in Nakashima Y. et al. (1999) J: Bone Joint Surg. Am. 81 (5):603-15.

In another embodiment, modulators of SCNA expression are identified in a method wherein a cell is contacted with a candidate compound and the expression of SCNA mRNA or protein in the cell is determined. The level of expression of SCNA mRNA or protein in the presence of the candidate compound is compared to the level of expression of SCNA mRNA or protein in the absence of the candidate compound. The candidate compound can then be identified as a modulator of SCNA expression based on this comparison. For example, when expression of SCNA mRNA or protein is greater (statistically significantly greater) in the presence of the candidate compound than in its absence, the candidate compound is identified as a stimulator of SCNA mRNA or protein expression. Alternatively, when expression of SCNA mRNA or protein is less (statistically significantly less) in the presence of the candidate compound than in its absence, the candidate compound is identified as an inhibitor of SCNA mRNA or protein expression. The level of SCNA mRNA or protein expression in the cells can be determined by methods described herein or other methods known in the art for detecting SCNA mRNA or protein.

The assays described above may be used as initial or primary screens to detect promising lead compounds for further development. Often, lead compounds will be further assessed in additional, different screens. Therefore, this invention also includes secondary SCNA screens which may involve electrophysiological assays utilizing mammalian cell lines expressing the SCNA channels such as patch clamp technology or two electrode voltage clamp and FRET-based voltage sensor. Standard patch clamp assays express wild type and mutant channels in Xenopus oocytes, and examine their properties using voltage-clamp electrophysiological recording. Wild type sodium channels are closed at hyperpolarized membrane potentials. In response to membrane depolarization the channels open within a few hundred microseconds, resulting in an inward sodium flux, which is terminated within a few milliseconds by channel inactivation. In whole cell recordings, rapid activation and inactivation of thousands of sodium channels distributed throughout the cell membrane results in a transient inward sodium current that rises rapidly to peak amplitude and then decays to baseline within a few milliseconds.

Tertiary screens may involve the study of the identified modulators in rat and mouse models for epilepsy. Accordingly, it is within the scope of this invention to further use an agent identified as described herein in an appropriate animal model. For example, an test compound identified as described herein (e.g., a SCNA modulating agent, an antisense SCNA nucleic acid molecule, a SCNA-specific antibody, or a SCNA-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment (e.g. treatments of different types of epilepsy or CNS disorders), as described herein.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des. 12: 145, 1997). Examples of methods for the synthesis of molecular libraries can be found in the art, for example in: DeWift et al. (1993) Proc. Natl. Acad. Sci. USA. 90:6909; Erb et al. (1994) Proc. Natl. Acad. Sci. USA 91:11422; Zuckermann et al. (1994), J. Med. Chem. 37:2678; Cho et al. (1993) Science 261:1303; Carrell et al. (1994) Angew. Chem, Int. Ed Engl. 33:2059; Carell et al. (1994) Angew. Chem. Jnl. Ed. Engl. 33:2061; and in Gallop et al. (1994). Med Chem. 37:1233. Libraries of compounds may be presented in solution (e.g. Houghten (1992) Biotechniques 13:412-421). or on beads (Lam (199]) Nature 354:82-84), chips (Fodor (1993) Nature 364:555-556). bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990); Science 249:386-390). Examples of methods for the synthesis of molecular libraries can be found in the art, for example in: DeWitt et al. (1993) Proc. Natl. Acad. Sci. USA. 90:6909; Erb et al. (1994) Proc. Natl. Acad Sci. USA 91: 11422; Zuckermann et al. (1994), J: Med. Chem. 37:2678; Cho et al. (1993), Science 261:1303; Carrell et al. (1994) Angew. Chem Int. Ed. Engl. 33:2059, or luciferase, and the enzymatic label detected by determination of conversion of an appropriate substrate to product.

In summary, based on the disclosure herein, those skilled in the art can develop SCNA screening assays which are useful for identifying compounds which are useful for treating epilepsy and other disorders which relate to potentiation of SCNA expressing cells. The assays of this invention may be developed for low-throughput, high-throughput, or ultra-high throughput screening formats.

The assays of this invention employ either natural or recombinant SCNA protein. Cell fraction or cell free screening assays for modulators of SCNA biological activity can use in situ, purified, or purified recombinant SCNA proteins. Cell based assays can employ cells which express SCNA protein naturally, or which contain recombinant SCNA gene constructs, which constructs may optionally include inducible promoter sequences. In all cases, the biological activity of SCNA can be directly or indirectly measured; thus modulators of SCNA biological activity can be identified. The modulators themselves may be further modified by standard combinatorial chemistry techniques to provide improved analogs of the originally identified compounds.

Finally, portions or fragments of the SCNA cDNA sequences identified herein (and the corresponding complete gene sequences) can be used in numerous ways as polynucleotide reagents. For example, these sequences can be used to: (i) map their respective genes on a chromosome and thus, locate gene regions associated with genetic disease (mutations/polymorphisms) related to epilepsy or CNS disorders that involve SCNA directly or indirectly; (ii) identify an individual from a minute biological sample (tissue typing); and (iii) aid in forensic identification of a biological sample.

The present invention is illustrated in further detail by the following non-limiting examples.

EXAMPLE 1

Molecular Analysis

Genomic DNA was extracted from blood samples (Sambrook et al. 1989) or lymphoblastoid cell lines (Anderson and Gusella 1984) from each individual. A panel of 210 dinucleotide (CA)n repeat polymorphic markers with high heterozygosity (75%) were chosen from the 1993-94 Généthon map (Gyapay et al. 1994). Dinucleotide markers were spaced an average of 20 cM from each other throughout the 22 autosomes.

Genotyping of microsatellite markers was accomplished by polymerase chain reaction (PCR). The reaction mixture was prepared in a total volume of 13 μl, using 80 ng genomic DNA; 1.25 μl 10× buffer with 1.5 mM MgCl2; 0.65 μl BSA (2.0 mg/ml); 100 ng of each oligonucleotide primer; 200 mM dCTP, dGTP and dTTP; 25 mM dATP; 1.5 mCi [35S] dATP; and 0.5 units Taq DNA polymerase (Perkin-Elmer). Reaction samples were transferred to 96 well plates and were subjected to: 35 cycles of denaturation for 30 seconds at 94° C., annealing for 30 seconds at temperatures varying from 55° C. to 57° C. depending on the specificity of the oligonucleotide primers, and elongation for 30 seconds at 72° C. PCR reaction products were electrophoresed on 6% denaturing polyacrylamide sequencing gels.

EXAMPLE 2

Genetic Analysis

Two-point linkage analysis was carried out using the MLINK program version 5.1 from the LINKAGE computer package (Lathrop et al. 1984). Precise values for Zmax were calculated with the ILINK program from the same computer package. Lod scores were generated based on an autosomal dominant mode of inheritance, 80% penetrance, disease gene frequency of 1:500 and allele frequencies for all allele markers calculated from the pedigree using the computer program ILINK (Lathrop et al. 1984).

EXAMPLE 3

Mutations in SCN1A in IGE Patients

Genomic DNA from IGE and normal patients was obtained by conventional methods. Primers used to amplify the genomic DNA are shown in FIG. 2. Following PCR, SSCP analysis was performed and mutations in SCN1A were identified as follows (FIG. 3):

(1) Glu1238Asp; normal: GCA TTT GAA GAT ATA; (SEQ ID NO: 189) patient R10191 who has an idiopathic generalized epilepsy (IGE): GCA TTT GAC GAT ATA (SEQ ID NO: 190) found in 1 of 70 IGE patients). The mutation is thus a conservative aa change, in the extracellular domain between III-S1 and III-S2. Furthermore, this residue is located at the junction between the TM domain and the extracellular domain. It may thus influence gating activity. The aa change between adult and neonatal isoforms is at a similar juxta-TM domain position (between I-S3 and I-S4).

(2) Ser1773Tyr; normal: ATC ATA TcC TTC CTG (SEQ ID NO: 191), patient R9049 (affected with IGE): ATC ATA TmC TTC CTG:(TCC>TAC, (SEQ ID NO: 192) This mutation is in the middle of IV-S6 TM domain; found in 1/70 IGE patients, and 0/150 control subjects tested. This mutation is interesting from a biological point of view for a number of reasons. First, this region of SCN gene (IV-S6) has been found to play a critical role in fast inactivation of the SCN, by mutagenesis experiments in rat SCN (McPhee et al., 1998). This is highly relevant for pathophysiology of epilepsy, since this may increase neuronal hyperexcitability. Moreover, in patients with GEFs, a mutation has been found in the SCNB1 subunit, causing impairment of the fast inactivation of the SCN (Wallace et al, 1999). Finally, many of the antiepileptic drugs (e.g. phenytoin, carbamazepine) primarily act by reducing the repetitive firing of neuron, which also involves fast inactivation of the SCN.

EXAMPLE 4

Mutations in SCN2A in IGE Patients

Genomic DNA from IGE and normal patients was obtained by conventional methods. Primers used to amplify the genomic DNA are shown in FIG. 4. Following PCR, SSCP analysis was performed and mutations in SCN2A were identified as follows (FIG. 5):

(1) Lys908Arg: normal: TAC AAA GAA (SEQ ID NO: 307) for patient numbers always proceeded by R; R9782 (Patient with IGE): TAC AGA GAA (SEQ ID NO: 308). The mutation is thus a conservative aa change, located in an extracellular domain between TM domains IIS5 and IIS6; in 1/70 IGE patients; 0/96 normal controls. The mutation involves an important component of the SCN gene, since the S5 and S6 segments are thought to form the wall of the transmembrane pore which allows the sodium to enter the cell. This may have an influence on the gating control of the pore.

(2) Leu768Val, in individuals R8197, R9062 and R9822 (all IGE patients) (found in 3/70 IGE patients and 0/65 control subjects). The mutation is in the IV-S6 component of the sodium channel, which is important in the inactivation of the channel (see above for more detail).

EXAMPLE 5

Mutations in SCN3A in IGE Patients

Genomic DNA from IGE and normal patients was obtained by conventional methods. Primers used to amplify the genomic DNA are shown in FIG. 6. Following PCR, SSCP analysis was performed and mutations in SCN3A were identified as follows (FIG. 7):

(1) Asn43DEL: allele 1: CAA GAT AAT GAT GAT GAG (SEQ ID NO:400); allele 2: CAA GAT --- GAT GAT GAG (SEQ ID NO: 401); in open reading frame deletes 1 aa: DNDDEN→QDDDEN, in the cytoplasmic N-terminal segment; in IGE patients, the frequency of allele 1=131/146 (0.90); allele 2=15/146 (0.10); for IGE patients: homozygotes (22): R3958, R9632; heterozygotes (12): R9049, R9152, R9649, R9710, R9896, R10069, R10191, R10213, R9993, R10009, R10256. Of note, 2 patients are homozygous for the rare allele and all patients have IGE. In controls: allele 1=145/154 (0.94); allele 2=9/154 (0.06) and no 22 homozygotes were found.

(2) normal: tggtgtaaggtag (SEQ ID NO: 402), R10670 (1 GB patient): tggtataaggtag (SEQ ID NO: 403), in conserved intron between 5N & 5A exons, significance uncertain.

(3) normal: ccccttatatctccaac (SEQ ID NO: 404), R10250 (1 GB patient): ccccttatayctccaac (SEQ ID NO: 405); in conserved intron between 5N & 5A exons, significance uncertain.

(4) Val1035Ile: normal: AAA TAC GTA ATC GAT (SEQ ID NO: 406), R9269 (IGE patient): AAA TAC RTA ATC GAT, (GTA>ATA=Val>Ile); (SEQ ID NOs: 407 and 408). The mutation is thus a conservative aa change which destroys a SnaBI site (this could thus be used as a polymorphism identifiable by restriction enzyme digestion). In SCN1A, this Val is a Ile, therefore probably not a causative mutation. In cytoplasmic domain bw II-S6 & III-S1 TMs; found in 1/70 IGE alleles; and 0/70 controls.

EXAMPLE 6

SCN1A is Involved in Idiopathic Generalized Epilepsy

The assumption that SCN1A gene is involved in idiopathic generalised epilepsy in humans is based on many sets of evidence. First, a mutation has been found in a large Australian family with autosomal dominant epilepsy. The phenotype is idiopathic generalised epilepsy that is associated with febrile seizures (GEFS syndrome). The gene for this family has been previously mapped to the long arm of chromosome 2. The maximum lod score is 6.83 for marker D2S111. The candidate region is very large, spanning 21 cM between markers, D2S156 and D2S311. However, within this interval, there is a cluster of sodium channel genes, including SCN1A which was hypothesized to be a candidate gene for the disease.

Screening by SSCP of a small panel of three (3) affected patients form the family, and 3 normal controls was carried-out at first. All the exons of the SCN1A gene have been amplified by PCR, and a SSCP variant in exon 4 was found for all of the affected individuals, and none of the controls. By sequencing an affected patient and a control, an A-T substitution at nucleotide 565 was found. This variation destroys a BamHI restriction site, this enzyme was thus used as a diagnostic test to screen all the affected patients from the family, as well as more control cases. All affected patients from the family have A565T substitution, and none of the unaffected patients in the same kindred. An A565T substitution was not found in more than 400 control chromosomes.

The A565T substitution correspond to a nonconservative amino acid change (D188V). This amino acid is conserved in all sodium channels thus far identified, in all species. The only exception is SCN2A identified in rat by Numa et al, where the aspartic acid is replaced by asparagine. However, it is likely that this represents an error during replication of cDNA, since other investigators have cloned the same gene in rat and found that the aspartic acid is conserved at position 188. Moreover, the same group has shown that D188N has a functional effect on channel activation in oocytes (Escayg et al., *Nature Genetics*. 24(4):343-5, 2000). Of note, this A565T substitution has not been found in 150 epileptic patients and in 200 control patients. Thus, this substitution has yet to be identified after 700 chromosomes assessments.

In view of proving that D188V in SCN1A, identified in the large Australian family studied, is a pathogenic mutation, the oligonucleotide mismatch mutagenesis technique was used to introduce the mutation in rat SCN1A clone. RNA was isolated from mutant and wild-type clones, and injected into oocytes in view of recording sodium currents by the patch-clamp technique. The amplitude of the currents was dramatically reduced for the mutant. Also, a small shift in the inactivation curve was observed for the mutant, as compared to the wild-type. Taken together, these preliminary results confirm a functional effect of D188V mutation on SCN1A gene. (more detail below).

The results presented herein are corroborated by studies from other investigators. For example, several other groups have also found linkage to the same locus on chromosome 2 for families with GEFS or very similar syndromes. Mutations in SCN1A (Thr875Met mutation; Arg1648His) have been found to be the cause of the epileptic syndrome in at least two (2) of these families (Escayg et al., *Nature Genetics*. 24(4):343-5, 2000). Also, GEFS syndrome has been shown to be caused by mutation in SCN1B gene. It is demonstrated that the beta subunits interact with alpha subunits of voltage-gated sodium channels to alter kinetics of sodium currents in cells. These data suggest a common mechanism for generating abnormal neuronal discharges in the brain of patients with idiopathic generalised epilepsy.

Finally, in the process of screening patients from the large kindred with GEFS described above, a large cohort of patients with idiopathic generalised epilepsy was also screened by SSCP. Two (2) SSCP variants, that were subsequently sequenced were thereby identified. The variation observed are shown in Table 3:

TABLE 3

| exon | DNA variation | IGE alleles | Control alleles |
|---|---|---|---|
| 1Ax17 | Glu1238Asp; conservative AA change in extracellular domain between III-S1 and III-S2 | 3/254 | 0/284 |
| 1Ax24.2 | Ser1773Tyr; middle of IV-S6 TM domain | 1/252 | 0/334 |

Previous functional studies have shown that amino acid substitution in the IV-S6 transmembrane domain of SCN2A significantly affects the rate of inactivation of the channel. It is thus likely that Ser1773Tyr will have an effect on the SCN1A gene function. Such functional studies are currently underway.

EXAMPLE 7

Further Validation of the Role of SCN1A, SCN2A, SCN3A, and Specific Mutations thereof in IGE and Epilepsy in General A number of methods could be used to further validate the role of SCN1A, SCN2A, SCN3A, and specific mutations thereof in IGE. For example, additional patients could be screened for mutations in SCN1A, SCN2A, or SCN3A. Furthermore, additional normal patients could be screened in order to validate that the mutations identified significantly correlate with disease, as opposed to reflecting a polymorphism which is not linked to IGE. Polymorphisms which are not directly linked to IGE, if in linkage disequilibrium with a functional mutation linked to IGE, could still be useful in diagnosis and/or prognosis assays. In addition, functional studies can be carried. Numerous methods are amenable to the skilled artisan. One particularly preferred functional assay involves the use of *Xenopus oocytes* and recombinant constructs harboring normal or mutant sequence of SCN1A, SCN2A, or SCN3A. *Xenopus oocytes* have been used in functional assays to dissect the structure-function relationship of the cyclic AMP-modulated potassium channel using recombinant KCNQ2 and KCNQ3 (Schroeder et al., 1998). As well, it has been used to dissect the structure-function relationship of the beta subunit of the sodium channel (SCN1B gene; Wallace et al. 1998).

One such example of functional studies was investigated by assessing the effects of mutation D188V in the SCN1A gene on sodium channel function by introducing the mutation into a cDNA encoding the rat ortholog SCN1A gene. This rat gene shares >95% identity with the human SCN1A gene. The expression of wild type and mutant channels in Xenopus oocytes, and the examination of their properties using voltage-clamp electrophysiological recording is amenable to this Xenopus system. Wild type sodium channels are closed at hyperpolarized membrane potentials. In response to membrane depolarization the channels open within a few hundred microseconds, resulting in an inward sodium flux, which is terminated within a few milliseconds by channel inactivation. In whole cell recordings, rapid activation and inactivation of thousands of sodium channels distributed throughout the cell membrane results in a transient inward sodium current that rises rapidly to peak amplitude and then decays to baseline within a few milliseconds. Among the channel properties that are likely to be altered by mutations linked to epilepsy are: 1) the voltage-dependence of activation, a measure of the strength of membrane depolarization necessary to open the channels; 2) the voltage-dependence of steady state inactivation, a measure of the fraction of channels available to open at the resting membrane potential; and 3) the time course of inactivation. Preliminary results indicate that D188V mutant channels are identical to wild type channels with respect to the voltage-dependence of activation and to inactivation time course. However, steady state inactivation for the mutant channels is shifted to membrane potentials that are slightly more positive than observed in wild type channels. This positive shift should increase the fraction of channels available to open at rest. This could increase neuronal excitability and contribute to epileptogenesis. Thus, a functional consequence of a naturally occurring mutation in a sodium channel gene has been tentatively identified. Thus, the functional consequence of the D188M mutant could at least in part explain its role in epilepsy. Such a functional consequence is expected to be observed with other mutations identified above in SCNA1, SCNA2 and SCNA3.

It is recognized by the inventors that certain therapeutic agents have been identified for cardiac, muscular, chronic pain, acute pain and other disorders, and analgesics and anesthetics that are modulators of sodium channels. Use of these sodium channel modulators for treating epilepsy and related neurological disorders also falls within the scope of this invention. In one embodiment of this invention, sodium channel blockers are modified to achieve improved transport across the blood brain barrier in order to have direct effect on neuronal SCNA proteins and genes. Descriptions of such compounds are found at Hunter, J C et al. Current Opinion in CPNS Invest. Drugs. 1999 1(1):72-81; Muir K W et al. 2000. Cerebrovasc. Disc. 10(6):431436; Winterer, G. 2000. Pharmacopsychiatry 33(5):182-8; Clare et al. 2000. Drug. Discov. Today 5(11):506-520; Taylor C P et al. 2000. Adv. Pharmacol. 39:47-98, and Pugsley M K et al. 1998. Eur. J. Pharmacol. 342(1)93-104.

It is also recognized by the inventors that compounds which modulate (i.e. either upregulate or downregulate) transcription and translation of SCNA genes are useful for treating epilepsy or related neurological disorders. According to this invention, test compounds which modulate the activity of promoter elements and regulatory elements of sodium channel genes are useful for treating these disorders.

Although the present invention has been described hereinabove by way of preferred embodiments thereof, it can be modified, without departing from the spirit and nature of the subject invention as defined in the appended claims.

REFERENCES

Andermann E (1982) Multifactorial inheritance of generalized and focal epilepsy. In: Anderson V E, Hauser W A, Penry J K, Sing C F (eds) GeneticBasis of the Epilepsies. New York, Raven Press, pp: 355-374

Anderson M A and Gusella J F (1984) Use of cyclosporin A in establishing Epstein Barr virus-transformed human lymphoblastoid cell lines. In Vitro 20:856-858

Anneger J F, Hauser W A, Anderson V E (1982) Risk of seizures among relatives of patients with epilepsy: families in a defined population. In: Anderson V E, Hauser W A, Sing L, Porter R (eds) The Genetic Basis of the Epilepsies, Raven Press, New York, pp 151-159

Barnard E A, Darlison M G, Seeburg P (1987) Molecular biology of the GABAA receptor: the receptor/channel superfamily. Trends Neurosci 10:502-509.

Berkovic S F, et al. Epilepsies in twins: genetics of the major epileptic syndromes. Ann Neurol. 43:435-445 (1998).

Bievert C, Schoeder B C, Kubisch C, Berkovic S F, Propping P, Jentsch T J, Steinlein O K (1998) A potassium channel mutation in neonatal human epilepsy. Science 279:403-406

Bu D F, Tobin A J (1994) The exon-intron organization of the genes (GAD1 and GAD2) encoding two human glutamate decarboxylases (GAD67 and GAD65) suggests that they derive from a common ancestral GAD. Genomics 1:222-228.

Charlier C, et al. A pore mutation in a novel KGT-like potassium channel gene in an idiopathic epilepsy family. Nat. Genet. 18:53-55 (1998).

Commission on Classification and Terminology of the International League against Epilepsy (1989) Proposal for revised clinical and eletroencephalographic classification of epileptic seizures. Epilepsia 22:489-501

Corey L A, Berg K, Pellock J M, Solaas M H, Nance W E, DeLorenzo R J (1991) The occurrence of epilepsy and febrile seizures in Virginian and Norwegian twins. Neurology 41:433-436

Elmslie F V, Rees M, Williamson M P, Kerr M, Kjeldsen M J, Pang K A, Sundqvist A, et al (1997) Genetic mapping of a major susceptibility locus for juvenile myoclonic epilepsy on chromosome 15q. Hum Mol Genet 6:1329-1334

Engel J J, Pedley T A (1998) What is epilepsy? In: Engel J J, Pedley T A (eds) Epilepsy a Comprehensive Textbook, Lippincott-Raven Publishers, Philadelphia, pp: 1-10.

Escayg et al., *Nature Genetics*. 24(4):343-5, 2000.

Greenberg D A, Delgado-Escueta A V, Widelitz H, Sparkes R S, Treiman L, Maldonado H M, et al (1988) Juvenile myoclonic epilepsy (JME) may be linked to the BF and HLA loci on human chromosome 6. Am J Hum Genet 31:185-192

Guipponi M, Rivier F, Vigevano F, Beck C, Crespel A, Echenne B, Lucchini P, et al (1997) Linkage mapping of benign familial infantile seizures (BFIS) to chromosome 19q. Hum Mol Genet 6:473-477

Gyapay G, Morissette J, Vighal A, et al. (1994) The 1993-94 Genethon human genetic linkage map. Nat Genet 7:246-339

Harvald B and Hauge M (1965) Hereditary factors elucidated by twin studies. In: Neel J V, Shaw M W, Schull W J (eds) Genetics and the Epidemiology of Chronic Diseases, Washington Public Health Service Publications 1163:61-76

Inouye E. (1960) Observations on forty twin index cases with chronic epilepsy and their co-twins. J Nerv Ment Dis 130: 401-416

Lathrop G M, Lalouel J M, (1984) Easy calculations of lod scores and genetic risks on small computers. Am J Hum Genet 36:460-465

Lennox W G, Lennox M A (1960) Epilepsy and related disorders. Boston, Little Brown.

Leppert M, Anderson V E, Quattlebaum T, Staufe D, O'Connell P, Nakamura Y, Lalouel J M, et al (1989) Benign familial neonatal convulsions linked to genetic markers on chromosome 20. Nature 337:647-648

Lewis T B, Leach R J, Ward K, O'Connell P, Ryan S G (1993) Genetic Heterogeneity in benign familial neonatal convulsions: identification of a new locus on chromosome 8q. Am J Hum Genet 53:670-675

McPhee et al., 1998, J. Biol. Chem. 273:1121-1129

Ottman R, Annegers J F, Hauser W A, Kurland L T (1989) Seizure risk in offspring of parents with generalized versus partial epilepsy. Epilepsia 30:157-161

Ottman R, Hauser W A, Barker-Cummings C, Lee J H, Risch N (1997) Segregation analysis of cryptogenic epilepsy and an empirical test of the validity of the results. Am J Hum Genet 60:667-675

Sambrook J, Fritsch E F, Maniatis T (eds) (1989) Molecular cloning: a laboratory manual, 2nd ed. Cold Spring Harbor Laboratory, Cold Spring Harbor, N.Y., pp E.3-E.4

Scheffer I E and Berkovic S F (1997) Generalised epilepsy with febrile seizures plus: a genetic disorder with heterogeneous clinical phenotypes. Brain 120: 479-490.

Schroeder et al., 1998, Nature 396:687-690.

Silanpaa M, Koskenvuo M, Romanov K, Kaprio J (1991) Genetic factors in epileptic seizures: evidence from a large twin population. Acta Neurol Scand 84:523-526

Singh N A, Charlier C, Stauffer D, DuPont B R, Leach R J, Melis R, Ronen G M, et al (1998) A novel potassium channel gene, KCNQ2, is mutated in an inherited epilepsy of newborns. Nat Genet 18:25-29

Steinlein O K, et al. A missense mutation in the neuronal nicotinic acetylcholine receptor alpha 4 subunit is associated with autosomal dominant nocturnal frontal lobe epilepsy. Nat. Genet. 11:201-203 (1995).

Wallace R H, Wang D W, Sing R, Scheffer I E, George-Jr A L, Phillips H A, Saar K, et al (1998) Febrile seizures and generalized epilepsy associated with a mutation in the Na+-channel (1 subunit gene SCN1B. Nat Genet 19:366-370

What is claimed is:

1. A purified human alpha subunit of an SCN1A sodium channel nucleic acid selected from the group consisting of:

(a) a nucleic acid comprising a sequence encoding an alpha subunit of SCN1A selected from the group consisting of:

(i) an alpha subunit of SCN1A as set forth in SEQ ID NO:3, comprising a mutation corresponding to amino acid position 188 which replaces an aspartic acid residue by a valine residue;

(ii) an alpha subunit of SCN1A as set forth in SEQ ID NO:3, comprising a mutation corresponding to amino acid position 1238 which replaces a glutamic acid residue by an aspartic acid residue;

(iii) an alpha subunit of SCN1A as set forth in SEQ ID NO:3, comprising a mutation corresponding to amino acid position 1773 which replaces a serine residue by a tyrosine residue; and (iv) an alpha subunit of SCN1A being at least 95% identical to the SCN1A alpha subunits in (i)-(iii) and comprising one of the mutations at amino acid position 188, 1238 or 1773;

(b) an SCN1A nucleic acid fragment selected from the group consisting of:

(v) an amplified segment consisting of the nucleic acid sequence from nucleotide 739 to 867 of SEQ ID NO: 1, (vi) an amplified segment comprising the nucleic acid sequence from nucleotide 739 to 867 of SEQ ID NO: 1 having a mutation at nucleotide 828, (vii) an amplified segment consisting of the nucleic acid sequence from nucleotide 3970 to 4143 of SEQ ID NO: 1, (viii) an amplified segment comprising the nucleic acid sequence from nucleotide 3970 to 4143 of SEQ ID NO: 1 having a mutation at position 3978, (ix) an amplified segment consisting of the nucleic acid sequence from nucleotide 5521 to 5747 of SEQ ID NO: 1, and (x) an amplified segment comprising the nucleic acid sequence from nucleotide 5521 to 5747 of SEQ ID NO: 1 having a mutation at position 5582; and (c) a full-length complement of (a) or (b).

2. The purified nucleic acid of claim 1, wherein said alpha subunit SCN1A nucleic acid encodes:

(a) an alpha subunit of SCN1A as set forth in SEQ ID NO:3, comprising a mutation corresponding to amino acid position 188 which replaces an aspartic acid residue by a valine residue; or (b) an alpha subunit of SCN1A at least 95% identical to the alpha subunit of SCN1A as set forth in SEQ ID NO:3 and comprising a mutation corresponding to amino acid position 188 which replaces an aspartic acid residue by a valine residue.

3. The purified nucleic acid of claim 1, wherein said SCN1A nucleic acid fragment comprises a the nucleotide sequence as set forth in SEQ ID NO:190 or the nucleotide sequence as set forth in SEQ ID NO:192.

4. The purified nucleic acid of claim 1, encoding the alpha subunit of SCN1A set forth in SEQ ID NO:3, wherein an aspartic acid residue at position 188 is replaced by a valine residue.

5. The purified nucleic acid of claim 1, encoding the alpha subunit of SCN1A set forth in SEQ ID NO:3, wherein a glutamic acid residue at position 1238 is replaced by an aspartic acid residue.

6. The purified nucleic acid of claim 1, encoding the alpha subunit of SCN1A set forth in SEQ ID NO:3, wherein a serine residue at position 1773 is replaced by a tyrosine residue.

7. A vector comprising any one of the nucleic acids of claim 1.

8. An isolated cell harboring a vector of claim 7.

9. A vector comprising any one of the nucleic acids of claim 2.

10. An isolated cell harboring the vector of claim 9.

11. A vector comprising any one of the nucleic acids of claim 3.

12. An isolated cell harboring the vector of claim 11.

13. A vector comprising the nucleic acid of claim 4.

14. An isolated cell harboring the vector of claim 13.

15. A vector comprising the nucleic acid of claim 5.

16. An isolated cell harboring the vector of claim 15.

17. A vector comprising the nucleic acid of claim 6.

18. An isolated cell harboring the vector of claim 17.

19. A purified human SCN1A nucleic acid comprising a nucleic acid sequence selected from the group consisting of:

(a) a nucleic acid sequence encoding an alpha subunit of SCN1A selected from the group consisting of:

(i) an alpha subunit of SCN1A as set forth in SEQ ID NO:3, comprising a mutation corresponding to amino acid position 188 which replaces an aspartic acid residue by a valine residue;

(ii) an alpha subunit of SCN1A as set forth in SEQ ID NO:3, comprising a mutation corresponding to amino acid position 1238 which replaces a glutamic acid residue by an aspartic acid residue;

(iii) an alpha subunit of SCN1A as set forth in SEQ ID NO:3, comprising a mutation corresponding to amino acid position 1773 which replaces a serine residue by a tyrosine residue; and (iv) an alpha subunit of SCN1A being at least 95% identical to the SCN1A alpha subunits in (i)-(iii) and comprising one of the mutations at amino acid position 188, 1238 or 1773;

(b) an SCN1A nucleic acid fragment selected from the group consisting of:

(v) an amplified segment comprising the nucleic acid sequence from nucleotide 739 to 867 of SEQ ID NO: 1 having a mutation at position 828, (vi) an amplified segment comprising the nucleic acid sequence from nucleotide 3970 to 4143 of SEQ ID NO:1 having a mutation at position 3978, (vii) an amplified segment comprising the nucleic acid sequence from nucleotide 5521 to 5747 of SEQ ID NO: 1 having a mutation at position 5582; and (c) a full-length complement of (a) or (b).

20. The nucleic acid of claim 19, wherein said nucleic acid sequence is selected from the group consisting of:

(viii) an amplified segment consisting of the nucleic acid sequence from nucleotide 739 to 867 of SEQ ID NO: 1 having a mutation at position 828, (ix) an amplified segment consisting of the nucleic acid sequence from nucleotide 3970 to 4143 of SEQ ID NO:1 having a mutation at position 3978;

(x) an amplified segment consisting of the nucleic acid sequence from nucleotide 5521 to 5747 of SEQ ID NO: 1 having a mutation at position 5582; and (xi) a full-length complement of (viii)-(x).

21. A vector comprising any one of the nucleic acids of claim 19.

22. An isolated cell harboring the vector of claim 21.

23. A purified human alpha subunit of an SCN1A sodium channel nucleic acid comprising a nucleic acid sequence selected from the group consisting of:

(a) a nucleic acid sequence encoding an alpha subunit of SCN1A selected from the group consisting of:

(i) an alpha subunit of SCN1A as set forth in SEQ ID NO:409, comprising a mutation corresponding to amino acid position 188 which replaces an aspartic acid residue by a valine residue;

(ii) an alpha subunit of SCN1A as set forth in SEQ ID NO:410, comprising a mutation corresponding to amino acid position 1238 which replaces a glutamic acid residue by an aspartic acid residue;

(iii) an alpha subunit of SCN1A as set forth in SEQ ID NO:411, comprising a mutation corresponding to amino acid position 1773 which replaces a serine residue by a tyrosine residue; and (iv) an alpha subunit of SCN1A being at least 95% identical to the SCN1A alpha subunits in (ii)-(iii) and comprising one of the mutations at amino acid position 188, 1238 or 1773; and (b) a full-length complement of a).

* * * * *

UNITED STATES PATENT AND TRADEMARK OFFICE

CERTIFICATE OF CORRECTION

PATENT NO. : 7,655,460 B2
APPLICATION NO. : 10/664423
DATED : February 2, 2010
INVENTOR(S) : Rouleau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 622 days.

Signed and Sealed this

Twenty-third Day of November, 2010

David J. Kappos
*Director of the United States Patent and Trademark Office*